(12) United States Patent
Martinez Botella et al.

(10) Patent No.: US 10,172,871 B2
(45) Date of Patent: Jan. 8, 2019

(54) 19-NOR C3, 3-DISUBSTITUTED C21-N-PYRAZOLYL STEROIDS AND METHODS OF USE THEREOF

(71) Applicant: SAGE THERAPEUTICS, INC., Cambridge, MA (US)

(72) Inventors: Gabriel Martinez Botella, Wayland, MA (US); Boyd L. Harrison, Princeton Junction, NJ (US); Albert Jean Robichaud, Cambridge, MA (US); Francesco G. Salituro, Marlborough, MA (US); Richard Thomas Beresis, Shanghai (CN)

(73) Assignee: Sage Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/297,845

(22) Filed: Oct. 19, 2016

(65) Prior Publication Data

US 2017/0246191 A1 Aug. 31, 2017

Related U.S. Application Data

(62) Division of application No. 14/785,171, filed as application No. PCT/CN2014/075594 on Apr. 17, 2014, now Pat. No. 9,512,165.

(30) Foreign Application Priority Data

Apr. 17, 2013 (WO) ................ PCT/CN2013/074323

(51) Int. Cl.
| | | |
|---|---|---|
| A61K 31/58 | (2006.01) | |
| A61K 31/573 | (2006.01) | |
| C07J 3/00 | (2006.01) | |
| C07J 7/00 | (2006.01) | |
| C07J 15/00 | (2006.01) | |

(Continued)

(52) U.S. Cl.
CPC ............ *A61K 31/58* (2013.01); *A61K 9/0019* (2013.01); *A61K 31/573* (2013.01); *C07J 3/00* (2013.01); *C07J 5/0053* (2013.01); *C07J 7/00* (2013.01); *C07J 15/00* (2013.01); *C07J 43/003* (2013.01); *C07J 1/007* (2013.01); *C07J 1/0059* (2013.01); *C07J 1/0074* (2013.01); *C07J 5/0015* (2013.01); *C07J 7/002* (2013.01); *C07J 7/007* (2013.01); *C07J 7/0085* (2013.01); *C07J 13/007* (2013.01); *C07J 21/00* (2013.01); *C07J 31/006* (2013.01)

(58) Field of Classification Search
CPC .............................. A61K 31/58; A61K 31/573
USPC ........................................................ 514/176
See application file for complete search history.

(56) References Cited

U.S. PATENT DOCUMENTS

| 2,856,415 A | 10/1958 | Mihina |
| 3,169,134 A | 2/1965 | Klimstra et al. |

(Continued)

FOREIGN PATENT DOCUMENTS

| CN | 1190404 A | 8/1998 |
| CN | 101412742 A | 4/2009 |

(Continued)

OTHER PUBLICATIONS

Bandyopadhyaya et al., "Neurosteroid Analogs. 15. A Comparative Study of the Anesthetic and GABAergic Actions of Alphaxalone, D16-Alphaxalone and Their Corresponding 17-Carbonitrile Analogs, "Bioorganic & Medicinal Chemistry Letters 20:6680-6684 (2010).

Botella et al., "Neuroactive Steroids. 1. Positive Allosteric Modulators of the (g-Aminobutyric Acid)a Receptor: Structure-Activity Relationships of Heterocyclic Substitution at C-21" Journal of Medical Chemistry, 2015, 58 pp. 3500-3511.

Botella et al., "Neuroactive Steroid& 2. 3a-Hydroxy-3b-methyl-21-(4-cyano-1H-pyrazol-1-yl)-19-nor-5b-pregnan-20-one (SAGE-217): A Clinical Next Generation Neuroactive Steroid Positive Allosteric Modulator of the (g-Aminobutyric Acid)A Receptor" Journal of Medical Chemistry, 2017, 10 pp. A-J.

(Continued)

*Primary Examiner* — Yevgeny Valenrod
(74) *Attorney, Agent, or Firm* — Goodwin Procter LLP

(57) ABSTRACT

Provided herein are 19-nor C3,3-disubstituted C21-pyrazolyl steroids of Formula (I):

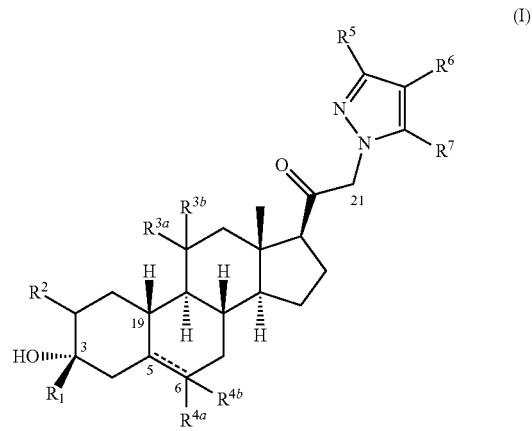

and pharmaceutically acceptable salts thereof; wherein ====, $R^1$, $R^2$, $R^{3a}$, $R^{3b}$, $R^{4a}$, $R^{4b}$, $R^5$, $R^6$, and $R^7$ are as defined herein. Such compounds are contemplated useful for the prevention and treatment of a variety of CNS-related conditions, for example, treatment of sleep disorders, mood disorders, schizophrenia spectrum disorders, convulsive disorders, disorders of memory and/or cognition, movement disorders, personality disorders, autism spectrum disorders, pain, traumatic brain injury, vascular diseases, substance abuse disorders and/or withdrawal syndromes, and tinnitus.

12 Claims, 52 Drawing Sheets

(51) Int. Cl.
  *C07J 43/00*   (2006.01)
  *A61K 9/00*    (2006.01)
  *C07J 5/00*    (2006.01)
  *C07J 1/00*        (2006.01)
  *C07J 13/00*       (2006.01)
  *C07J 21/00*       (2006.01)
  *C07J 31/00*       (2006.01)

(56) References Cited

U.S. PATENT DOCUMENTS

| | | |
|---|---|---|
| 3,206,459 A | 9/1965 | Cross |
| 3,580,937 A | 5/1971 | Campbell et al. |
| 3,943,124 A | 3/1976 | Phillipps et al. |
| 3,983,111 A | 9/1976 | Phillipps et al. |
| 3,998,829 A | 12/1976 | Phillips et al. |
| 4,071,625 A | 1/1978 | Grunwell et al. |
| 4,179,336 A | 12/1979 | Weber et al. |
| 4,192,871 A | 3/1980 | Phillipps et al. |
| 4,389,345 A | 6/1983 | Lenz |
| 5,593,983 A | 1/1997 | Campbell |
| 5,721,227 A | 2/1998 | Melloni et al. |
| 5,925,630 A | 7/1999 | Upasani et al. |
| 5,935,545 A | 8/1999 | Leary et al. |
| 5,939,545 A * | 8/1999 | Upasani ............... A61K 31/56 540/106 |
| 6,133,280 A | 10/2000 | Brodie et al. |
| 6,143,736 A | 11/2000 | Upasani et al. |
| 6,277,838 B1 | 8/2001 | Upasani et al. |
| 6,717,002 B2 | 4/2004 | Yano et al. |
| 6,844,456 B2 | 1/2005 | Covey |
| 7,064,116 B2 | 6/2006 | Calogeropoulou et al. |
| 7,781,421 B2 | 8/2010 | Covey et al. |
| 8,759,330 B2 | 6/2014 | Covey et al. |
| 8,939,545 B2 | 1/2015 | Tunmore et al. |
| 9,156,876 B2 | 10/2015 | Covey |
| 9,365,611 B2 | 6/2016 | Martinez Botella et al. |
| 9,512,165 B2 | 12/2016 | Martinez Botella et al. |
| 9,630,986 B2 | 4/2017 | Covey et al. |
| 9,725,481 B2 | 8/2017 | Martinez Botella et al. |
| 9,765,110 B2 | 9/2017 | Covey |
| 2002/0091112 A1 | 7/2002 | Menzenbach et al. |
| 2005/0176976 A1 | 8/2005 | Calogeropoulou et al. |
| 2006/0094696 A1 | 5/2006 | Leese et al. |
| 2007/0014719 A1 | 1/2007 | Reading et al. |
| 2008/0269183 A1 | 10/2008 | Mellon et al. |
| 2009/0048218 A1 | 2/2009 | Kuhnke et al. |
| 2010/0152840 A1 | 6/2010 | Seguin et al. |
| 2010/0234335 A1 | 9/2010 | Gravanis et al. |
| 2010/0317638 A1 | 12/2010 | Covey et al. |
| 2011/0152840 A1 | 6/2011 | Lee et al. |
| 2011/0172242 A1 | 7/2011 | Helton et al. |
| 2014/0017675 A1 | 1/2014 | Ito |
| 2014/0050789 A1 | 2/2014 | Rogawski et al. |
| 2014/0094619 A1 | 4/2014 | Runyon et al. |
| 2014/0148412 A1 | 5/2014 | Hogenkamp |
| 2014/0235600 A1 | 8/2014 | Covey et al. |
| 2014/0275241 A1 | 9/2014 | Covey |
| 2015/0291654 A1 | 10/2015 | Upasani et al. |
| 2015/0315230 A1 | 11/2015 | Covey et al. |
| 2016/0068563 A1 | 3/2016 | Martinez Botella et al. |
| 2016/0083418 A1 | 3/2016 | Martinez Botella et al. |
| 2016/0108080 A1 | 4/2016 | Martinez Botella et al. |
| 2016/0229887 A1 | 8/2016 | Martinez Botella et al. |

FOREIGN PATENT DOCUMENTS

| | | |
|---|---|---|
| CN | 101624414 A | 1/2010 |
| CN | 104136452 A | 11/2014 |
| DE | 2330342 A1 | 1/1974 |
| DE | 2526373 A1 | 12/1976 |
| DE | 2700267 A1 | 7/1977 |
| DE | 2632677 A1 | 1/1978 |
| EP | 0104489 A1 | 4/1984 |
| EP | 0554436 A1 | 8/1993 |
| EP | 0656365 A1 | 6/1995 |
| EP | 0701444 A1 | 3/1996 |
| EP | 1038880 A2 | 9/2000 |
| FR | 1994 M | 9/1963 |
| GB | 1380246 A | 1/1975 |
| GB | 1430942 A | 4/1976 |
| GB | 1570394 A | 7/1980 |
| GB | 1581234 A | 12/1980 |
| RU | 2194712 C2 | 12/2002 |
| RU | 2010100334 A | 7/2011 |
| WO | 1991016897 A1 | 11/1991 |
| WO | 9303732 A1 | 3/1993 |
| WO | 9305786 A1 | 4/1993 |
| WO | 9318053 A1 | 9/1993 |
| WO | 9427608 A1 | 12/1994 |
| WO | 1995021617 A1 | 8/1995 |
| WO | 1996003421 A1 | 2/1996 |
| WO | 1996016076 A1 | 5/1996 |
| WO | 9640043 A2 | 12/1996 |
| WO | 9805337 A1 | 2/1998 |
| WO | 0066614 A1 | 11/2000 |
| WO | 2005051972 A1 | 6/2005 |
| WO | 2005105822 A2 | 11/2005 |
| WO | 2006037016 A2 | 4/2006 |
| WO | 2006131392 A1 | 12/2006 |
| WO | 2008151745 A1 | 12/2008 |
| WO | 2008157460 A1 | 12/2008 |
| WO | 2010003391 A2 | 1/2010 |
| WO | 2010107815 A1 | 9/2010 |
| WO | 2012013816 A1 | 2/2012 |
| WO | 2012083090 A2 | 6/2012 |
| WO | 2012109752 A1 | 8/2012 |
| WO | 2012110010 A1 | 8/2012 |
| WO | 2012116290 A2 | 8/2012 |
| WO | 2013019711 A2 | 2/2013 |
| WO | 2013036835 A1 | 3/2013 |
| WO | 2013056181 A1 | 4/2013 |
| WO | 2013188792 A2 | 12/2013 |
| WO | 2014058736 A1 | 4/2014 |
| WO | 2014071449 A1 | 5/2014 |
| WO | 2014100228 A1 | 6/2014 |
| WO | 2014169831 A1 | 10/2014 |
| WO | 2014169832 A1 | 10/2014 |
| WO | 2014169833 A1 | 10/2014 |
| WO | 2014169836 A1 | 10/2014 |
| WO | 2015010054 A2 | 1/2015 |
| WO | 2015027227 A1 | 2/2015 |
| WO | 2015180679 A1 | 12/2015 |
| WO | 2015195962 A1 | 12/2015 |
| WO | 2016061527 A1 | 4/2016 |
| WO | 2016061537 A1 | 4/2016 |
| WO | 2016082789 A1 | 6/2016 |
| WO | 2016123056 A1 | 8/2016 |
| WO | 2016134301 A2 | 8/2016 |
| WO | 2016209847 A1 | 12/2016 |
| WO | 2017044659 A1 | 3/2017 |
| WO | 2017066626 A1 | 4/2017 |
| WO | 2017087864 A1 | 5/2017 |
| WO | 2017156418 A1 | 9/2017 |
| WO | 2018013613 A1 | 1/2018 |
| WO | 2018013615 A1 | 1/2018 |

OTHER PUBLICATIONS

Dorwald, "Side Reactions in Organic Synthesis", 2005, Wiley-VCH, Preface, p. IX.
Extended European Search Report for application PCT/CN2014075593 dated Aug. 26, 2016.
Extended European Search Report for application PCT/CN2014075594 dated Aug. 26, 2016.
Hu et al., "Journal of Medicinal Chemistry, Neurosteroid Analogues: Structure-Activity Studies of Benz(e] indene Modulators of GABM Receptor Function. 1. The Effect of 6-Melhyl Substitution on the Electrophysiological Activity of 7-Substituted Benz[e]indene-3-carbonitriles", 1993, 36 pp. 3956-3967.
International Search Report and Written Opinion for Corresponding International Application No. PCT/US2016/018748 dated Aug. 29, 2016.

(56) References Cited

OTHER PUBLICATIONS

International Search Report and Written Opinion for International Application No. PCT/US14/47246, dated Jan. 22, 2015.
Notification of Transmittal of the International Search Report and the Written Opinion of the International Searching authority, or the Declaration, International Application No. PCT/US13/45933, dated Dec. 3, 2013, 5 Pages.
Phillipps et al., "A New Series of Steroidal Antidysrhythmic Agents," J. Steroid Biochem. 19(1):759-765 (1983).
Runyon et al., "European Journal of Pharmacology, 17b-Nitro-5a-androstan-3a-ol and its 3b-methyl derivative: Neurosteroid analogs with potent anticonvulsant and anxiolytic activities", 2009, 617 pp. 68-73.
Shu et al., "Characteristics of concatemeric GABM receptors containing alpha4/d subunits expressed in Xenopus oocytes" British Journal of Pharmacology (2012) 165, 2228-2243.
Supplemental European Search Report, European Patent Application No. 14826212.4, dated Feb. 16, 2017.
Atack, "Development of Subtype-Selective GABAA Receptor Compounds for the Treatment of Anxiety, Sleep Disorders and Epilepsy", GABA and Sleep. Molecular, Functional and Clinical Aspects. 2010, pp. 25-72.
Banday et al., "D-ring substituted 1,2,3-triazolyl 20-keto pregnenanes as potential anticancer agents: Synthesis and biological evaluation", Steroids, (2010), vol. 75, No. 12, pp. 801-804, Abstract.
Bernstein, "Rett Syndrome Medication", Medscape, (2017).
CAS registry No. 162882-77-1.
CAS registry No. 162883-68-3.
Chodounska et al., "Epalons: Synthesis of 3a, 7a-Dihydroxy-5a-Pregnan-20-One", Collection Symposium Series, vol. 33, no. 10, (1998), pp. 1543-1548.
Database CAPLUS in STN, Acc. No. 1995:986323, Upasani et al., WO 9521617 A1 (Aug. 17, 1995) (abstract). [Upasani, Ravindra B. "Androstanes and pregnanes for allosteric modulation of GABA receptor, and preparation and therapeutic uses of compounds".].
Database CAPLUS in STN, Acc. No. 1998:112239, Lan, WO 9805337 A1 (Feb. 12, 1998) (abstract). [Lan, Nancy C., "Use of GABA agonists and NMDA receptor antagonists for the treatment of migraine headache".].
Deluca et al., "Synthesis of 3b-Hydroxy[21-14C] -5b-pregn-8(14)-en-20-one from Chenodeoxycholic Acid", Helvetica Chemica Acta, vol. 69, (1986), pp. 1844-1850.
Edgar et al., "CCD-3693: An Orally Bioavailable Analog of the Endogenous Neuroactive Steroid, Pregnanolone, Demonstrates Potent Sedative Hypnotic Actions in the Rat" The Journal of Pharmacology and Experimental Therapeutics (1997) vol. 282, No. 1, pp. 420-429.
Gasior et al., "Neuroactive steroids: potential therapeutic use in neurological and psychiatric disorders", Trends in Pharmacological Science, (1999), vol. 20, No. 3, pp. 107-112.
Harrison et al., "Structure-Activity Relationships for Steroid Interaction with the y-Aminobutyric AcidA Receptor Complex" The Journal of Pharmacology and Experimental Therapeutics (1987) vol. 241, No. 1, pp. 346-353.
Hawkinson et al, "3a-Hydroxy-3b-trifluoromethyl-5a-pregnan-20-one (Co 2-1970): A Partial Agonist at the Neuroactive Steroid Site of the y-Aminobutyric acidA Receptor" Molecular Pharmacology (1996) vol. 49, pp. 897-906.
Hawkinson et al, "Correlation of Neuroactive Steroid Modulation of [35S]t-Butylbicyclophosphorothionate and [3H] Flunitrazepam Binding and y-Aminobutyric AcidA Receptor Function", Molecular Pharmacology (1994) vol. 46, pp. 977-985.
Hawkinson et al, "Substituted 3b-Phenylethynyl Derivatives of 3a-Hydroxy-5a-pregnan-20-one: Remarkably Potent Neuroactive Steroid Modulators of y-Aminobutyric AcidA Receptors", The Journal of Pharmacology and Experimental Therapeutics(1998), vol. 287, No. 1, pp. 198-207.
Hogenkamp et al., "Pharmacological profile of a 17b-heteroaryl-substituted neuroactive steroid", Psychopharmacology, vol. 231, (2014), pp. 3517-3524.
Hogenkamp et al., "Synthesis and in Vitro Activity of 3b-Substituted-3a-hydroxypregnan-20-ones: Allosteric Modulators of the GABAA Receptor", Journal of Medicinal Chemistry, (1997), vol. 40, pp. 61-72.
International Search Report and Written Opinion for Corresponding International Application No. PCT/CN2014/078820 dated Feb. 27, 2015.
International Search Report and Written Opinion for Corresponding International Application No. PCT/CN2015/080216 dated Aug. 3, 2015.
International Search Report and Written Opinion for Corresponding International Application No. PCT/CN2015/095765 dated Mar. 4, 2016.
International Search Report and Written Opinion for Corresponding International Application No. PCT/US15/36500 dated Sep. 11, 2015.
International Search Report and Written Opinion for Corresponding International Application No. PCT/US15/56054 dated Feb. 9, 2016.
International Search Report and Written Opinion for Corresponding International Application No. PCT/US2013/076214 dated Aug. 29, 2016.
International Search Report and Written Opinion for Corresponding International Application No. PCT/US2014/052417 dated Nov. 19, 2014.
International Search Report and Written Opinion for Corresponding International Application No. PCT/US2014/092369 dated Aug. 25, 2015.
International Search Report and Written Opinion for Corresponding International Application No. PCT/US2015/056066 dated Feb. 8, 2016.
International Search Report and Written Opinion for Corresponding International Application No. PCT/US2016/014835 dated Jun. 9, 2016.
International Search Report and Written Opinion for Corresponding International Application No. PCT/US2016/062874 dated Jan. 30, 2017.
International Search Report and Written Opinion for Corresponding International Application No. PCT/US2017/041600 dated Dec. 1, 2017.
International Search Report and Written Opinion for Corresponding International Application No. PCT/US2017/041605 dated Dec. 12, 2017.
International Search Report and Written Opinion for Corresponding International Application No. PCT/US2017/048267 dated Aug. 29, 2016.
International Search Report and Written Opinion for International Application No. PCT/CN2013/074312 dated Jan. 23, 2014.
International Search Report and Written Opinion for International Application No. PCT/CN2013/074319 dated Jan. 23, 2014.
International Search Report and Written Opinion for International Application No. PCT/CN2013/074323 dated Jan. 30, 2014.
International Search Report and Written Opinion for International Application No. PCT/CN2013/074325 dated Jan. 23, 2014.
International Search Report and Written Opinion for International Application No. PCT/CN2014/075585 dated Aug. 1, 2014.
International Search Report and Written Opinion for International Application No. PCT/CN2014/075593 dated Jul. 22, 2014.
International Search Report and Written Opinion for International Application No. PCT/CN2014/075594 dated Jul. 16, 2014.
International Search Report and Written Opinion for International Application No. PCT/CN2014/075600 dated Jul. 29, 2014.
International Search Report for International Application No. PCT/US2012/060136 dated Mar. 27, 2013.
Jungmann et al., "7-Keto-5b-ätiansäure-Derivate. über Gallensäuren und verwandte Stoffe, 51 Mitteilung [Bile acids and related substances. LI. 7-0xo-5. beta.-etianic acid derivatives]", Helvetica Chimica Acta, vol. 41, No. 5, (1958), pp. 1206-1233.
Krafft et al., "Synthesis of the C/D/E and A/B Rings of Xestobergsterol—(A)", Journal of Organic Chemistry, American Chemical Society, vol. 64, No. 7, (1999), pp. 2475-2485.
Lehmann et al., "Schweinegallensäuren Der Abbau von Hyocholsäure zu Pregnanderivaten", vol. 32, No. 3-4, (1966), pp. 217-224.

(56) References Cited

OTHER PUBLICATIONS

Mangialasche et al., "Alzheimer's disease: clinical trials and drug development", Lance Neurology, vol. 9 (2010), pp. 702-716.
Matsui et al., "Comparative fate of testosterone and testosterone sulfate in female rats: C1902 and C1903 steroid metabolites in the bile", Journal of Steroid Biochemistry, 1977, 8(4), pp. 323-328.
Paul et al., "Neuroactive Steroids", The Journal of the Federation of American Societies for Experimental Biology, (1992), pp. 2311-2322.
Peart et al., "Hydroxylation of steroids by Fusarium oxysporum, Exophiala jeanselmei and Ceratocystis paradoxa", Steroids, vol. 76, No. 12, (2011), pp. 1317-1330.
Phillipps et al., "Water-soluble Steroidal Anaesthetics", Journal of Steroid Biochemistry 11:79-86 (1979).
Phillipps, "Structure-Activity Relationships in Steroidal Anaesthetics", Journal of Steroid Biochemistry, (1975), vol. 6, pp. 607-613.
Phillipps, "Structure-Activity Relationships in Steroidal Anaesthetics", Nol. Mech. Gen. Anaesth. Glaxo Symposium, (1974), pp. 32-47.
PubChem-70249446 (2012), entire document.
Rogawski et al., "Neuroactive steroids for the treatment of status epilepticus", Epilepsia, 54:(2013), pp. 93-98.
Slavikovéet al., "Allopregnanolone (3a-Hydroxy-5a-pregnan-20-one) Derivatives with a Polar Chain in Position 16a: Synthesis and Activity", Journal of Medicinal Chemistry, vol. 52, No. 7, (2009), 2119-2125.
Stastna et al., "Synthesis of C3, C5, and C7 pregnane derivatives and their effect on NMDA receptor responses in cultured rat hippocampal neurons", Steroids, Elsevier Science Publishers, vol. 74, No. 2, (2008), pp. 256-263.
Tsai et al., "Synthesis and antiproliferative activity of 3a-hydroxyl-3b-methoxymethyl-5a-pregnan-20-one with a C-21 hydrophilic substituent", Heteroatom Chemistry, (2017), pp. 1-9.
Upasani et al., "3a-Hydroxy-3β-(phenylethynyl)-5β-pregnan-20-ones: Synthesis and Pharmacological Activity of Neuroactive Steroids with High Affinity for GABAA Receptors", J. Med. Chem. (1997) vol. 40, No. 1, pp. 73-84.
Vanover et al., "Behavioral characterization of Co 134444 (3a-hydroxy-21-(1'-imidazolyl)-3b-methoxymethyl-5a-pregnan-20-one), a novel sedative-hypnotic neuroactive steroid", Psychopharmacology (2001), vol. 155, pp. 285-291.
Vanover et al., "Characterization of the Anxiolytic Properties of a Novel Neuroactive Steroid, Co 2-6749 (GMA-839; WAY-141839; 3a, 21-Dihydroxy-3b-trifluoromethyl-19-nor-5b-pregnan-20-one), a Selective Modulator of y-Aminobutyric AcidA Receptors", The Journal of Pharmacology and Experimental Therapeutics, (2000), vol. 295, No. 1, pp. 337-345.
Vanover et al., "Response-Rate Suppression in Operant Paradigm as Predictor of Soporific Potency in Rats and Identification of Three Novel Sedative-Hypnotic Neuroactive Steroids", The Journal of Pharmacology and Experimental Therapeutics, (1999), vol. 291, No. 3, pp. 1317-1323.
Zeng et al., "Neurosteroid Analogues. 10. The Effect of Methyl Group Substitution at the C-6 and C-7 Positions on the GABA Modulatory and Anesthetic Actions of (3a,5a) -and (3a, 5b)-3-Hydroxypregnan-20-one", Journal of Medicinal Chemistry, (2005). vol. 48, pp. 3051-3059.
Zonana et al., "The Neurobiology of Postpartum Depression", CNS Spectrums, (2005), pp. 792-799, 805.
Anderson et al., "Anesthetic Activity of Novel Water-Soluble 2b-Morpholinyl Steroids and Their Modulatory Effects at GABA-A Receptors", Journal of Medicinal Chemistry., 1997, vol. 40, pp. 1668-1681.
Anderson et al., "Conformationally Constrained Anesthetic Steroids That Modulate GABAA Receptors," Journal of Medicinal Chemistry, 2000, vol. 43, No. 22, pp. 4118-4125.
Berge et al., J. Pharmaceutical Sciences, 1977, vol. 66, pp. 1-19.
Bjorkhem et al., "Steroid hormone metabolism in developing rates", Eur. J.Biochem., 1972, vol. 27, No. 2, pp. 318-326.
CAS registry No. 1040410-23-8.
Caspi et al., "Stereochemistry of 19-hydroxy-19alpha-methyl steroids," Chemical Communications, 1966, vol. 7, pp. 209-210.
Cerny et al., "Syntheses of 19-[O-(carboxymethyl)oxime] haptens of epipregnanolone and pregnanolone", Steroids, 2006, vol. 71(2), pp. 120-128.
Cerny et al., "Synthetic approach to 5alpha-pregnanolone 19-[0-(carboxymethyl) oxime] derivatives", Collection of Czechoslovak Chemical Communications, 2004, vol. 69, No. 9, pp. 1805-1817.
Deniau et al., "Synthesis of fluorinated analogues of the neurosteroid GABA receptor antagonist, 17-PA", Journal of Fluorine Chemistry, (2008), vol. 129, No. 9, pp. 881-887.
Evers et al., "A Synthetic 18-Norsleroid Distinguishes Between Two Neuroactive Steroid Binding Sites on GABAA Receptors", Journal of Pharmacology and Experimental Therapeutics, 2010, vol. 333, No. 2, pp. 404-413.
Fajkos et al., "Steroids. XXIII. Synthesis and configuration of the two stereoisomeric 3b-hydroxy-16-acetylandrostanes", Chemicke Listy pro Vedu a Prumysl, 1956, vol. 50, pp. 791-799.
Fesik et al., "Geometric Requirements for Membrance Perturbation and Anesthetic Activity", Molecular Pharmacology, 1985, vol. 27, pp. 624-629.
Green et al., "The nonfeminizing enantiomer of 17b-estradiol exerts protective effects in neuronal cultures and a rat model of cerebral ischemia", Endocrinology, 2001, vol. 142, pp. 400-406.
Gustafsson et al., "Steroid excretion patterns in urine from ovariectomized and adrenalectomized rats", Biochmica ET Biophysica ACTA—Lipids and Lipid Metabolism, Elsevier Science BV, 1972, vol. 280, No. 1, pp. 182-186.
Gustafsson et al., "Steroids in Germfree and Conventional Rats. 7. Identification of C19 and C21 Steroids in faeces from Conventional Rats", European Journal of Biochemistry, 1968, vol. 6, No. 2, pp. 248-255.
Gyermek et al., "Steroids, CCCX. 1 Structure-Activity Relationship of Some Steroidal Hypnotic Agents", Journal of Medicinal Chemistry, 1968, vol. 11, No. 1, pp. 117-125.
Han et al., "Neurosteroid Analogs. 3. The Synthesis and Electrophysiological Evaluation of Benz[e]indene Congeners of Neuroactive Steroids Having the 5b-Configuration", Journal of of Medicinal Chemistry, 1995, vol. 38, No. 22, pp. 4548-4556.
Hauser et al., "Steroids. CCV. Fragmentations and intramolecular abstractions of tertiary hydrogen atoms by primary oxy radicals with fixed reaction centers", Helv. Chim. Acta, 1964, vol. 47, pp. 1961-1979.
Heard et al., "Steroids. VII. Preparation of of androstan-3(b)-ol-7-one from from dehydroisoandrosterone", Journal of Thological Chemistry, 1946, vol. 165, pp. 677-685.
Hewett et al., "Amino steroids. Part III. 2- and 3-Amino-5a-androstanes", Journal of the Chemical Society, 1968, vol. 9, pp. 1134-1140.
Hill et al, "Pholochemische Reaktionen. 32 Milleilung. UV-Bestrahlung von gesattigten and bela,gamma- ngesalligten, homoallylisch konjugierten steroidaldehyden", Helvetica Chimica Acta, 1946, vol. 49, No. 1, pp. 292-311.
Hu et al, "Neurosteroid analogues. Part 5. Enantiomers of neuroactive steroids and benz[e]indenes: total synthesis,18 electrophysiological effects on GABAA receptor function and anesthetic actions in tadpoles", J. Chem. Soc. Perkin Trans 1, 1997, pp. 3665-3671.
Im et al., "Studies on the Mechanism of Interactions between Anesthetic Steroids and y-Aminobutyric AcidA Receptors", Molecular Pharmacology (1990), 37(3), pp. 429-434.
Jiang et al., "Neurosteroid analogues. 9. Conformationally constrained pregnanes: structure-activity studies of 13,24-cyclo-18, 21-dinorcholane analogues of the GABA modulatory and anesthetic steroids (3a,5a)- and (3a,5a)-3-hydroxypregnan-20-one", Journal of Medicinal Chemistry, 2003, vol. 46, pp. 5334-5348.
Kaji et al., "Synthesis of 3-epi-6, 7- dideoxyxestobergsterol A", Chem. & Pharm. Bulletin, 2000, vol. 48, No. 10, pp. 1480-1483.
Katona et al., "Neurosteroid analogues. 12. Potent enhancement of GABA-mediated chloride currents at GABAA receptors by ent-androgens", European Journal of Medicinal Chemistry, 2008, vol. 43, pp. 107-113.

(56) References Cited

OTHER PUBLICATIONS

Knox et al., "Steroids. CCLXXVII. Reductions of 19-substituted androst-4-en-3-ones and related compounds", Journal of Organic Chemistry, 1965, vol. 30, No. 7, pp. 2198-2205.
Krishnan et al., "Neurosteroid Analogues. Chapter 17. Inverted Binding Orientations of Androsterone Enantiomers at the Steroid Potentiation Site on y-Aminobutyric Acid Type A Receptors", Journal of Medicinal Chemistry, 2012, vol. 55, No. 3, pp. 1334-1345.
Lan et al, "Neurosteroid Analogues. 4. The Effect of Methyl Substitution at the C-5 and C-10 Positions of Neurosteroids on Electrophysiological Activity at GABAA Receptors", Journal of Medicinal Chemistry, (1996), vol. 39, pp. 4218-4232.
Lewbart et al., "Oxidation of Steroidal a-Ketols to Glyoxals with Cupric Acetate", Journal of Organic Chemistry, (1963), vol. 28, No. 8, pp. 2001-2006.
Li et al., "Neuroactive Steroids and Human Recombinant p1 GABAc Receptors", Journal of Pharmacology and Experimental Therapeutics, (2007), vol. 323, pp. 236-247.
Mok et al., "Evidence that 5a-pregnan-3a-ol-20-one is the metabolite responsible for progesterone anesthesia", Brain Research (1990), 533(1), pp. 42-45.
Morrow et al., "Characterization of Steroid Interactions with gamma-Aminobutyric Acid Receptor-Gated Chloride Ion Channels: Evidence for Multiple Steroid Recognition Sites", 1989, Molecular Pharmacology, 37, pp. 263-270.
Nilsson et al., "Neurosteroid analogues. 6. The synthesis and GABAA receptor pharmacology of enantiomers of dehydroepiandrosterone sulfate, pregnenolone sulfate, and (3a,5b)-3-hydroxypregnan-20-one sulfate", Journal of Medicinal Chemistry, 1998, vol. 41, pp. 2604-2613.
Paradiso et al., "Steroid Inhibition of Rat Neuronal Nicotinic a4B2 Receptors Expressed in HEK 293 Cells", Journal of Molecular Pharmacology, (2000), vol. 58, pp. 341-351.
Pechet et al., "Metabolism of 19-hydroxycorticosterone. Isolation and characterization of three metabolites", Journal of Biological Chemistry, Jan. 1, 1961, vol. 236, No. 10, pp. PC68-PC69.
Purdy et al., "Synthesis, Metabolism, and Pharmacological Activity of 3a-Hydroxy Steroids Which Potentiate GABA-Receptor-Mediated Chloride Ion Uptake in Rat Cerebral Cortical Synaptoneurosomes", Journal of Medicinal Chemistry, (1990), vol. 33, pp. 1572-1581.
Qian et al., "Neurosteroid Analogues, 18. Structure-Activity Studies of ent-Steroid Potentiators of y-Aminobutyric Acid Type A Receptors and Comparison of Their Activities with Those of Alphaxalone and Allopregnanolone", Journal of Medicinal Chemistry, 2014, vol. 57, No. 1, pp. 171-190.
Qian et al., "The efficient and enantiospecific total synthesis of cyclopenta[b]phenanthrenes structurally related to neurosteroids", Adv. Syn. & Cata., 2010, vol. 352, Nos. 11-12, pp. 2057-2061.
Ruzicka et al., "Steroids and sex hormones. CXXXIX. The relation between constitution and odor of steroids. Methylandrostane and allopregnane derivatives", Helvetica Chimica Acta, 1947, vol. 30, pp. 867-878.
Rychnovsky et al., "Synthesis of ent-cholesterol, the unnatural enantiomer", Journal of Organic Chemistry, 1992, vol. 57, No. 9, pp. 2732-2736.
Santaniello & Caspi, "Reduction of certain steroidal 19-sulfonic esters with metal hydrides", J. of Ster. Biochem, 1976, vol. 7, No. 3, pp. 223-227.

Sarett., "A new method for the preparation of 17(alpha)-hydroxy-20-ketopregnanes", J. Am. Chem. Soc., 1948, vol. 70, pp. 1454-1458.
Scaglione et al., "Neurosteroid Analogues. 14. Alternative Ring System Scaffolds: GABA Modulatory and Anesthetic Actions of Cyclopenta[b]phenanthrenes and Cyclopenta[b]anthracenes", 2008, Journal of Medicinal Chemistry, vol. 51, pp. 1309-1318.
Shen et al., "Microbial aromatization of 19-hydroxymethylepidehydroandrosterone acetate by Corynebacterium simplex", Huaxue Xuebao, 1983, vol. 41, No. 5, pp. 473-474.
Spiegel et al., "Use of Nonaqueous Solvents in Parenteral Products", Journal of Pharmaceutical Sciences, 1963, vol. 52, No. 10, pp. 917-927.
Starnes et al., "Thin-Layer Chromatography of 17-Kelosteroid 2,4-Dinitrophenylhydrazones", Journal of Clinical Endocrinology and Metabolism, 1966, vol. 26, No. 11, pp. 1245-1250.
Stastna et al., "Neurosteroid Analogues. 16. A New Explanation for the Lack of Anesthetic Effects in D16—Alphaxalone and Identification of a D17(20) Analogue with Potent Anesthetic Activity", Journal of Medicinal Chemistry, 2011, vol. 54, No. 11, pp. 3926-3934.
Stastna et al., "Stereoselectivity of sodium borohydride reduction of saturated steroidal ketones utilizing conditions of Luche reduction", Steroids, 2010, vol. 75, No. 10, pp. 721-725.
Stastna et al., "The use of symmetry in enantioselective synthesis: Four pairs of chrysene enantiomers prepared from 19-nortestosterone", Org. Biomol. Chem., 2011, vol. 9, pp. 4685-4694.
U.S. Appl No. 14/132,386, dated Dec. 18, 2013, issued.
U.S. Appl. No. 14/652,717, dated Dec. 18, 2013, issued.
U.S. Appl. No. 15/459,492, dated Mar. 15, 2017, pending.
U.S. Appl. No. 15/586,853, dated May 4, 2017, pending.
U.S. Appl. No. 14/408,045, dated Dec. 15, 2014, pending.
Wicha et al., "Transformations of steroidal neopentyl systems. II. Migration of acetate from the 3beta- to the 19-hydroxyl in delta 5 and A/B-trans steroids", Canadian Journal of Chemistry, 1967, vol. 45, No. 7, pp. 707-711.
Wicha et al., "Transformations of steroidal neopentyl systems. IV. Stereochemistry of Products of Reaction of Methyllithium with Steroidal A5-19-aldehydes", Journal of the Chemical Society (Section) C: Organic, 1968, vol. 14, 1740-1746.
Wicha et al., "Transformations of steroidal neopentyl systems. V. Synthesis and proof of the configuration of 19amethyl-19S-alcohols", Journal of the Chemical Society [Section] C: Organic, 1969, vol. 6, pp. 947-951.
Wicha et al., "Transformations of steroidal neopentyl systems. VI. Intramolecular Claisen condensation of 19R-acetoxy- 19A-methyl-3-ones of the 5alpha series", Tetrahedron, 1969, vol. 25, No. 17, pp. 3961-3968.
Wicha et al., "Transformations of steroidal neopentyl systems. VII. Mechanism of the transformation of (19R)-(19)hydroxy-19-methyl-3-oxo-5alpha-to 3alpha-hydroxy-19-methyl-19—oxo-5alpha-analogs", Journal of Organic Chemistry, 1973, vol. 38 No. 7, pp. 1280-1283.
Wu, "A New Classification of Prodrugs: Regulatory Perspectives", Pharmaceuticals, 2009, vol. 2, pp. 77-81.
Zorumski et al., "Enantioselective Modulation of GABAergic Synaptic Transmission by Steroids and Benz[dindenes in Hippocampal Microcultures", Synapse, (1998), vol. 29, pp. 162-171.

* cited by examiner

19-NOR C3, 3-DISUBSTITUTED C21-N-PYRAZOLYL STEROIDS AND METHODS OF USE THEREOF

CLAIM OF PRIORITY

This application is a divisional of U.S. Ser. No. 14/785,171 filed Apr. 17, 2014, which is a national stage application under U.S.C. § 371 of International Application No. PCT/CN2014/075594, filed Apr. 17, 2014, published as International Publication No. WO2014/169833 on Oct. 23, 2014, which claims priority to International Application No. PCT/CN2013/074323, filed Apr. 17, 2013, the contents of each of which is incorporated herein by reference in its entirety.

BACKGROUND OF THE INVENTION

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −70 mV, the cell interior being negative with respect to the cell exterior. The potential (voltage) is the result of ion ($K^+$, $Na^+$, $Cl^-$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization (change of potential from −70 mV to −50 mV). This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the GABA receptor complex (GRC), the effect on brain excitability is mediated by GABA, a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs (i.e., reduced neuron excitability). In other words, the higher the chloride ion concentration in the neuron, the lower the brain excitability (the level of arousal).

It is well-documented that the GRC is responsible for the mediation of anxiety, seizure activity, and sedation. Thus, GABA and drugs that act like GABA or facilitate the effects of GABA (e.g., the therapeutically useful barbiturates and benzodiazepines (BZs), such as Valium®) produce their therapeutically useful effects by interacting with specific regulatory sites on the GRC. Accumulated evidence has now indicated that in addition to the benzodiazepine and barbiturate binding site, the GRC contains a distinct site for neuroactive steroids (Lan, N. C. et al., Neurochem. Res. 16:347-356 (1991)).

Neuroactive steroids can occur endogenously. The most potent endogenous neuroactive steroids are 3α-hydroxy-5-reduced pregnan-20-one and 3α-21-dihydroxy-5-reduced pregnan-20-one, metabolites of hormonal steroids progesterone and deoxycorticosterone, respectively. The ability of these steroid metabolites to alter brain excitability was recognized in 1986 (Majewska, M. D. et al., Science 232: 1004-1007 (1986); Harrison, N. L. et al., J Pharmacol. Exp. Ther. 241:346-353 (1987)).

The ovarian hormone progesterone and its metabolites have been demonstrated to have profound effects on brain excitability (Backstrom, T. et al., Acta Obstet. Gynecol. Scand. Suppl. 130:19-24 (1985); Pfaff, D. W and McEwen, B. S., Science 219:808-814 (1983); Gyermek et al., J Med Chem. 11: 117 (1968); Lambert, J. et al., Trends Pharmacol. Sci. 8:224-227 (1987)). The levels of progesterone and its metabolites vary with the phases of the menstrual cycle. It has been well documented that the levels of progesterone and its metabolites decrease prior to the onset of menses. The monthly recurrence of certain physical symptoms prior to the onset of menses has also been well documented. These symptoms, which have become associated with premenstrual syndrome (PMS), include stress, anxiety, and migraine headaches (Dalton, K., Premenstrual Syndrome and Progesterone Therapy, 2nd edition, Chicago Yearbook, Chicago (1984)). Subjects with PMS have a monthly recurrence of symptoms that are present in premenses and absent in postmenses.

In a similar fashion, a reduction in progesterone has also been temporally correlated with an increase in seizure frequency in female epileptics, i.e., catamenial epilepsy (Laidlaw, J., Lancet, 1235-1237 (1956)). A more direct correlation has been observed with a reduction in progesterone metabolites (Rosciszewska et al., J. Neurol. Neurosurg. Psych. 49:47-51 (1986)). In addition, for subjects with primary generalized petit mal epilepsy, the temporal incidence of seizures has been correlated with the incidence of the symptoms of premenstrual syndrome (Backstrom, T. et al., J. Psychosom. Obstet. Gynaecol. 2:8-20 (1983)). The steroid deoxycorticosterone has been found to be effective in treating subjects with epileptic spells correlated with their menstrual cycles (Aird, R. B. and Gordan, G., J. Amer. Med. Soc. 145:715-719 (1951)).

A syndrome also related to low progesterone levels is postnatal depression (PND). Immediately after birth, progesterone levels decrease dramatically leading to the onset of PND. The symptoms of PND range from mild depression to psychosis requiring hospitalization. PND is also associated with severe anxiety and irritability. PND-associated depression is not amenable to treatment by classic antidepressants, and women experiencing PND show an increased incidence of PMS (Dalton, K., Premenstrual Syndrome and Progesterone Therapy, 2nd edition, Chicago Yearbook, Chicago (1984)).

Collectively, these observations imply a crucial role for progesterone and deoxycorticosterone and more specifically their metabolites in the homeostatic regulation of brain excitability, which is manifested as an increase in seizure activity or symptoms associated with catamenial epilepsy, PMS, and PND. The correlation between reduced levels of progesterone and the symptoms associated with PMS, PND, and catamenial epilepsy (Backstrom, T. et al., J Psychosom. Obstet. Gynaecol. 2:8-20 (1983)); Dalton, K., Premenstrual Syndrome and Progesterone Therapy, 2nd edition, Chicago Yearbook, Chicago (1984)) has prompted the use of progesterone in their treatment (Mattson et al., "Medroxyprogesterone therapy of catamenial epilepsy," in Advances in Epileptology: XVth Epilepsy International Symposium, Raven Press, New York (1984), pp. 279-282, and Dalton, K., Premenstrual Syndrome and Progesterone Therapy, 2nd edition, Chicago Yearbook, Chicago (1984)). However, progesterone is not consistently effective in the treatment of the aforementioned syndromes. For example, no dose-response relationship exists for progesterone in the treatment of PMS (Maddocks et al., *Obstet. Gynecol.* 154:573-581 (1986); Dennerstein et al., *Brit. Med J* 290:16-17 (1986)).

New and improved neuroactive steroids are needed that act as modulating agents for brain excitability, as well as agents for the prevention and treatment of CNS-related diseases. The compounds, compositions, and methods described herein are directed toward this end.

SUMMARY OF THE INVENTION

The present invention is based, in part, on the desire to provide novel 19-nor (i.e., C19 desmethyl) compounds, e.g., related to progesterone, deoxycorticosterone, and their metabolites, with good potency, pharmacokinetic (PK) properties, oral bioavailability, formulatability, stability, safety, clearance and/or metabolism. One key feature of the compounds as described herein is disubstitution at the C3 position (e.g., with one substituent being a 3α hydroxy moiety. The inventors envision disubstitution at C-3 will eliminate the potential for oxidation of the hydroxy moiety to the ketone, prevent further metabolism, and reduce the potential for secondary elimination pathways, such as glucuronidation. The inventors further envision the overall effect of C3 disubstitution should be of improving the overall PK parameters and reducing potential toxicities and side effects, which may allow, in certain embodiments, administration orally and/or chronically. Another key feature of the compounds as described herein is the presence of a hydrogen at the C19 position ("19-nor") rather than a methyl group. The inventors envision 19-nor compounds, as compared to their C19-methyl counterparts, will have improved physical properties, such as improved solubility. The inventors envision further enhancement of solubility, for example, when the AB ring system is in the cis configuration.

Thus, in one aspect, provided herein are 19-nor C3,3-disubstituted C21-pyrazolyl steroids of Formula (I):

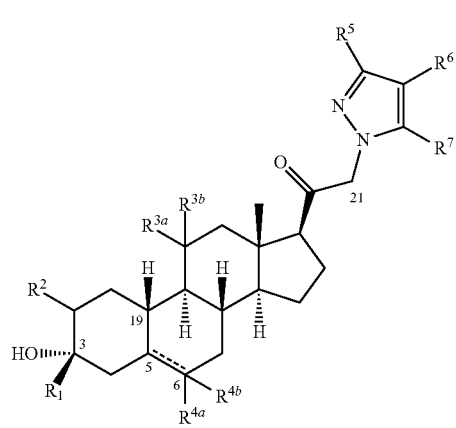

and pharmaceutically acceptable salts thereof;
wherein:
- - - - - represents a single or double bond;
$R^1$ is substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl;

$R^2$ is hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, or —$OR^{A2}$, wherein $R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl;

$R^{3a}$ is hydrogen or —$OR^{A3}$, wherein $R^{A3}$ is hydrogen or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, and $R^{3b}$ is hydrogen; or $R^{3a}$ and $R^{3b}$ are joined to form an oxo (=O) group;

each instance of $R^{4a}$ and $R^{4b}$ is independently hydrogen, substituted or unsubstituted $C_{1-6}$ alkyl, or halogen, provided if the - - - - - between C5 and C6 is a single bond, then the hydrogen at C5 and $R^{4a}$ are each independently provided in the alpha or beta configuration, and $R^{4b}$ is absent;

each instance of $R^5$, $R^6$, and $R^7$ is, independently, hydrogen, halogen, —$NO_2$, —$CN$, —$OR^{GA}$, —$N(R^{GA})_2$, —$C(=O)R^{GA}$, —$C(=O)OR^{GA}$, —$OC(=O)R^{GA}$, —$OC(=O)OR^{GA}$, —$C(=O)N(R^{GA})_2$, —$N(R^{GA})C(=O)R^{GA}$, —$OC(=O)N(R^{GA})_2$, —$N(R^{GA})C(=O)OR^{GA}$, —$N(R^{GA})C(=O)N(R^{GA})_2$, —$SR^{GA}$, —$S(O)R^{GA}$, e.g., —$S(=O)R^{GA}$, —$S(=O)_2R^{GA}$, —$S(=O)_2OR^{GA}$, —$OS(=O)_2R^{GA}$, —$S(=O)_2N(R^{GA})_2$, —$N(R^{GA})S(=O)_2R^{GA}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, or substituted or unsubstituted 3- to 6-membered heterocylyl; and each instance of $R^{GA}$ is independently hydrogen, substituted or unsubstituted $C_{1-6}$ alkyl, or unsubstituted $C_{2-6}$ alkenyl, substituted or unsubstituted $C_{2-6}$ alkynyl, substituted or unsubstituted $C_{3-6}$ carbocyclyl, substituted or unsubstituted 3- to 6-membered heterocylyl, substituted or unsubstituted aryl, substituted or unsubstituted heteroaryl, an oxygen protecting group when attached to oxygen, nitrogen protecting group when attached to nitrogen, or two $R^{GA}$ groups are taken with the intervening atoms to form a substituted or unsubstituted heterocylyl or heteroaryl ring.

Steroids of Formula (I), sub-genera thereof, and pharmaceutically acceptable salts thereof are collectively referred to herein as "compounds of the present invention."

In another aspect, provided is a pharmaceutical composition comprising a compound of the present invention and a pharmaceutically acceptable excipient. In certain embodiments, the compound of the present invention is provided in an effective amount in the pharmaceutical composition. In certain embodiments, the compound of the present invention is provided in a therapeutically effective amount. In certain embodiments, the compound of the present invention is provided in a prophylactically effective amount.

Compounds of the present invention as described herein, act, in certain embodiments, as GABA modulators, e.g., effecting the $GABA_A$ receptor in either a positive or negative manner. As modulators of the excitability of the central nervous system (CNS), as mediated by their ability to modulate $GABA_A$ receptor, such compounds are expected to have CNS-activity.

Thus, in another aspect, provided are methods of treating a CNS-related disorder in a subject in need thereof, comprising administering to the subject an effective amount of a compound of the present invention. In certain embodiments, the CNS-related disorder is selected from the group consisting of a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, and tinnitus. In certain embodiments, the compound is administered orally, subcutaneously, intravenously, or intramuscularly. In certain embodiments, the compound is administered chronically.

Other objects and advantages will become apparent to those skilled in the art from a consideration of the ensuing Detailed Description, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N.Y., 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

As used herein, "alkylene," "alkenylene," and "alkynylene," refer to a divalent radical of an alkyl, alkenyl, and alkynyl group, respectively. When a range or number of carbons is provided for a particular "alkylene," "alkenylene," and "alkynylene" group, it is understood that the range or number refers to the range or number of carbons in the linear carbon divalent chain. "Alkylene," "alkenylene," and "alkynylene" groups may be substituted or unsubstituted with one or more substituents as described herein.

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—CH(CH$_3$)—, (—C(CH$_3$)$_2$—), substituted ethylene (—CH(CH$_3$)CH$_2$—, —CH$_2$CH(CH$_3$)—, —C(CH$_3$)$_2$CH$_2$—, —CH$_2$C(CH$_3$)$_2$—), substituted propylene (—CH(CH$_3$)CH$_2$CH$_2$—, —CH$_2$CH(CH$_3$)CH$_2$—, —CH$_2$CH$_2$CH(CH$_3$)—, —C(CH$_3$)$_2$CH$_2$CH$_2$—, —CH$_2$C(CH$_3$)$_2$CH$_2$—, —CH$_2$CH$_2$C(CH$_3$)$_2$—), and the like.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("C$_{2-20}$ alkenyl"). In certain embodiments, alkenyl does not contain any triple bonds. In some embodiments, an alkenyl group has 2 to 10 carbon atoms ("C$_{2-10}$ alkenyl"). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted C$_{2-10}$ alkenyl. In certain embodiments, the alkenyl group is substituted C$_{2-10}$ alkenyl.

"Alkenylene" refers to an alkenyl group wherein two hydrogens are removed to provide a divalent radical, and which may be substituted or unsubstituted. Exemplary unsubstituted divalent alkenylene groups include, but are not limited to, ethenylene (—CH=CH—) and propenylene (e.g., —CH=CHCH$_2$—, —CH$_2$—CH=CH—). Exemplary substituted alkenylene groups, e.g., substituted with one or more alkyl (methyl) groups, include but are not limited to, substituted ethylene (—C(CH$_3$)=CH—, —CH=C(CH$_3$)—), substituted propylene (e.g., —C(CH$_3$)=CHCH$_2$—, —CH=C(CH$_3$)CH$_2$—, —CH=CHCH(CH$_3$)—, —CH=CHC(CH$_3$)—, —CH(CH$_3$)—CH=CH—, —C(CH$_3$)$_2$—CH=CH—, —CH$_2$—C(CH$_3$)=CH—, —CH$_2$—CH=C(CH$_3$)—), and the like.

"Alkynyl" refers to a radical of a straight-chain or branched hydrocarbon group having from 2 to carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("C$_{2-20}$ alkynyl"). In certain embodiments, alkynyl does not contain any double bonds. In some embodiments, an alkynyl group has 2 to 10 carbon atoms ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkynyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted C$_{2-10}$ alkynyl. In certain embodiments, the alkynyl group is substituted C$_{2-10}$ alkynyl.

"Alkynylene" refers to a linear alkynyl group wherein two hydrogens are removed to provide a divalent radical, and which may be substituted or unsubstituted. Exemplary divalent alkynylene groups include, but are not limited to, substituted or unsubstituted ethynylene, substituted or unsubstituted propynylene, and the like.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("heteroC$_{1-10}$ alkyl"). In some embodiments, a heteroalkyl group is a saturated group having 1 to 9 carbon atoms and 1, 2, 3, or 4 heteroatoms ("heteroC$_{1-9}$ alkyl"). In some embodiments, a heteroalkyl group is a saturated group having 1 to 8 carbon atoms and 1, 2, 3, or 4 heteroatoms ("heteroC$_{1-8}$ alkyl"). In some embodiments, a heteroalkyl group is a saturated group having 1 to 7 carbon atoms and 1, 2, 3, or 4 heteroatoms ("heteroC$_{1-7}$ alkyl"). In some embodiments, a heteroalkyl group is a group having 1 to 6 carbon atoms and 1, 2, or 3 heteroatoms ("heteroC$_{1-6}$ alkyl"). In some embodiments, a heteroalkyl group is a saturated group having 1 to 5 carbon atoms and 1 or 2 heteroatoms ("heteroC$_{1-5}$ alkyl"). In some embodiments, a heteroalkyl group is a saturated group having 1 to 4 carbon atoms and 1 or 2 heteroatoms ("heteroC$_{1-4}$ alkyl"). In some embodiments, a heteroalkyl group is a saturated group having 1 to 3 carbon atoms and 1 heteroatom ("heteroC$_{1-3}$ alkyl"). In some embodiments, a heteroalkyl group is a saturated group having 1 to 2 carbon atoms and 1 heteroatom ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "heteroalkenyl," as used herein, refers to an alkenyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkenyl group refers to a group having from 2 to 10 carbon atoms, at least one double bond, and 1, 2, 3, or 4 heteroatoms ("heteroC$_{2-10}$ alkenyl"). In some embodiments, a heteroalkenyl group has 2 to 9 carbon atoms at least one double bond, and 1, 2, 3, or 4 heteroatoms ("heteroC$_{2-9}$ alkenyl"). In some embodiments, a heteroalkenyl group has 2 to 8 carbon atoms, at least one double bond, and 1, 2, 3, or 4 heteroatoms ("heteroC$_{2-8}$ alkenyl"). In some embodiments, a heteroalkenyl group has 2 to 7 carbon atoms, at least one double bond, and 1, 2, 3, or 4 heteroatoms ("heteroC$_{2-7}$ alkenyl"). In some embodiments, a heteroalkenyl group has 2 to 6 carbon atoms, at least one double bond, and 1, 2, or 3 heteroatoms ("heteroC$_{2-6}$ alkenyl"). In some embodiments, a heteroalkenyl group has 2 to 5 carbon atoms, at least one double bond, and 1 or 2 heteroatoms ("heteroC$_{2-5}$ alkenyl"). In some embodiments, a heteroalkenyl group has 2 to 4 carbon atoms, at least one double bond, and 1 or 2 heteroatoms ("heteroC$_{2-4}$ alkenyl"). In some embodiments, a heteroalkenyl group has 2 to 3 carbon atoms, at least one double bond, and 1 heteroatom ("heteroC$_{2-3}$ alkenyl"). In some embodiments, a heteroalkenyl group has 2 to 6 carbon atoms, at least one double bond, and 1 or 2 heteroatoms ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "heteroalkynyl," as used herein, refers to an alkynyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkynyl group refers to a group having from 2 to 10 carbon atoms, at least one triple bond, and 1, 2, 3, or 4 heteroatoms ("heteroC$_{2-10}$ alkynyl"). In some embodiments, a heteroalkynyl group has 2 to 9 carbon atoms, at least one triple bond, and 1, 2, 3, or 4 heteroatoms ("heteroC$_{2-9}$ alkynyl"). In some embodiments, a heteroalkynyl group has 2 to 8 carbon atoms, at least one triple bond, and 1, 2, 3, or 4 heteroatoms ("heteroC$_{2-8}$ alkynyl"). In some embodiments, a heteroalkynyl group has 2 to 7 carbon atoms, at least one triple bond, and 1, 2, 3, or 4 heteroatoms ("heteroC$_{2-7}$ alkynyl"). In some embodiments, a heteroalkynyl group has 2 to 6 carbon atoms, at least one triple bond, and 1, 2, or 3 heteroatoms ("heteroC$_{2-6}$ alkynyl"). In some embodiments, a heteroalkynyl group has 2 to 5 carbon atoms, at least one triple bond, and 1 or 2 heteroatoms ("heteroC$_{2-5}$ alkynyl"). In some embodiments, a heteroalkynyl group has 2 to 4 carbon atoms, at least one triple bond, and 1 or 2 heteroatoms ("heteroC$_{2-4}$ alkynyl"). In some embodiments, a heteroalkynyl group has 2 to 3 carbon atoms, at least one triple bond, and 1 heteroatom ("heteroC$_{2-3}$ alkynyl"). In some embodiments, a heteroalkynyl group has 2 to 6 carbon atoms, at least one triple bond, and 1 or 2 heteroatoms ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "alkylene," "alkenylene," "alkynylene," "heteroalkylene," "heteroalkenylene," and "heteroalkynylene," refer to a divalent radical of an alkyl, alkenyl, alkynyl group, heteroalkyl, heteroalkenyl, and heteroalkynyl group respectively. When a range or number of carbons is provided for a particular "alkylene," "alkenylene," "alkynylene," "heteroalkylene," "heteroalkenylene," or "heteroalkynylene," group, it is understood that the range or number refers to the range or number of carbons in the linear carbon divalent chain. "Alkylene," "alkenylene," "alkynylene," "heteroalkylene," "heteroalkenylene," and "heteroalkynylene" groups may be substituted or unsubstituted with one or more substituents as described herein.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C$_{6-14}$ aryl. In certain embodiments, the aryl group is substituted C$_{6-14}$ aryl.

In certain embodiments, an aryl group substituted with one or more of groups selected from halo, C$_1$-C$_8$ alkyl, C$_1$-C$_8$ haloalkyl, cyano, hydroxy, C$_1$-C$_8$ alkoxy, and amino.

Examples of representative substituted aryls include the following

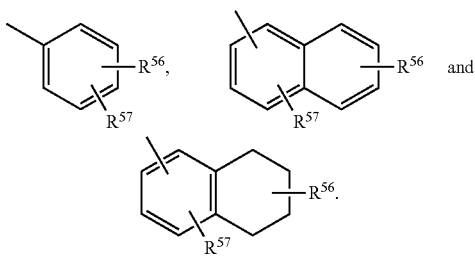

wherein one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$ haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

Other representative aryl groups having a fused heterocyclyl group include the following:

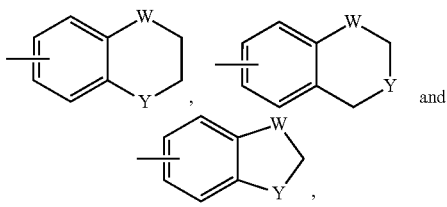

wherein each W is selected from $C(R^{66})_2$, $NR^{66}$, O, and S; and each Y is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Fused aryl" refers to an aryl having two of its ring carbon in common with a second aryl or heteroaryl ring or with a carbocyclyl or heterocyclyl ring.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10 n electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

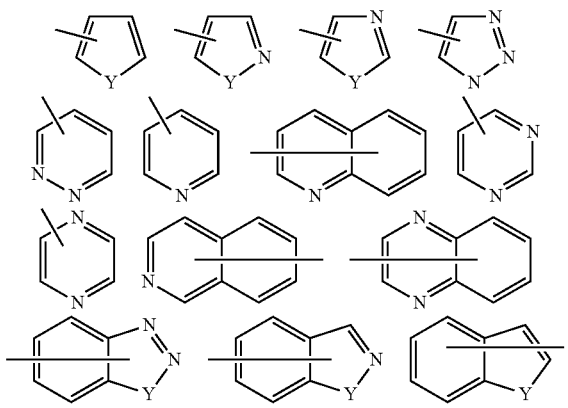

wherein each Y is selected from carbonyl, N, NR$^{65}$, O, and S; and R$^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Heteroaralkyl" is a subset of alkyl and heteroaryl, as defined herein, and refers to an optionally substituted alkyl group substituted by an optionally substituted heteroaryl group.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cycloprodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

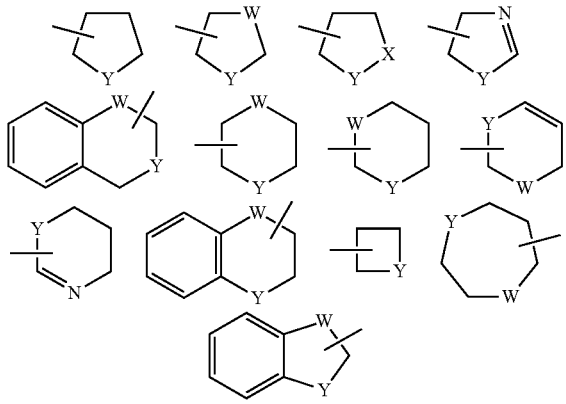

wherein each W is selected from $CR^{67}$, $C(R^{67})_2$, $NR^{67}$, O, and S; and each Y is selected from $NR^{67}$, O, and S; and $R^{67}$ is independently hydrogen, $C_1$-$C_8$ alkyl, $C_3$-$C_{10}$ cycloalkyl, 4-10 membered heterocyclyl, $C_6$-$C_{10}$ aryl, 5-10 membered heteroaryl. These heterocyclyl rings may be optionally substituted with one or more groups selected from the group consisting of acyl, acylamino, acyloxy, alkoxy, alkoxycarbonyl, alkoxycarbonylamino, amino, substituted amino, aminocarbonyl (carbamoyl or amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g, heteroaryl, cycloalkenyl, e.g, cycloheteroalkenyl, and the like having from 1 to 5, and particularly from 1 to 3 heteroatoms.

"Acyl" refers to a radical —C(O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—$C_1$-$C_8$ alkyl, —C(O)—(CH$_2$)$_t$($C_6$-$C_{10}$ aryl), —C(O)—(CH$_2$)$_t$(5-10 membered heteroaryl), —C(O)—(CH$_2$)$_t$($C_3$-$C_{10}$ cycloalkyl), and —C(O)—(CH$_2$)$_t$(4-10 membered heterocyclyl), wherein t is an integer from 0 to 4. In certain embodiments, $R^{21}$ is $C_1$-$C_8$ alkyl, substituted with halo or hydroxy; or $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Acylamino" refers to a radical —$NR^{22}$C(O)$R^{23}$, where each instance of $R^{22}$ and R23 is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein, or $R^{22}$ is an amino protecting group. Exemplary "acylamino" groups include, but are not limited to, formylamino, acetylamino, cyclohexylcarbonylamino, cyclohexylmethyl-carbonylamino, benzoylamino and benzylcarbonylamino. Particular exemplary "acylamino" groups are —$NR^{24}$C(O)—$C_1$-$C_8$ alkyl, —$NR^{24}$C(O)—(CH$_2$)$_t$($C_6$-$C_{10}$ aryl), —$NR^{24}$C(O)—(CH$_2$)$_t$(5-10 membered heteroaryl), —$NR^{24}$C(O)—(CH$_2$)$_t$($C_3$-$C_{10}$ cycloalkyl), and —$NR^{24}$C(O)—(CH$_2$)$_t$(4-10 membered heterocyclyl), wherein t is an integer from 0 to 4, and each $R^{24}$ independently represents H or $C_1$-$C_8$ alkyl. In certain embodiments, $R^{25}$ is H, $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; and $R^{26}$ is H, $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl; provided at least one of $R^{25}$ and $R^{26}$ is other than H.

"Acyloxy" refers to a radical —OC(O)$R^{27}$, where $R^{27}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. Representative examples include, but are not limited to, formyl, acetyl, cyclohexylcarbonyl, cyclohexylmethylcarbonyl, benzoyl and benzylcarbonyl. In certain embodiments, $R^{28}$ is $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Alkoxy" refers to the group —$OR^{29}$ where $R^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—(CH$_2$)$_t$($C_6$-$C_{10}$ aryl), —O—(CH$_2$)$_t$(5-10 membered heteroaryl), —O—(CH$_2$)$_t$($C_3$-$C_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Substituted amino" refers to an amino group of the formula —N($R^{38}$)$_2$ wherein $R^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{38}$ is not a hydrogen. In certain embodiments, each $R^{38}$ is independently selected from hydrogen, $C_1$-$C_8$ alkyl, $C_3$-$C_8$ alkenyl, $C_3$-$C_8$ alkynyl, $C_6$-$C_{10}$ aryl, 5-membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl), or —(CH$_2$)$_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both $R^{38}$ groups are joined to form an alkylene group.

Exemplary "substituted amino" groups include, but are not limited to, —$NR^{39}$—$C_1$-$C_8$ alkyl, —$NR^{39}$—(CH$_2$)$_t$($C_6$-$C_{10}$ aryl), —$NR^{39}$—(CH$_2$)$_t$(5-10 membered heteroaryl), —$NR^{39}$—(CH$_2$)$_t$($C_3$-$C_{10}$ cycloalkyl), and —$NR^{39}$—(CH$_2$)$_t$(4-10 membered heterocyclyl), wherein t is an integer from 0 to 4, for instance 1 or 2, each $R^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Azido" refers to the radical —N$_3$.

"Carbamoyl" or "amido" refers to the radical —C(O)NH$_2$.

"Substituted carbamoyl" or "substituted amido" refers to the radical —C(O)N($R^{62}$)$_2$ wherein each $R^{62}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{62}$ is not a hydrogen. In certain embodiments, $R^{62}$ is selected from H, $C_1$-$C_8$ alkyl, $C_3$-$C_{10}$ cycloalkyl, 4-10 membered heterocyclyl, $C_6$-$C_{10}$ aryl, aralkyl, 5-10 membered heteroaryl, and heteroaralkyl; or $C_1$-$C_8$ alkyl substituted with halo or hydroxy; or $C_3$-$C_{10}$ cycloalkyl, 4-10 membered heterocyclyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided that at least one $R^{62}$ is other than H.

Exemplary "substituted carbamoyl" groups include, but are not limited to, —C(O) $NR^{64}$—$C_1$-$C_8$ alkyl, —C(O)$NR^{64}$—(CH$_2$)$_t$($C_6$-$C_{10}$ aryl), —C(O)$N^{64}$—(CH$_2$)$_t$(5-10 membered heteroaryl), —C(O)$NR^{64}$—(CH$_2$)$_t$($C_3$-$C_{10}$ cycloalkyl), and —C(O)$NR^{64}$—(CH$_2$)$_t$(4-10 membered heterocyclyl), wherein t is an integer from 0 to 4, each $R^{64}$ independently represents H or $C_1$-$C_8$ alkyl and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Hydroxy" refers to the radical —OH.

"Nitro" refers to the radical —NO$_2$.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Cycloalkenyl" refers to substituted or unsubstituted carbocyclyl group having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Fused cycloalkenyl" refers to a cycloalkenyl having two of its ring carbon atoms in common with a second aliphatic or aromatic ring and having its olefinic unsaturation located to impart aromaticity to the cycloalkenyl ring.

"Ethylene" refers to substituted or unsubstituted —(C—C)—.

"Ethenyl" refers to substituted or unsubstituted —(C═C)—.

"Ethynyl" refers to —(C≡C)—.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Thioketo" refers to the group ═S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or such other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR, —SSR$^{cc}$, —C(═O)R$^{aa}$, —CO$_2$H, —CHO, —C(OR$^{cc}$)$_2$, —CO$_2$R$^{aa}$, —OC(═O)R$^{aa}$, —OCO$_2$R$^{aa}$, —C(═O)N(R$^{bb}$)$_2$, —OC(═O)N(R$^{bb}$)$_2$, —NR$^{bb}$C(═O)R$^{aa}$, —NR$^{bb}$CO$_2$R$^{aa}$, —NR$^{bb}$C(═O)N(R$^{bb}$)$_2$, —C(═NR$^{bb}$)R$^{aa}$, —C(═NR$^{bb}$)OR$^{aa}$, —OC(═NR$^{bb}$)R$^{aa}$, —OC(═NR$^{bb}$)OR$^{aa}$, —C(═NR$^{bb}$)N(R$^{bb}$)$_2$, —OC(═NR$^{bb}$)N(R$^{bb}$)$_2$, —NR$^{bb}$C(═NR$^{bb}$)N(R$^{bb}$)$_2$, —C(═O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(O)R$^{aa}$, e.g., —S(═O)$^{aa}$, —OS(═O)R$^{aa}$, —Si(R$^{aa}$)$_3$, —OSi(R$^{aa}$)$_3$ —C(═S)N(R$^{bb}$)$_2$, —C(═O)SR$^{aa}$, —C(═S)SR$^{aa}$, —SC(═S)SR$^{aa}$, —SC(═O)SR$^{aa}$, —OC(═O)SR$^{aa}$, —SC(═O)OR$^{aa}$, —SC(═O)R$^{aa}$, —P(═O)$_2$R, —OP(═O)$_2$R, —P(═O)(R$^{aa}$)$_2$, —OP(═O)(R$^{aa}$)$_2$, —OP(═O)(OR$^{cc}$)$_2$, —P(═O)$_2$N(R$^{bb}$)$_2$, —OP(═O)$_2$N(R$^{bb}$)$_2$, —P(═O)(NR$^{bb}$)$_2$, —OP(═O)(NR$^{bb}$)$_2$, —NR$^{bb}$P(═O)(OR$^{cc}$)$_2$, —NR$^{bb}$P(═O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group ═O, ═S, ═NN(R$^{bb}$)$_2$, ═NNR$^{bb}$C(═O)R$^{aa}$, ═NNR$^{bb}$C(═O)OR$^{aa}$, ═NNR$^{bb}$S(═O)$_2$R, ═NR$^{bb}$, or ═NOR$^{cc}$;

each instance of R$^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(═O)R$^{aa}$, —C(═O)N(R$^{cc}$)$_2$, —CO$_2$R, —SO$_2$R, —C(═NR$^{cc}$)OR$^{aa}$, —C(═NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(═S)N(R$^{cc}$)$_2$, —C(═O)SR$^{cc}$, —C(═S)SR$^{cc}$, —P(═O)$_2$R, —P(═O)(R$^{aa}$)$_2$, —P(═O)$_2$N(R$^{cc}$)$_2$, —P(═O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O) R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(O) R$^{ee}$, e.g., —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$ X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH) O(C$_{1-6}$ alkyl), —OC(=NH)(C$_{1-6}$ alkyl), —OC(=NH) OC$_{1-6}$ alkyl, —C(=NH)N(C$_{1-6}$ alkyl)$_2$, —C(=NH) NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH (C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP (=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 5-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, SO$_4^{-2}$ sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O) N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O) (R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

These and other exemplary substituents are described in more detail in the Detailed Description, Examples, and claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of the present invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

Figure 1:
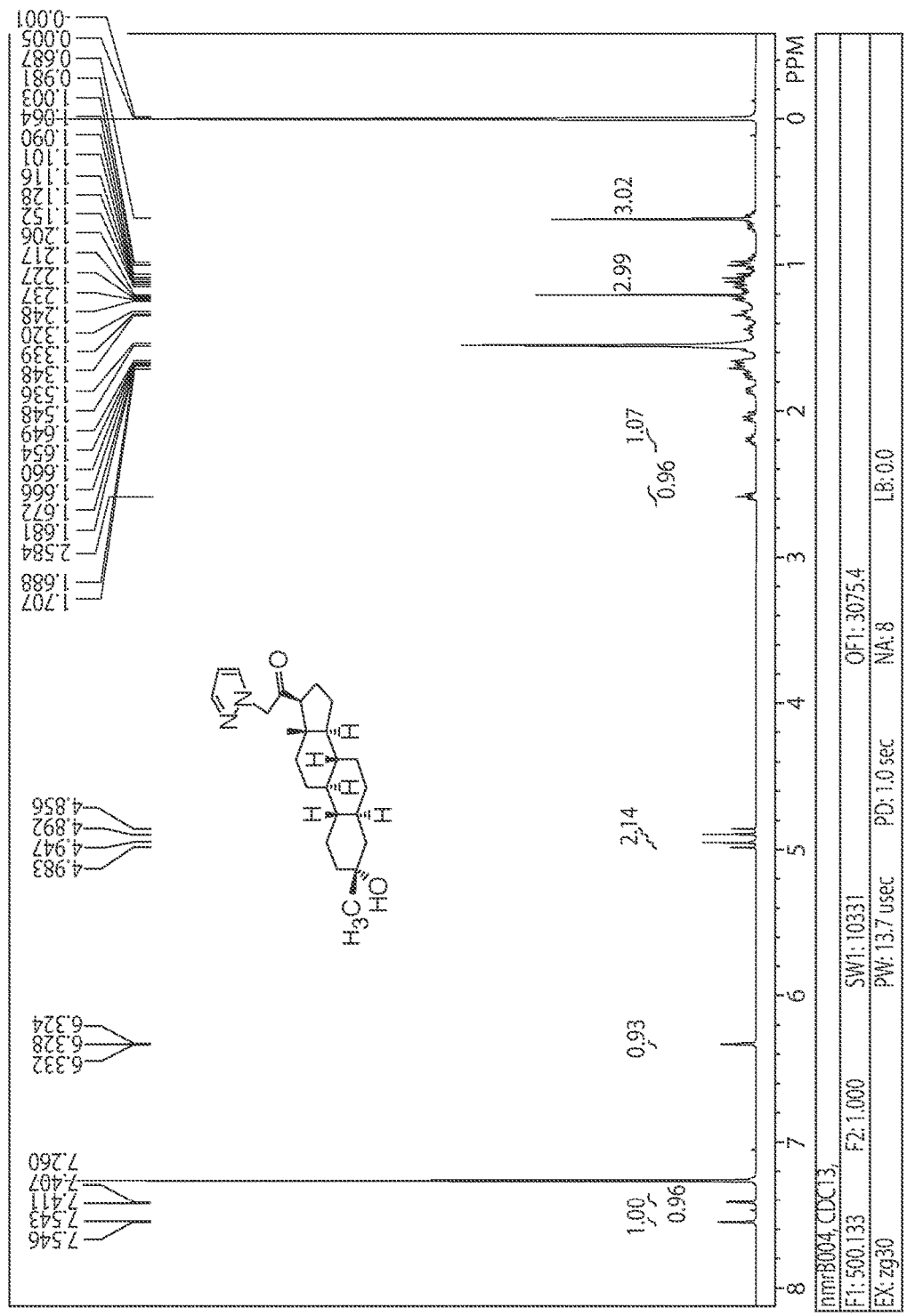
FIGS. 1-52 depict representative $^1$H NMR spectra of exemplary compounds described herein.
Figure 2:
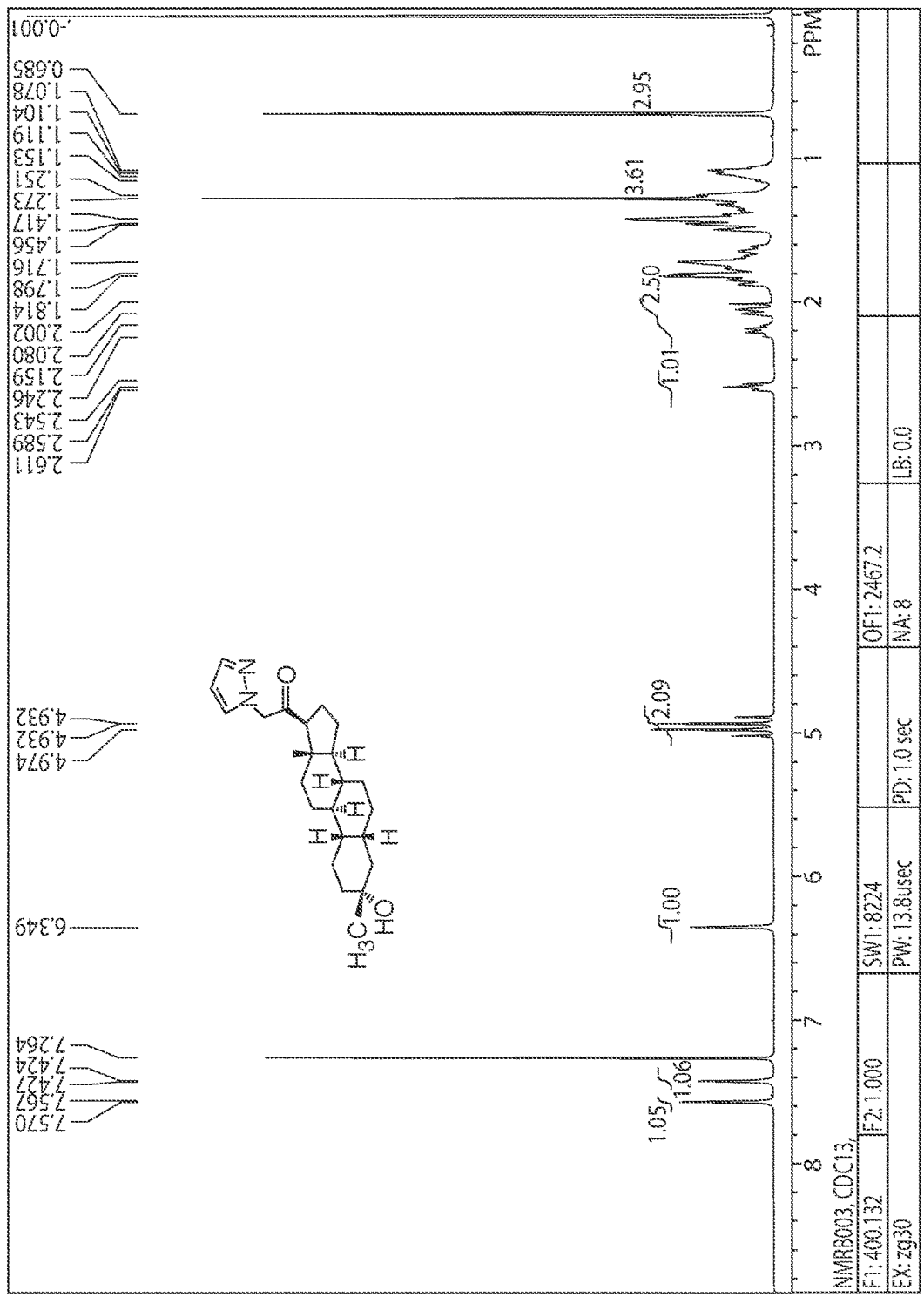
Figure 3:
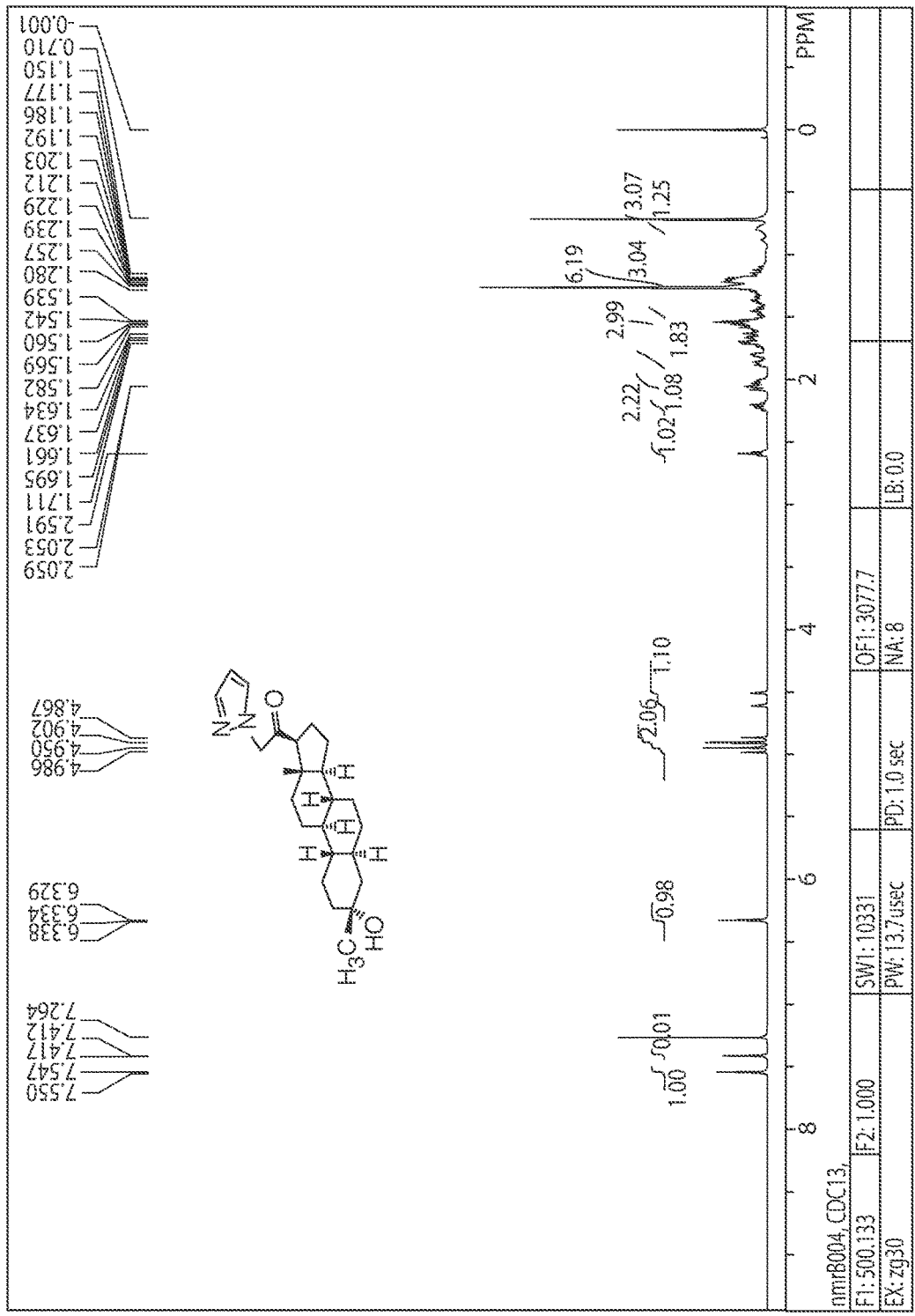
Figure 4:
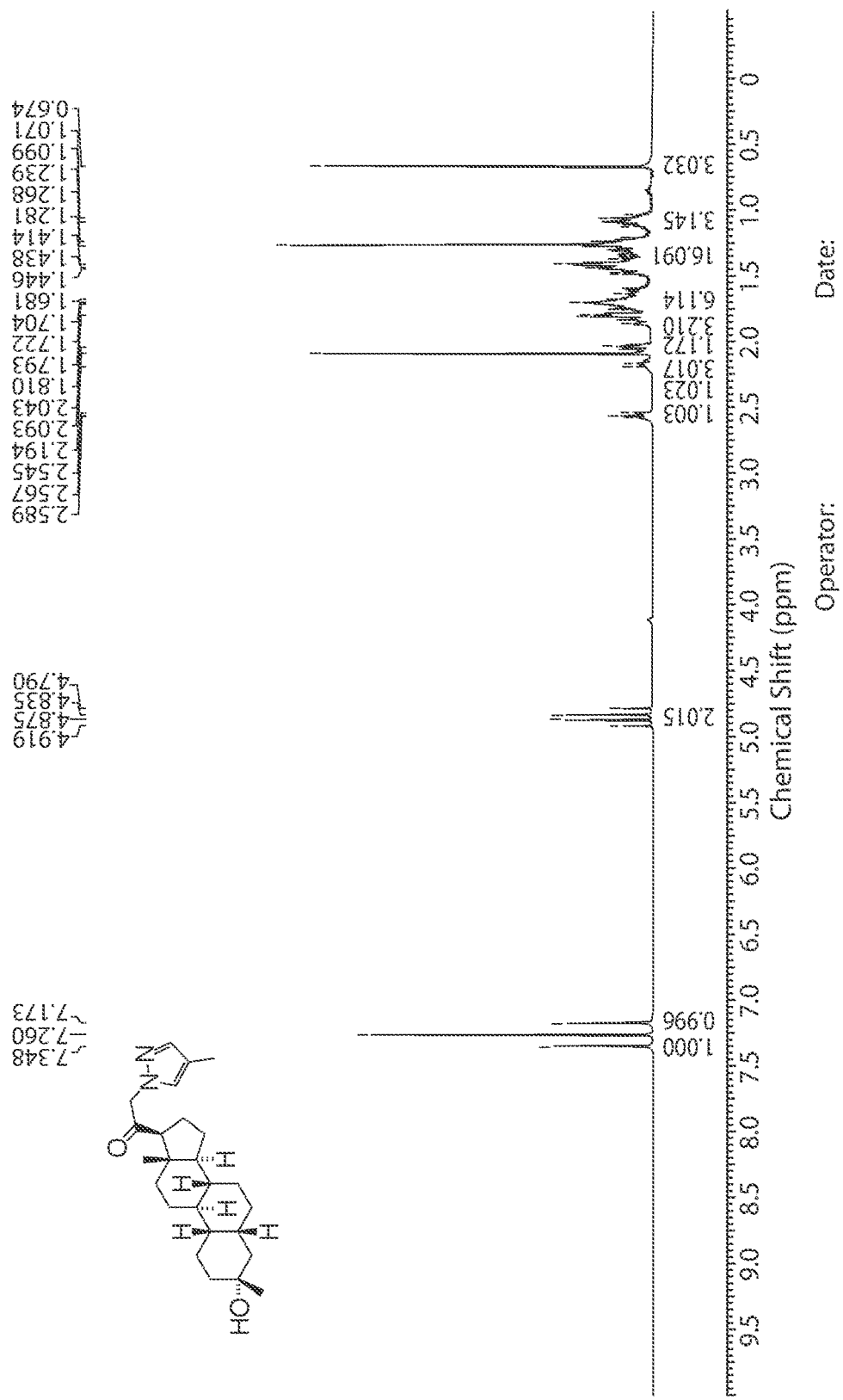
Figure 5:
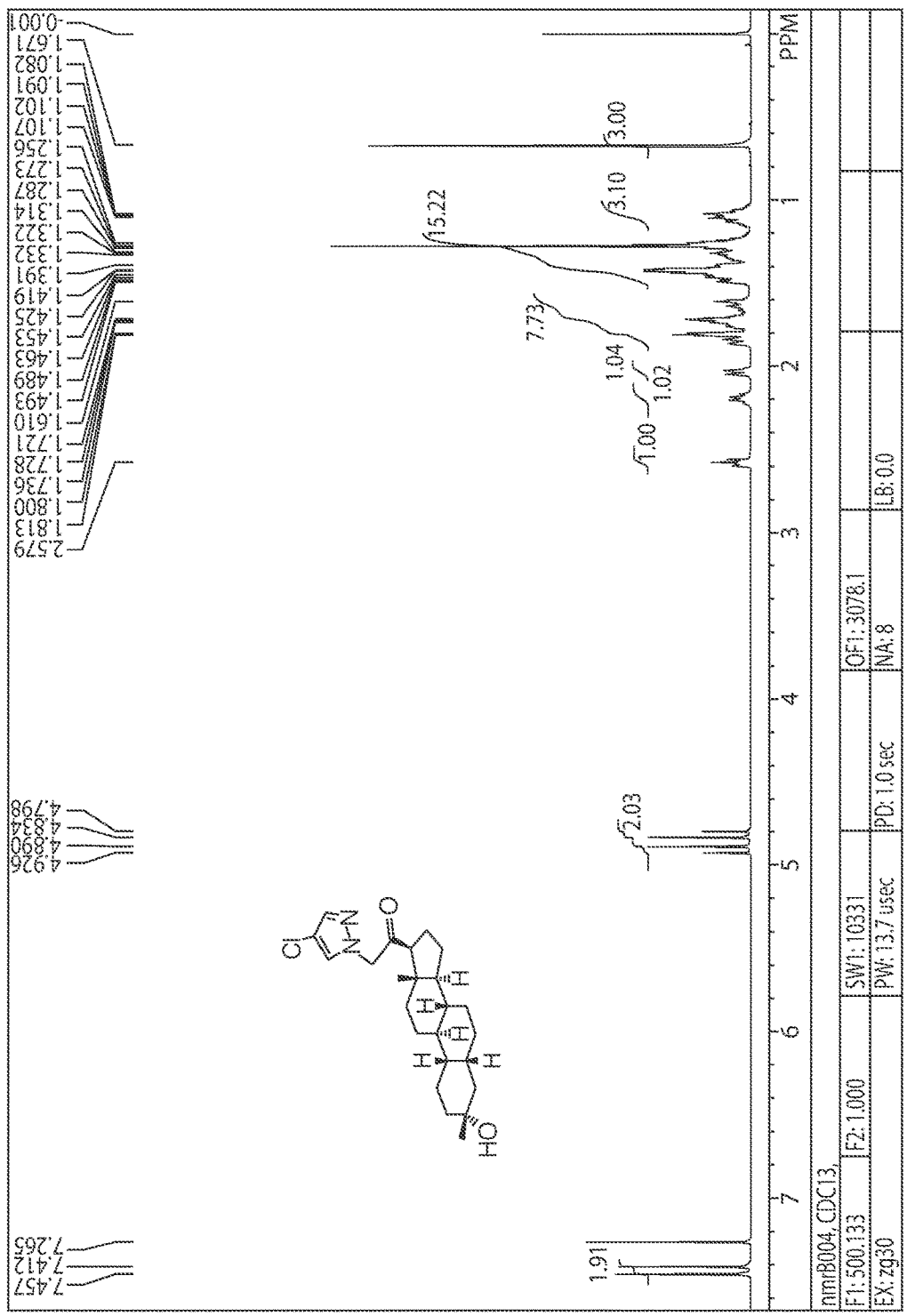
Figure 6:
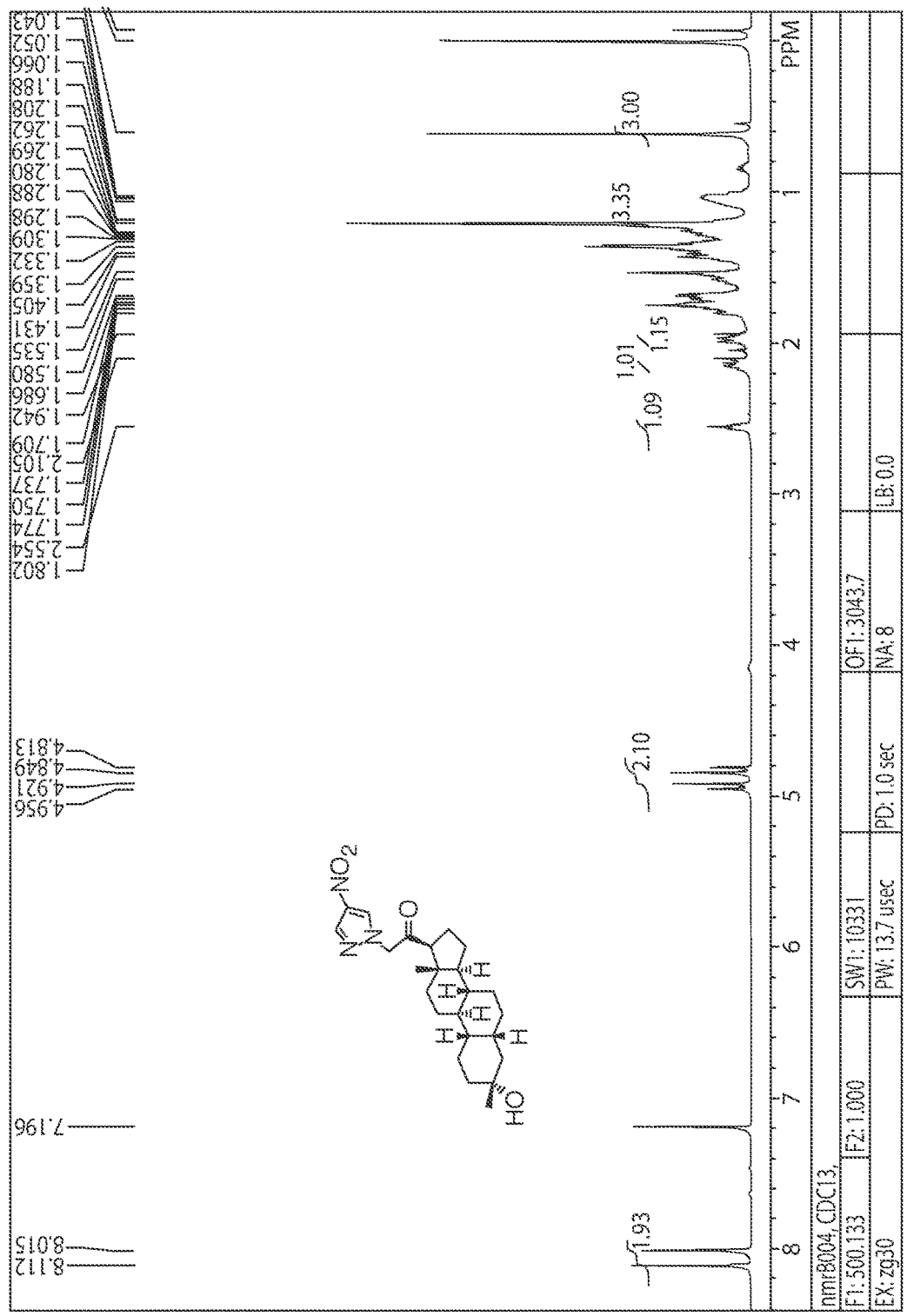
Figure 7:
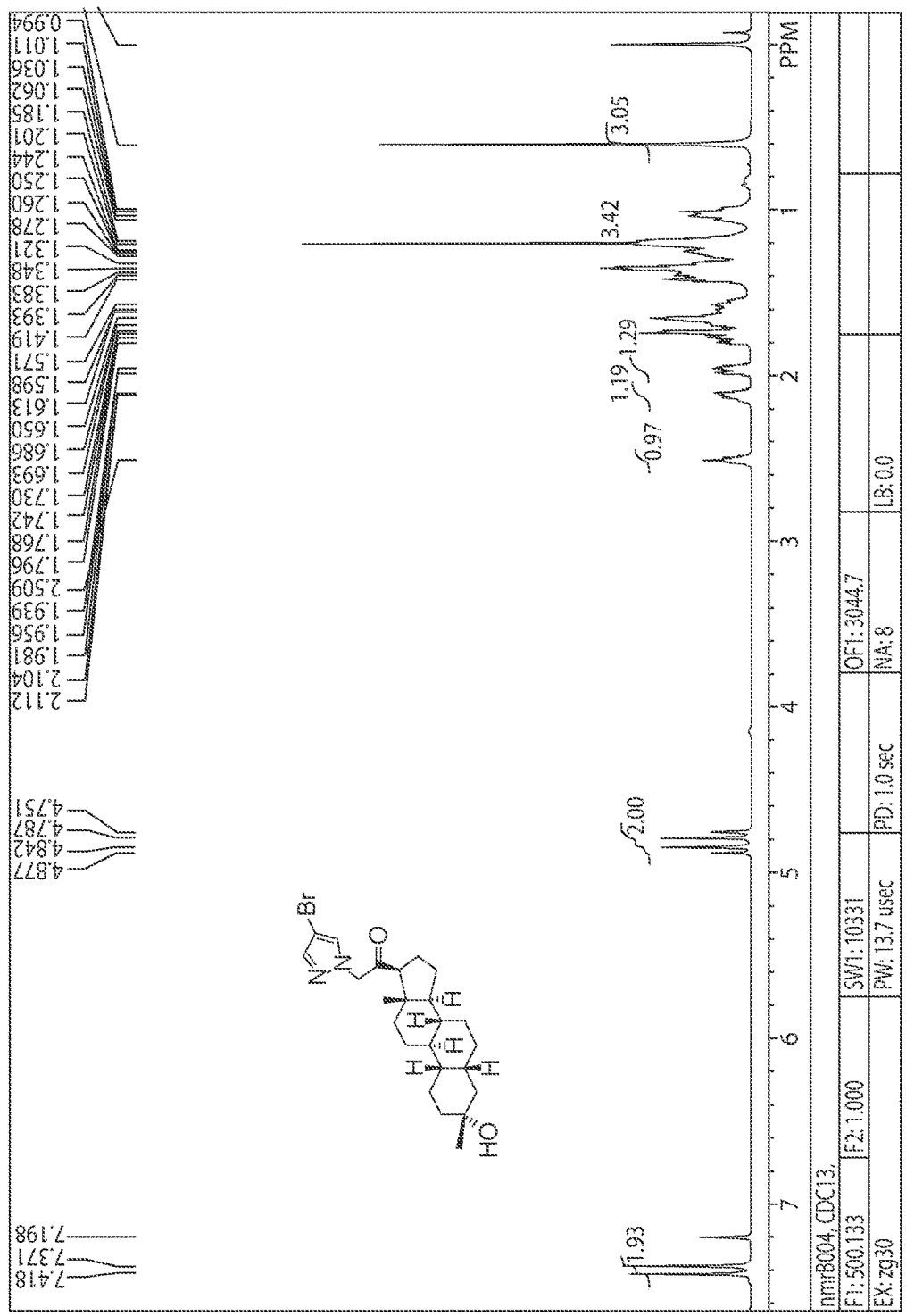
Figure 8:
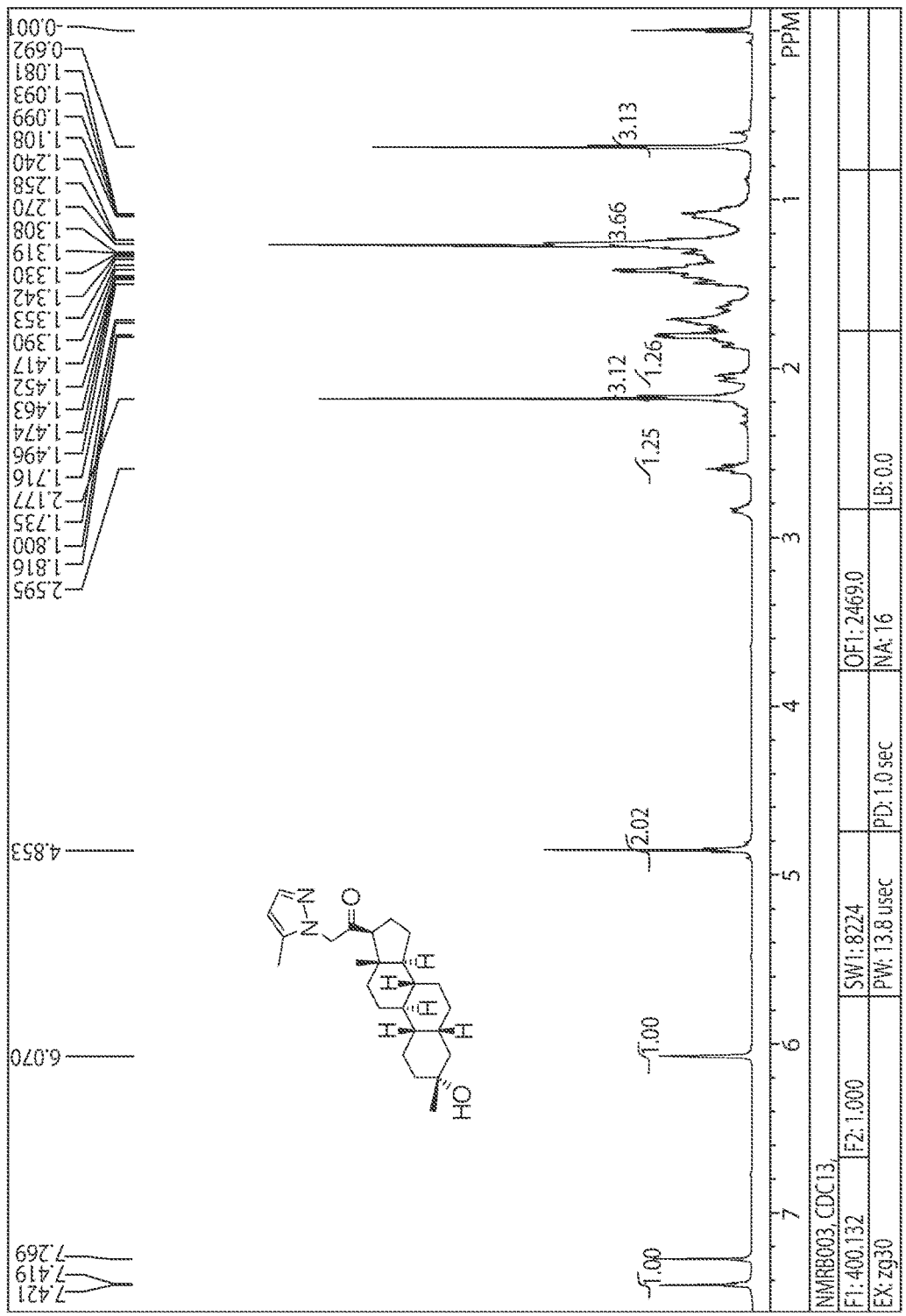
Figure 9:
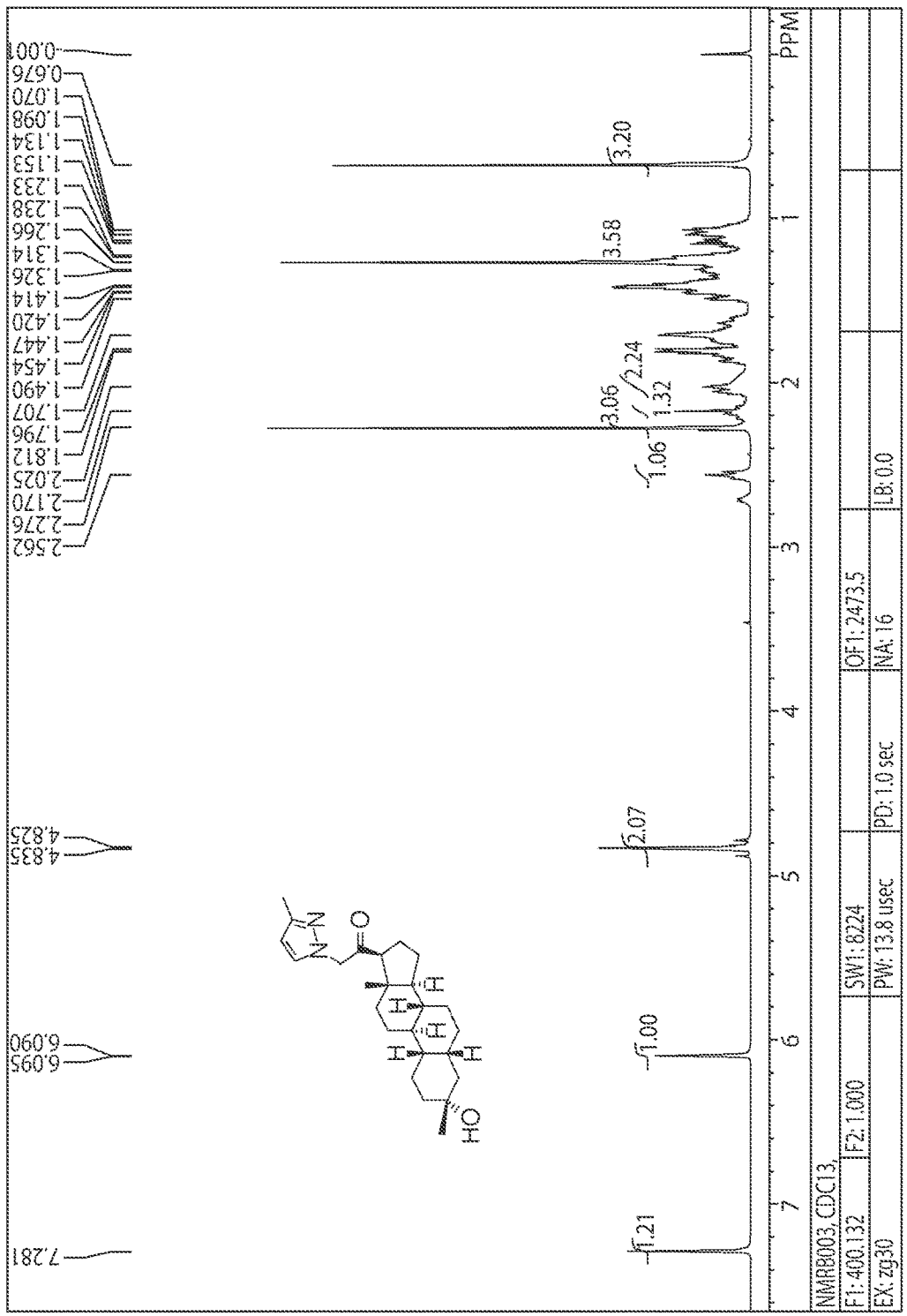
Figure 10:
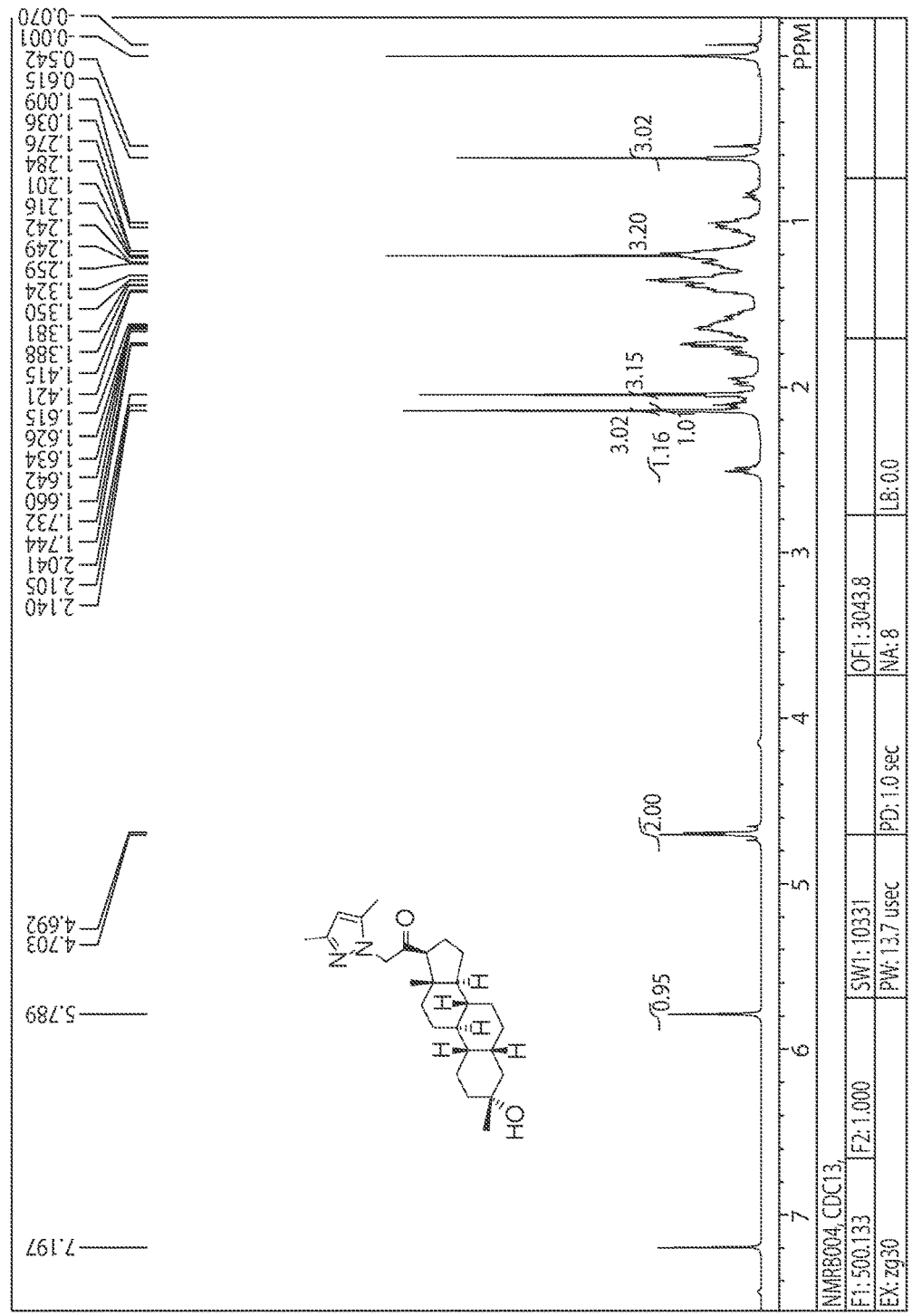
Figure 11:
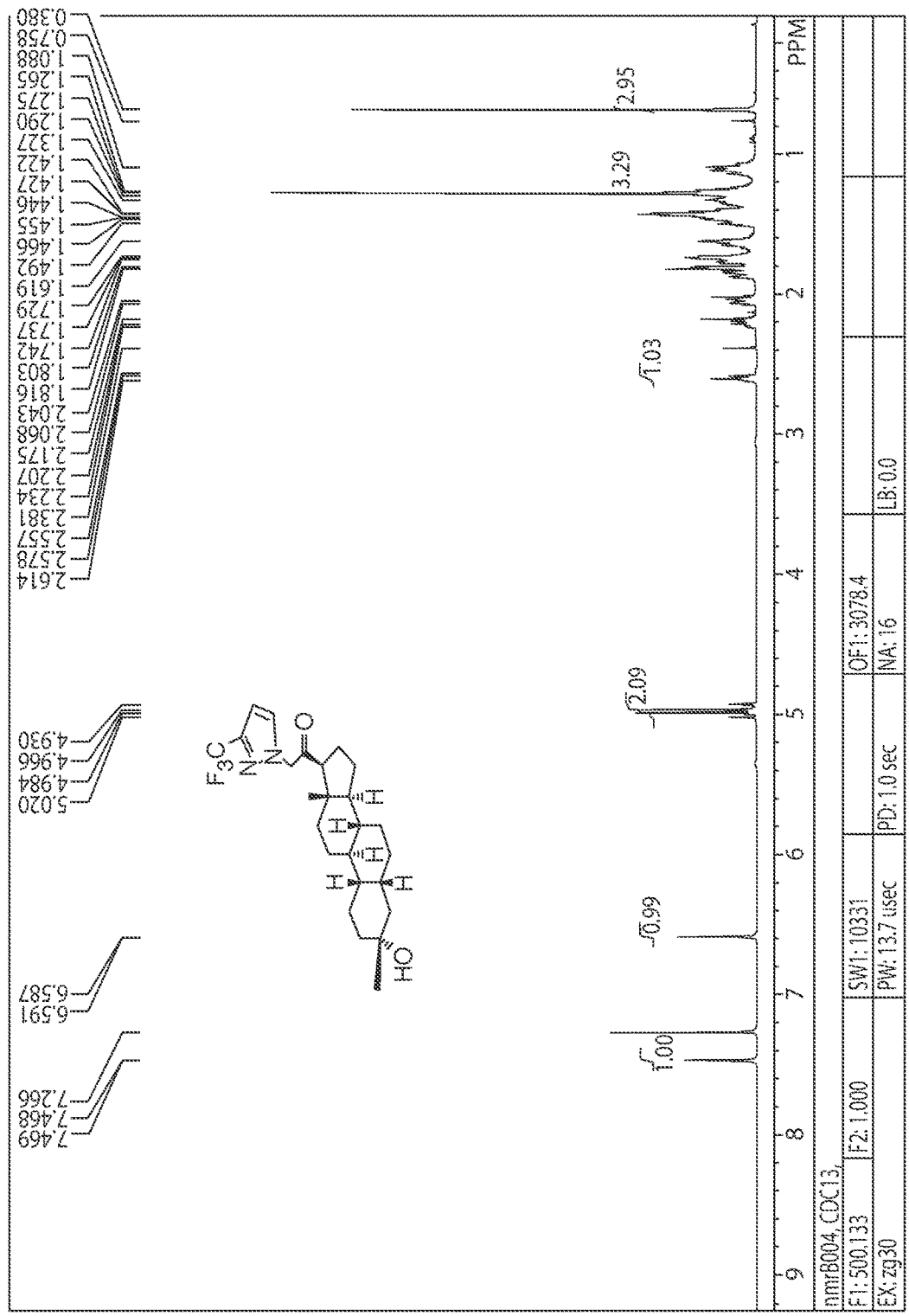
Figure 12:
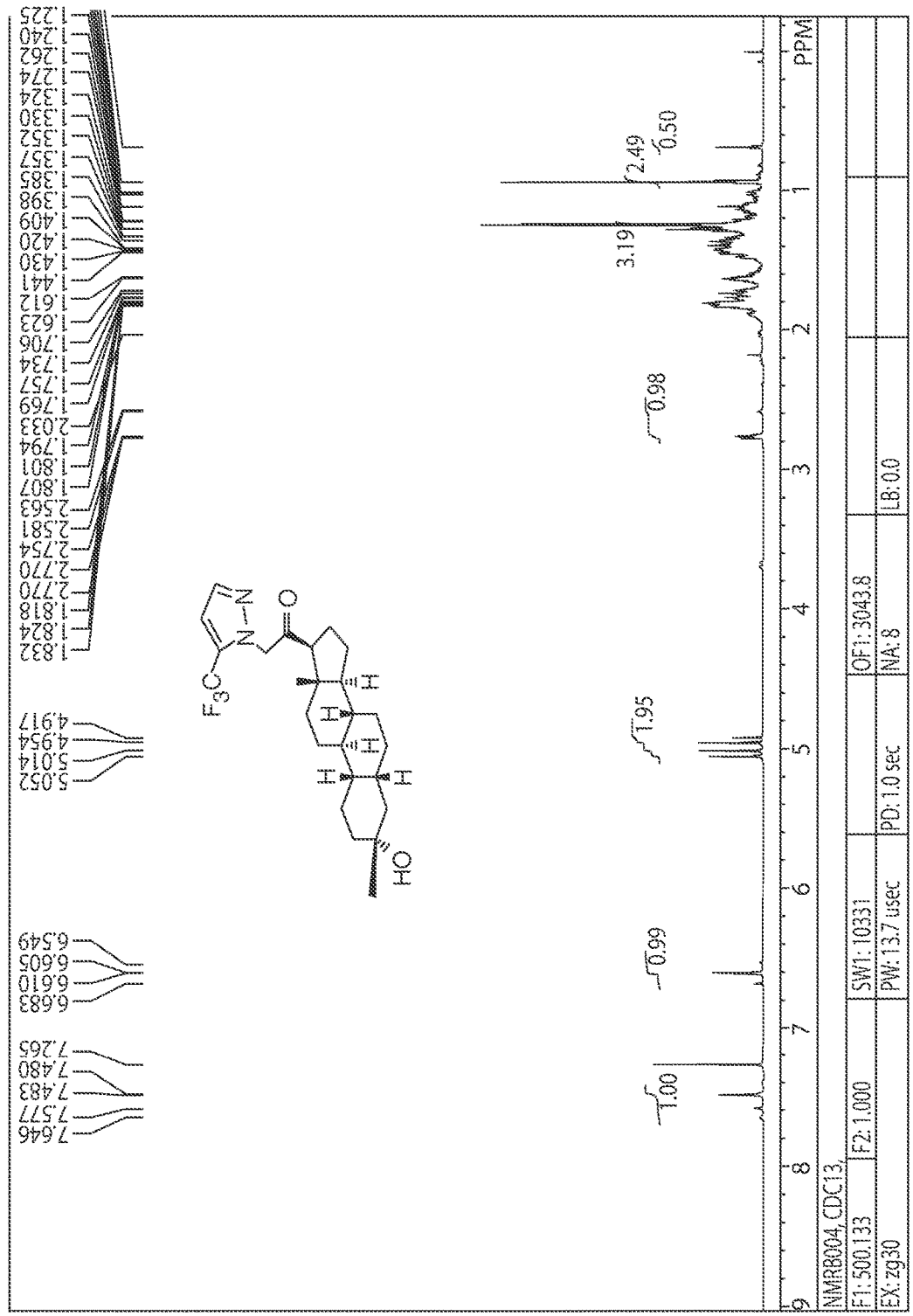
Figure 13:
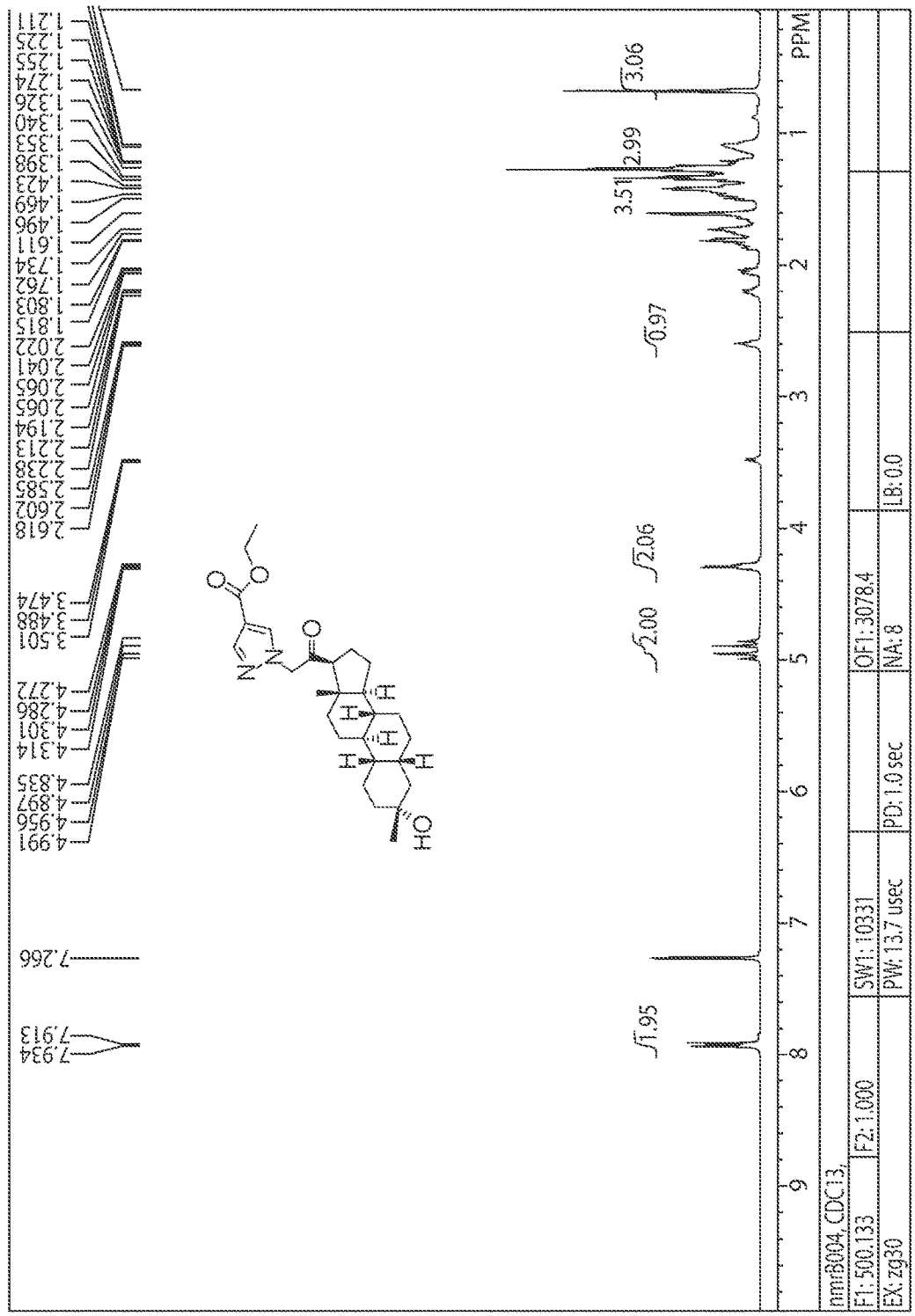
Figure 14:
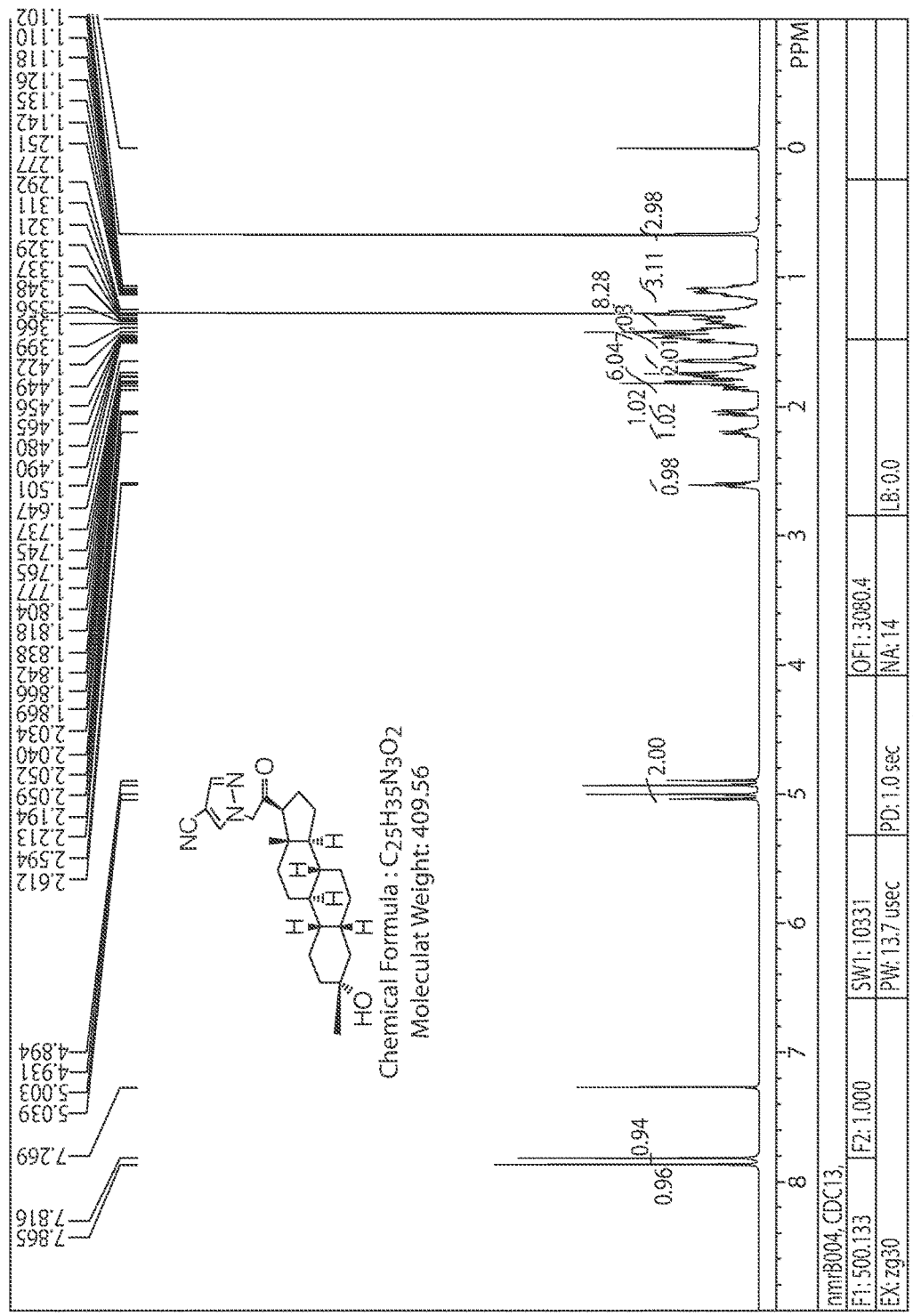
Figure 15:
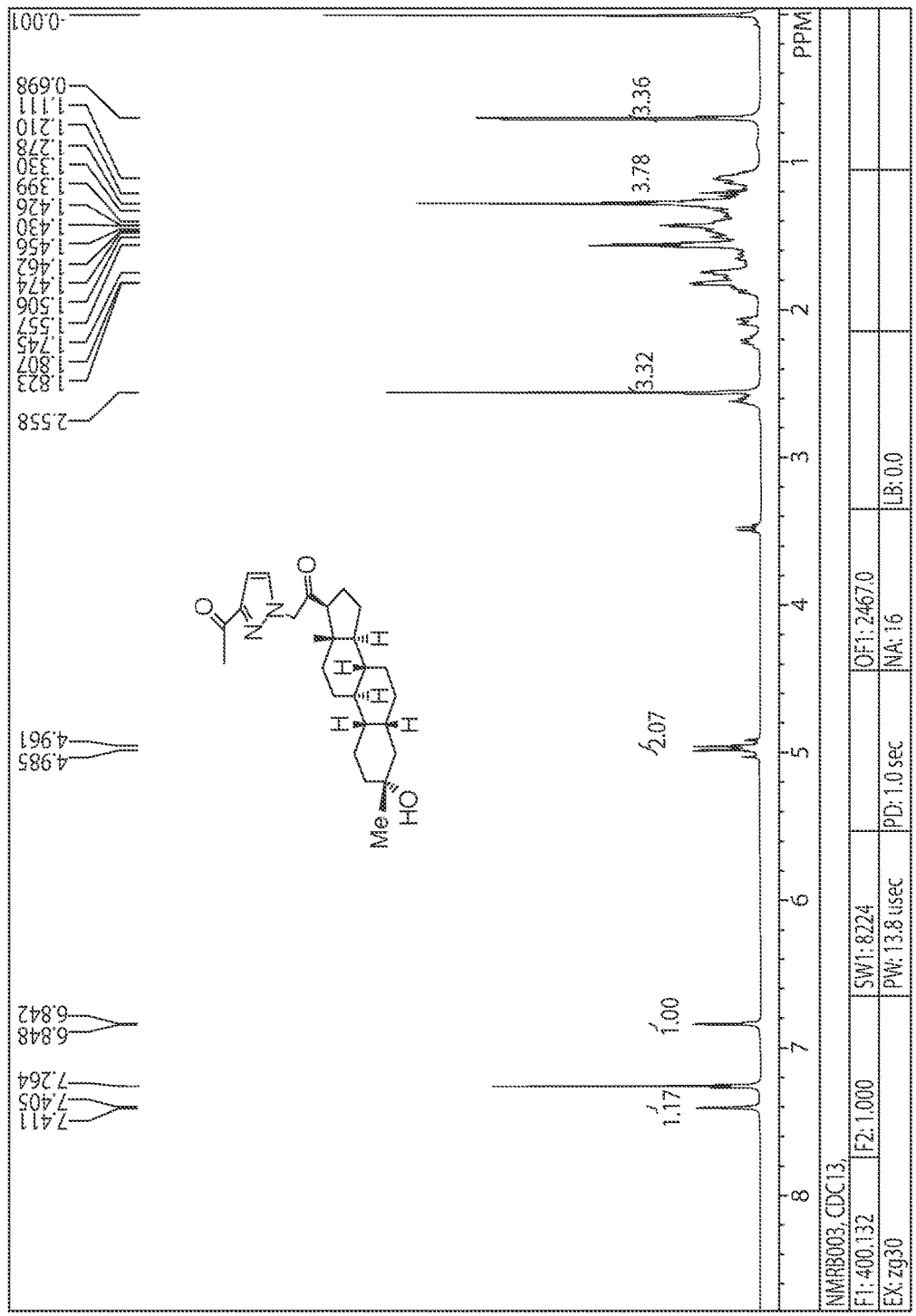
Figure 16:
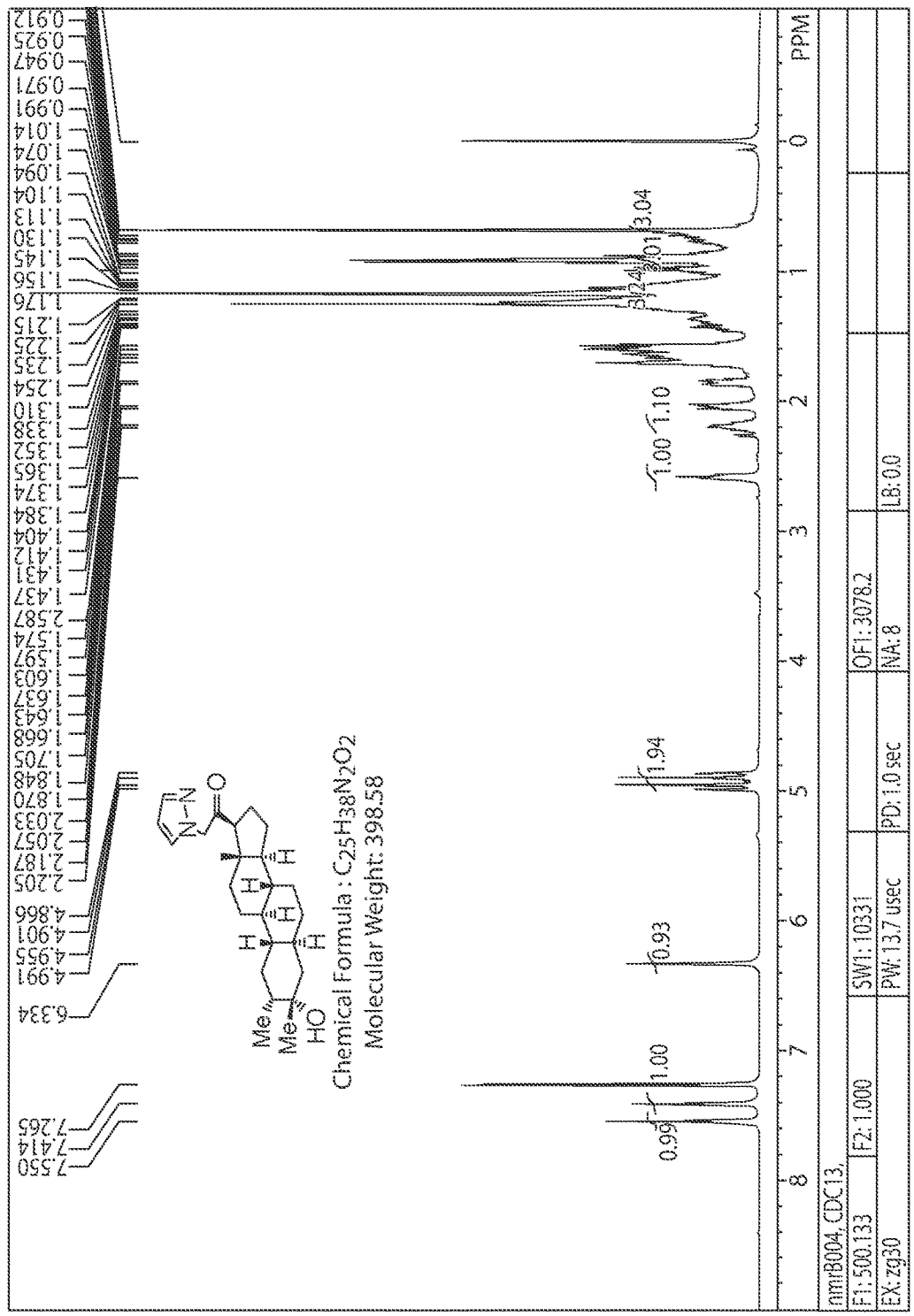
Figure 17:
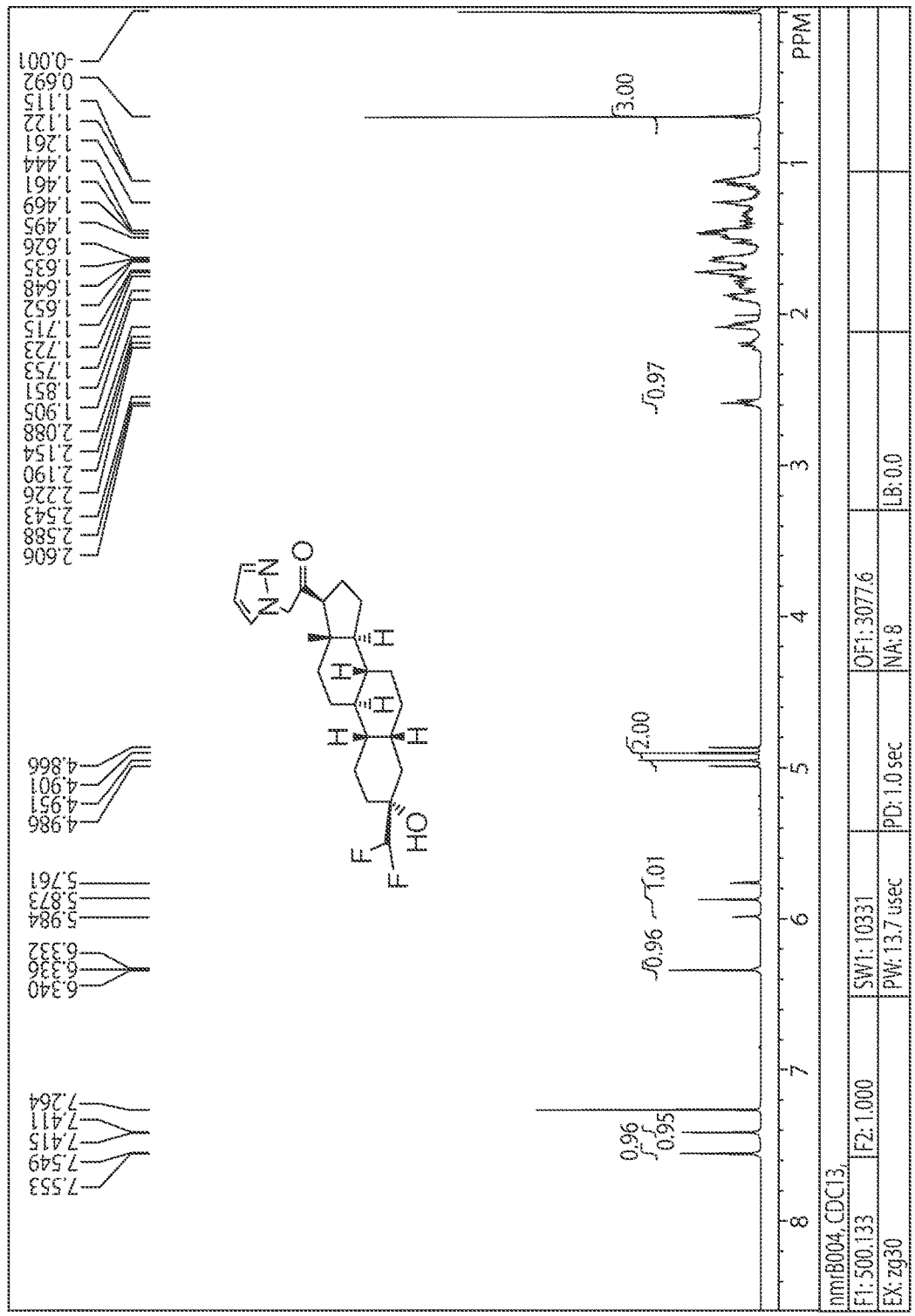
Figure 18:
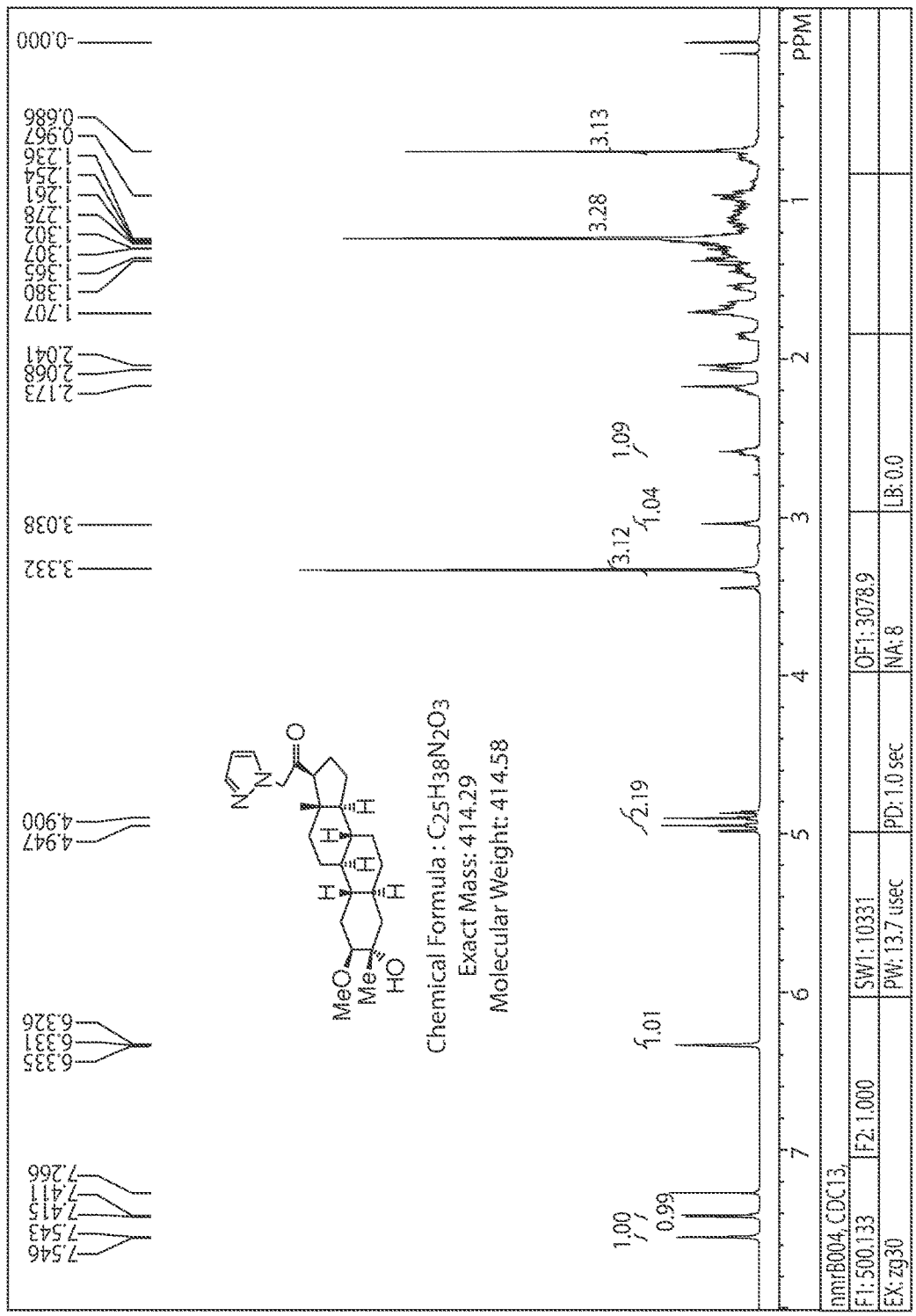
Figure 19:
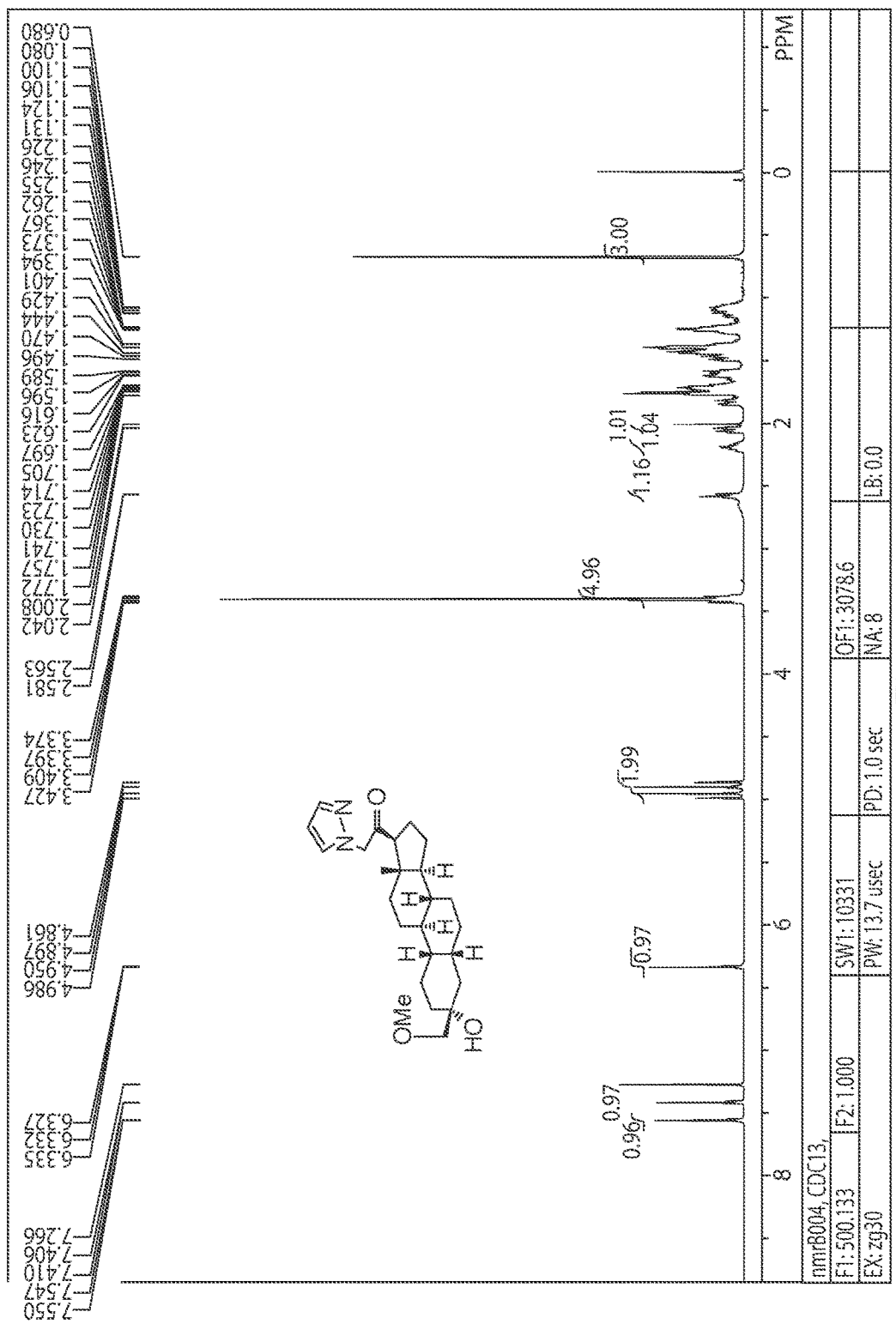
Figure 20:
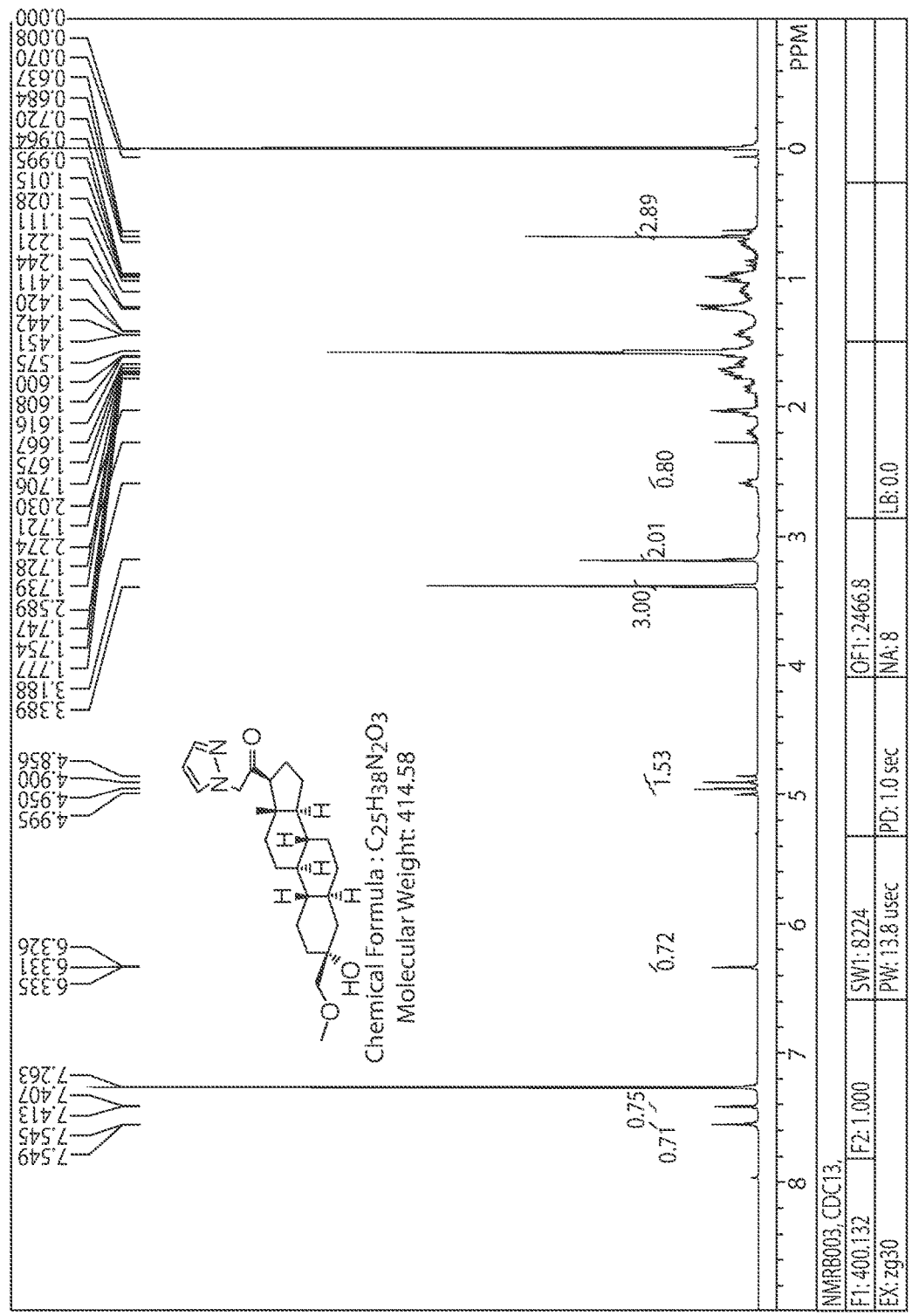
Figure 21:
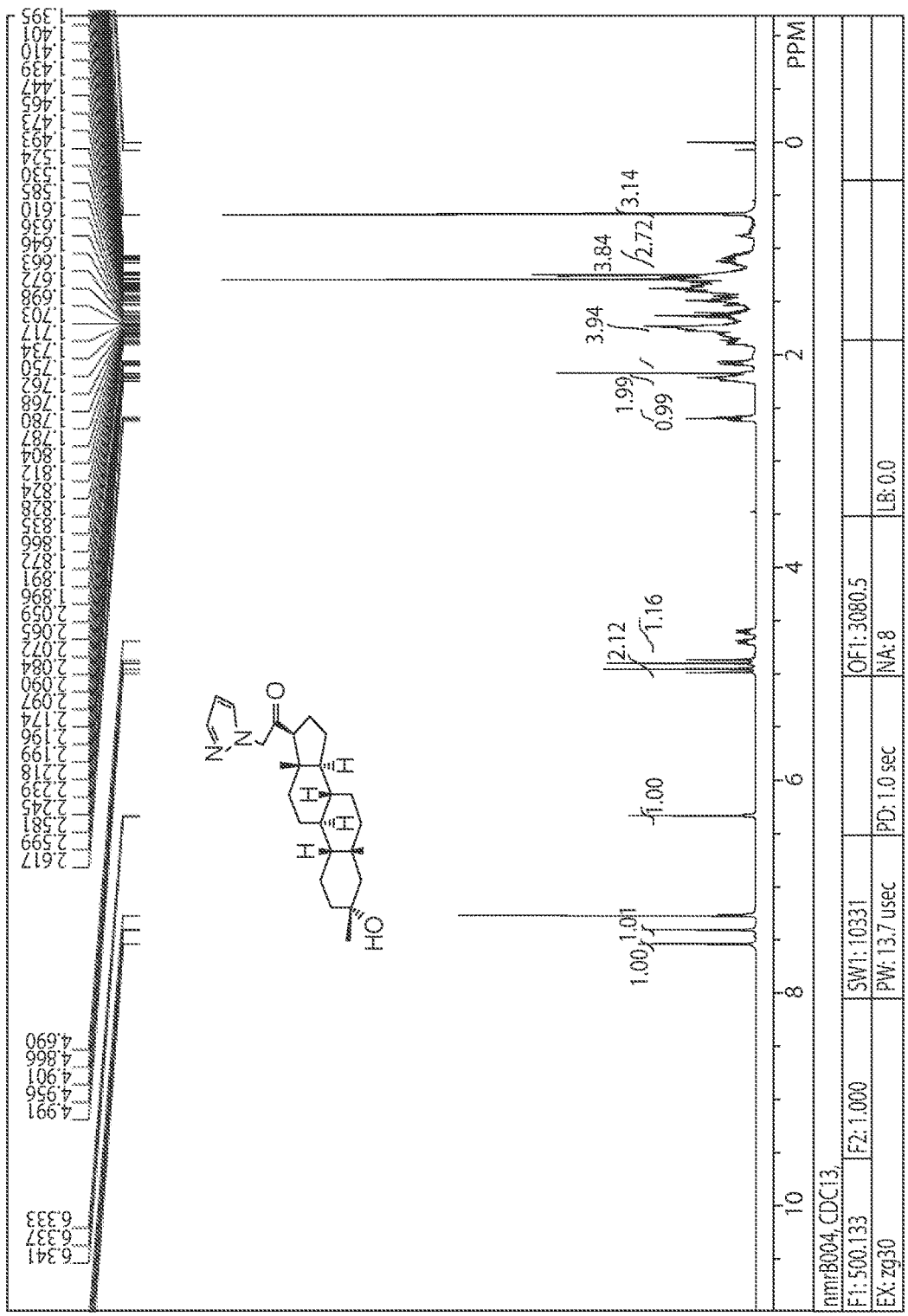
Figure 22:
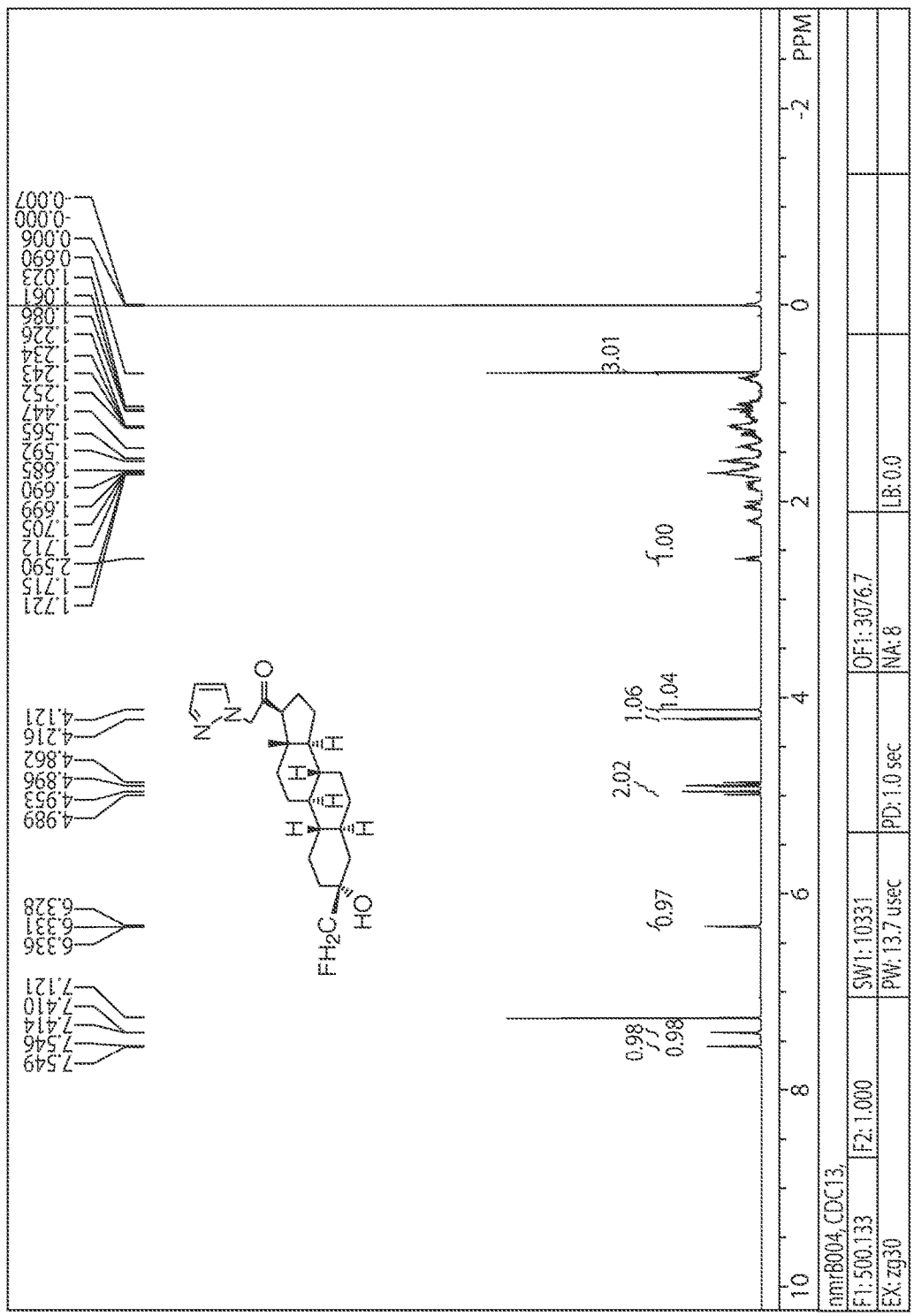
Figure 23:
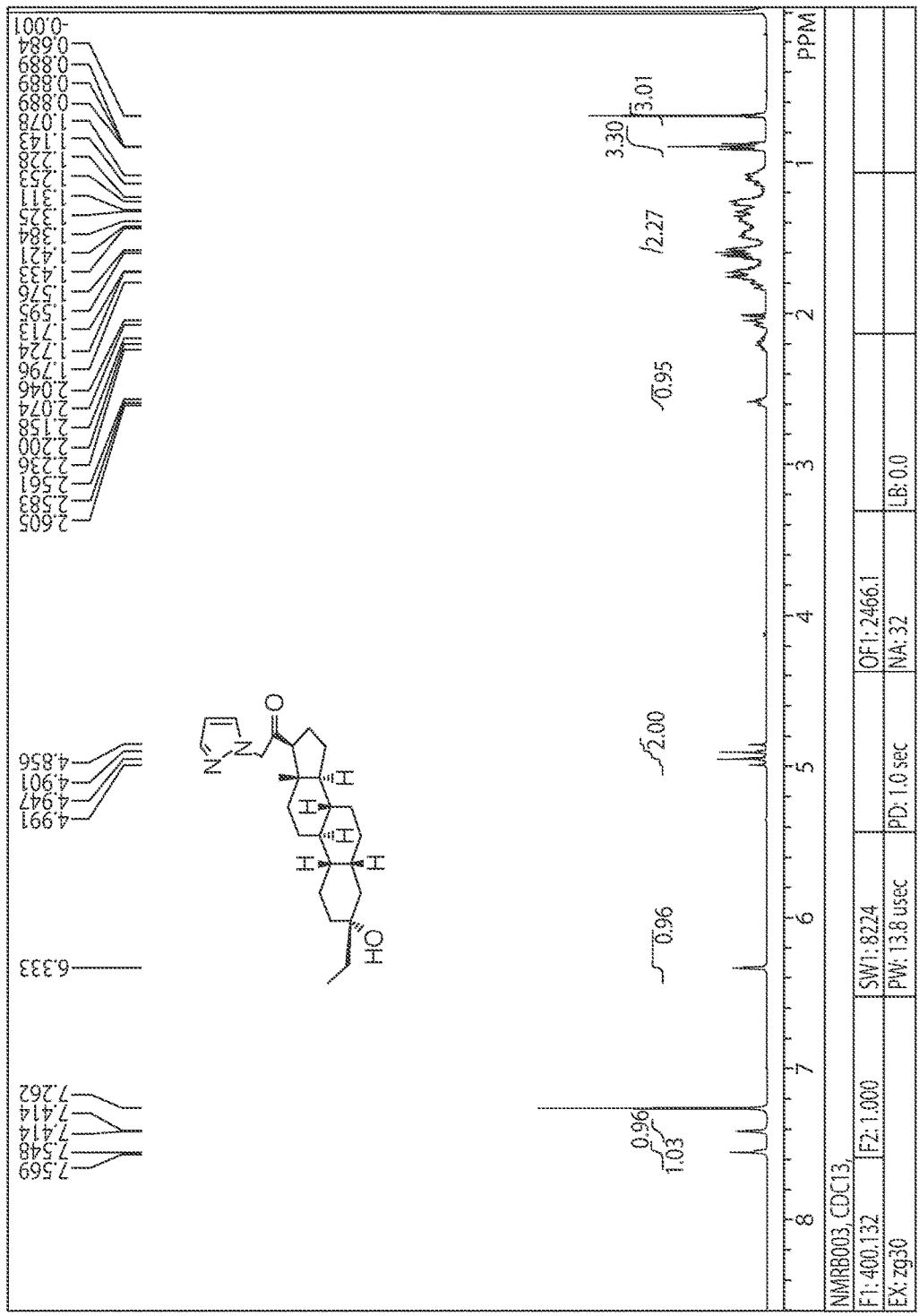
Figure 24:
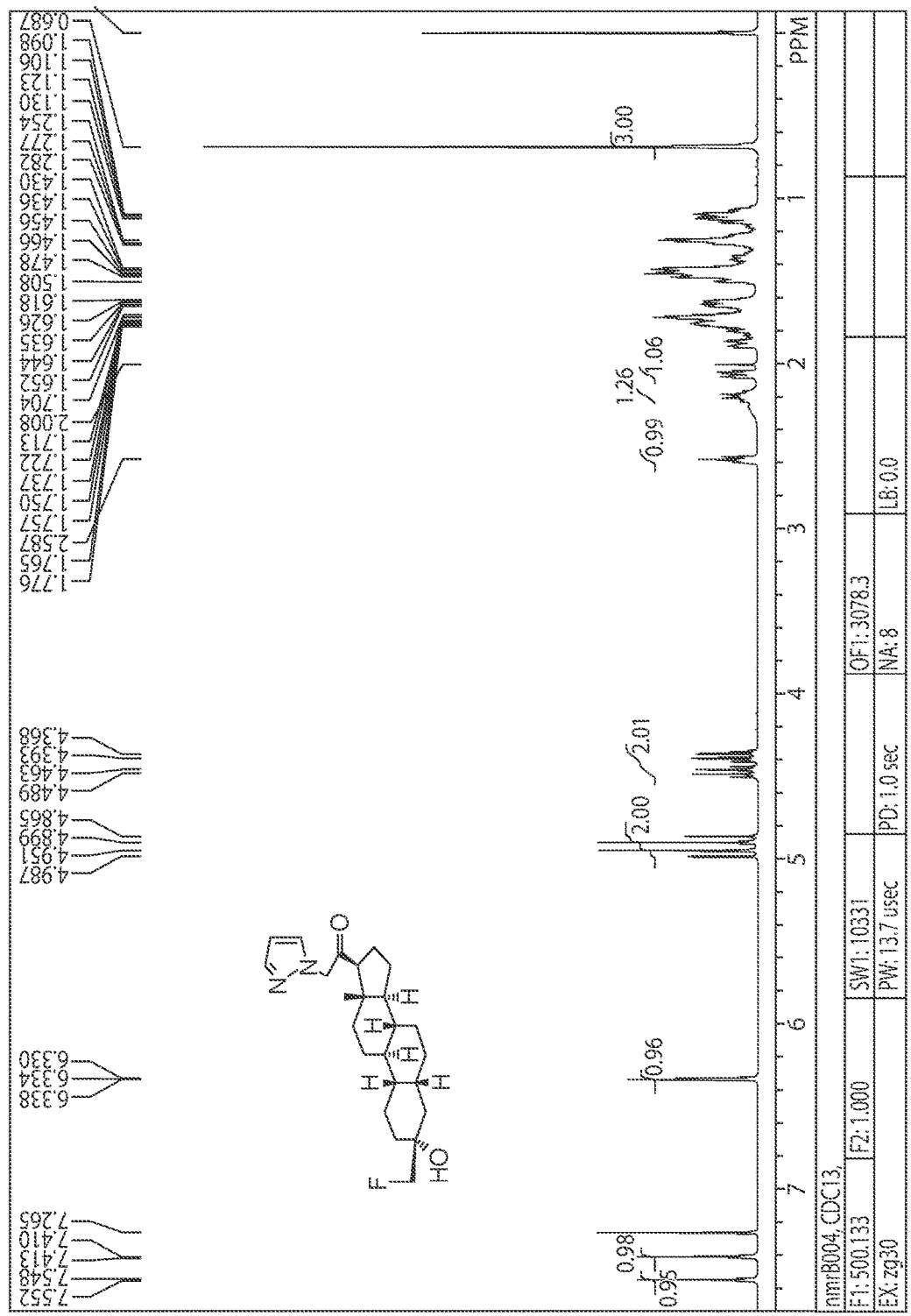
Figure 25:
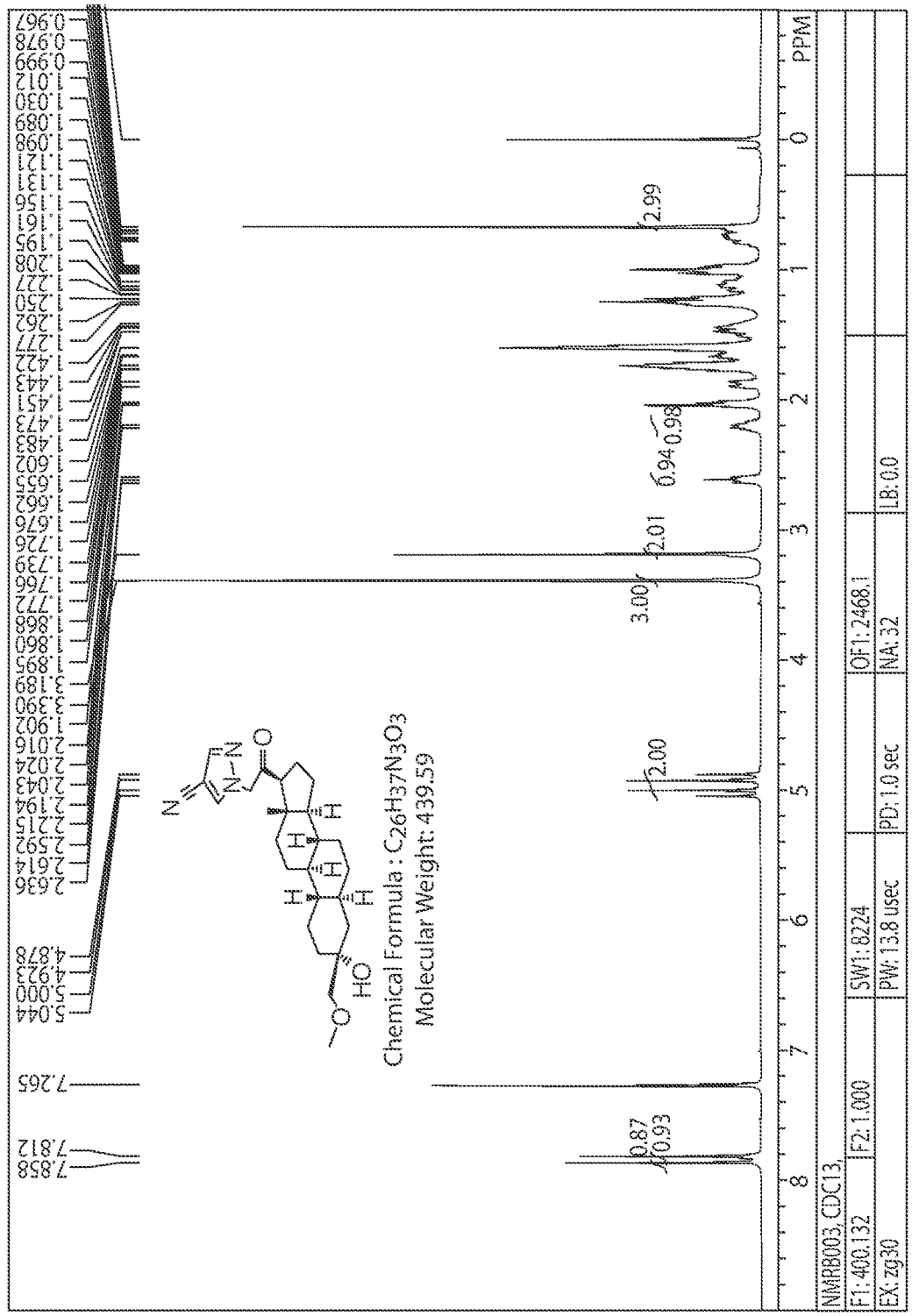
Figure 26:
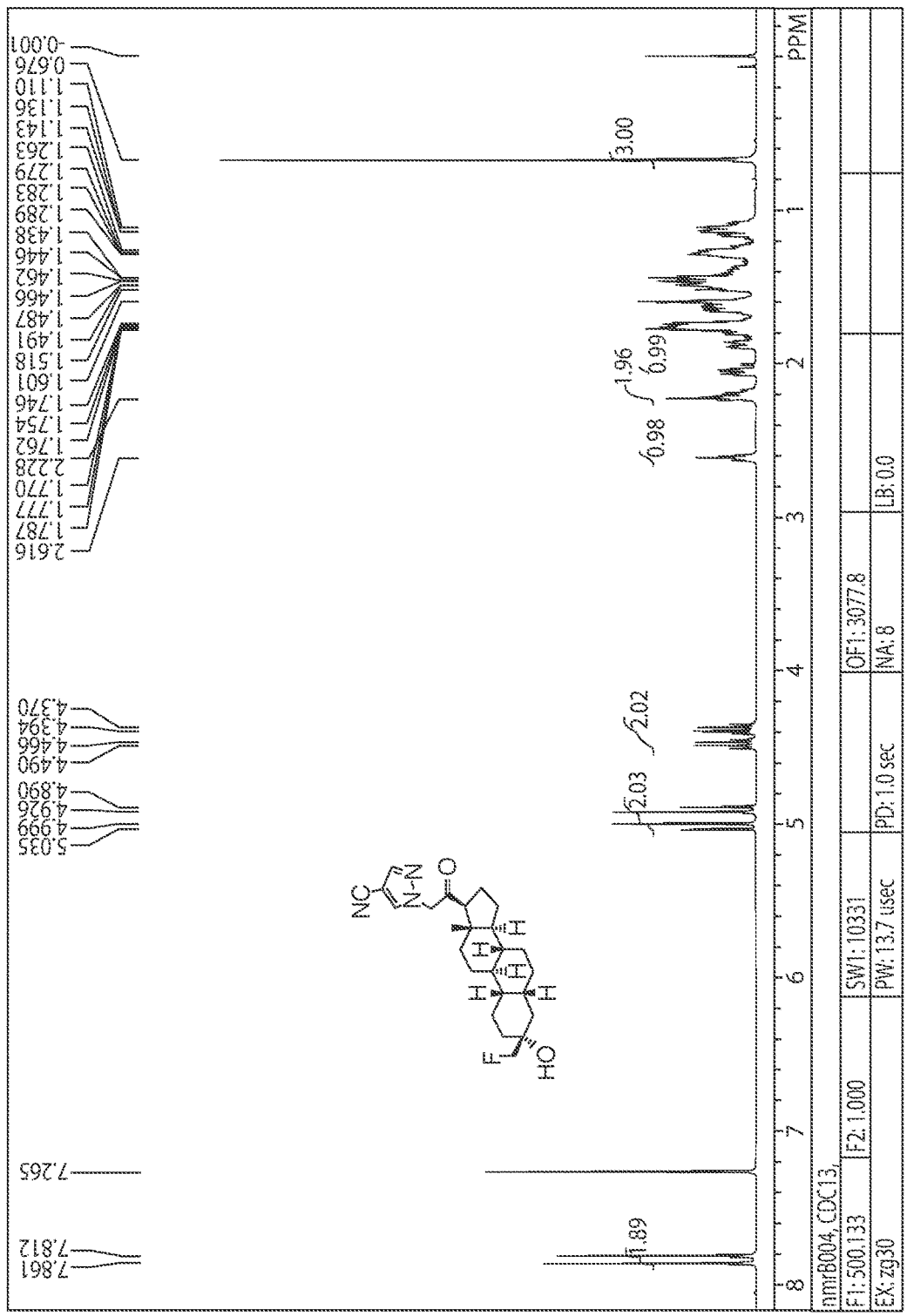
Figure 27:
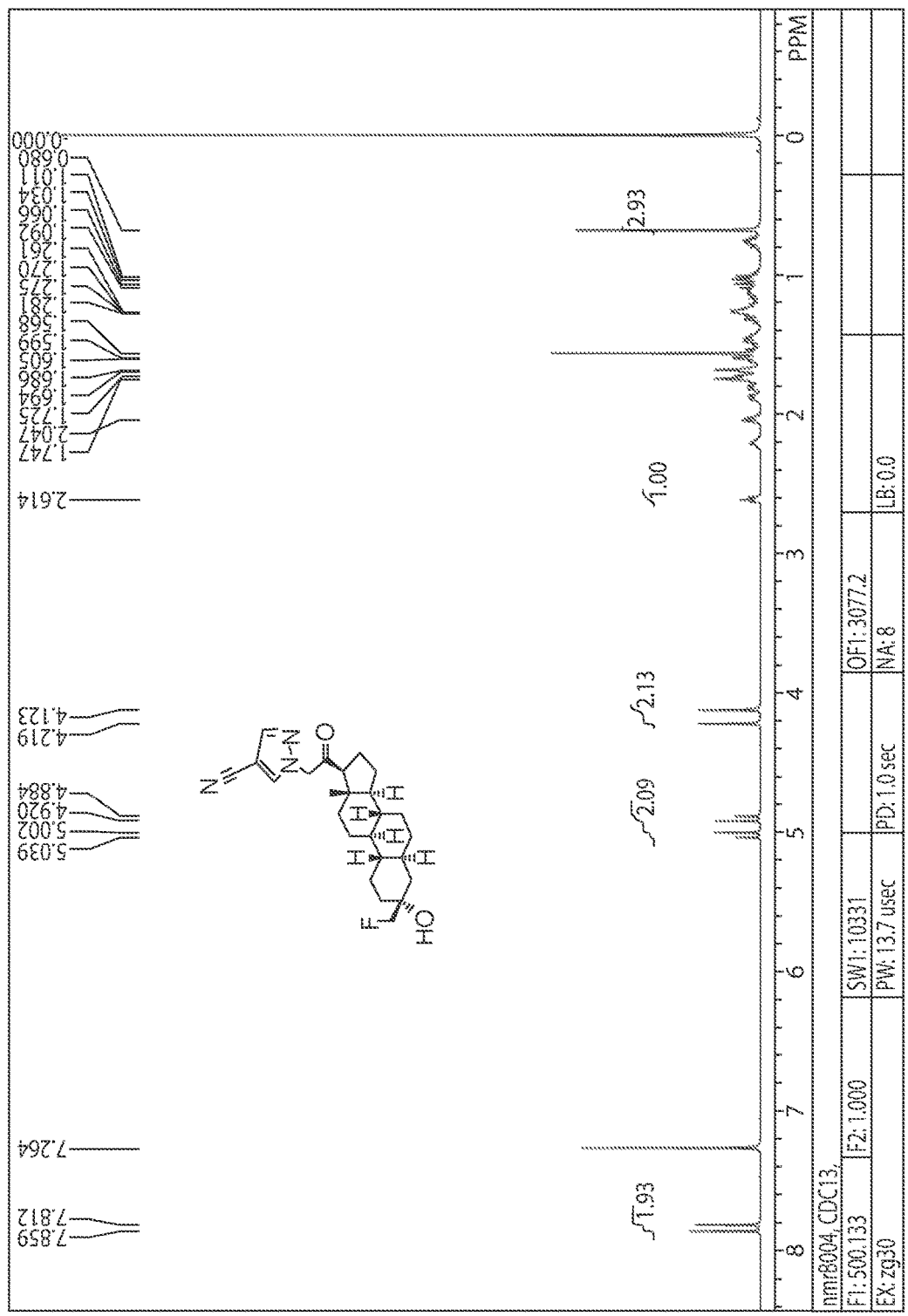
Figure 28:
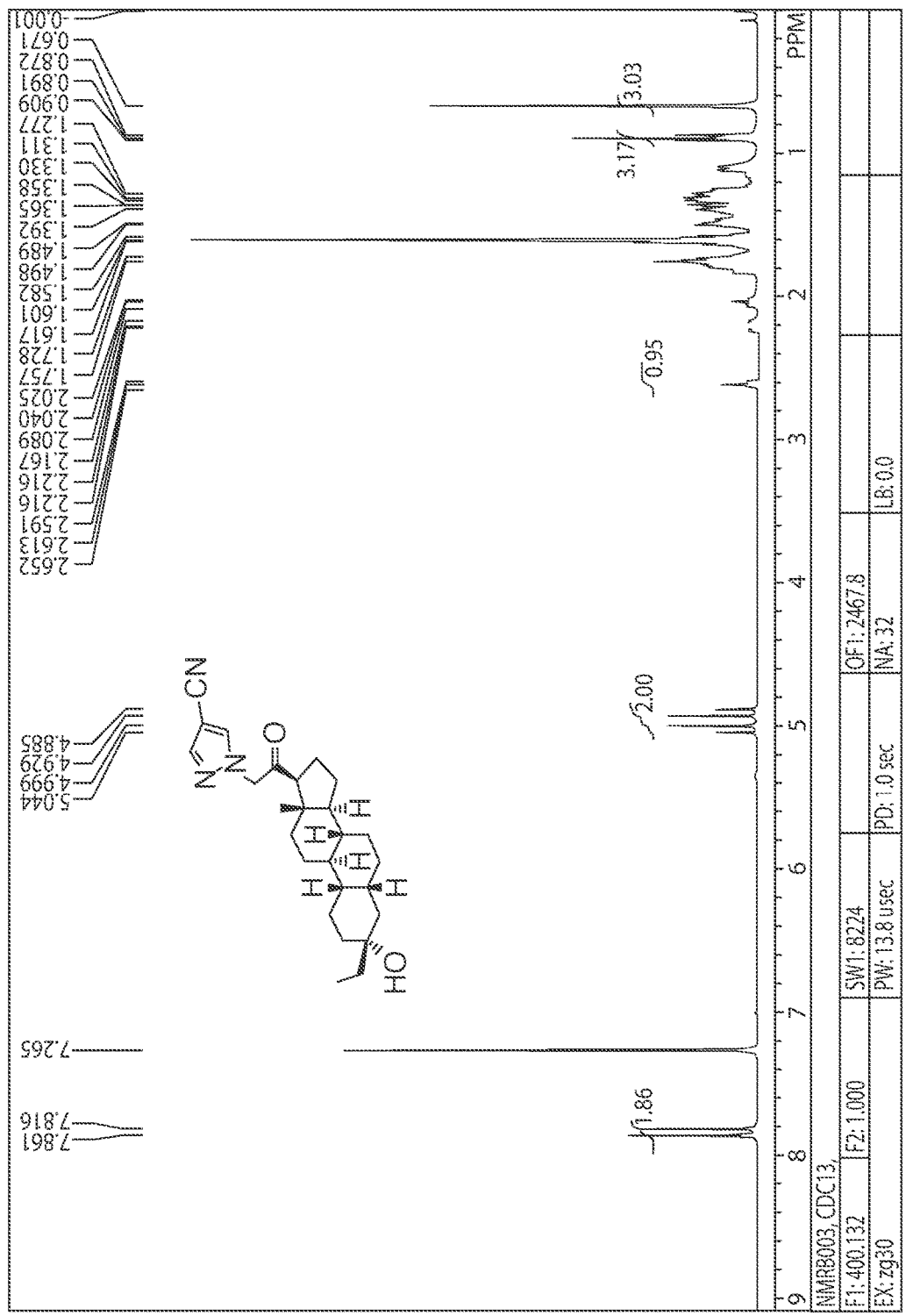
Figure 29:
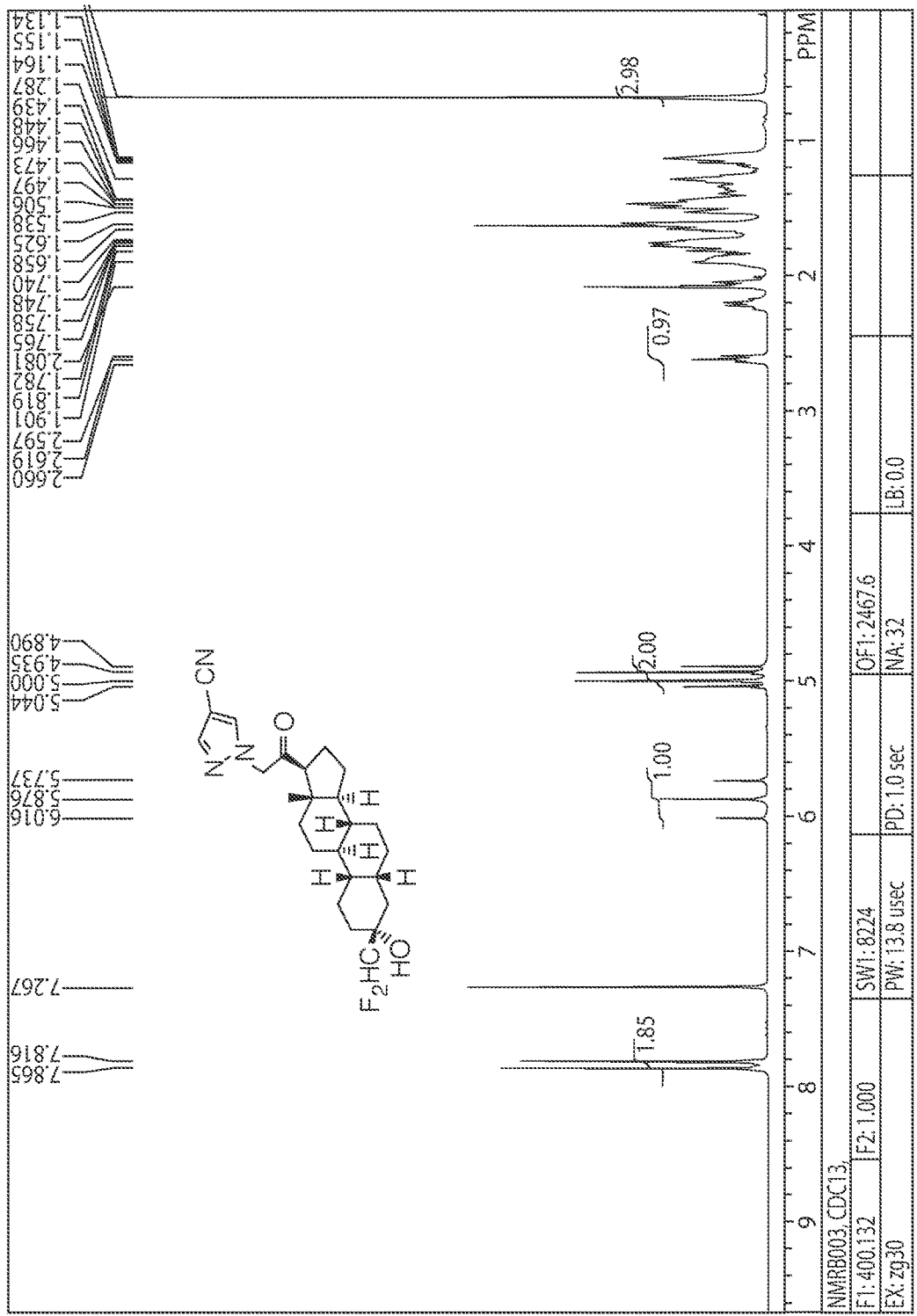
Figure 30:
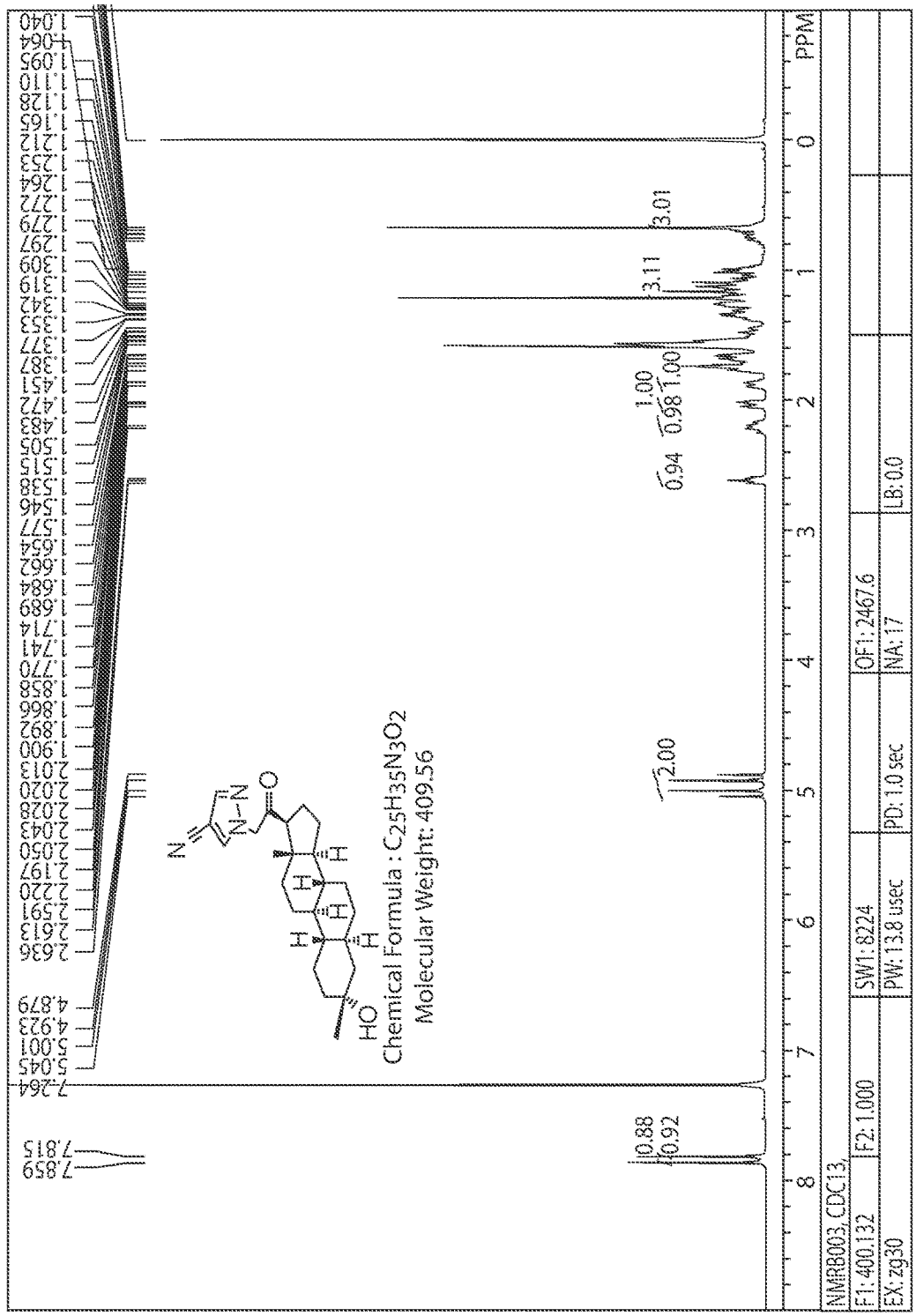
Figure 31:
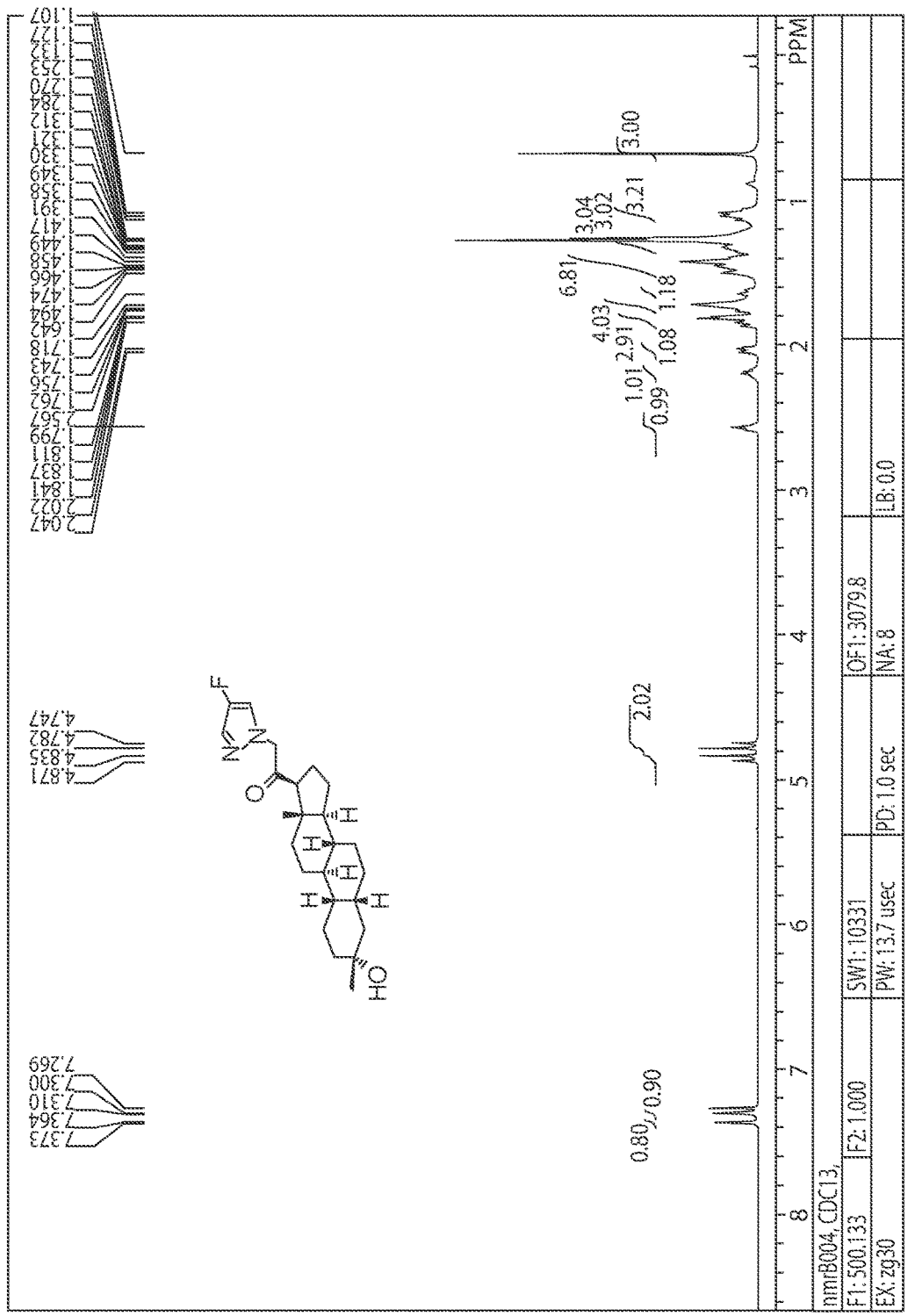
Figure 32:
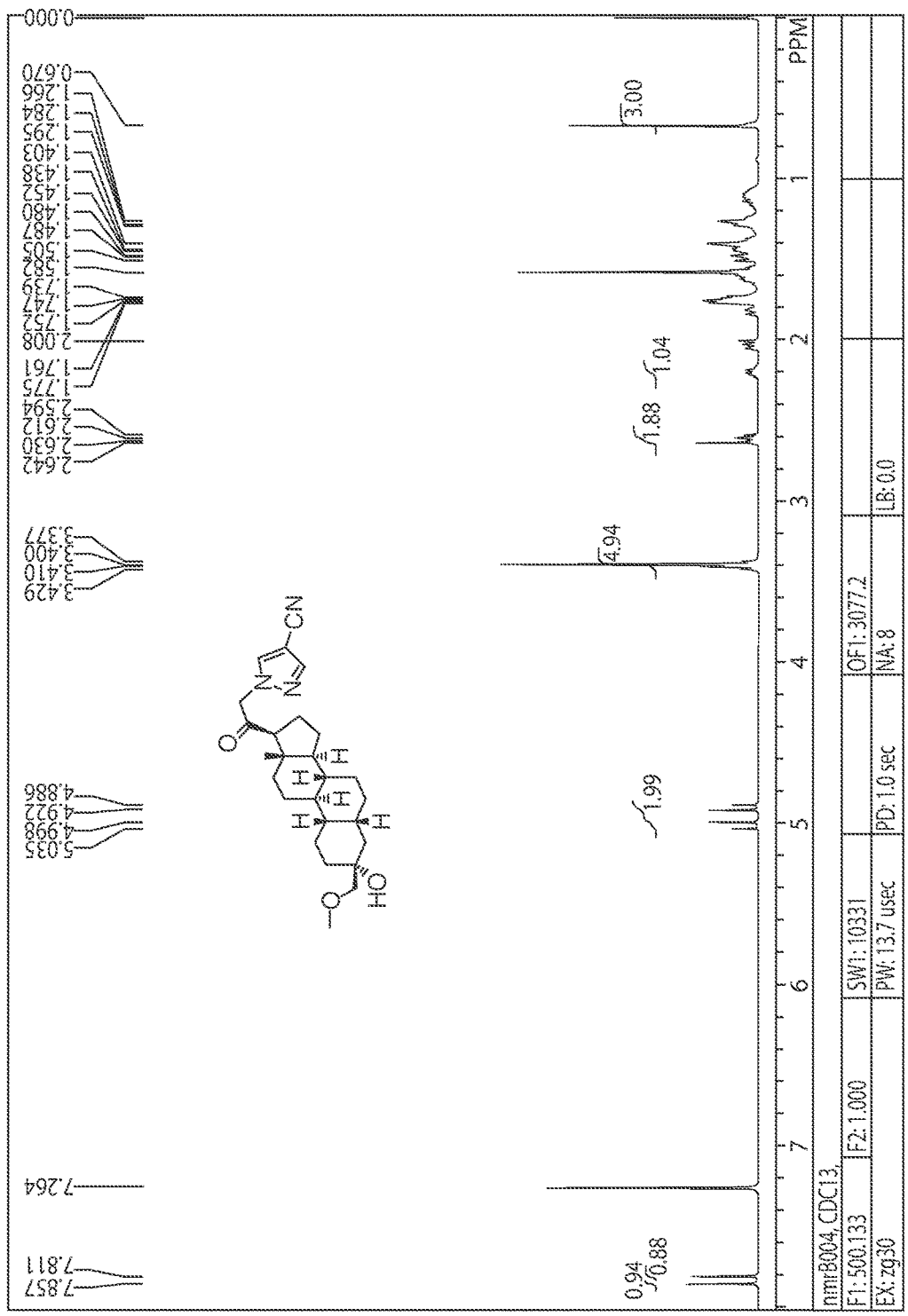
Figure 33:
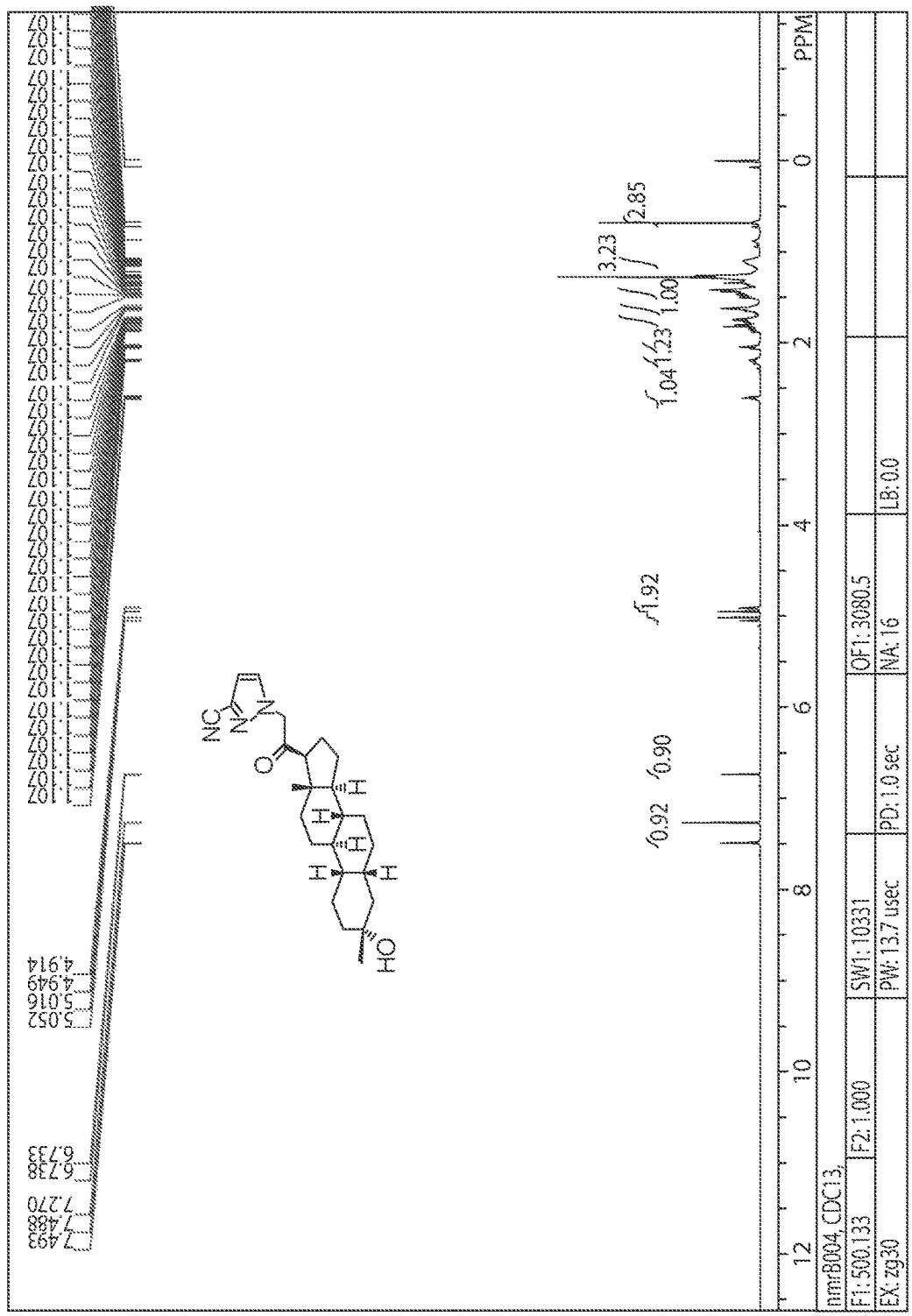
Figure 34:
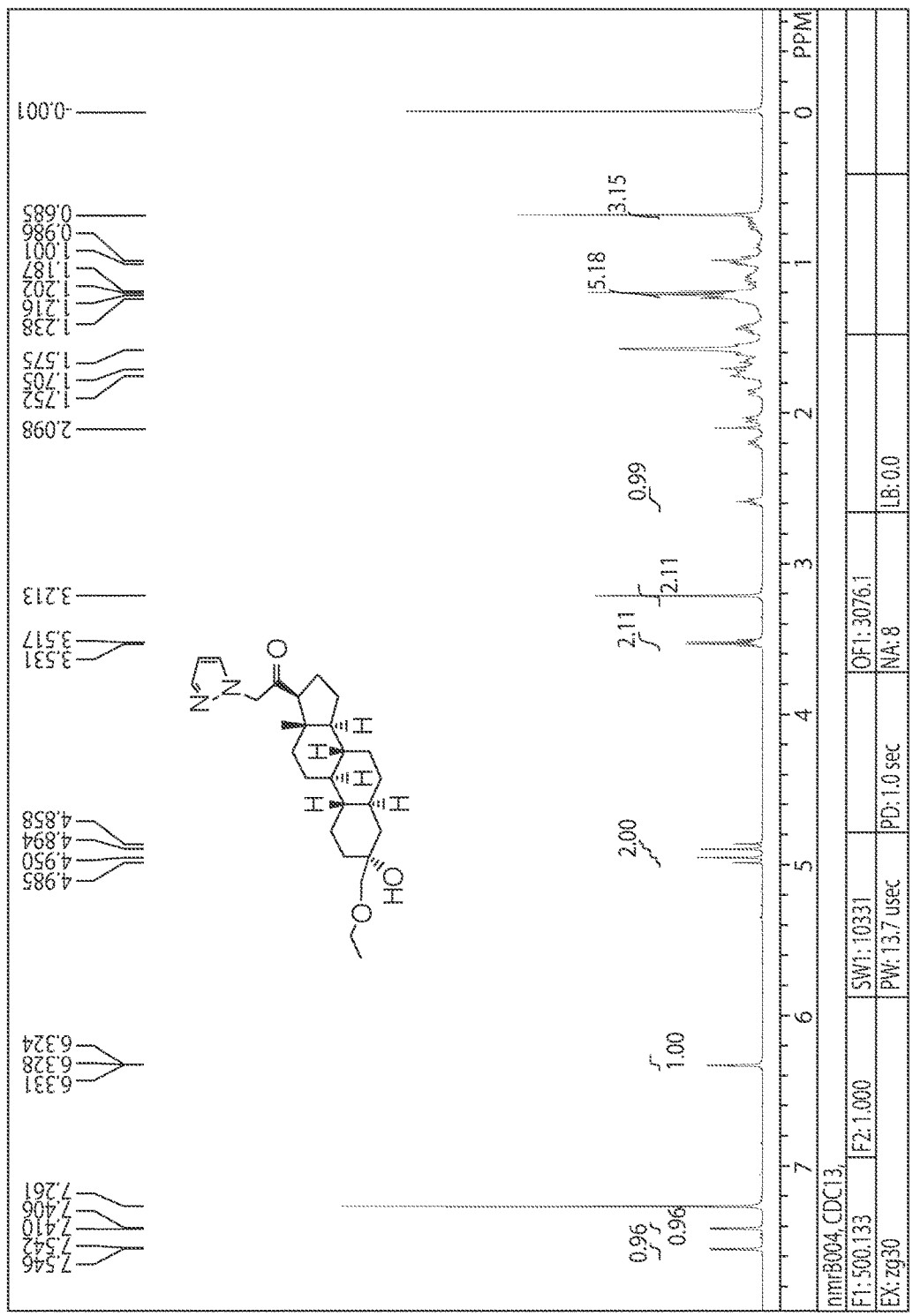
Figure 35:
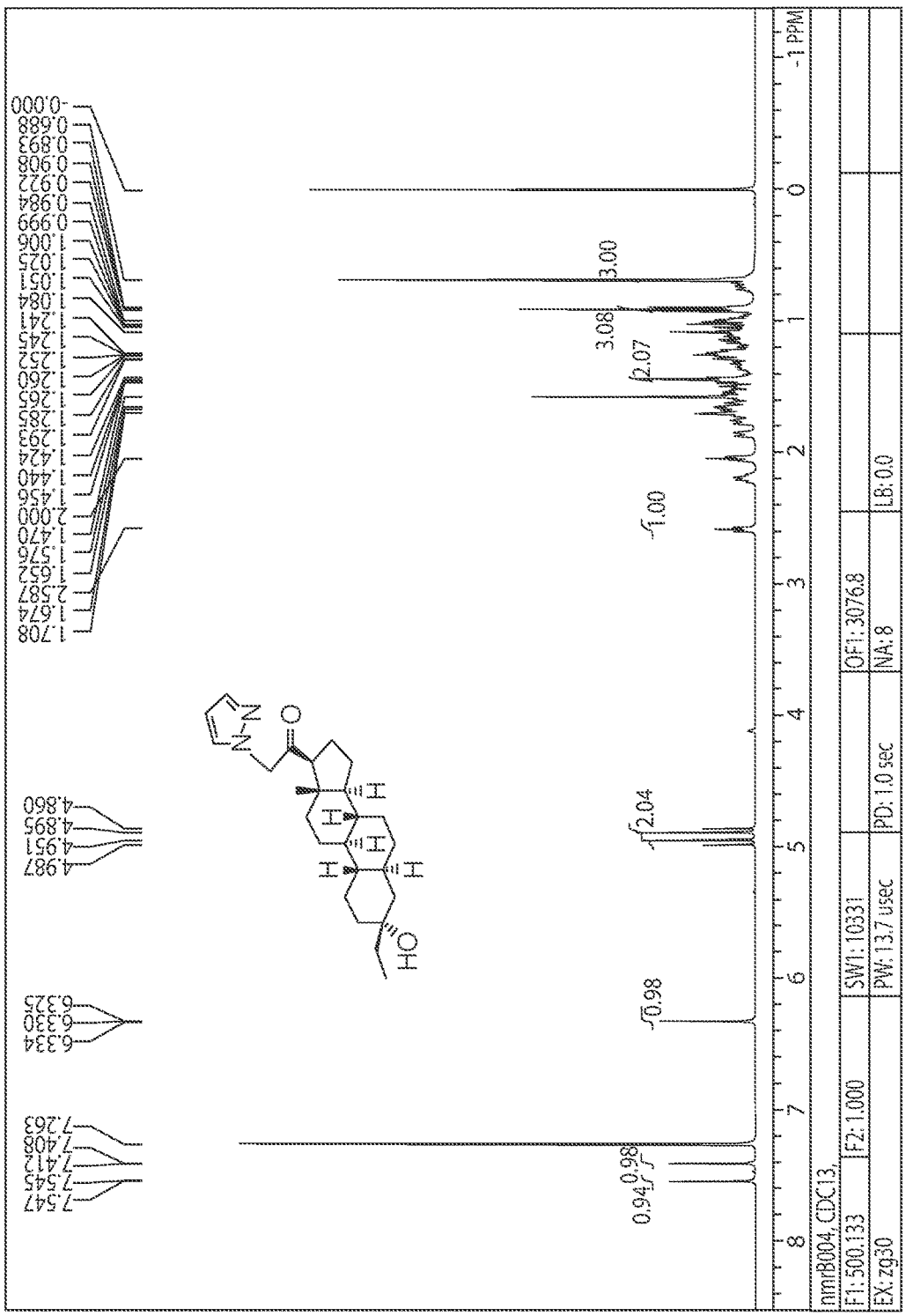
Figure 36:
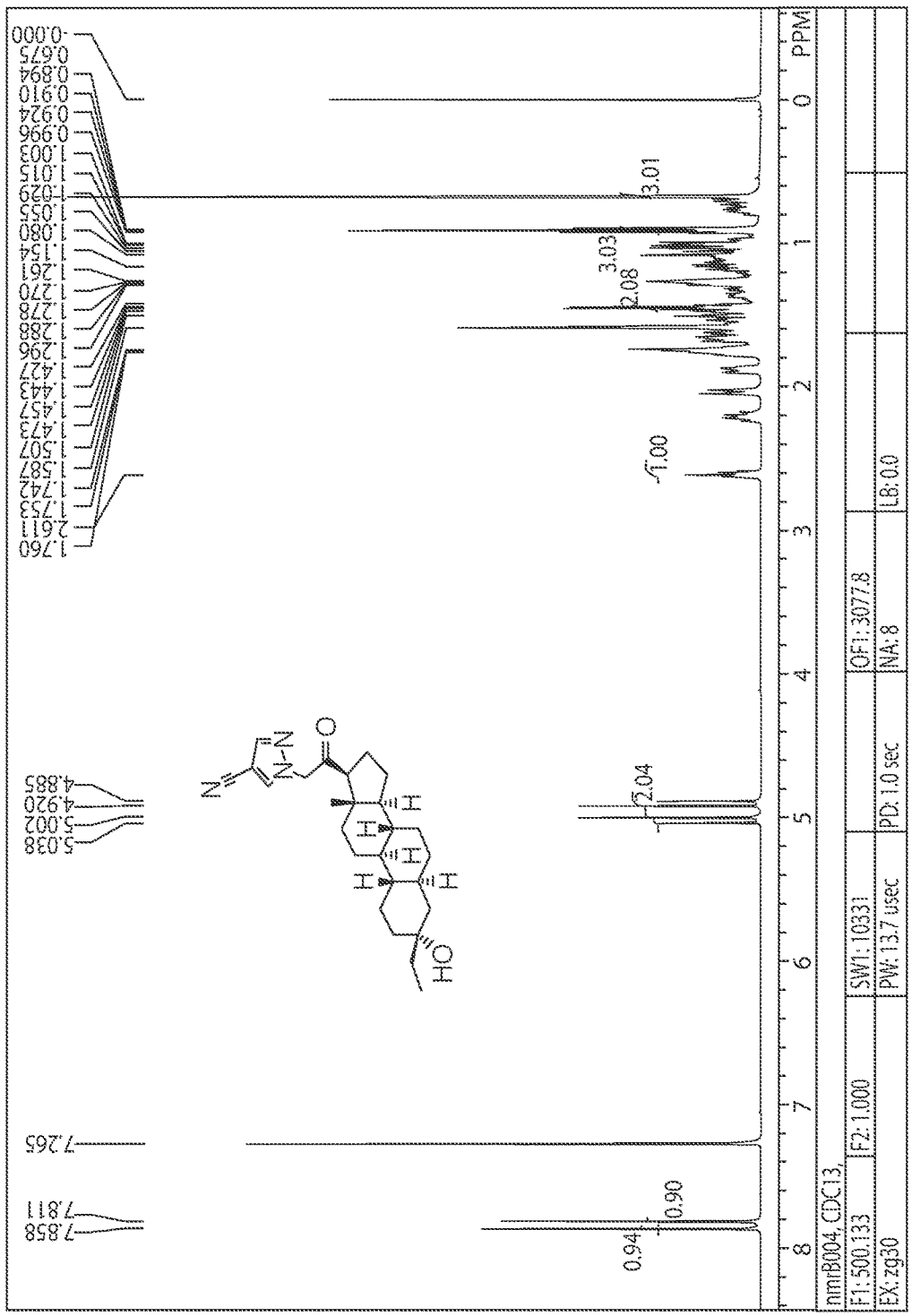
Figure 37:
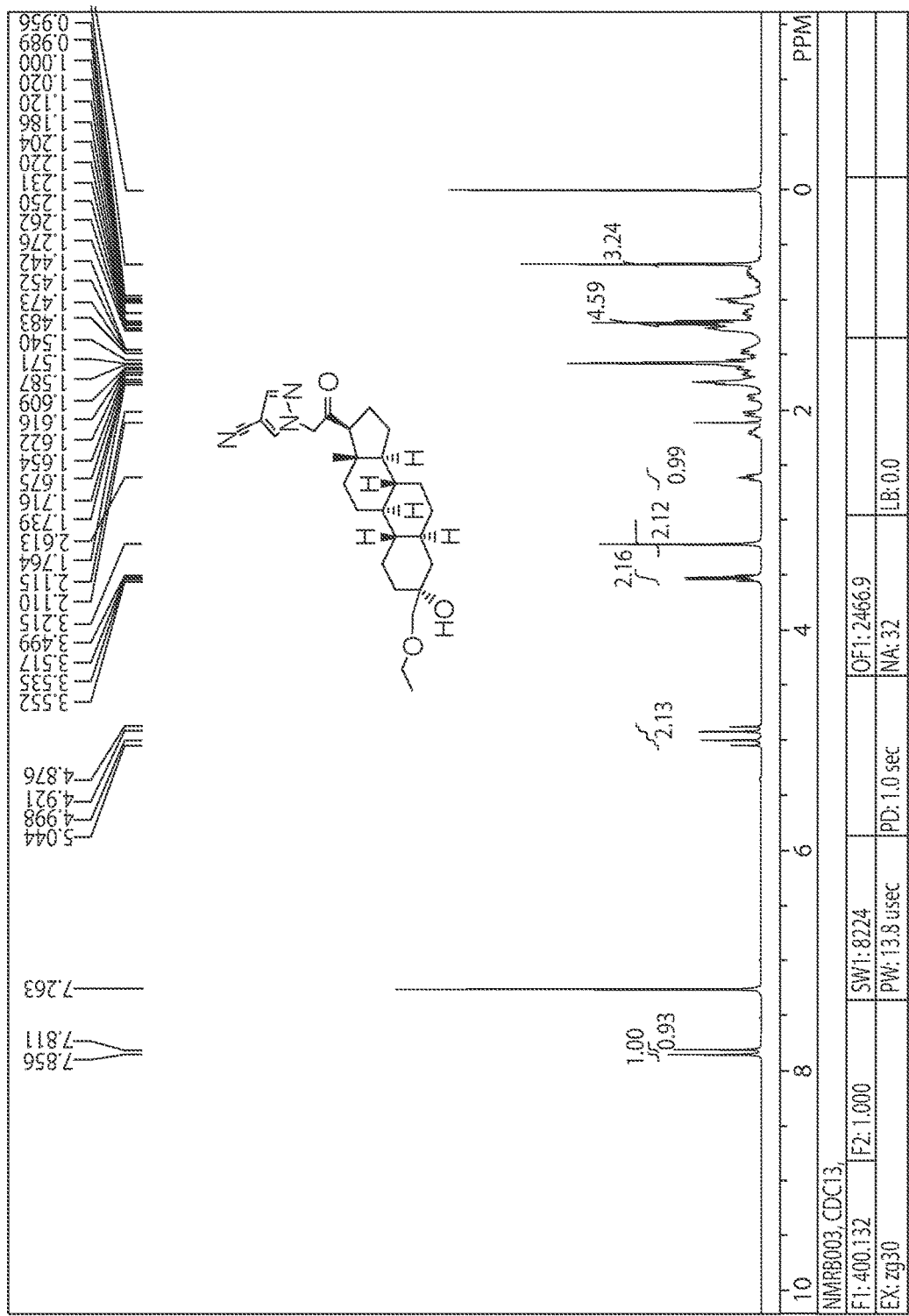
Figure 38:
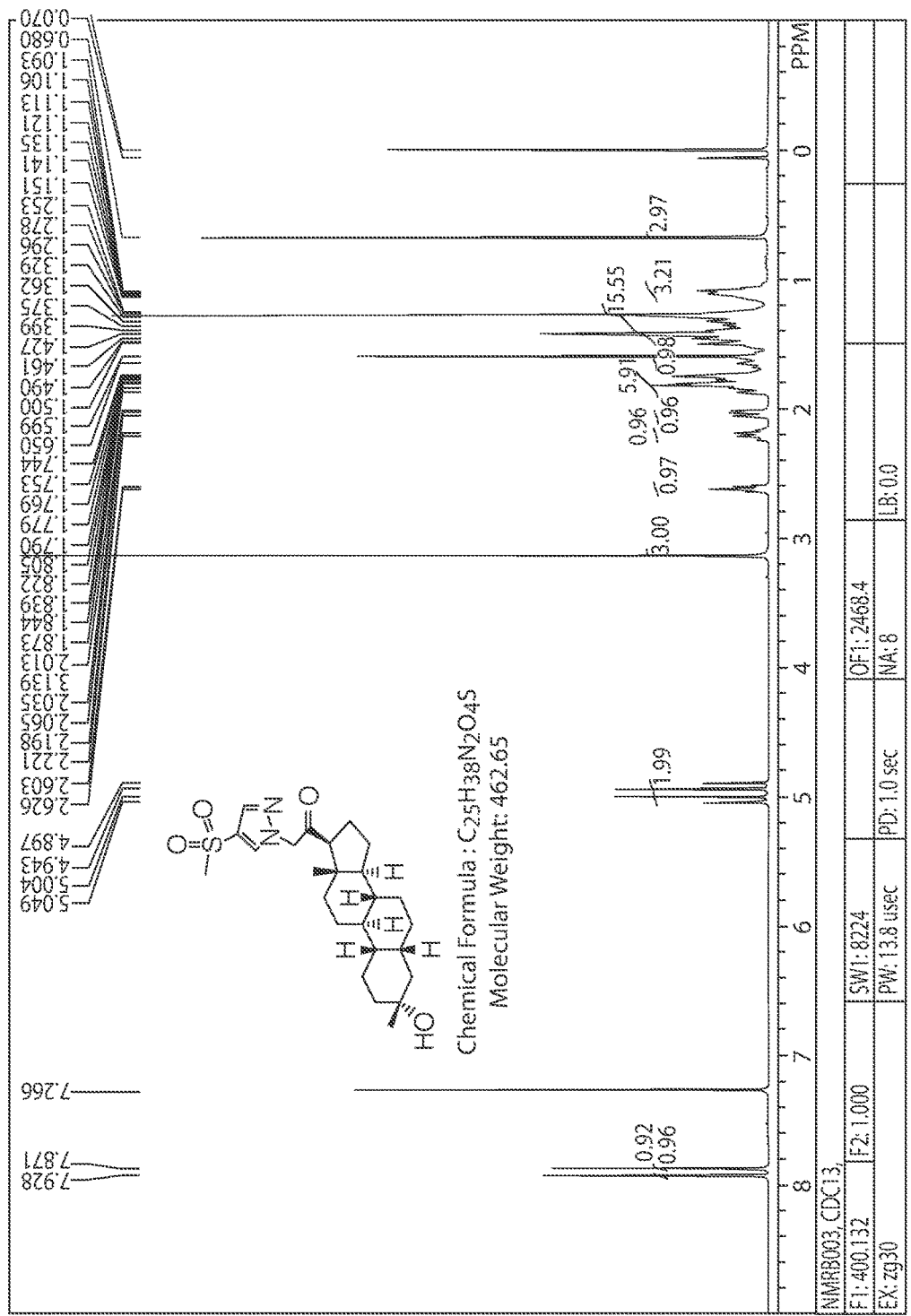
Figure 39:
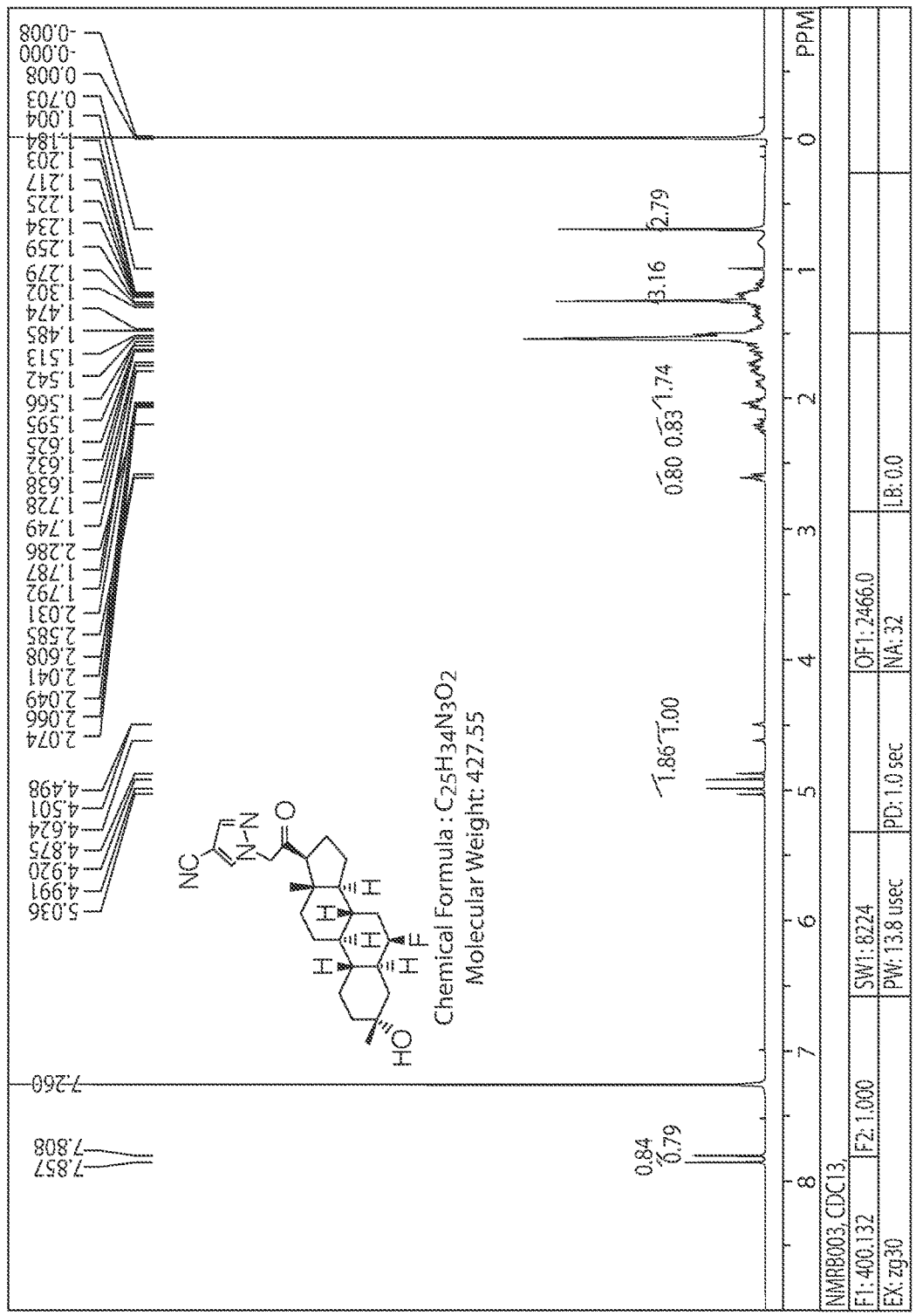
Figure 40:
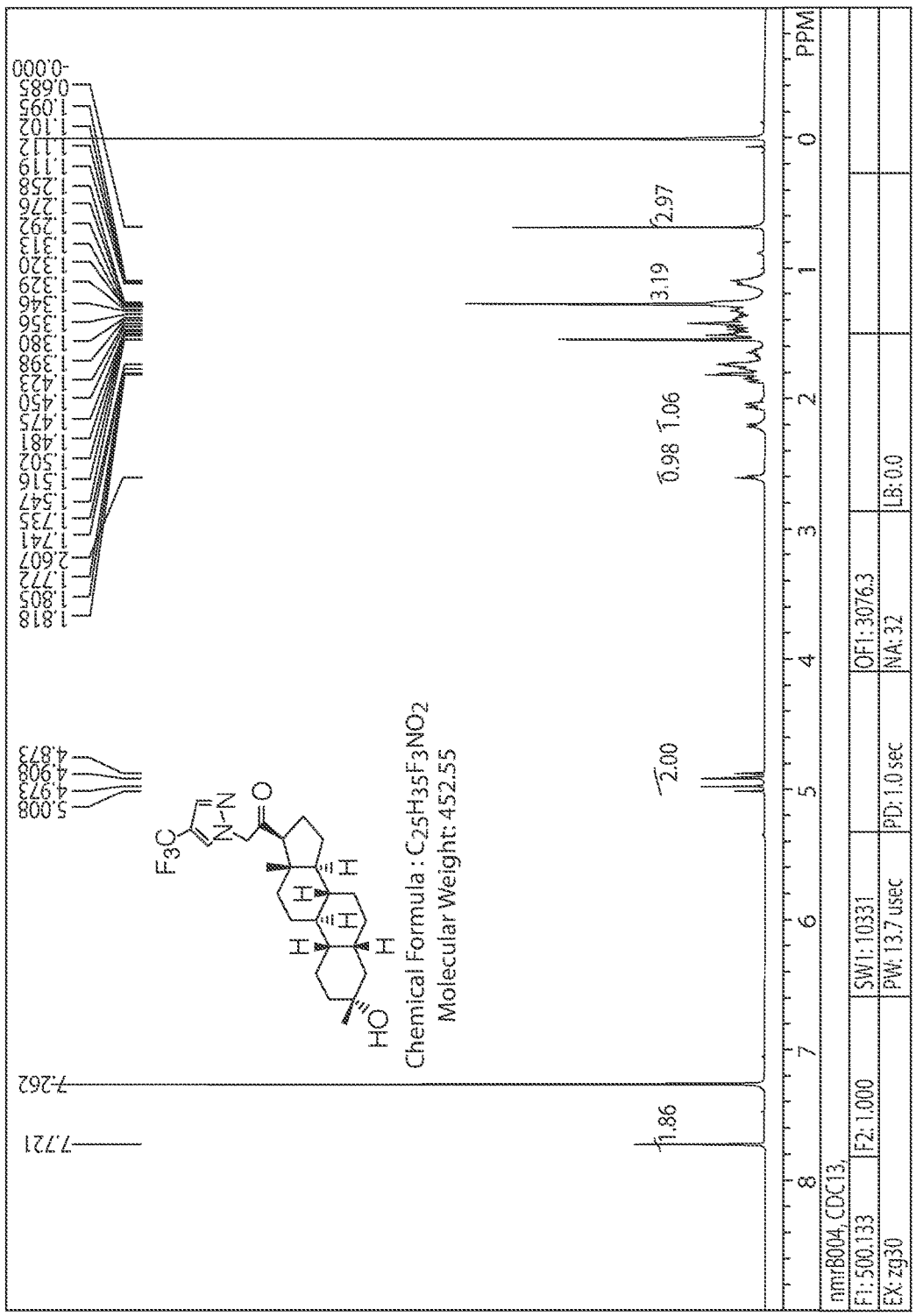
Figure 41:
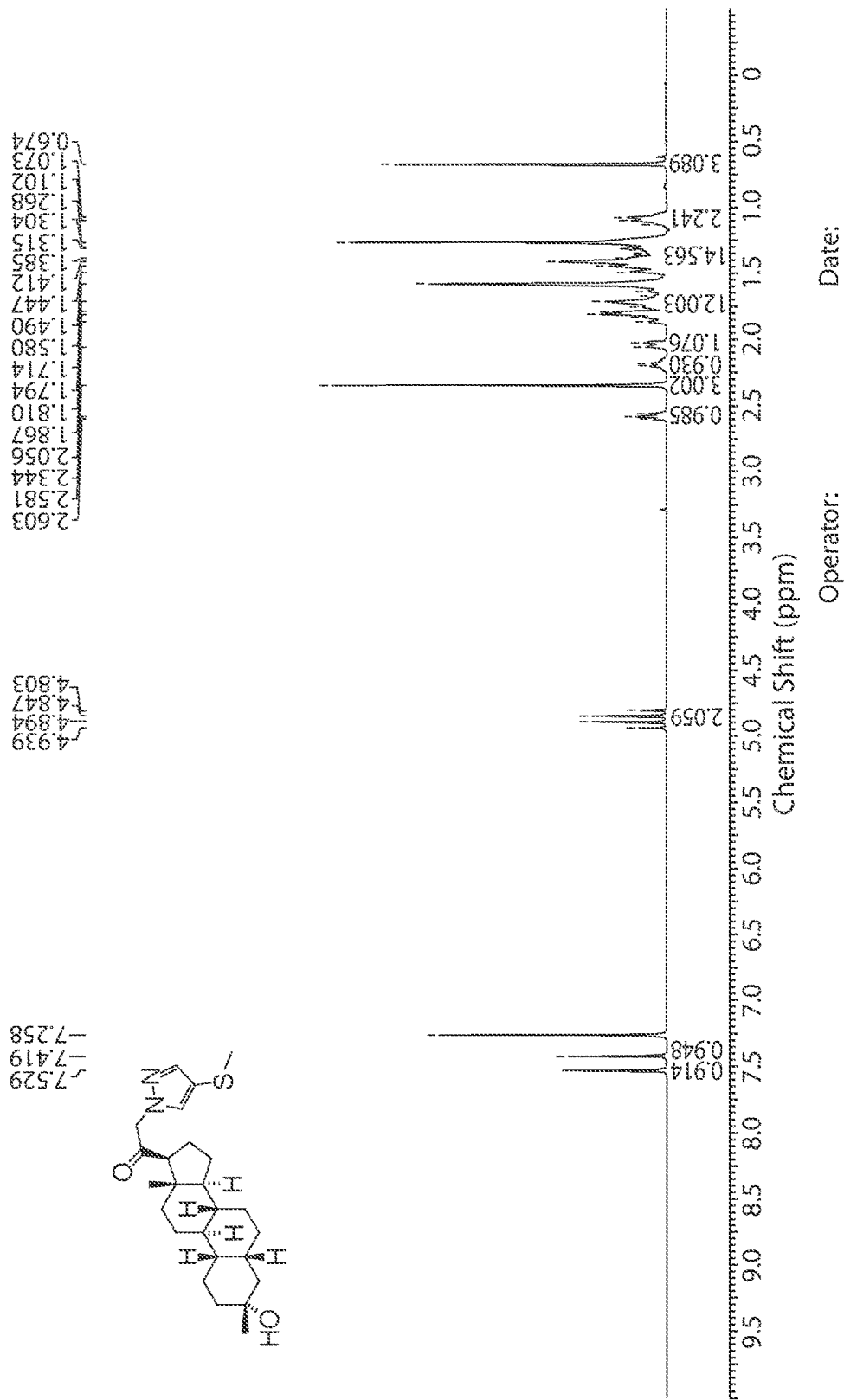
Figure 42:
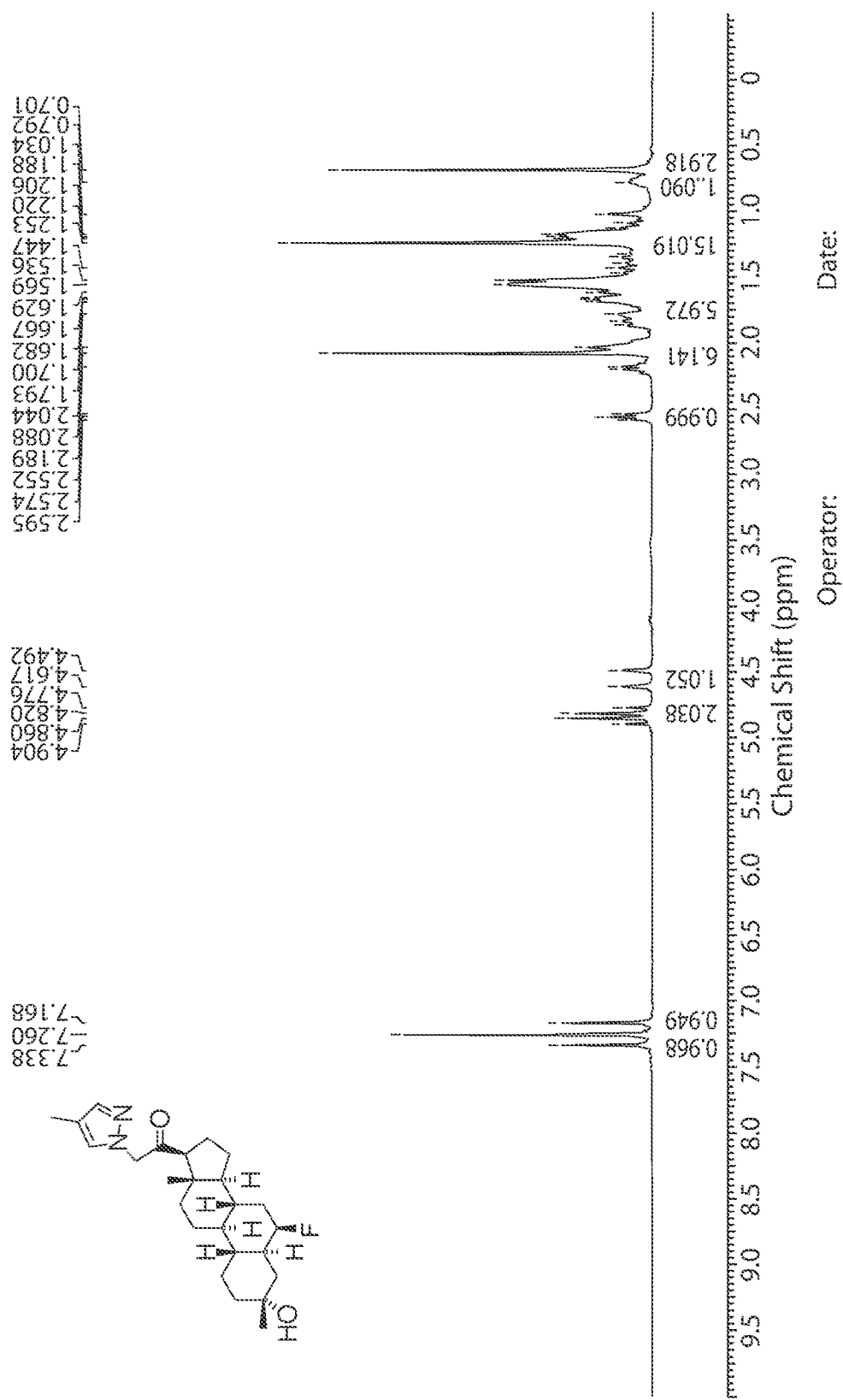
Figure 43:
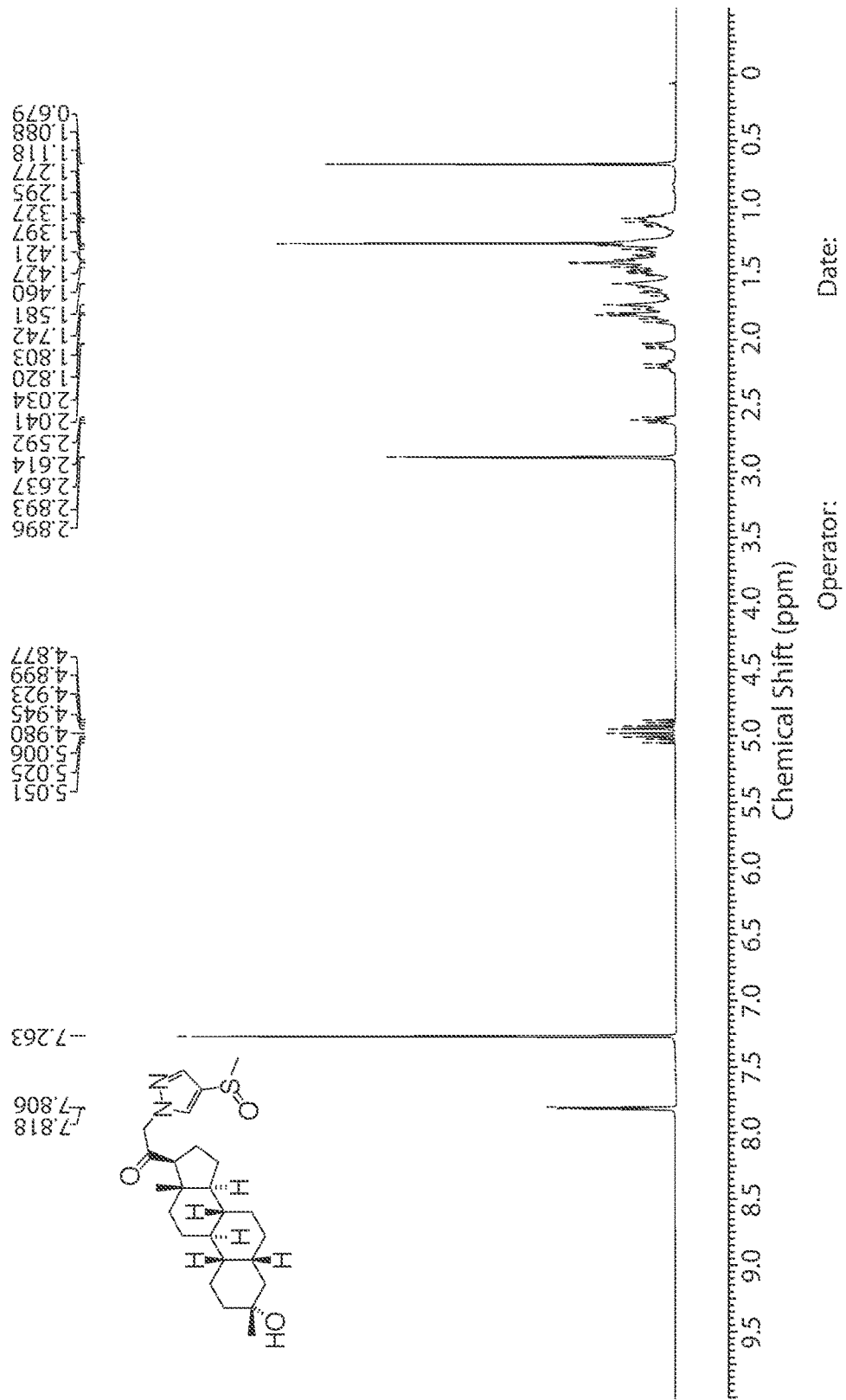
Figure 44:
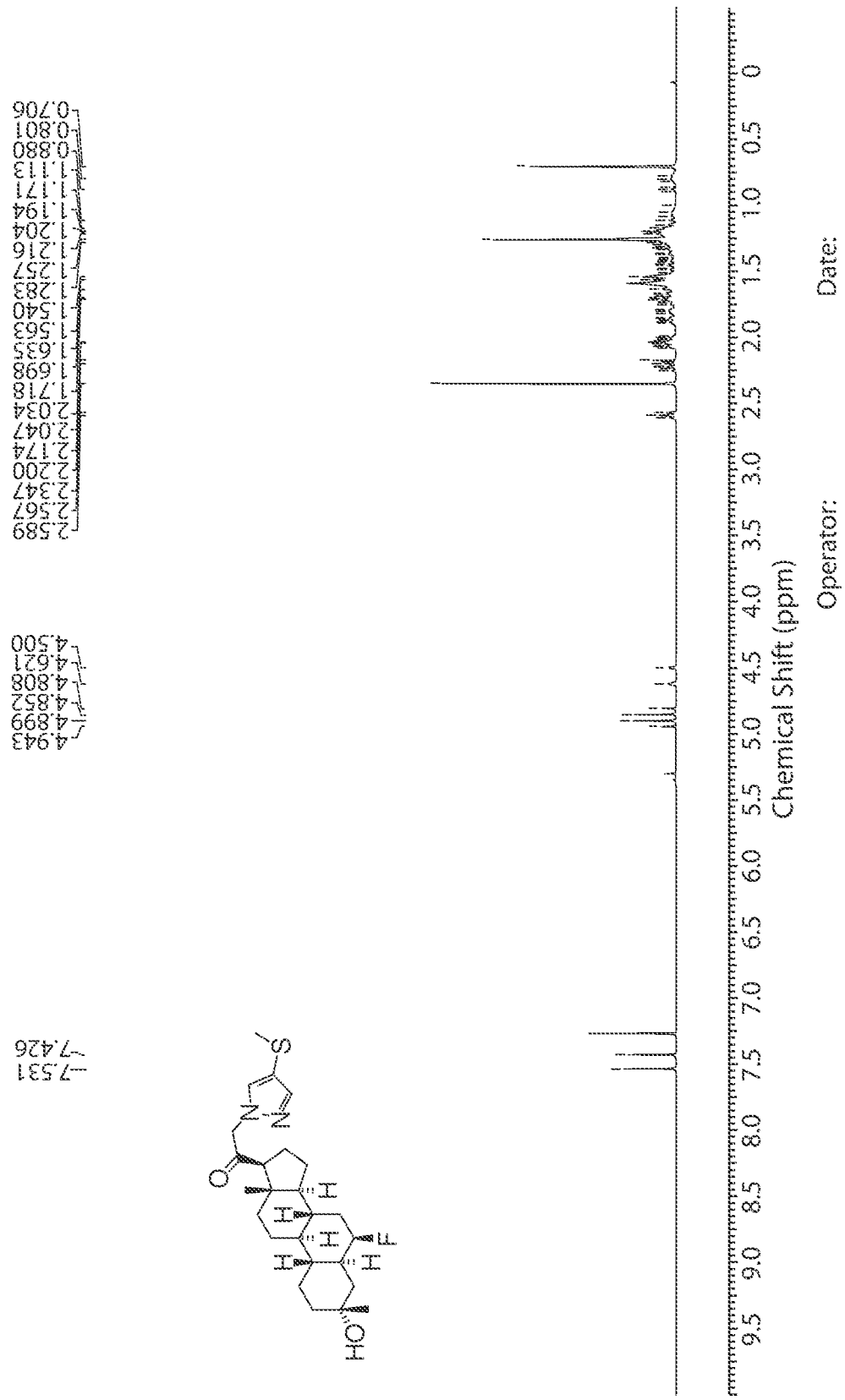
Figure 45:
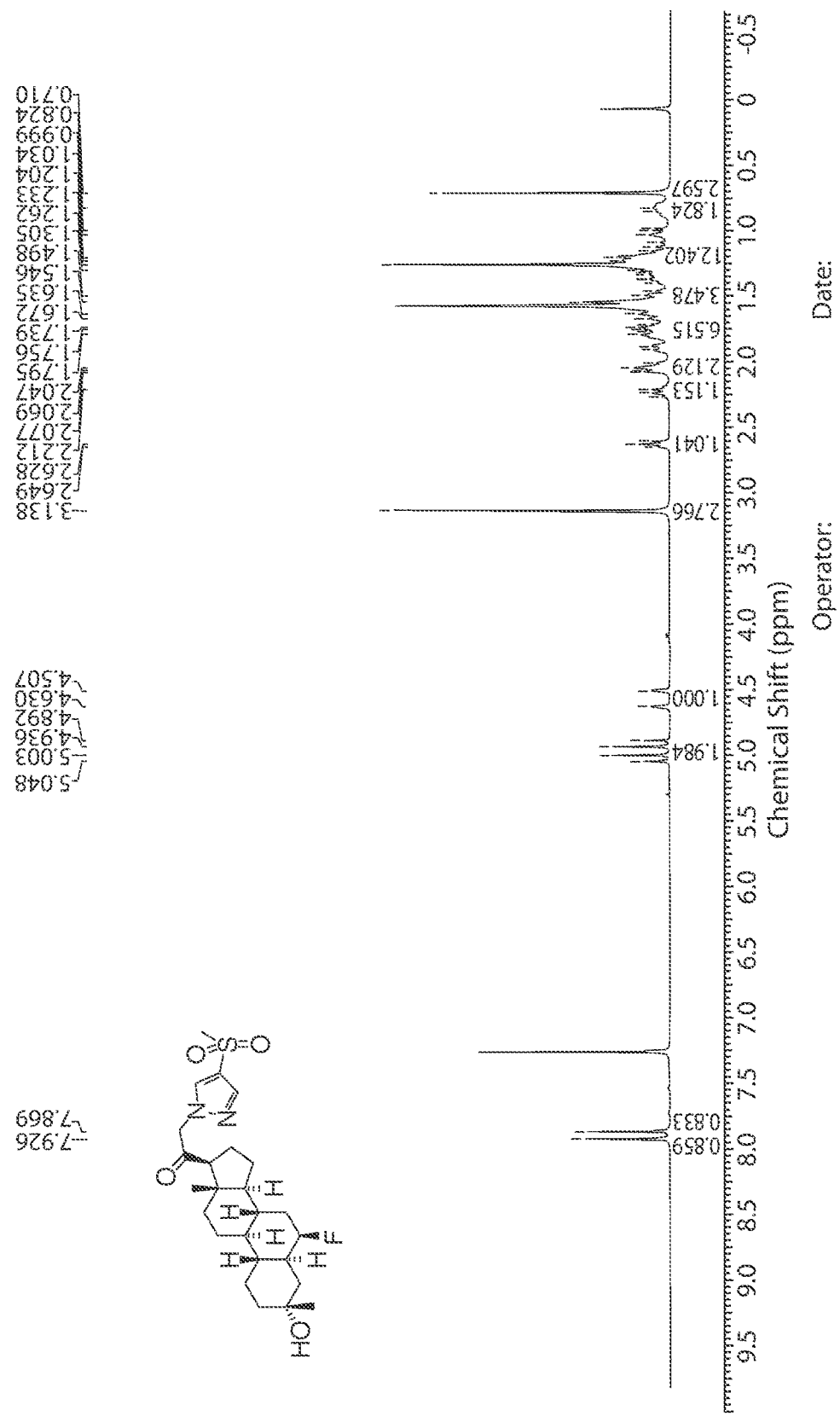
Figure 46:
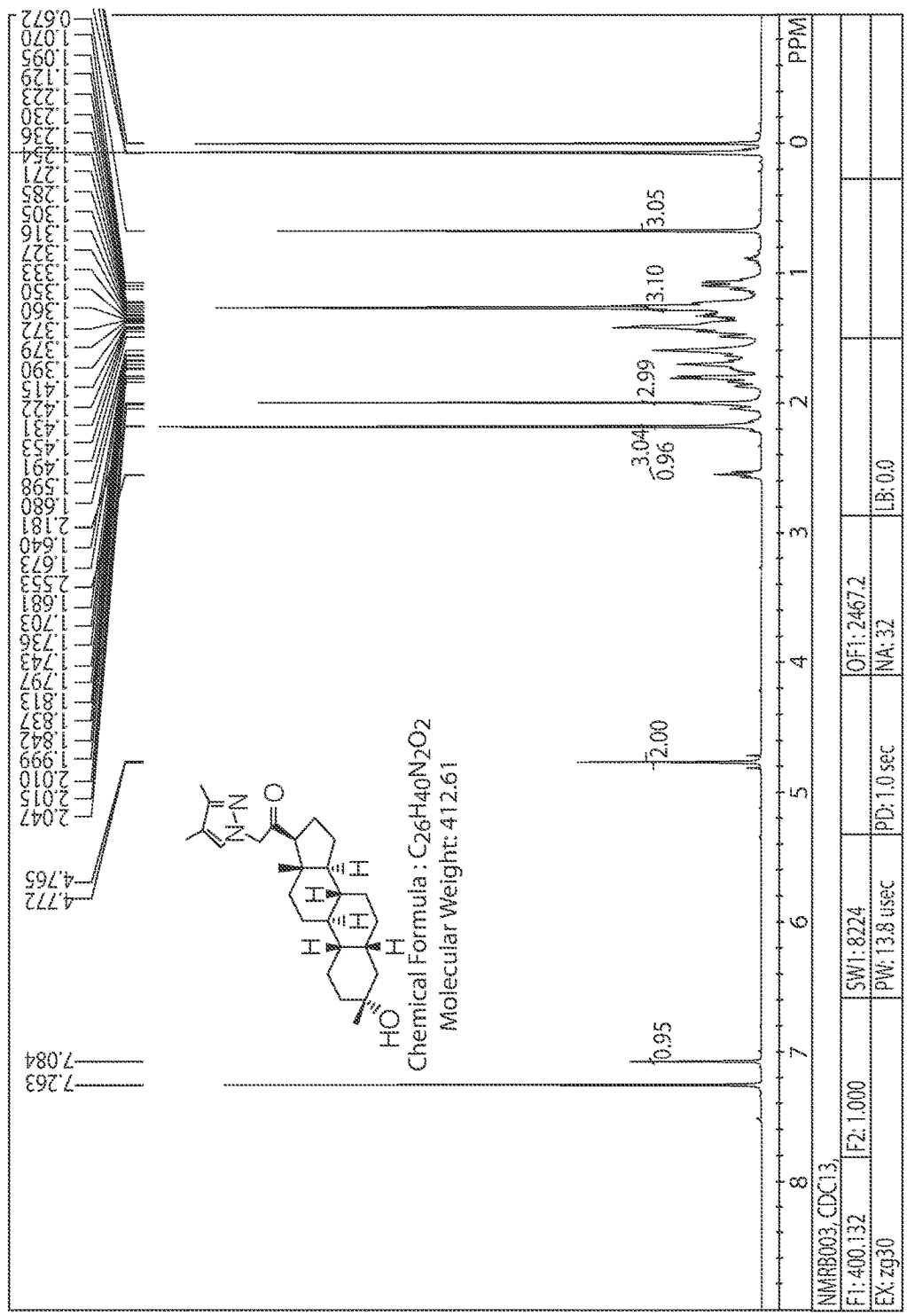
Figure 47:
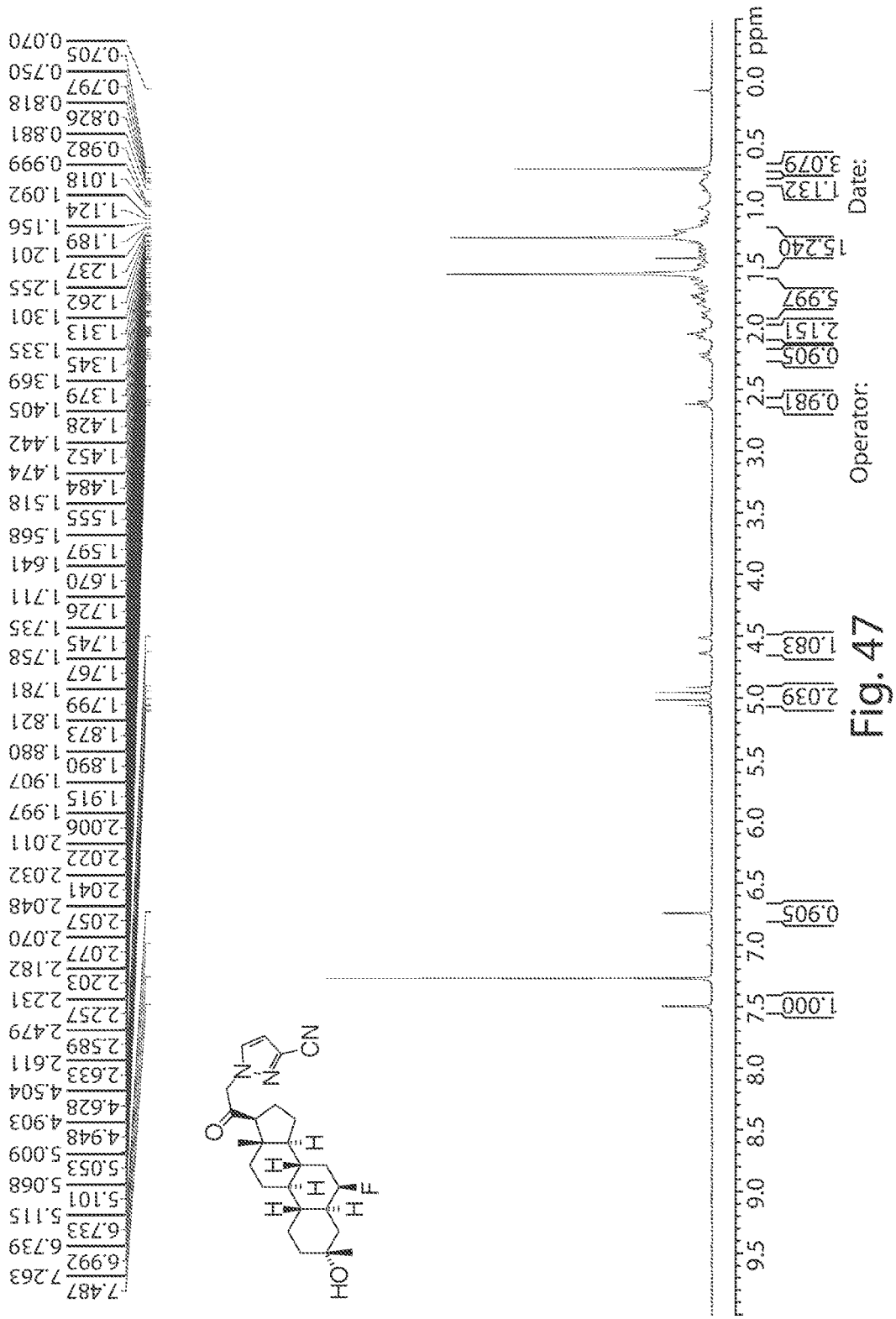
Figure 48:
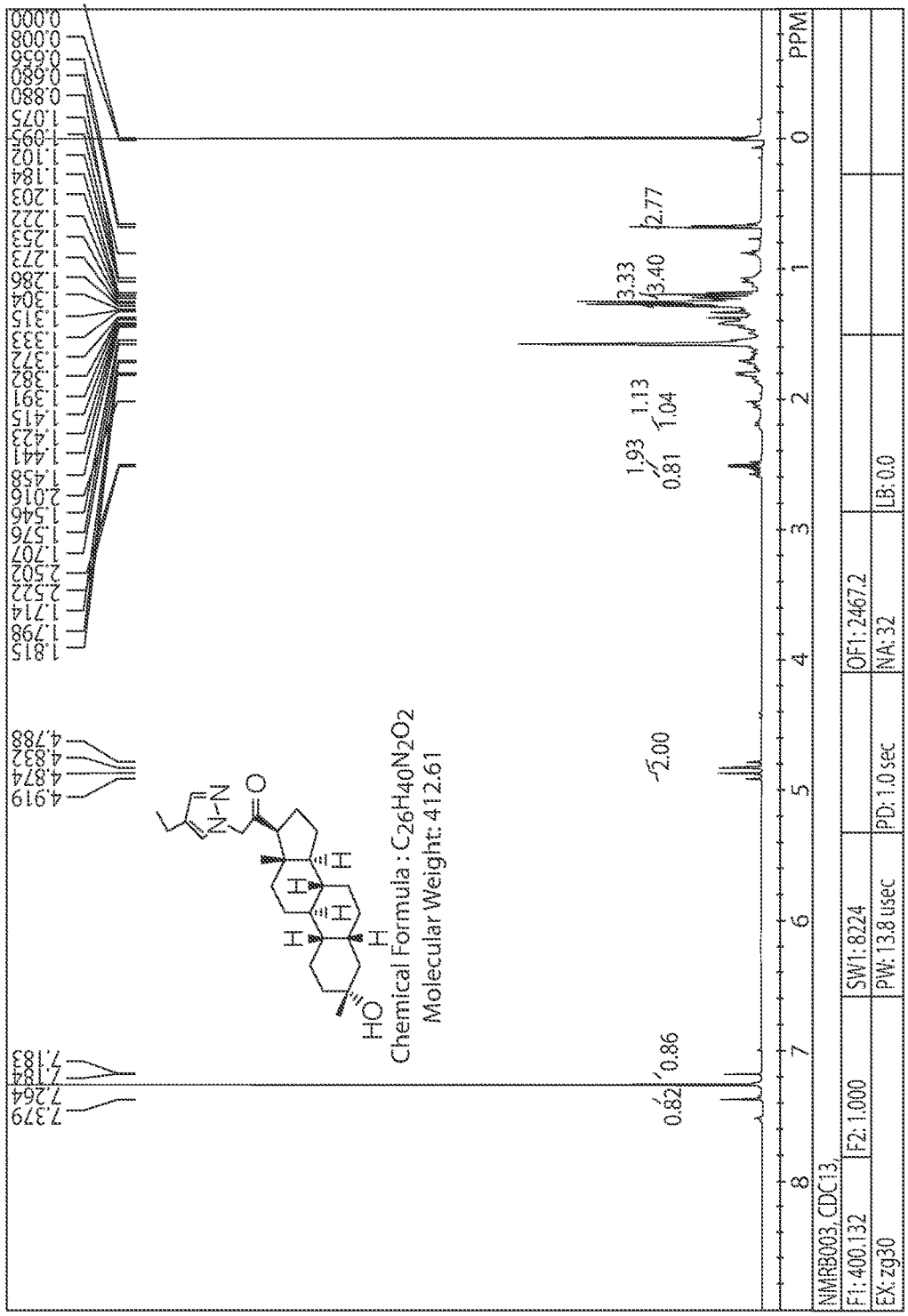
Figure 49:
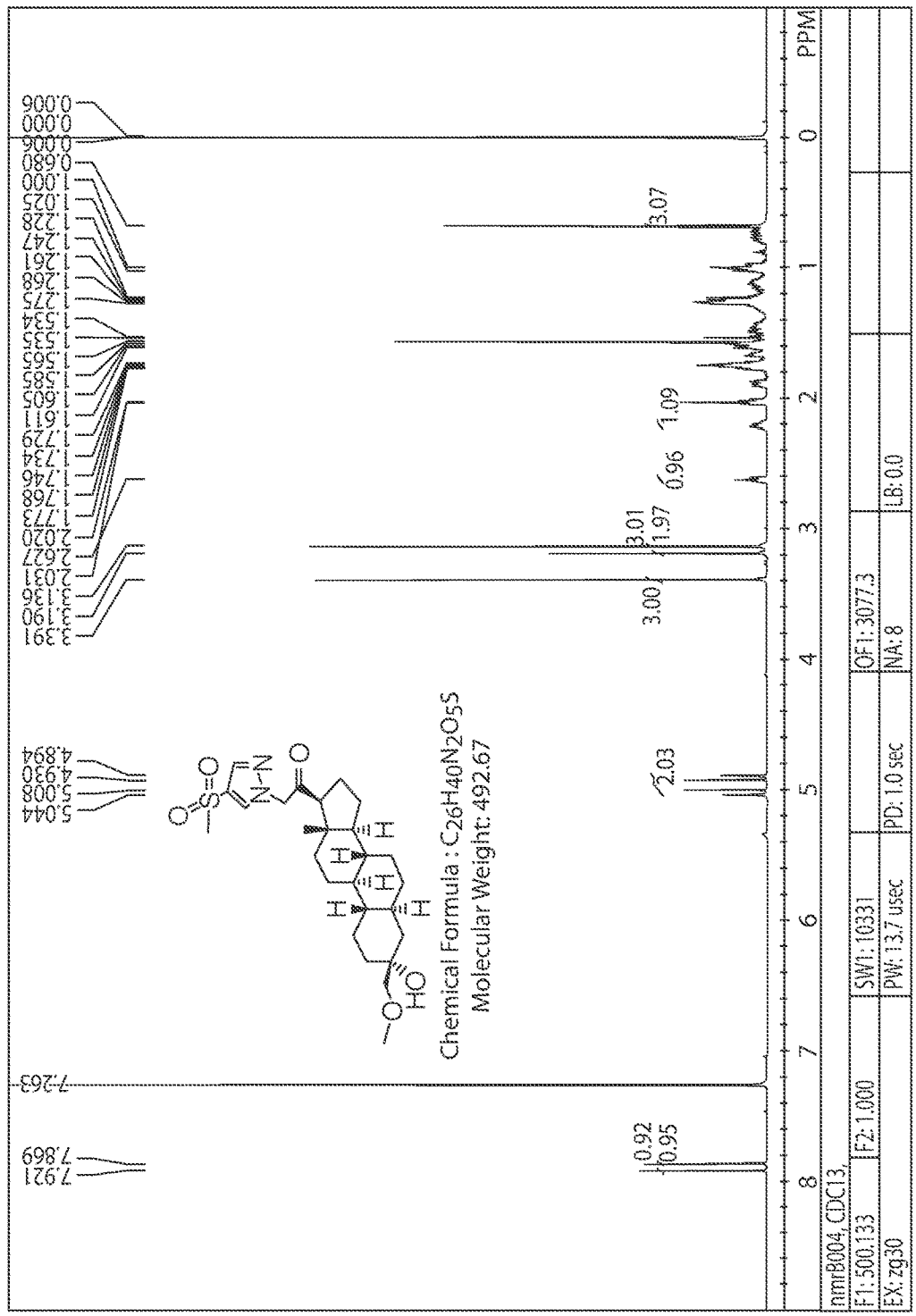
Figure 50:
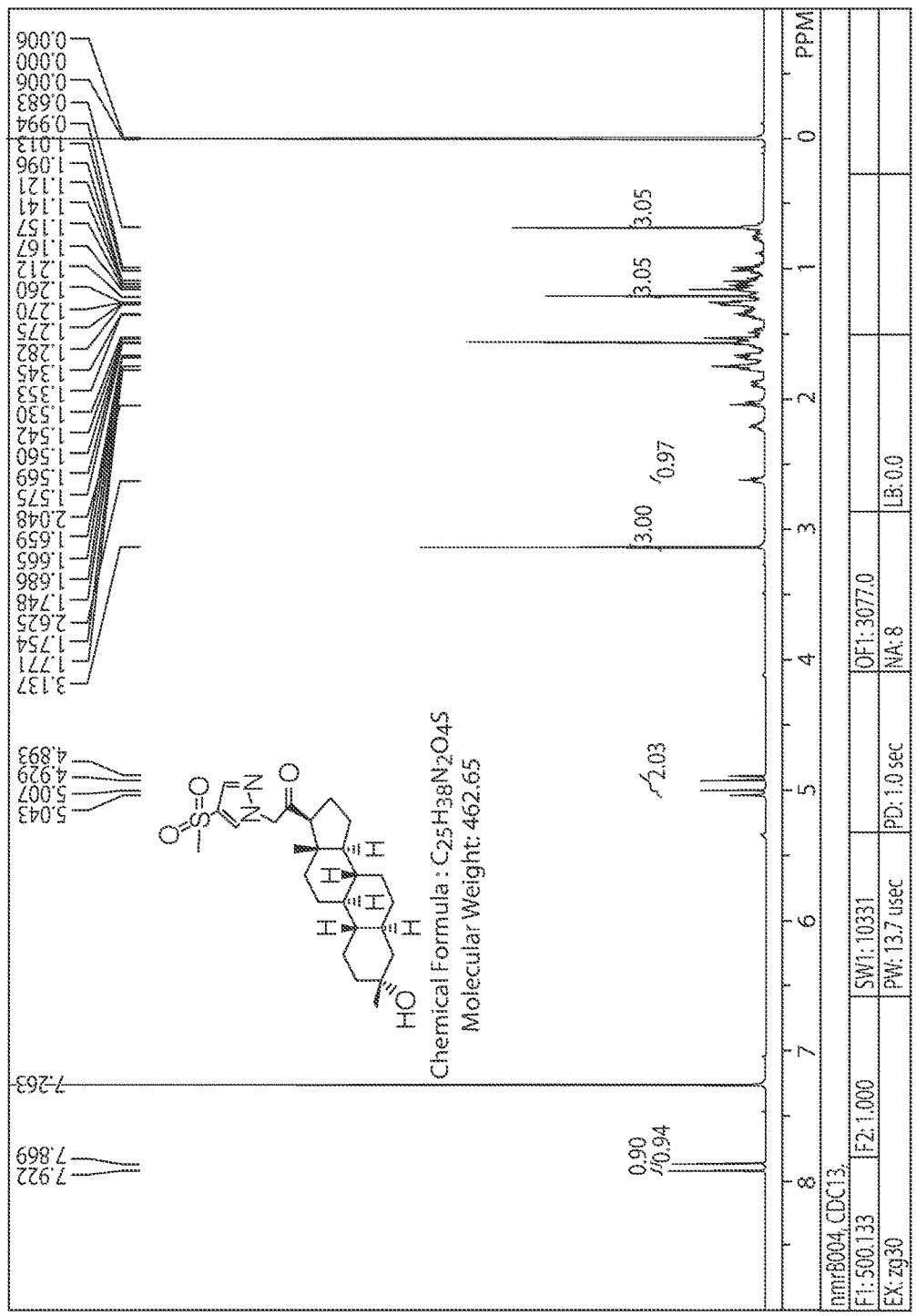
Figure 51:
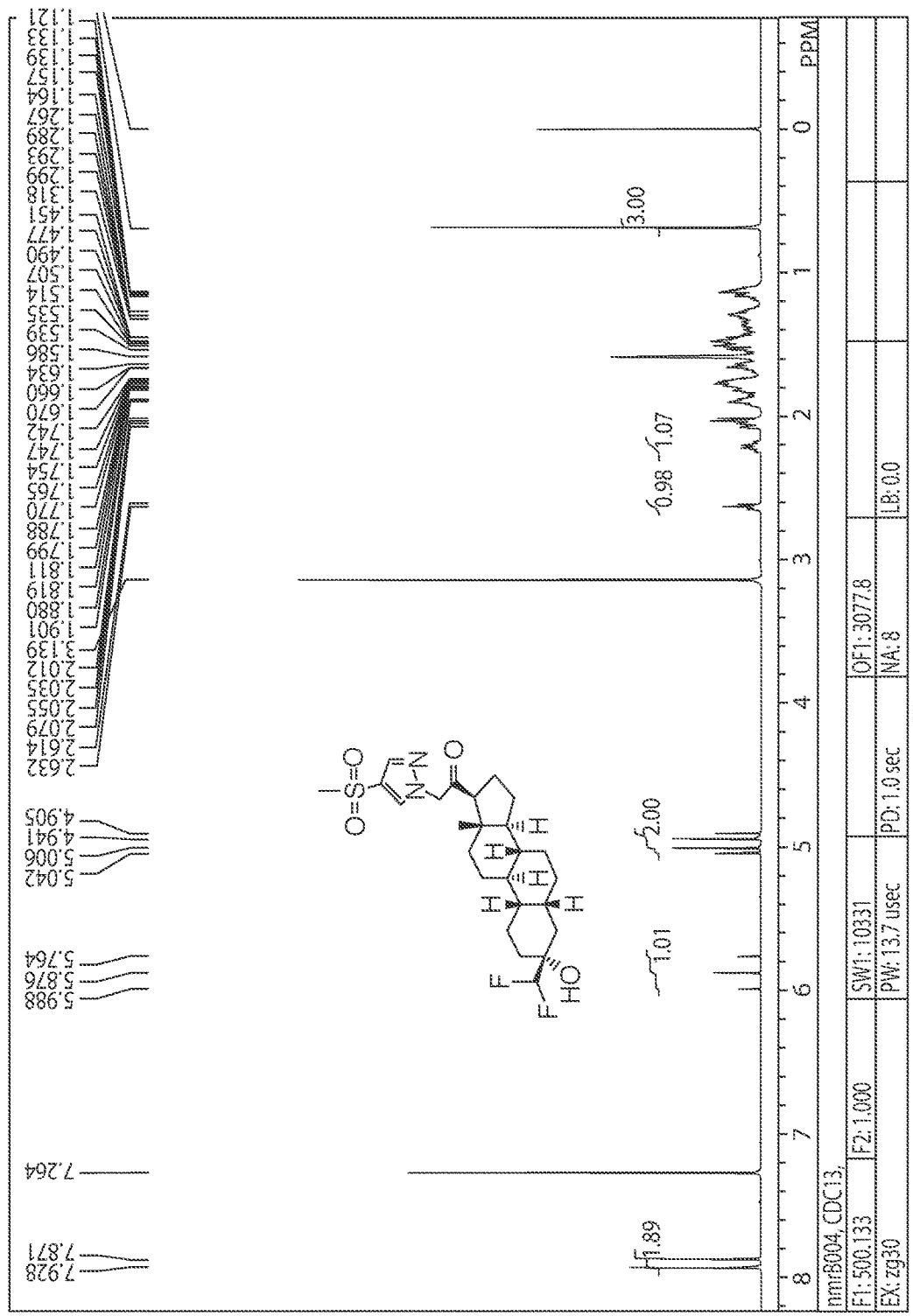
Figure 52:
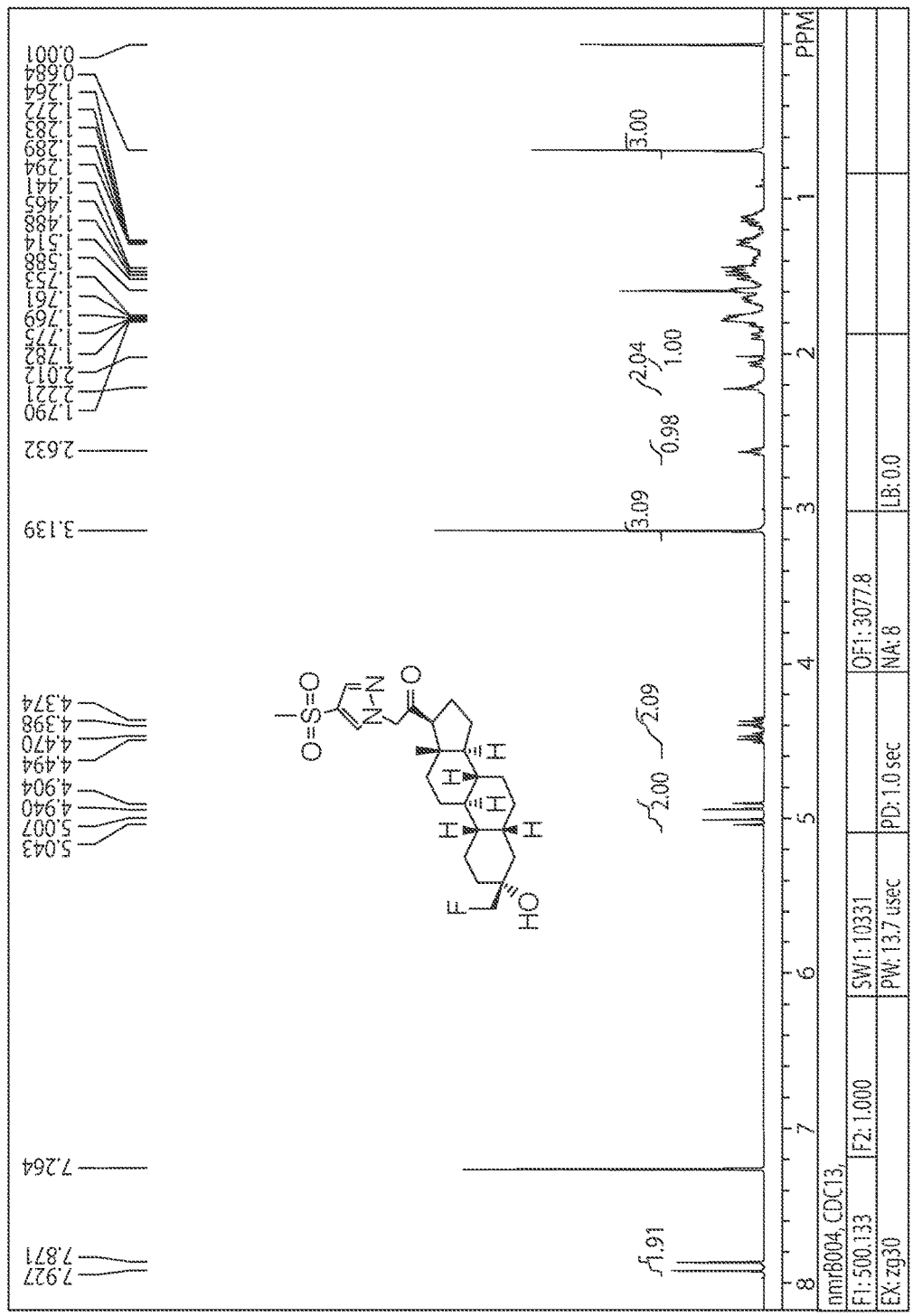

As described herein, the present invention provides 19-nor C3,3-disubstituted C21-pyrazolyl neuroactive steroids of Formula (I):

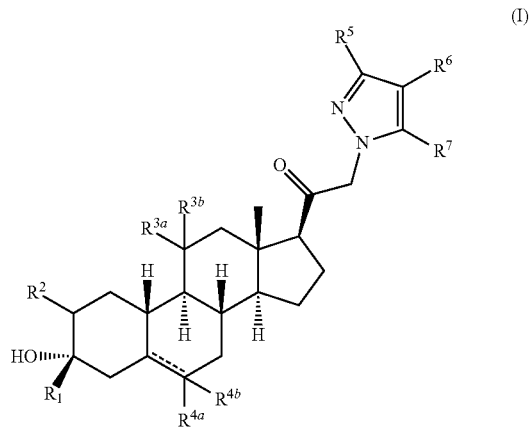

and pharmaceutically acceptable salts thereof;
wherein:
  ----- represents a single or double bond;
  $R^1$ is substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl;
  $R^2$ is hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, or —$OR^{A2}$, wherein $R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl;
  $R^{3a}$ is hydrogen or —$OR^{A3}$, wherein $R^{A3}$ is hydrogen or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, and $R^{3b}$ is hydrogen; or $R^{3a}$ and $R^{3b}$ are joined to form an oxo (=O) group;
  each instance of $R^{4a}$ and $R^{4b}$ is independently hydrogen, substituted or unsubstituted $C_{1-6}$ alkyl, or halogen, provided if the ----- between C5 and C6 is a single bond, then the hydrogen at C5 and $R^{4a}$ are each independently provided in the alpha or beta configuration, and $R^{4b}$ is absent;
  each instance of $R^5$, $R^6$, and $R^7$ is, independently, hydrogen, halogen, —$NO_2$, —CN, —$OR^{GA}$, —$N(R^{GA})_2$, —C(=O)$R^{GA}$, —C(=O)O$R^{GA}$, —OC(=O)$R^{GA}$, —OC(=O)OR$^{GA}$, —C(=O)N(R$^{GA}$)$_2$, —N(R$^{GA}$)C(=O)R$^{GA}$, —OC(=O)N(R$^{GA}$)$_2$, —N(R$^{GA}$)C(=O)OR$^{GA}$, —N(R$^{GA}$)C(=O)N(R$^{GA}$)$_2$, —SR$^{GA}$, —S(O)R$^{GA}$, e.g., —S(=O)R$^{GA}$, —S(=O)$_2$R$^{GA}$, —S(=O)$_2$OR$^{GA}$, —OS(=O)$_2$R$^{GA}$, —S(=O)$_2$N(R$^{GA}$)$_2$, —N(R$^{GA}$)S(=O)$_2$R$^{GA}$, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ carbocylyl, or substituted or unsubstituted 3- to 6-membered heterocylyl; and each instance of R$^{GA}$ is independently hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ carbocylyl, substituted or unsubstituted 3- to 6-membered heterocylyl, substituted or unsubstituted aryl, substituted or unsubstituted heteroaryl, an oxygen protecting group when attached to oxygen, nitrogen protecting group when attached to nitrogen, or two R$^{GA}$ groups are taken with the intervening atoms to form a substituted or unsubstituted heterocylyl or heteroaryl ring.

In certain embodiments, R$^1$ is C$_{1-6}$ alkyl optionally substituted with alkoxy or one to two halo groups (e.g., fluoro), or at least one of R$^5$, R$^6$, and R$^7$ is halogen (e.g., —F, —Cl, —Br), —NO$_2$, —CN, —OR$^{GA}$, —N(R$^{GA}$)$_2$, —C(=O)R$^{GA}$, —C(=O)OR$^{GA}$, —SR$^{GA}$, —S(=O) R$^{GA}$, —S(=O)$_2$R$^{GA}$, —S(=O)$_2$OR$^{GA}$, —OS(=O)$_2$R$^{GA}$, —S(=O)$_2$N(R$^{GA}$)$_2$, substituted or unsubstituted C$_{1-6}$ alkyl (e.g., —CH$_3$, —CH$_2$CH$_3$, haloalkyl, e.g., —CF$_3$), wherein R$^{GA}$ is substituted or unsubstituted C$_{1-2}$ alkyl.

In certain embodiments, R$^1$ is C$_{1-6}$ alkyl optionally substituted with alkoxy or one to two halo groups (e.g., fluoro), and at least one of R$^5$, R$^6$, and R$^7$ is halogen (e.g., —F, —Cl, —Br), —NO$_2$, —CN, —OR$^{GA}$, —N(R$^{GA}$)$_2$, —C(=O)R$^{GA}$, —C(=O)OR$^{GA}$, —SR$^{GA}$, —S(=O) R$^{GA}$, —S(=O)$_2$R$^{GA}$, —S(=O)$_2$OR$^{GA}$, —OS(=O)$_2$R$^{GA}$, —S(=O)$_2$N(R$^{GA}$)$_2$, substituted or unsubstituted C$_{1-6}$ alkyl (e.g., —CH$_3$, —CH$_2$CH$_3$, haloalkyl, e.g., —CF$_3$), wherein R$^{GA}$ is substituted or unsubstituted C$_{1-2}$ alkyl.

It is understood, based on the aforementioned description, that steroids of Formula (I) encompass 3,3-disubstituted 19-nor neuroactive steroids wherein the A/B ring system of the compound is cis (as provided in Formula (I-A), wherein the A/B ring system of the compound is trans (as provided in Formula (I-B), and wherein the B ring of the compound comprises a C5-C6 double bond (as provided in Formula (I-C)):

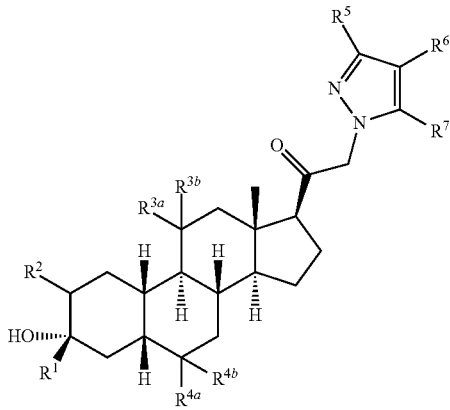

(I-A)

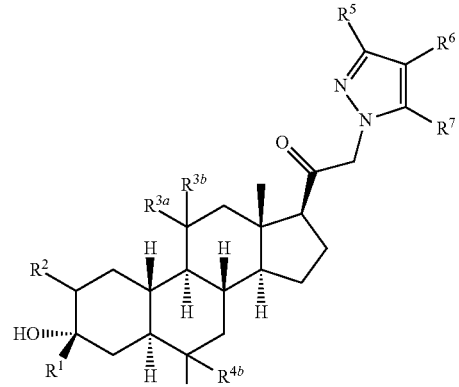

(I-B)

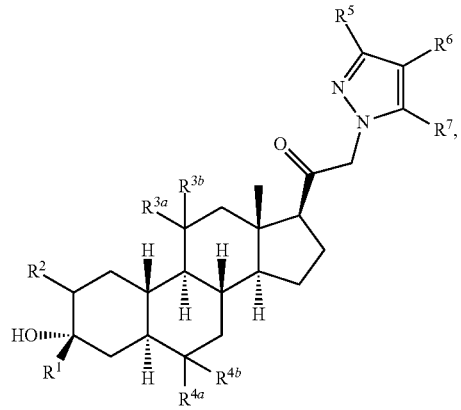

(I-C)

and pharmaceutically acceptable salts thereof.

Group R$^1$

As generally defined herein, R$^1$ is substituted or unsubstituted C$_{1-6}$ alkyl, substituted or unsubstituted C$_{2-6}$ alkenyl, substituted or unsubstituted C$_{2-6}$ alkynyl, or substituted or unsubstituted C$_{3-6}$ carbocyclyl.

In certain embodiments, R$^1$ is substituted or unsubstituted C$_{1-6}$ alkyl, e.g., substituted or unsubstituted C$_{1-2}$alkyl, substituted or unsubstituted C$_{2-3}$alkyl, substituted or unsubstituted C$_{3-4}$alkyl, substituted or unsubstituted C$_{4-5}$alkyl, or substituted or unsubstituted C$_{5-6}$alkyl. Exemplary R$^1$C$_{1-6}$alkyl groups include, but are not limited to, substituted or unsubstituted methyl (C$_1$), ethyl (C$_2$), n-propyl (C$_3$), isopropyl (C$_3$), n-butyl (C$_4$), tert-butyl (C$_4$), sec-butyl (C$_4$), isobutyl (C$_4$), n-pentyl (C$_5$), 3-pentanyl (C), amyl (C$_5$), neopentyl (C$_5$), 3-methyl-2-butanyl (C$_5$), tertiary amyl (C$_5$), n-hexyl (C$_6$), C$_{1-6}$ alkyl substituted with 1, 2, 3, 4, 5, 6, 7, 8, 9, 10, or more fluoro groups (e.g., —CF$_3$, —CH$_2$F, —CHF$_2$, difluoroethyl, and 2,2,2-trifluoro-1,1-dimethylethyl), C$_{1-6}$ alkyl substituted with 1, 2, 3, 4, 5, 6, 7, 8, 9, 10, or more chloro groups (e.g., —CH$_2$Cl, —CHCl$_2$), and C$_{1-6}$ alkyl substituted with alkoxy groups (e.g., —CH$_2$OCH$_3$ and —CH$_2$OCH$_2$CH$_3$). In certain embodiments, R$^1$ is substituted C$_{1-6}$ alkyl, e.g., R$^1$ is haloalkyl, alkoxyalkyl, or aminoalkyl. In certain embodiments, R$^1$ is Me, Et, n-Pr, n-Bu, i-Bu, fluoromethyl, chloromethyl, difluoromethyl, trifluoromethyl, trifluoroethyl, difluoroethyl, 2,2,2-trifluoro-1,1-dimethyl-ethyl, methoxymethyl, methoxyethyl, or ethoxymethyl.

In certain embodiments, R$^1$ is unsubstituted C$_{1-3}$ alkyl, e.g., R$^1$ is —CH$_3$, —CH$_2$CH$_3$, or —CH$_2$CH$_2$CH$_3$.

In certain embodiments, $R^1$ is $C_{1-6}$ alkyl substituted with one or more fluorine atoms; e.g., $R^1$ is —$CH_2F$, —$CHF_2$, or —$CF_3$. In certain embodiments, $R^1$ is $C_{1-6}$ alkyl substituted with one or two fluorine atoms; e.g., $R^1$ is —$CH_2F$ or —$CHF_2$.

In certain embodiments, $R^1$ is $C_{1-6}$ alkyl substituted with one or more —$OR^{A1}$ groups, wherein $R^{A1}$ is hydrogen or substituted or unsubstituted alkyl. In certain embodiments, $R^1$ is —$CH_2OR^{A1}$, e.g., wherein $R^{A1}$ is hydrogen, —$CH_3$, —$CH_2CH_3$, or —$CH_2CH_2CH_3$, e.g., to provide a group $R^1$ of formula —$CH_2OH$, —$CH_2OCH_3$, —$CH_2OCH_2CH_3$, or —$CH_2OCH_2CH_3$.

In certain embodiments, $R^1$ is substituted or unsubstituted $C_{2-6}$ alkenyl, e.g., substituted or unsubstituted $C_{2-3}$alkenyl, substituted or unsubstituted $C_{3-4}$alkenyl, substituted or unsubstituted $C_{4-5}$alkenyl, or substituted or unsubstituted $C_{5-6}$alkenyl. In certain embodiments, $R^1$ is ethenyl ($C_2$), propenyl ($C_3$), or butenyl ($C_4$), unsubstituted or substituted with one or more substituents selected from the group consisting of alkyl, halo, haloalkyl, alkoxyalkyl, or hydroxyl. In certain embodiments, $R^1$ is ethenyl, propenyl, or butenyl, unsubstituted or substituted with alkyl, halo, haloalkyl, alkoxyalkyl, or hydroxy. In certain embodiments, $R^1$ is ethenyl.

In certain embodiments, $R^1$ is substituted or unsubstituted $C_{2-6}$ alkynyl, e.g., substituted or unsubstituted $C_{2-3}$alkynyl, substituted or unsubstituted $C_{3-4}$alkynyl, substituted or unsubstituted $C_{4-5}$alkynyl, or substituted or unsubstituted $C_{5-6}$alkynyl. In certain embodiments, $R^1$ is ethynyl, propynyl, or butynyl, unsubstituted or substituted with alkyl, halo, haloalkyl (e.g., $CF_3$), alkoxyalkyl, cycloalkyl (e.g., cyclopropyl or cyclobutyl), or hydroxyl. In certain embodiments, $R^1$ is selected from the group consisting of trifluoroethynyl, cyclopropylethynyl, cyclobutylethynyl, and propynyl, fluoropropynyl, and chloroethynyl. In certain embodiments, $R^1$ is ethynyl ($C_2$), propynyl ($C_3$), or butynyl ($C_4$), unsubstituted or substituted with one or more substituents selected from the group consisting of substituted or unsubstituted aryl, substituted or unsubstituted heteroaryl, substituted or unsubstituted carbocyclyl, and substituted or unsubstituted heterocyclyl. In certain embodiments, $R^1$ is ethynyl ($C_2$), propynyl ($C_3$), or butynyl ($C_4$) substituted with substituted phenyl. In certain embodiments, the phenyl substituent is further substituted with one or more substituents selected from the group consisting of halo, alkyl, trifluoroalkyl, alkoxy, acyl, amino or amido. In certain embodiments, $R^1$ is ethynyl ($C_2$), propynyl ($C_3$), or butynyl ($C_4$) substituted with substituted or unsubstituted pyrrolyl, imidazolyl, pyrazolyl, oxazoyl, thiazolyl, isoxazoyl, 1,2,3-triazolyl, 1,2,4-triazolyl, oxadiazolyl, thiadiazolyl, or tetrazolyl.

In certain embodiments, $R^1$ is ethynyl, propynyl, or butynyl, unsubstituted or substituted with alkyl, halo, haloalkyl, alkoxyalkyl, or hydroxyl. In certain embodiments, $R^1$ is ethynyl or propynyl, substituted with substituted or unsubstituted aryl. In certain embodiments, $R^1$ is ethynyl or propynyl, substituted with phenyl unsubstituted or substituted with halo, alkyl, alkoxy, haloalkyl, trihaloalkyl, or acyl. In certain embodiments, $R^1$ is ethynyl or propynyl, substituted with substituted or unsubstituted carbocyclyl. In certain embodiments, $R^{3a}$ is ethynyl or propynyl, substituted with substituted or unsubstituted cyclopropyl, cyclobutyl, cyclopentyl, or cyclohexyl. In certain embodiments, $R^1$ is ethynyl or propynyl, substituted with substituted or unsubstituted heteroaryl. In certain embodiments, $R^1$ is ethynyl or propynyl, substituted with substituted or unsubstituted pyridinyl, or pyrimidinyl. In certain embodiments, $R^1$ is ethynyl or propynyl, substituted with substituted or unsubstituted pyrrolyl, imidazolyl, pyrazolyl, oxazoyl, thiazolyl, isoxazoyl, 1,2,3-triazolyl, 1,2,4-triazolyl, oxadiazolyl, thiadiazolyl, tetrazolyl. In certain embodiments, $R^1$ is ethynyl or propynyl, substituted with substituted or unsubstituted heterocyclyl. In certain embodiments, $R^1$ is ethynyl or propynyl, substituted with substituted or unsubstituted pyrrolidinyl, piperidinyl, piperazinyl, or mopholinyl. In certain embodiments, $R^1$ is propynyl or butynyl, substituted with hydroxyl or alkoxy. In certain embodiments, $R^1$ is propynyl or butynyl, substituted with methoxy or ethoxy. In certain embodiments, $R^1$ is ethynyl or propynyl, substituted with chloro. In certain embodiments, $R^1$ is ethynyl or propynyl, substituted with trifluoromethyl.

In certain embodiments, $R^1$ is substituted or unsubstituted $C_{3-6}$ carbocyclyl, e.g., substituted or unsubstituted $C_{3-4}$carbocyclyl, substituted or unsubstituted $C_{4-5}$ carbocyclyl, or substituted or unsubstituted $C_{5-6}$ carbocyclyl. In certain embodiments, $R^1$ is substituted or unsubstituted cyclopropyl or substituted or unsubstituted cyclobutyl.

Groups -----, $R^2$, $R^{3a}$, $R^{3b}$, $R^{4a}$, and $R^{4b}$

As generally defined herein, $R^2$ is hydrogen, halogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, or —$OR^2$, wherein $R^{A2}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl.

In certain embodiments, $R^2$ is hydrogen. In certain embodiments, $R^2$ is halogen, e.g., fluoro, chloro, bromo, or iodo. In certain embodiments, $R^2$ is fluoro or chloro. In certain embodiments, $R^2$ is substituted or unsubstituted $C_{1-6}$alkyl, e.g., substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. For example, in some embodiments, $R^2$ is $C_{1-6}$alkyl optionally substituted with halo (e.g., bromo, chloro, fluoro (i.e., to provide a group $R^2$ of formula —$CH_2F$, —$CHF_2$, —$CF_3$)) or —$OR^{A2}$. In certain embodiments, $R^{A2}$ is —$CH_3$, —$CH_2CH_3$, or —$CH_2CH_2CH_3$, i.e., to provide a group $R^2$ of formula —$OH$, —$OCH_3$, —$OCH_2CH_3$, or —$OCH_2CH_2CH_3$. In certain embodiments, $R^2$ is substituted or unsubstituted $C_{2-6}$ alkenyl, In certain embodiments, $R^2$ is substituted or unsubstituted $C_{2-6}$ alkynyl, e.g., substituted or unsubstituted $C_{2-3}$alkynyl, substituted or unsubstituted $C_{3-4}$alkynyl, substituted or unsubstituted $C_{4-5}$alkynyl, or substituted or unsubstituted $C_{5-6}$alkynyl. In certain embodiments, $R^2$ is substituted or unsubstituted $C_{3-6}$ carbocyclyl, e.g., substituted or unsubstituted $C_{3-4}$carbocyclyl, substituted or unsubstituted $C_{4-5}$ carbocyclyl, or substituted or unsubstituted $C_{5-6}$ carbocyclyl. In certain embodiments, $R^2$ is substituted or unsubstituted cyclopropyl or substituted or unsubstituted cyclobutyl. In certain embodiments, $R^2$ is —$CH_3$, —$CH_2CH_3$, —$CH_2CH_2CH_3$, or substituted or unsubstituted cyclopropyl.

In certain embodiments, $R^2$ is —$OR^{A2}$. In certain embodiments, $R^{A2}$ is hydrogen. In certain embodiments, $R^{A2}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. In certain embodiments, $R^{A2}$ is hydrogen, —$CH_3$, —$CH_2CH_3$, or —$CH_2CH_2CH_3$, i.e., to provide a group $R^2$ of formula —$OH$, —$OCH_3$, —$OCH_2CH_3$, or —$OCH_2CH_2CH_3$. In certain embodiments, $R^2$ is a non-hydrogen substituent in the alpha configuration. In certain embodiments, $R^2$ is a non-hydrogen substituent in the beta configuration.

As generally defined herein, $R^{3a}$ is hydrogen or $-OR^{A3}$, wherein $R^{A3}$ is hydrogen or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl, and $R^{3b}$ is hydrogen; or $R^{3a}$ and $R^{3b}$ are joined to form an oxo (=O) group.

In certain embodiments, both $R^{3a}$ and $R^{3b}$ are both hydrogen.

In certain embodiments, $R^{3a}$ and $R^{3b}$ are joined to form an oxo (=O) group.

In certain embodiments, $R^{3a}$ is $-OR^{A3}$ and $R^{3b}$ is hydrogen. In certain embodiments, wherein $R^{3a}$ is $-OR^{A3}$, $R^{3a}$ is in the alpha or beta configuration. In certain embodiments, wherein $R^{3a}$ is $-OR^{A3}$, $R^{3a}$ is in the alpha configuration. In certain embodiments, wherein $R^{3a}$ is $-OR^{A3}$, $R^{3a}$ is in the beta configuration. In certain embodiments, $R^{A3}$ is hydrogen. In certain embodiments, $R^{A3}$ is substituted or unsubstituted $C_{1-6}$ alkyl, e.g., substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. In certain embodiments, $R^{A3}$ is hydrogen, $-CH_3$, $-CH_2CH_3$, or $-CH_2CH_2CH_3$, i.e., to provide a group $R^{3a}$ of formula $-OH$, $-OCH_3$, $-OCH_2CH_3$, or $-OCH_2CH_2CH_3$.

As generally defined herein, each instance of $R^{4a}$ and $R^{4b}$ is independently hydrogen, substituted or unsubstituted $C_{1-6}$ alkyl, or halogen, provided if the ---- between C5 and C6 is a single bond, then the hydrogen at C5 and $R^{4a}$ are each independently provided in the alpha or beta configuration, and $R^{4b}$ is absent.

In certain embodiments, ---- is a single bond, at least one of $R^{4a}$ and $R^{4b}$ is hydrogen. In certain embodiments, ---- is a single bond, at least one of $R^{4a}$ and $R^{4b}$ is substituted or unsubstituted $C_{1-6}$ alkyl, e.g., substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. In certain embodiments, ---- is a single bond, at least one of $R^{4a}$ and $R^{4b}$ is $C_1$ alkyl, e.g., $-CH_3$ or $-CF_3$. In certain embodiments, ---- is a single bond, at least one of $R^{4a}$ and $R^{4b}$ is halogen, e.g., fluoro.

In certain embodiments, ---- is a single bond, and both of $R^{4a}$ and $R^{4b}$ are hydrogen. In certain embodiments, ---- is a single bond, and both of $R^{4a}$ and $R^{4b}$ are independently substituted or unsubstituted $C_{1-6}$ alkyl, e.g., substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. In certain embodiments, ---- is a single bond, and both of $R^{4a}$ and $R^{4b}$ are independently $C_1$ alkyl, e.g., $-CH_3$ or $-CF_3$. In certain embodiments, ---- is a single bond, and both of $R^{4a}$ and $R^{4b}$ are halogen, e.g., fluoro.

In certain embodiments, wherein ---- represents a single bond, $R^{4a}$ is a non-hydrogen substituent in the alpha configuration. In certain embodiments, wherein ---- represents a single bond, $R^{4a}$ is a non-hydrogen substituent in the beta configuration.

In certain embodiments, ---- is a double bond, and $R^{4a}$ is hydrogen. In certain embodiments, ---- is a double bond, and $R^{4a}$ is substituted or unsubstituted $C_{1-6}$ alkyl, e.g., substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. In certain embodiments, ---- is a double bond, and $R^{4a}$ is $C_1$ alkyl, e.g., $-CH_3$ or $-CF_3$. In certain embodiments, ---- is a double bond, and $R^{4a}$ is halogen, e.g., fluoro.

Groups $R^5$, $R^6$, and $R^7$

As generally defined herein, each instance of $R^5$, $R^6$, and $R^7$ is, independently, hydrogen, halogen, $-NO_2$, $-CN$, $-OR^{GA}$, $-N(R^{GA})_2$, $-C(=O)R^{GA}$, $-C(=O)OR^{GA}$, $-OC(=O)R^{GA}$, $-OC(=O)OR^{GA}$, $-C(=O)N(R^{GA})_2$, $-N(R^{GA})C(=O)R^{GA}$, $-OC(=O)N(R^{GA})_2$, $-N(R^{GA})C(=O)OR^{GA}$, $N(R^{GA})C(=O)N(R^{GA})_2$, $-SR^{GA}$, $-S(O)R^{GA}$, e.g., $-S(=O)R^{GA}$, $-S(=O)_2R^{GA}$, $-S(=O)_2OR^{GA}$, $-OS(=O)_2R^{GA}$, $-S(=O)_2N(R^{GA})_2$, $-N(R^{GA})S(=O)_2R^{GA}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, or substituted or unsubstituted 3- to 6-membered heterocylyl.

Furthermore, as generally defined herein, each instance of $R^{GA}$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, substituted or unsubstituted 3- to 6-membered heterocylyl, substituted or unsubstituted aryl, substituted or unsubstituted heteroaryl, an oxygen protecting group when attached to oxygen, nitrogen protecting group when attached to nitrogen, or two $R^{GA}$ groups are taken with the intervening atoms to form a substituted or unsubstituted heterocylyl or heteroaryl ring. In certain embodiments, each instance of $R^{GA}$ is independently hydrogen, substituted or unsubstituted $C_{1-6}$ alkyl (e.g., substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl), substituted or unsubstituted aryl, or substituted or unsubstituted heteroaryl. In certain embodiments, each instance of $R^{GA}$ is hydrogen, $-CH_3$, $-CH_2CH_3$, or substituted or unsubstituted phenyl.

In certain embodiments, at least one of $R^5$, $R^6$, and $R^7$ is hydrogen. In certain embodiments, at least two of $R^5$, $R^6$, and $R^7$ are hydrogen. In certain embodiments, all of $R^5$, $R^6$, and $R^7$ are hydrogen to provide an unsubstituted pyrazolyl.

In certain embodiments, at least one of $R^5$, $R^6$, and $R^7$ is a non-hydrogen substituent. As used herein, a $R^5$, $R^6$, and $R^7$ "non-hydrogen substituent" means that $R^5$, $R^6$, and $R^7$ are not hydrogen, but are any one of halogen, $-NO_2$, $-CN$, $-CF_3$, $-OR^{GA}$, $-N(R^{GA})_2$, $-C(=O)R^{GA}$, $-C(=O)OR^{GA}$, $-OC(=O)R^{GA}$, $-OC(=O)OR^{GA}$, $-C(=O)N(R^{GA})_2$, $-N(R^{GA})C(=O)R^{GA}$, $-OC(=O)N(R^{GA})_2$, $-N(R^{GA})C(=O)OR^{GA}$, $-SR^{GA}$, $-S(O)R^{GA}$, e.g., $-S(=O)R^{GA}$, $-S(=O)_2R^{GA}$, $-S(=O)_2OR^{GA}$, $-OS(=O)_2R^{GA}$, $-S(=O)_2N(R^{GA})_2$, or $-N(R^{GA})S(=O)_2R^{GA}$; substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, or substituted or unsubstituted 3- to 6-membered heterocylyl.

In certain embodiments, at least one of $R^5$, $R^6$, and $R^7$ is halogen, e.g., fluoro, bromo, iodo, or chloro. In certain embodiments, one of $R^5$, $R^6$, and $R^7$ is halogen. In certain embodiments, $R^5$ is halogen, e.g., fluoro, bromo, iodo, or chloro. In certain embodiments, $R^6$ is halogen, e.g., fluoro, bromo, iodo, or chloro. In certain embodiments, $R^7$ is halogen, e.g., fluoro, bromo, iodo, or chloro.

In certain embodiments, at least one of $R^5$, $R^6$, and $R^7$ is $-NO_2$. In certain embodiments, one of $R^5$, $R^6$, and $R^7$ is $-NO_2$. In certain embodiments, $R^5$ is $-NO_2$. In certain embodiments, $R^6$ is $-NO_2$. In certain embodiments, $R^7$ is $-NO_2$.

In certain embodiments, at least one of $R^5$, $R^6$, and $R^7$ is —CN. In certain embodiments, one of $R^5$, $R^6$, and $R^7$ is —CN. In certain embodiments, $R^5$ is —CN. In certain embodiments, $R^6$ is —CN. In certain embodiments, $R^7$ is —CN.

In certain embodiments, at least one of $R^5$, $R^6$, and $R^7$ is —OR$^{GA}$, e.g., wherein R$^{GA}$ is hydrogen or substituted or unsubstituted $C_{1-6}$ alkyl (e.g., —CH$_3$ or —CF$_3$). In certain embodiments, one of $R^5$, $R^6$, and $R^7$ is —OR$^{GA}$, e.g., —OH, —OCH$_3$, or —OCF$_3$. In certain embodiments, $R^5$ is —OR$^{GA}$, e.g., —OH, —OCH$_3$, or —OCF$_3$. In certain embodiments, $R^6$ is —OR$^{GA}$. In certain embodiments, $R^7$ is —OR$^{GA}$, e.g., —OH, —OCH$_3$, or —OCF$_3$.

In certain embodiments, at least one of $R^5$, $R^6$, and $R^7$ is —N(R$^{GA}$)$_2$, e.g., wherein R$^{GA}$ is hydrogen or substituted or unsubstituted $C_{1-6}$ alkyl (e.g., —CH$_3$ or —CF$_3$). In certain embodiments, one of $R^5$, $R^6$, and $R^7$ is —N(R$^{GA}$)$_2$, e.g., —NH$_2$, —NHCH$_3$, or —N(CH$_3$)$_2$. In certain embodiments, $R^5$ is —N(R$^{GA}$)$_2$, e.g., —NH$_2$, —NHCH$_3$, or —N(CH$_3$)$_2$. In certain embodiments, $R^6$ is —N(R$^{GA}$)$_2$, e.g., —NH$_2$, —NHCH$_3$, or —N(CH$_3$)$_2$. In certain embodiments, $R^7$ is —N(R$^{GA}$)$_2$, e.g., —NH$_2$, —NHCH$_3$, or —N(CH$_3$)$_2$.

In certain embodiments, at least one of $R^5$, $R^6$, and $R^7$ is —C(=O)R$^{GA}$, —C(=O)OR$^{GA}$, or —C(=O)N(R$^{GA}$)$_2$, e.g., wherein R$^{GA}$ is hydrogen or substituted or unsubstituted $C_{1-6}$ alkyl (e.g., —CH$_3$ or —CF$_3$). In certain embodiments, one of $R^5$, $R^6$, and $R^7$ is —C(=O)R$^{GA}$, e.g., —CHO, —C(=O)CH$_3$, or —C(=O)CH$_2$CH$_3$. In certain embodiments, $R^5$ is —C(=O)R$^{GA}$, e.g., —CHO, —C(=O)CH$_3$, or —C(=O)CH$_2$CH$_3$. In certain embodiments, $R^6$ is —C(=O)R$^{GA}$, e.g., —CHO, —C(=O)CH$_3$, or —C(=O)CH$_2$CH$_3$. In certain embodiments, $R^7$ is —C(=O)R$^{GA}$, e.g., —CHO, —C(=O)CH$_3$, or —C(=O)CH$_2$CH$_3$. In certain embodiments, one of $R^5$, $R^6$, and $R^7$ is —C(=O)OR$^{GA}$, e.g., —C(=O)OH, —C(=O)OCH$_3$, or —C(=O)OCH$_2$CH$_3$. In certain embodiments, $R^5$ is —C(=O)OR$^{GA}$, e.g., —C(=O)OH, —C(=O)OCH$_3$, or —C(=O)OCH$_2$CH$_3$. In certain embodiments, $R^6$ is —C(=O)OR$^{GA}$, e.g., —C(=O)OH, —C(=O)OCH$_3$, or —C(=O)OCH$_2$CH$_3$. In certain embodiments, $R^7$ is —C(=O)OR$^{GA}$, e.g., —C(=O)OH, —C(=O)OCH$_3$, or —C(=O)OCH$_2$CH$_3$. In certain embodiments, one of $R^5$, $R^6$, and $R^7$ is —C(=O)N(R$^{GA}$)$_2$, e.g., —C(=O)NH$_2$, —C(=O)NHCH$_3$, or —C(=O)N(CH$_3$)$_2$. In certain embodiments, $R^5$ is —C(=O)N(R$^{GA}$)$_2$, e.g., —C(=O)NH$_2$, —C(=O)NHCH$_3$, or —C(=O)N(CH$_3$)$_2$. In certain embodiments, $R^6$ is —C(=O)N(R$^{GA}$)$_2$, e.g., —C(=O)NH$_2$, —C(=O)NHCH$_3$, or —C(=O)N(CH$_3$)$_2$. In certain embodiments, $R^7$ is —C(=O)N(R$^{GA}$)$_2$, e.g., —C(=O)NH$_2$, —C(=O)NHCH$_3$, or —C(=O)N(CH$_3$)$_2$.

In certain embodiments, at least one of $R^5$, $R^6$, and $R^7$ is —OC(=O)R$^{GA}$, —OC(=O)OR$^{GA}$, or, —OC(=O)N(R$^{GA}$)$_2$, e.g., wherein R$^{GA}$ is hydrogen or substituted or unsubstituted $C_{1-6}$ alkyl (e.g., —CH$_3$ or —CF$_3$). In certain embodiments, one of $R^5$, $R^6$, and $R^7$ is —OC(=O)R$^{GA}$, e.g., —OC(=O)CH$_3$. In certain embodiments, $R^5$ is —OC(=O)R$^{GA}$, e.g., —OC(=O)CH$_3$. In certain embodiments, $R^6$ is —OC(=O)R$^{GA}$, e.g., —OC(=O)CH$_3$. In certain embodiments, $R^7$ is —OC(=O)R$^{GA}$, e.g., —OC(=O)CH$_3$. In certain embodiments, one of $R^5$, $R^6$, and $R^7$ is —OC(=O)OR$^{GA}$, e.g., —OC(=O)OCH$_3$. In certain embodiments, $R^5$ is —OC(=O)OR$^{GA}$, e.g., —OC(=O)OCH$_3$. In certain embodiments, $R^6$ is —OC(=O)OR$^{GA}$, e.g., —OC(=O)OCH$_3$. In certain embodiments, $R^7$ is —OC(=O)OR$^{GA}$, e.g., —OC(=O)OCH$_3$. In certain embodiments, one of $R^5$, $R^6$, and $R^7$ is —OC(=O)N(R$^{GA}$)$_2$, e.g., —OC(=O)NHCH$_3$ or —OC(=O)N(CH$_3$)$_2$. In certain embodiments, $R^5$ is —OC(=O)N(R$^{GA}$)$_2$, e.g., —OC(=O)NHCH$_3$ or —OC(=O)N(CH$_3$)$_2$. In certain embodiments, $R^6$ is —OC(=O)N(R$^{GA}$)$_2$, e.g., —OC(=O)NHCH$_3$ or —OC(=O)N(CH$_3$)$_2$. In certain embodiments, $R^7$ is —OC(=O)N(R$^{GA}$)$_2$, e.g., —OC(=O)NHCH$_3$ or —OC(=O)N(CH$_3$)$_2$.

In certain embodiments, at least one of $R^5$, $R^6$, and $R^7$ is —N(R$^{GA}$)C(=O)R$^{GA}$, —N(R$^{GA}$)C(=O)OR$^{GA}$, or —N(R$^{GA}$)C(=O)N(R$^{GA}$)$_2$, e.g., wherein R$^{GA}$ is hydrogen or substituted or unsubstituted $C_{1-6}$ alkyl (e.g., —CH$_3$ or —CF$_3$). In certain embodiments, one of $R^5$, $R^6$, and $R^7$ is —N(R$^{GA}$)C(=O)R$^{GA}$, e.g., —NHC(=O)CH$_3$. In certain embodiments, $R^5$ is —N(R$^{GA}$)C(=O)R$^{GA}$, e.g., —NHC(=O)CH$_3$. In certain embodiments, $R^6$ is —N(R$^{GA}$)C(=O)R$^{GA}$, e.g., —NHC(=O)CH$_3$. In certain embodiments, $R^7$ is —N(R$^{GA}$)C(=O)R$^{GA}$, e.g., —NHC(=O)CH$_3$. In certain embodiments, one of $R^5$, $R^6$, and $R^7$ is —N(R$^{GA}$)C(=O)OR$^{GA}$, e.g., —NHC(=O)OCH$_3$. In certain embodiments, $R^5$ is —N(R$^{GA}$)C(=O)OR$^{GA}$, e.g., —NHC(=O)OCH$_3$. In certain embodiments, $R^6$ is —N(R$^{GA}$)C(=O)OR$^{GA}$, e.g., —NHC(=O)OCH$_3$. In certain embodiments, $R^7$ is —N(R$^{GA}$)C(=O)OR$^{GA}$, e.g., —NHC(=O)OCH$_3$. In certain embodiments, one of $R^5$, $R^6$, and $R^7$ is —N(R$^{GA}$)C(=O)N(R$^{GA}$)$_2$, e.g., —NHC(=O)NH$_2$ or —NHC(=O)N(CH$_3$)$_2$. In certain embodiments, $R^5$ is —N(R$^{GA}$)C(=O)N(R$^{GA}$)$_2$, e.g., —NHC(=O)NH$_2$ or —NHC(=O)N(CH$_3$)$_2$. In certain embodiments, $R^6$ is —N(R$^{GA}$)C(=O)N(R$^{GA}$)$_2$, e.g., —NHC(=O)NH$_2$ or —NHC(=O)N(CH$_3$)$_2$. In certain embodiments, $R^7$ is —N(R$^{GA}$)C(=O)N(R$^{GA}$)$_2$, e.g., —NHC(=O)NH$_2$ or —NHC(=O)N(CH$_3$)$_2$.

In certain embodiments, at least one of $R^5$, $R^6$, and $R^7$ is —SR$^{GA}$, —S(O)R$^{GA}$, e.g., —S(=O)R$^{GA}$, —S(=O)$_2$R$^{GA}$, —S(=O)$_2$OR$^{GA}$, —OS(=O)$_2$R$^{GA}$, —S(=O)$_2$N(R$^{GA}$)$_2$, or —N(R$^{GA}$)S(=O)$_2$R$^{GA}$, e.g., wherein R$^{GA}$ is hydrogen, substituted or unsubstituted $C_{1-6}$ alkyl (e.g., —CH$_3$ or —CF$_3$), substituted or unsubstituted aryl, or substituted or unsubstituted heteroaryl. In certain embodiments, one of $R^5$, $R^6$, and $R^7$ is —SR$^{GA}$, e.g., —SCH$_3$, or —S-Aryl, wherein Aryl is substituted or unsubstituted aryl or heteroaryl. In certain embodiments, one of $R^5$, $R^6$, and $R^7$ is —S(O)R$^{GA}$, e.g., —S(=O)R$^G$, e.g., —S(=O)CH$_3$, —S(=O)CF$_3$, or —S(=O)-Aryl, wherein Aryl is substituted or unsubstituted aryl or heteroaryl. In certain embodiments, one of $R^5$, $R^6$, and $R^7$ is —S(=O)$_2$R$^{GA}$, e.g., —S(=O)$_2$CH$_3$, —S(=O)$_2$CF$_3$, or —S(=O)$_2$-Aryl, wherein Aryl is substituted or unsubstituted aryl or heteroaryl. In certain embodiments, $R^5$ is —SR$^{GA}$, e.g., —SCH$_3$, —SCF$_3$; —S(O)R$^{GA}$, e.g., —S(=O)R$^{GA}$, e.g., —S(=O)CH$_3$, —S(=O)CF$_3$; —S(=O)$_2$R$^{GA}$, e.g., —S(=O)$_2$CH$_3$, —S(=O)$_2$CF$_3$, or —S(=O)$_2$-Aryl, wherein Aryl is substituted or unsubstituted aryl or heteroaryl. In certain embodiments, $R^6$ is —SR$^{GA}$, e.g., —SCH$_3$, —SCF$_3$; —S(O)R$^{GA}$, e.g., —S(=O)R$^{GA}$, e.g., —S(=O)CH$_3$, —S(=O)CF$_3$; —S(=O)$_2$R$^{GA}$, e.g., —S(=O)$_2$CH$_3$, —S(=O)$_2$CF$_3$, or —S(=O)$_2$-Aryl, wherein Aryl is substituted or unsubstituted aryl or heteroaryl. In certain embodiments, $R^7$ is —SR$^{GA}$, e.g., —SCH$_3$, —SCF$_3$; —S(O)R$^{GA}$, e.g., —S(=O)R$^{GA}$, e.g., —S(=O)CH$_3$, —S(=O)CF$_3$; —S(=O)$_2$R$^{GA}$, e.g., —S(=O)$_2$CH$_3$, —S(=O)$_2$CF$_3$, or —S(=O)$_2$-Aryl, wherein Aryl is substituted or unsubstituted aryl or heteroaryl. In certain embodiments, one of $R^5$, $R^6$, and $R^7$ is —S(=O)$_2$OR$^{GA}$. In certain embodiments, $R^5$ is —S(=O)$_2$OR$^{GA}$, e.g., —S(=O)$_2$OCH$_3$, —S(=O)$_2$OCF$_3$, or —S(=O)$_2$OAryl, wherein Aryl is substituted or unsubstituted aryl or heteroaryl. In certain embodiments, $R^6$ is —S(=O)$_2$OR$^{GA}$, e.g., —S(=O)$_2$OCH$_3$, —S(=O)$_2$OCF$_3$, or —S(=O)$_2$OAryl, wherein Aryl is substituted or unsubstituted aryl or heteroaryl. In certain embodiments, $R^7$ is —S(=O)$_2$OR$^{GA}$, e.g., —S(=O)$_2$OCH$_3$, —S(=O)$_2$OCF$_3$, or —S(=O)$_2$OAryl, wherein Aryl is substituted or unsubstituted aryl or heteroaryl. In certain embodiments, one of R$^5$, R$^6$, and R$^7$ is —OS(=O)$_2$R$^{GA}$. In certain embodiments, R$^5$ is —OS(=O)$_2$R$^{GA}$, e.g., —OS(=O)$_2$CH$_3$, —OS(=O)$_2$CF$_3$, or —OS(=O)$_2$-Aryl, wherein Aryl is substituted or unsubstituted aryl or heteroaryl. In certain embodiments, R$^6$ is —OS(=O)$_2$R$^{GA}$, e.g., —OS(=O)$_2$CH$_3$, —OS(=O)$_2$CF$_3$, or OS(=O)$_2$-Aryl, wherein Aryl is substituted or unsubstituted aryl or heteroaryl. In certain embodiments, R$^7$ is —OS(=O)$_2$R$^{GA}$, e.g., —OS(=O)$_2$CH$_3$, —OS(=O)$_2$CF$_3$, or —OS(=O)$_2$-Aryl, wherein Aryl is substituted or unsubstituted aryl or heteroaryl. In certain embodiments, one of R$^5$, R$^6$, and R$^7$ is —S(=O)$_2$N(R$^{GA}$)$_2$. In certain embodiments, R$^5$ is —S(=O)$_2$N(R$^{GA}$)$_2$, e.g., —S(=O)$_2$NHCH$_3$, —S(=O)$_2$NHCF$_3$, or —S(=O)$_2$—NH-Aryl, wherein Aryl is substituted or unsubstituted aryl or heteroaryl. In certain embodiments, R$^6$ is —S(=O)$_2$N(R$^{GA}$)$_2$, e.g., —S(=O)$_2$NHCH$_3$, —S(=O)$_2$NHCF$_3$, or —S(=O)$_2$—NH-Aryl, wherein Aryl is substituted or unsubstituted aryl or heteroaryl. In certain embodiments, R$^7$ is —S(=O)$_2$N(R$^{GA}$)$_2$, e.g., —S(=O)$_2$NHCH$_3$, —S(=O)$_2$NHCF$_3$, or —S(=O)$_2$—NH-Aryl, wherein Aryl is substituted or unsubstituted aryl or heteroaryl. In certain embodiments, one of R$^5$, R$^6$, and R$^7$ is —N(R$^{GA}$)S(=O)$_2$R$^{GA}$. In certain embodiments, R$^5$ is —N(R$^{GA}$)S(=O)$_2$R$^{GA}$, e.g., —NHS(=O)$_2$CH$_3$, —NHS(=O)$_2$CF$_3$, or —NHS(=O)$_2$-Aryl, wherein Aryl is substituted or unsubstituted aryl or heteroaryl. In certain embodiments, R$^6$ is —N(R$^{GA}$)S(=O)$_2$R$^{GA}$, e.g., —NHS(=O)$_2$CH$_3$, —NHS(=O)$_2$CF$_3$, or —NHS(=O)$_2$-Aryl, wherein Aryl is substituted or unsubstituted aryl or heteroaryl. In certain embodiments, R$^7$ is —N(R$^{GA}$)S(=O)$_2$R$^{GA}$, e.g., —NHS(=O)$_2$CH$_3$, —NHS(=O)$_2$CF$_3$, or —NHS(=O)$_2$-Aryl, wherein Aryl is substituted or unsubstituted aryl or heteroaryl.

In certain embodiments, at least one of R$^5$, R$^6$, and R$^7$ is substituted or unsubstituted C$_{1-6}$ alkyl, e.g., substituted or unsubstituted C$_{1-2}$alkyl, substituted or unsubstituted C$_{2-3}$alkyl, substituted or unsubstituted C$_{3-4}$alkyl, substituted or unsubstituted C$_{4-5}$alkyl, or substituted or unsubstituted C$_{5-6}$alkyl. Exemplary C$_{1-6}$alkyl groups include, but are not limited to, substituted or unsubstituted methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C$_5$), amyl (C$_5$), neopentyl (C$_5$), 3-methyl-2-butanyl (C$_5$), tertiary amyl (C$_5$), n-hexyl (C$_6$), C$_{1-6}$ alkyl substituted with 1, 2, 3, 4, 5, 6, 7, 8, 9, 10, or more fluoro groups (e.g., —CF$_3$, —CH$_2$F, —CHF$_2$, difluoroethyl, and 2,2,2-trifluoro-1,1-dimethyl-ethyl), C$_{1-6}$ alkyl substituted with 1, 2, 3, 4, 5, 6, 7, 8, 9, 10, or more chloro groups (e.g., —CH$_2$Cl, —CHCl$_2$), and C$_{1-6}$ alkyl substituted with alkoxy groups (e.g., —CH$_2$OCH$_3$ and —CH$_2$OCH$_2$CH$_3$). In certain embodiments, at least one of R$^5$, R$^6$, and R$^7$ is substituted C$_{1-6}$ alkyl, e.g., at least one of R$^5$, R$^6$, and R$^7$ is haloalkyl, alkoxyalkyl, or aminoalkyl. In certain embodiments, at least one of R$^5$, R$^6$, and R$^7$ is Me, Et, n-Pr, n-Bu, i-Bu, fluoromethyl, chloromethyl, difluoromethyl, trifluoromethyl, trifluoroethyl, difluoroethyl, 2,2,2-trifluoro-1,1-dimethyl-ethyl, methoxymethyl, methoxyethyl, or ethoxymethyl.

In certain embodiments, at least one of R$^5$, R$^6$, and R$^7$ is substituted or unsubstituted C$_{2-6}$ alkenyl, e.g., substituted or unsubstituted C$_{2-3}$alkenyl, substituted or unsubstituted C$_{3-4}$alkenyl, substituted or unsubstituted C$_{4-5}$alkenyl, or substituted or unsubstituted C$_{5-6}$alkenyl. In certain embodiments, at least one of R$^5$, R$^6$, and R$^7$ is ethenyl (C$_2$), propenyl (C$_3$), or butenyl (C$_4$), unsubstituted or substituted with one or more substituents selected from the group consisting of alkyl, halo, haloalkyl, alkoxyalkyl, or hydroxyl. In certain embodiments, at least one of R$^5$, R$^6$, and R$^7$ is ethenyl, propenyl, or butenyl, unsubstituted or substituted with alkyl, halo, haloalkyl, alkoxyalkyl, or hydroxy.

In certain embodiments, at least one of R$^5$, R$^6$, and R$^7$ is substituted or unsubstituted C$_{2-6}$ alkynyl, e.g., substituted or unsubstituted C$_{2-3}$alkynyl, substituted or unsubstituted C$_{3-4}$alkynyl, substituted or unsubstituted C$_{4-5}$alkynyl, or substituted or unsubstituted C$_{5-6}$alkynyl. In certain embodiments, at least one of R$^5$, R$^6$, and R$^7$ is ethynyl, propynyl, or butynyl, unsubstituted or substituted with alkyl, halo, haloalkyl (e.g., CF$_3$), alkoxyalkyl, cycloalkyl (e.g., cyclopropyl or cyclobutyl), or hydroxyl.

In certain embodiments, at least one of R$^5$, R$^6$, and R$^7$ is substituted or unsubstituted C$_{3-6}$ carbocyclyl, e.g., substituted or unsubstituted C$_{3-4}$carbocyclyl, substituted or unsubstituted C$_{4-5}$ carbocyclyl, or substituted or unsubstituted C$_{5-6}$ carbocyclyl. In certain embodiments, at least one of R$^5$, R$^6$, and R$^7$ is substituted or unsubstituted cyclopropyl or substituted or unsubstituted cyclobutyl.

In certain embodiments, at least one of R$^5$, R$^6$, and R$^7$ is substituted or unsubstituted 3- to 6-membered heterocylyl, e.g., substituted or unsubstituted 3-4 membered heterocylyl, substituted or unsubstituted 4-5 membered heterocylyl, or substituted or unsubstituted 5-6 membered heterocylyl.

In certain embodiments, at least one of R$^5$, R$^6$, and R$^7$ is substituted or unsubstituted C$_{1-2}$ alkyl (e.g., —CH$_3$, —CF$_3$), —CO$_2$R$^{GA}$, —C(=O)R$^{GA}$, —CN, —NO$_2$, or halogen, wherein R$^{GA}$ is substituted or unsubstituted C$_{1-2}$ alkyl (e.g., —CH$_3$, —CF$_3$).

Exemplary combinations of R$^5$, R$^6$, and R$^7$ as non-hydrogen substituents are contemplated herein.

For example, in certain embodiments, the C21-pyrazolyl of formula

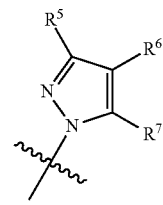

is a mono-substituted pyrazolyl ring of formula:

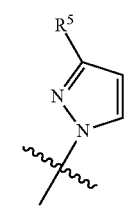

(i-a)

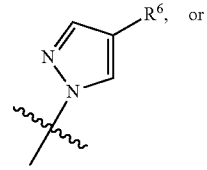

(i-b)

(i-c)

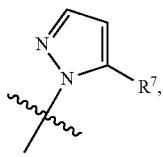

wherein $R^5$, $R^6$, and $R^7$ are each non-hydrogen substituents as defined herein.

In certain embodiments, the C21-pyrazolyl of formula

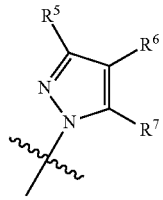

is a di-substituted pyrazolyl ring of formula:

(ii-a)

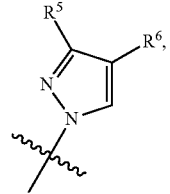

(ii-b)

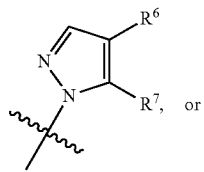

(ii-c)

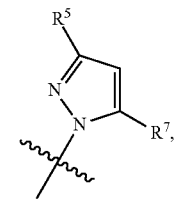

wherein $R^5$, $R^6$, and $R^7$ are each non-hydrogen substituents as defined herein.

In certain embodiments, the C21-pyrazolyl of formula

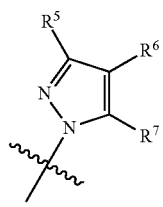

is a tri-substituted pyrazolyl ring wherein each of $R^5$, $R^6$, and $R^7$ are non-hydrogen substituents as defined herein.

Various Combinations of Certain Embodiments

Various combinations of certain embodiments are further contemplated herein.

For example, in certain embodiments, wherein $R^2$ is hydrogen or a non-hydrogen alpha substituent, provided is a steroid of Formula (I-A1), (I-B1), or (I-C1):

(I-A1)

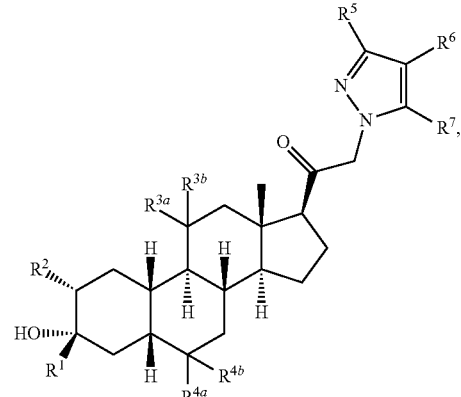

(I-B1)

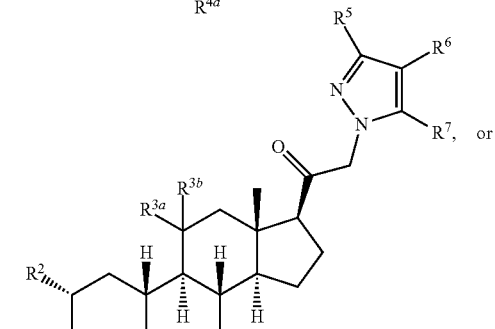

or (I-C1)

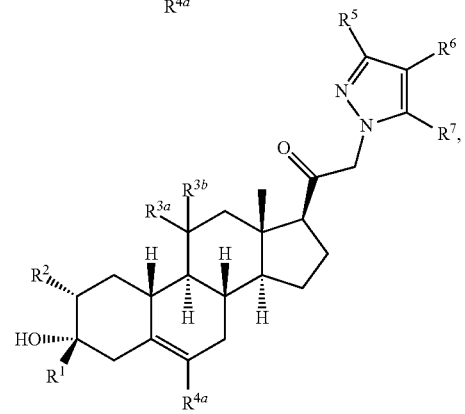

or a pharmaceutically acceptable salt thereof. In certain embodiments, $R^1$ is —$CH_3$, —$CH_2CH_3$, —$CH_2F$, —$CHF_2$, —$CF_3$, —$CH_2OCH_3$, or substituted or unsubstituted cyclopropyl. In certain embodiments, $R^2$ is —OH, —$OCH_3$, —$OCH_2CH_3$, —$OCH_2CH_2CH_3$, —$CH_3$, —$CH_2CH_3$, —$CH_2CH_2CH_3$, substituted or unsubstituted cyclopropyl, fluoro, or chloro. In certain embodiments, $R^{3a}$ and $R^{3b}$ are both hydrogen. In certain embodiments, $R^{3a}$ and $R^{3b}$ are joined to form =O (oxo). In certain embodiments, wherein Ring B comprises a C5-C6 double bond, $R^{4a}$ is hydrogen, fluoro, —$CH_3$, or —$CF_3$. In certain embodiments, wherein Ring B does not comprises a C5-C6 double bond, both of $R^{4a}$ and $R^{4b}$ are hydrogen. In certain embodiments, wherein Ring B does not comprises a C5-C6 double bond, both of $R^{4a}$ and $R^{4b}$ are —$CH_3$ or —$CF_3$. In certain embodiments, wherein Ring B does not comprises a C5-C6 double bond, both of $R^{4a}$ and $R^{4b}$ are fluoro. In certain embodiments, wherein Ring B does not comprises a C5-C6 double bond, $R^{4a}$ is a non-hydrogen substituent and $R^{4b}$ is hydrogen. In certain embodiments, the C21-pyrazolyl ring is a mono-substituted pyrazolyl. In certain embodiments, the C21-pyrazolyl ring is a di-substituted pyrazolyl. In certain embodiments, at least one of $R^5$, $R^6$, and $R^7$ is substituted or unsubstituted $C_{1-2}$ alkyl (e.g., —$CH_3$, —$CF_3$), —$CO_2R^{GA}$, —C(=O)$R^{GA}$, —CN, —$NO_2$, or halogen, wherein $R^{GA}$ is substituted or unsubstituted $C_{1-2}$ alkyl (e.g., —$CH_3$, —$CF_3$). In certain embodiments, the C21-pyrazolyl ring is an unsubstituted pyrazolyl, wherein each instance of $R^5$, $R^6$, and $R^7$ is hydrogen.

In certain embodiments, wherein $R^2$ is hydrogen or a non-hydrogen beta substituent, provided is a steroid of Formula (I-A2), (I-B2), or (I-C2):

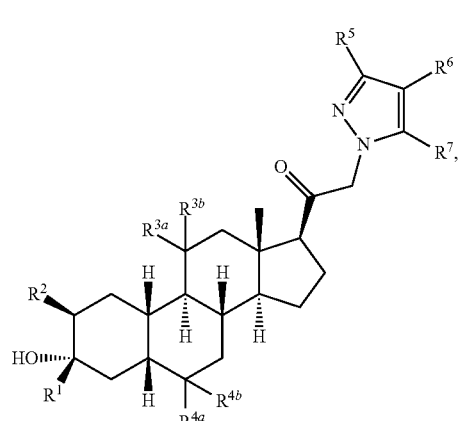

(I-A2)

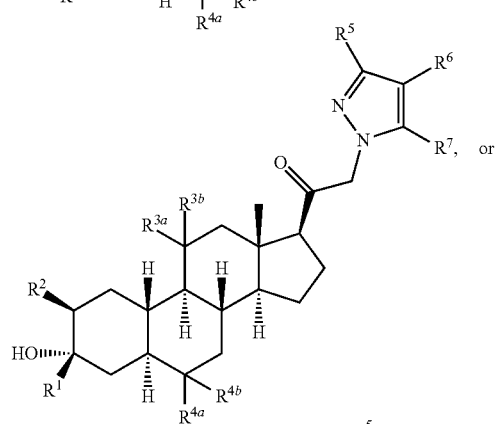

(I-B2), or

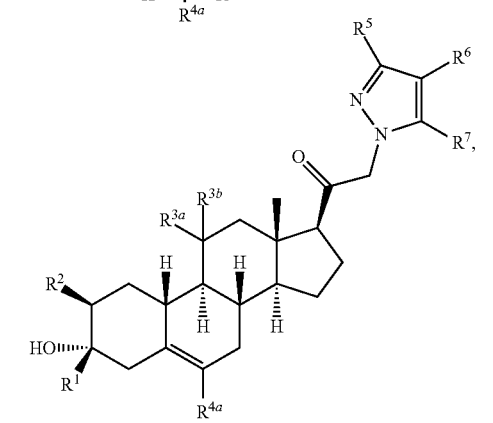

(I-C2)

or a pharmaceutically acceptable salt thereof. In certain embodiments, $R^1$ is —$CH_3$, —$CH_2CH_3$, —$CH_2F$, —$CHF_2$, —$CF_3$, —$CH_2OCH_3$, or substituted or unsubstituted cyclopropyl. In certain embodiments, $R^2$ is —OH, —$OCH_3$, —$OCH_2CH_3$, —$OCH_2CH_2CH_3$, —$CH_3$, —$CH_2CH_3$, —$CH_2CH_2CH_3$, substituted or unsubstituted cyclopropyl, fluoro, or chloro. In certain embodiments, $R^{3a}$ and $R^{3b}$ are both hydrogen. In certain embodiments, $R^{3a}$ and $R^{3b}$ are joined to form =O (oxo). In certain embodiments, wherein Ring B comprises a C5-C6 double bond, $R^{4a}$ is hydrogen, fluoro, —$CH_3$, or —$CF_3$. In certain embodiments, wherein Ring B does not comprises a C5-C6 double bond, both of $R^{4a}$ and $R^{4b}$ are hydrogen. In certain embodiments, wherein Ring B does not comprises a C5-C6 double bond, both of $R^{4a}$ and $R^{4b}$ are —$CH_3$ or —$CF_3$. In certain embodiments, wherein Ring B does not comprises a C5-C6 double bond, both of $R^{4a}$ and $R^{4b}$ are fluoro. In certain embodiments, wherein Ring B does not comprises a C5-C6 double bond, $R^{4a}$ is a non-hydrogen substituent and $R^{4b}$ is hydrogen. In certain embodiments, the C21-pyrazolyl ring is a mono-substituted pyrazolyl.

In certain embodiments, the C21-pyrazolyl ring is a di-substituted pyrazolyl. In certain embodiments, at least one of $R^5$, $R^6$, and $R^7$ is substituted or unsubstituted $C_{1-2}$ alkyl (e.g., —$CH_3$, —$CF_3$), —$CO_2R^{GA}$, —C(=O)$R^{GA}$, —CN, —$NO_2$, or halogen, wherein $R^{GA}$ is substituted or unsubstituted $C_{1-2}$ alkyl (e.g., —$CH_3$, —$CF_3$). In certain embodiments, the C21-pyrazolyl ring is an unsubstituted pyrazolyl, wherein each instance of $R^5$, $R^6$, and $R^7$ is hydrogen.

In certain embodiments, wherein $R^{3a}$ is hydrogen or a non-hydrogen alpha substituent, and $R^{3b}$ is hydrogen, provided is a steroid of Formula (I-A3), (I-B3), or (I-C3):

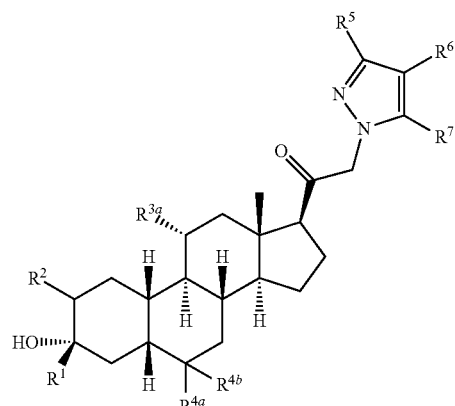

(I-A3)

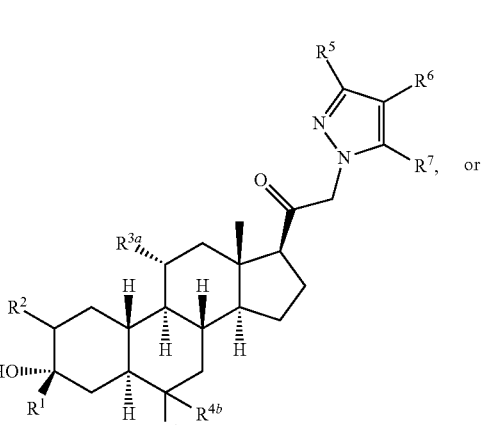

(I-B3), or

-continued (I-C3)

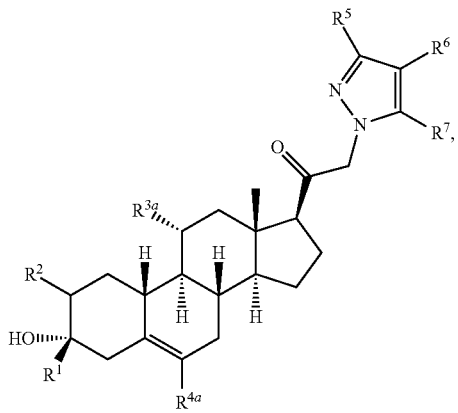

(I-B4)

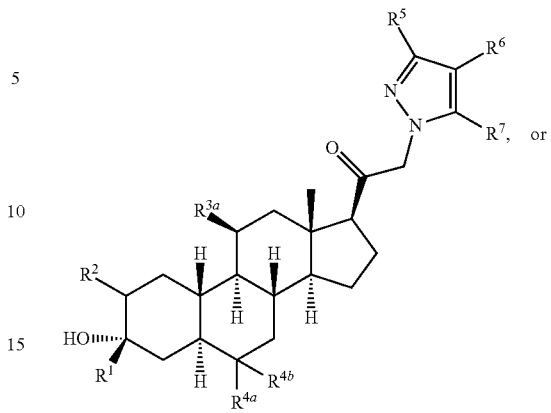

or (I-C4)

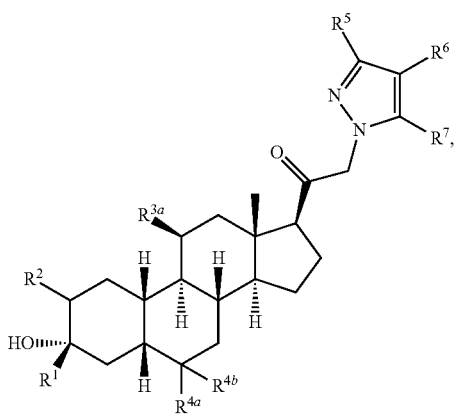

or a pharmaceutically acceptable salt thereof. In certain embodiments, $R^1$ is —$CH_3$, —$CH_2CH_3$, —$CH_2F$, —$CHF_2$, —$CF_3$, —$CH_2OCH_3$, or substituted or unsubstituted cyclopropyl. In certain embodiments, $R^2$ is —OH, —$OCH_3$, —$OCH_2CH_3$, —$OCH_2CH_2CH_3$, —$CH_3$, —$CH_2CH_3$, —$CH_2CH_2CH_3$, substituted or unsubstituted cyclopropyl, fluoro, or chloro. In certain embodiments, $R^2$ is a non-hydrogen substituent in the alpha configuration. In certain embodiments, $R^2$ is a non-hydrogen substituent in the beta configuration. In certain embodiments, wherein Ring B comprises a C5-C6 double bond, $R^{4a}$ is hydrogen, fluoro, —$CH_3$, or —$CF_3$. In certain embodiments, wherein Ring B does not comprises a C5-C6 double bond, both of $R^{4a}$ and $R^{4b}$ are hydrogen. In certain embodiments, wherein Ring B does not comprises a C5-C6 double bond, both of $R^{4a}$ and $R^{4b}$ are —$CH_3$ or —$CF_3$. In certain embodiments, wherein Ring B does not comprises a C5-C6 double bond, both of $R^{4a}$ and $R^{4b}$ are fluoro. In certain embodiments, wherein Ring B does not comprises a C5-C6 double bond, $R^{4a}$ is a non-hydrogen substituent and $R^{4b}$ is hydrogen. In certain embodiments, the C21-pyrazolyl ring is a mono-substituted pyrazolyl. In certain embodiments, the C21-pyrazolyl ring is a di-substituted pyrazolyl. In certain embodiments, at least one of $R^5$, $R^6$, and $R^7$ is substituted or unsubstituted $C_{1-2}$ alkyl (e.g., —$CH_3$, —$CF_3$), —$CO_2R^{GA}$, —$C(=O)R^{GA}$, —CN, —$NO_2$, or halogen, wherein $R^{GA}$ is substituted or unsubstituted $C_{1-2}$ alkyl (e.g., —$CH_3$, —$CF_3$). In certain embodiments, the C21-pyrazolyl ring is an unsubstituted pyrazolyl, wherein each instance of $R^5$, $R^6$, and $R^7$ is hydrogen.

In certain embodiments, wherein $R^{3a}$ is hydrogen or a non-hydrogen beta substituent, and $R^{3b}$ is hydrogen, provided is a steroid of Formula (I-A4), (I-B4), or (I-C4):

or a pharmaceutically acceptable salt thereof. In certain embodiments, $R^1$ is —$CH_3$, —$CH_2CH_3$, —$CH_2F$, —$CHF_2$, —$CF_3$, —$CH_2OCH_3$, or substituted or unsubstituted cyclopropyl. In certain embodiments, $R^2$ is —OH, —$OCH_3$, —$OCH_2CH_3$, —$OCH_2CH_2CH_3$, —$CH_3$, —$CH_2CH_3$, —$CH_2CH_2CH_3$, substituted or unsubstituted cyclopropyl, fluoro, or chloro. In certain embodiments, $R^2$ is a non-hydrogen substituent in the alpha configuration. In certain embodiments, $R^2$ is a non-hydrogen substituent in the beta configuration. In certain embodiments, wherein Ring B comprises a C5-C6 double bond, $R^{4a}$ is hydrogen, fluoro, —$CH_3$, or —$CF_3$. In certain embodiments, wherein Ring B does not comprises a C5-C6 double bond, both of $R^{4a}$ and $R^{4b}$ are hydrogen. In certain embodiments, wherein Ring B does not comprises a C5-C6 double bond, both of $R^{4a}$ and $R^{4b}$ are —$CH_3$ or —$CF_3$. In certain embodiments, wherein Ring B does not comprises a C5-C6 double bond, both of $R^{4a}$ and $R^{4b}$ are fluoro. In certain embodiments, wherein Ring B does not comprises a C5-C6 double bond, $R^{4a}$ is a non-hydrogen substituent and $R^{4b}$ is hydrogen. In certain embodiments, the C21-pyrazolyl ring is a mono-substituted pyrazolyl. In certain embodiments, the C21-pyrazolyl ring is a di-substituted pyrazolyl. In certain embodiments, at least one of $R^5$, $R^6$, and $R^7$ is substituted or unsubstituted $C_{1-2}$ alkyl (e.g., —$CH_3$, —$CF_3$), —$CO_2R^{GA}$, —$C(=O)R^{GA}$, —CN, —$NO_2$, or halogen, wherein $R^{GA}$ is substituted or unsubstituted $C_{1-2}$ alkyl (e.g., —$CH_3$, —$CF_3$). In certain embodiments, the C21-pyrazolyl ring is an unsubstituted pyrazolyl, wherein each instance of $R^5$, $R^6$, and $R^7$ is hydrogen.

In certain embodiments, wherein $R^{3a}$ and $R^{3b}$ are joined to form an oxo group, provided is a steroid of Formula (I-A5), (I-B5), or (I-C5):

(I-A4)

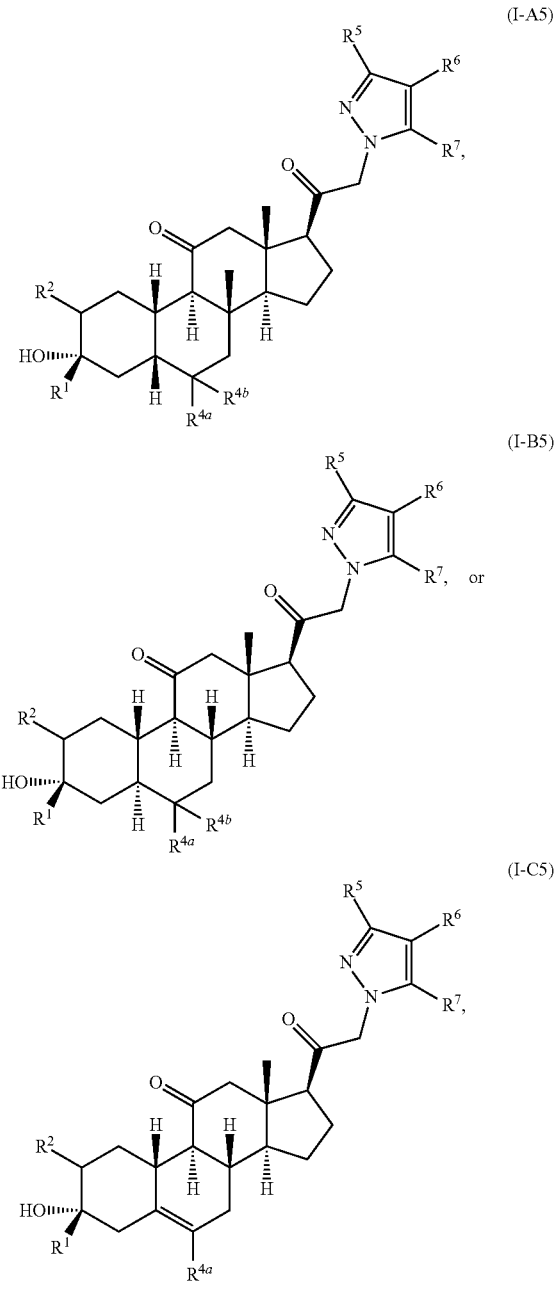

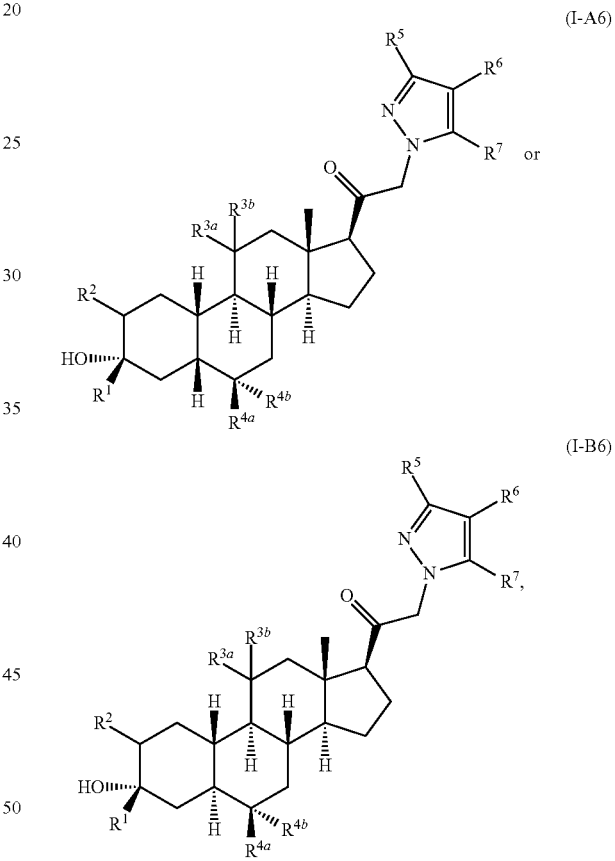

Ring B does not comprises a C5-C6 double bond, both of $R^{4a}$ and $R^{4b}$ are fluoro. In certain embodiments, wherein Ring B does not comprises a C5-C6 double bond, $R^{4a}$ is a non-hydrogen substituent and $R^{4b}$ is hydrogen. In certain embodiments, the C21-pyrazolyl ring is a mono-substituted pyrazolyl. In certain embodiments, the C21-pyrazolyl ring is a di-substituted pyrazolyl. In certain embodiments, at least one of $R^5$, $R^6$, and $R^7$ is substituted or unsubstituted $C_{1-2}$ alkyl (e.g., —$CH_3$, —$CF_3$), —$CO_2R^{GA}$, —$C(=O)R^{GA}$, —CN, —$NO_2$, or halogen, wherein $R^{GA}$ is substituted or unsubstituted $C_{1-2}$ alkyl (e.g., —$CH_3$, —$CF_3$). In certain embodiments, the C21-pyrazolyl ring is an unsubstituted pyrazolyl, wherein each instance of $R^5$, $R^6$, and $R^7$ is hydrogen.

In certain embodiments, wherein $R^{4a}$ is a non-hydrogen substituent, provided is a steroid of Formula (I-A6) or (I-B6):

or a pharmaceutically acceptable salt thereof. In certain embodiments, $R^1$ is —$CH_3$, —$CH_2CH_3$, —$CH_2F$, —$CHF_2$, —$CF_3$, —$CH_2OCH_3$, or substituted or unsubstituted cyclopropyl. In certain embodiments, $R^2$ is —OH, —$OCH_3$, —$OCH_2CH_3$, —$OCH_2CH_2CH_3$, —$CH_3$, —$CH_2CH_3$, —$CH_2CH_2CH_3$, substituted or unsubstituted cyclopropyl, fluoro, or chloro. In certain embodiments, $R^2$ is a non-hydrogen substituent in the alpha configuration. In certain embodiments, $R^2$ is a non-hydrogen substituent in the beta configuration. In certain embodiments, wherein Ring B comprises a C5-C6 double bond, $R^{4a}$ is hydrogen, fluoro, —$CH_3$, or —$CF_3$. In certain embodiments, wherein Ring B does not comprises a C5-C6 double bond, both of $R^{4a}$ and $R^{4b}$ are hydrogen. In certain embodiments, wherein Ring B does not comprises a C5-C6 double bond, both of $R^{4a}$ and $R^{4b}$ are —$CH_3$ or —$CF_3$. In certain embodiments, wherein or a pharmaceutically acceptable salt thereof. In certain embodiments, $R^1$ is —$CH_3$, —$CH_2CH_3$, —$CH_2F$, —$CHF_2$, —$CF_3$, —$CH_2OCH_3$, or substituted or unsubstituted cyclopropyl. In certain embodiments, $R^2$ is —OH, —$OCH_3$, —$OCH_2CH_3$, —$OCH_2CH_2CH_3$, —$CH_3$, —$CH_2CH_3$, —$CH_2CH_2CH_3$, substituted or unsubstituted cyclopropyl, fluoro, or chloro. In certain embodiments, $R^2$ is a non-hydrogen substituent in the alpha configuration. In certain embodiments, $R^2$ is a non-hydrogen substituent in the beta configuration. In certain embodiments, $R^{3a}$ and $R^{3b}$ are both hydrogen. In certain embodiments, $R^{3a}$ and $R^{3b}$ are joined to form =O (oxo). In certain embodiments, $R^{4a}$ is fluoro, —$CH_3$, or —$CF_3$ and $R^{4b}$ is hydrogen. In certain embodiments, $R^{4b}$ is fluoro, —$CH_3$, or —$CF_3$ and $R^{4a}$ is hydrogen.

In certain embodiments, both of $R^{4a}$ and $R^{4b}$ are —CH$_3$ or —CF$_3$. In certain embodiments, both of $R^{4a}$ and $R^{4b}$ are fluoro. In certain embodiments, the C21-pyrazolyl ring is a mono-substituted pyrazolyl. In certain embodiments, the C21-pyrazolyl ring is a di-substituted pyrazolyl. In certain embodiments, at least one of $R^5$, $R^6$, and $R^7$ is substituted or unsubstituted C$_{1-2}$ alkyl (e.g., —CH$_3$, —CF$_3$), —CO$_2$R$^{GA}$, —C(=O)R$^{GA}$, —CN, —NO$_2$, or halogen, wherein R$^{GA}$ is substituted or unsubstituted C$_{1-2}$ alkyl (e.g., —CH$_3$, —CF$_3$). In certain embodiments, the C21-pyrazolyl ring is an unsubstituted pyrazolyl, wherein each instance of $R^5$, $R^6$, and $R^7$ is hydrogen.

In certain embodiments, wherein $R^{4a}$ is a non-hydrogen substituent, provided is a steroid of Formula (I-A6) or (I-B6):

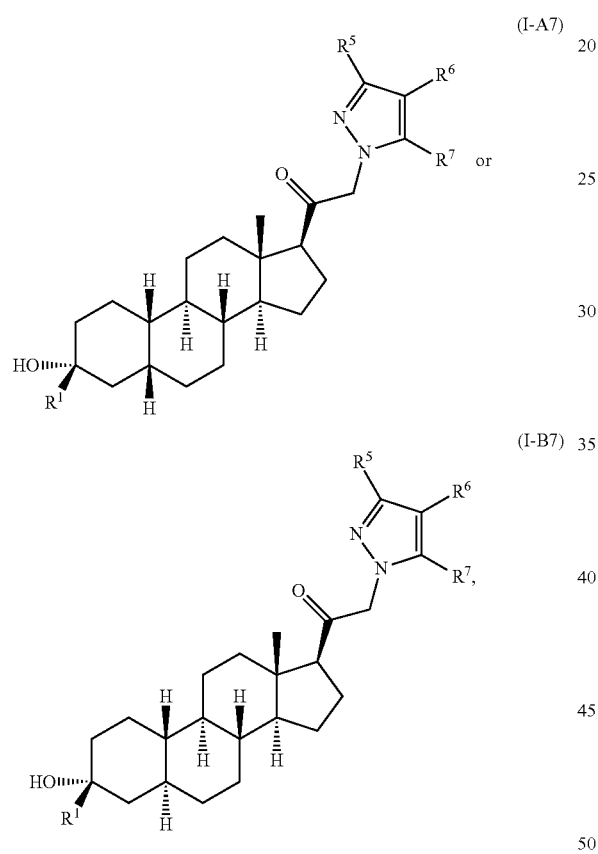

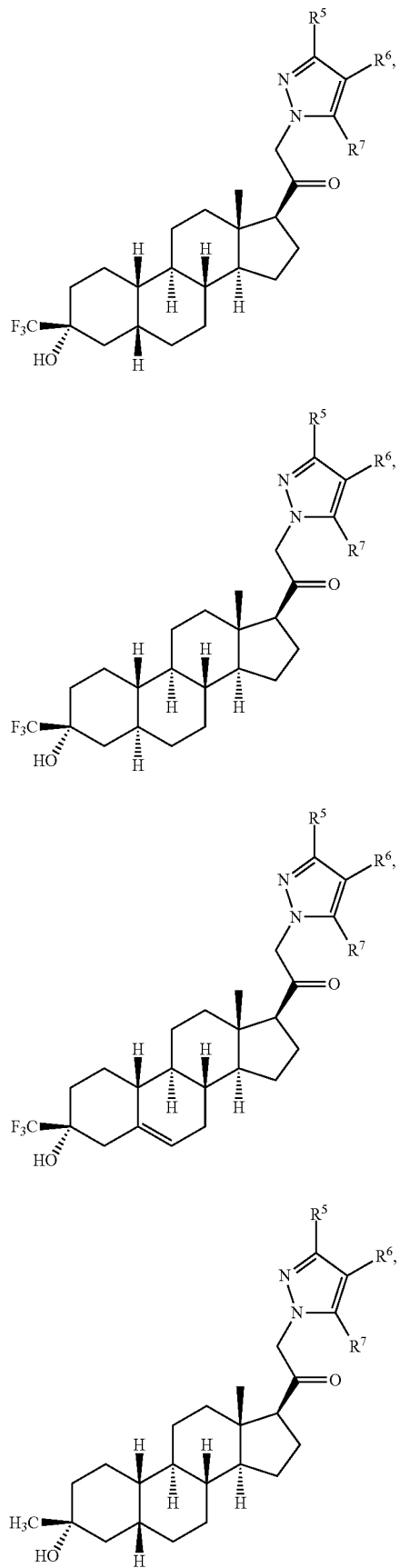

or a pharmaceutically acceptable salt thereof. In certain embodiments, $R^1$ is —CH$_3$, —CH$_2$CH$_3$, —CH$_2$F, —CHF$_2$, —CF$_3$, —CH$_2$OCH$_3$, or substituted or unsubstituted cyclopropyl. In certain embodiments, the C21-pyrazolyl ring is a mono-substituted pyrazolyl. In certain embodiments, the C21-pyrazolyl ring is a di-substituted pyrazolyl. In certain embodiments, at least one of $R^5$, $R^6$, and $R^7$ is substituted or unsubstituted C$_{1-2}$ alkyl (e.g., —CH$_3$, —CF$_3$), —CO$_2$R$^{GA}$, —C(=O)R$^{GA}$, —CN, —NO$_2$, or halogen, wherein R$^{GA}$ is substituted or unsubstituted C$_{1-2}$ alkyl (e.g., —CH$_3$, —CF$_3$). In certain embodiments, the C21-pyrazolyl ring is an unsubstituted pyrazolyl, wherein each instance of $R^5$, $R^6$, and $R^7$ is hydrogen.

In certain embodiments, a steroid of Formula (I) is selected from the group consisting of:

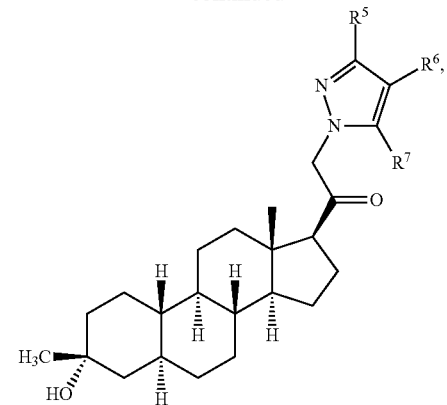
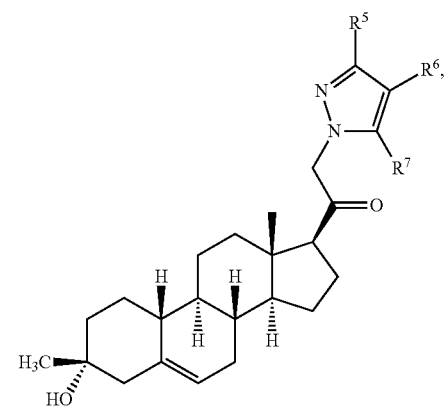
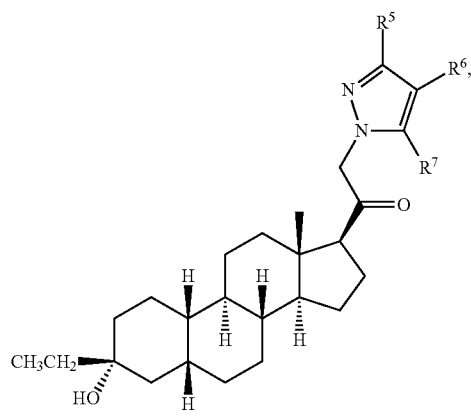
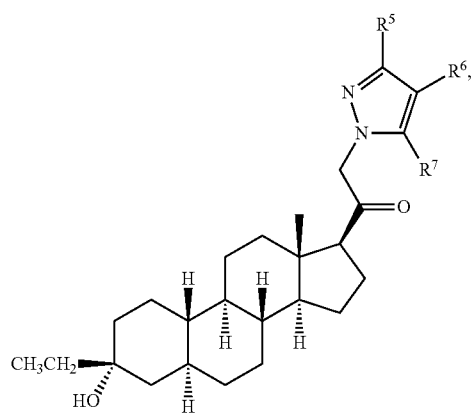
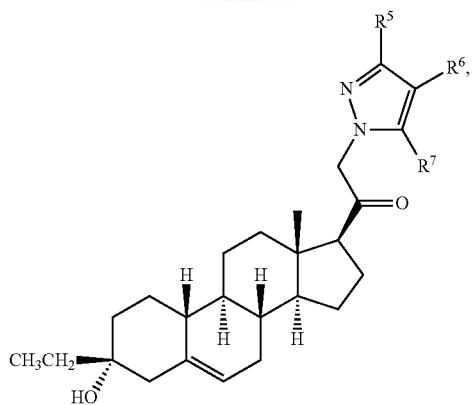
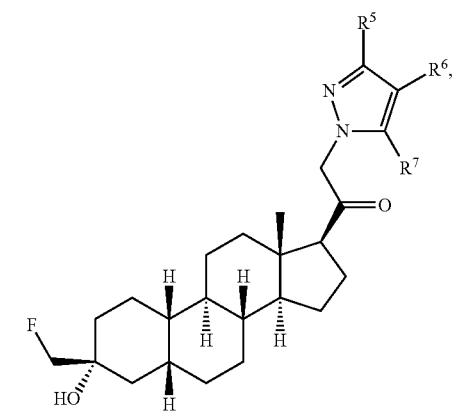
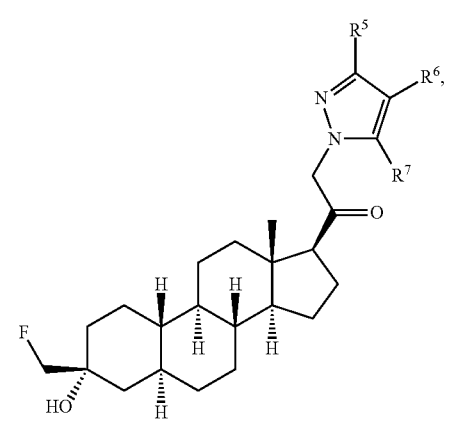
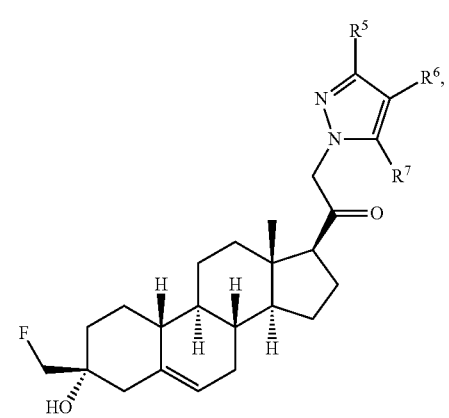

-continued
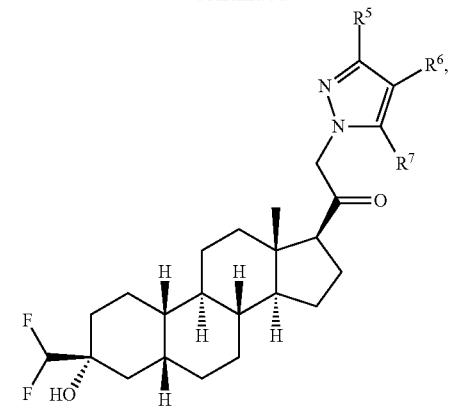
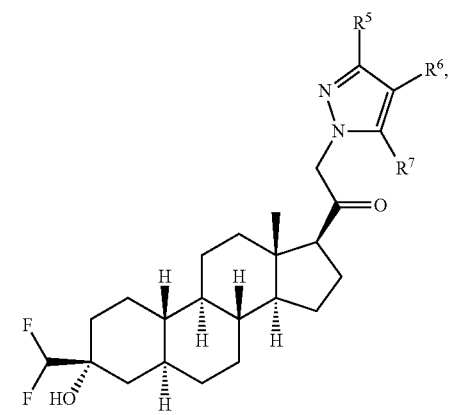
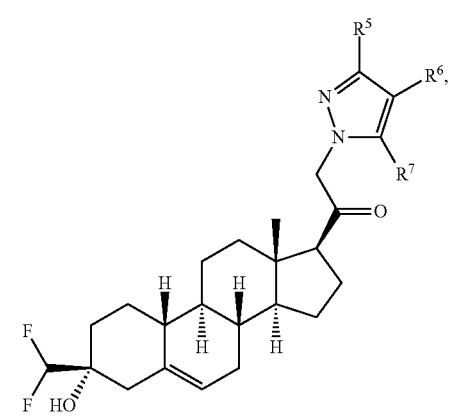
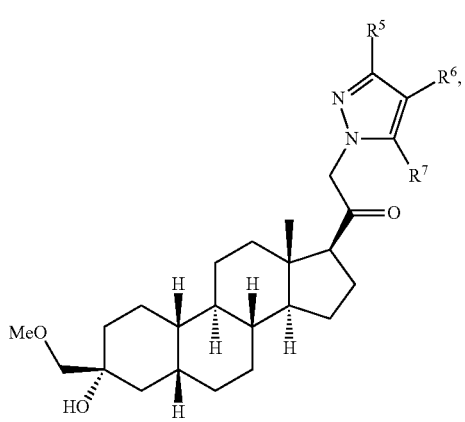
-continued
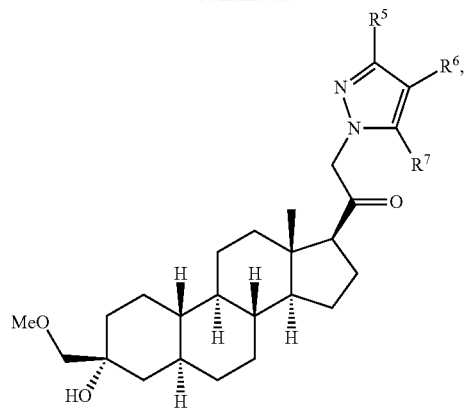
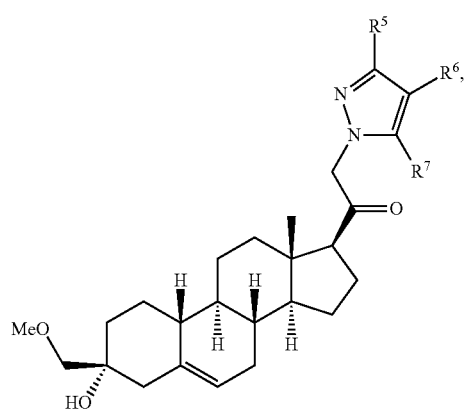
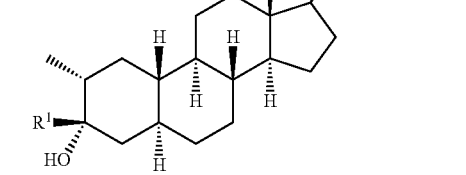
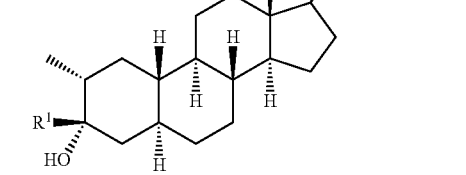

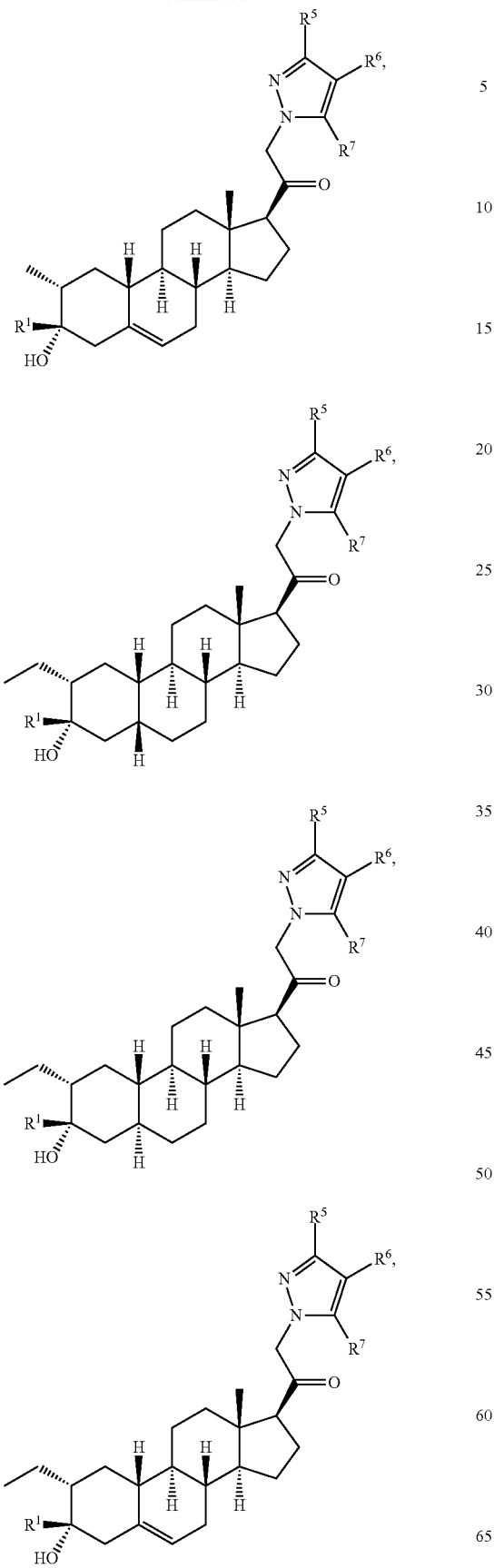
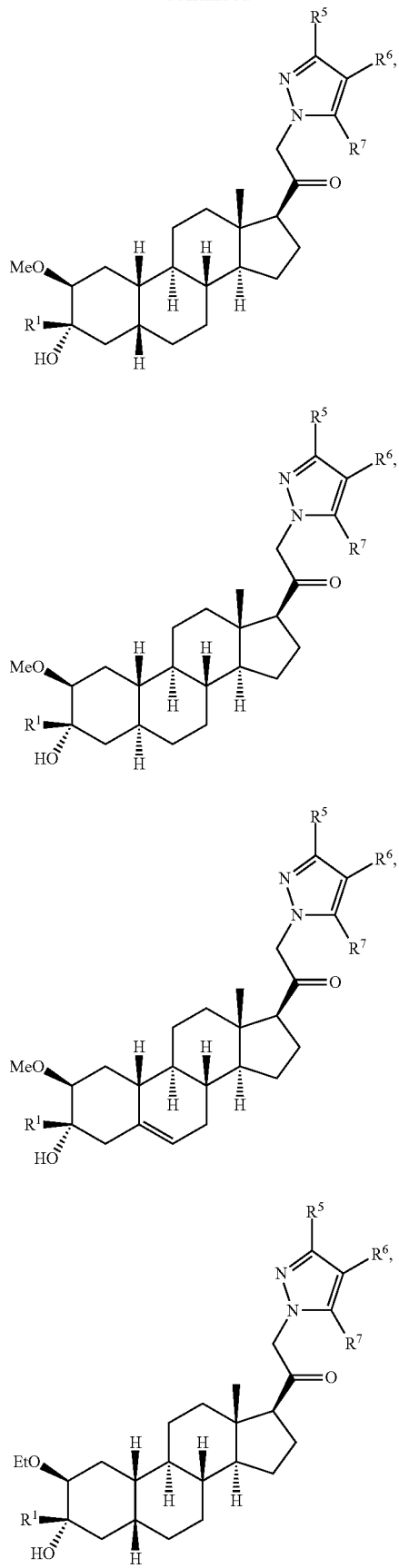

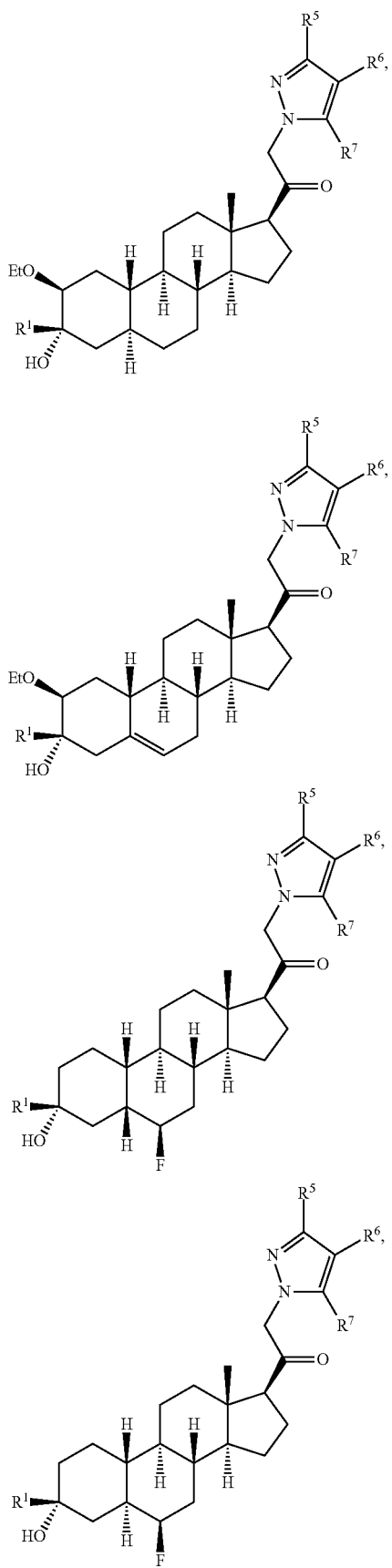
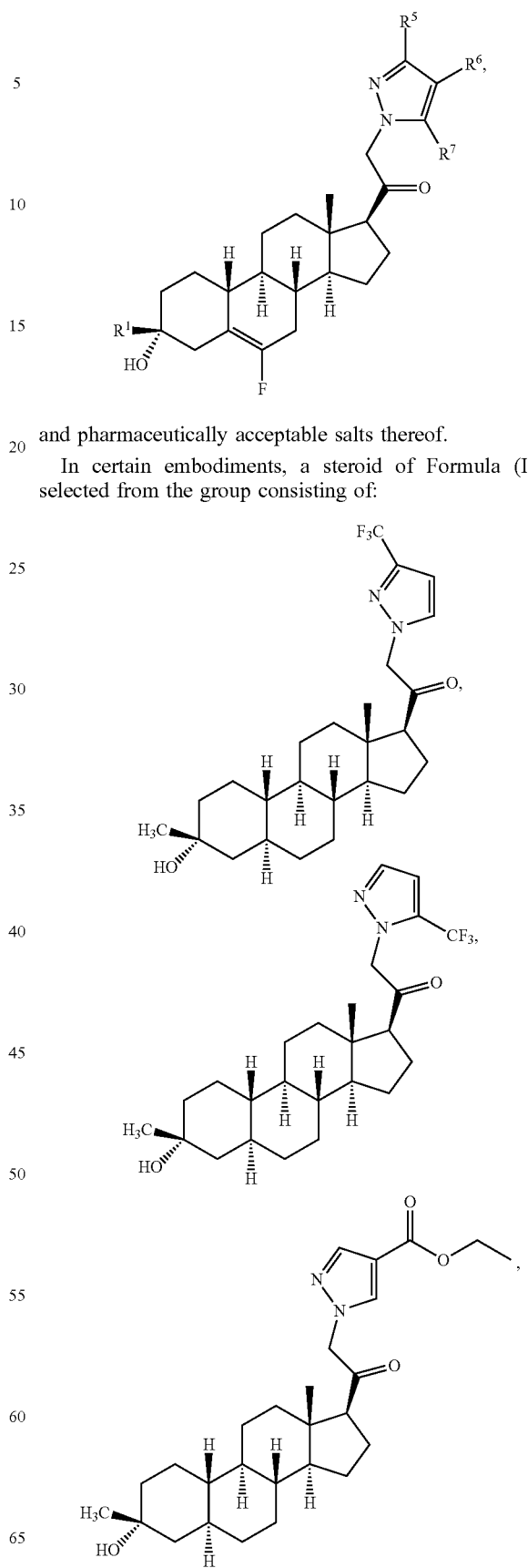
and pharmaceutically acceptable salts thereof.
In certain embodiments, a steroid of Formula (I) is selected from the group consisting of:

-continued
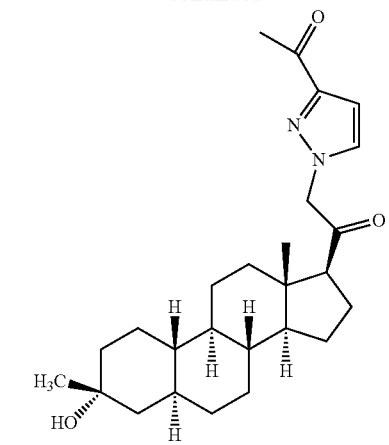
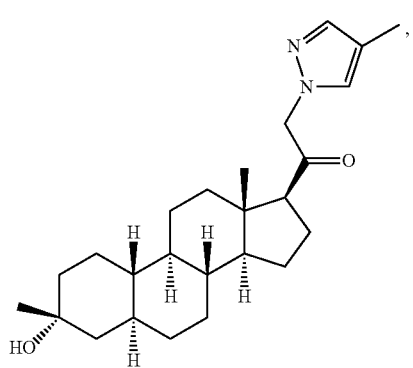
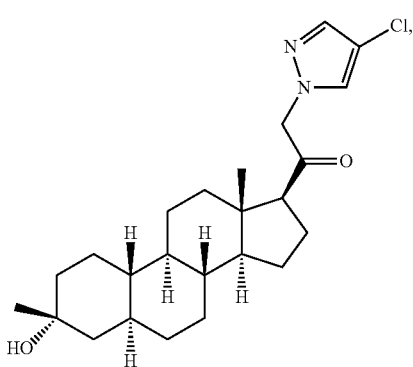
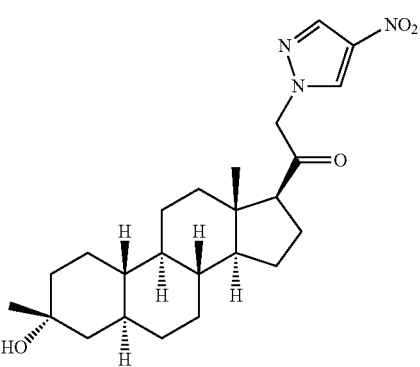
-continued
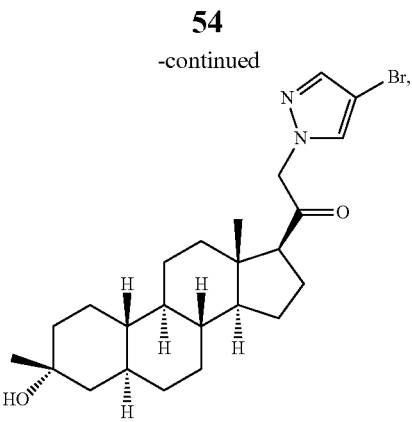
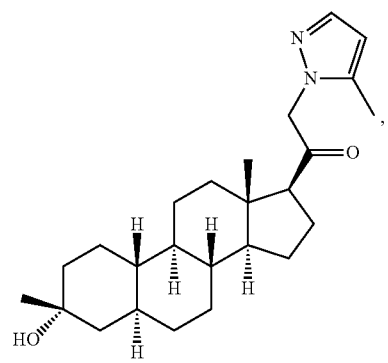
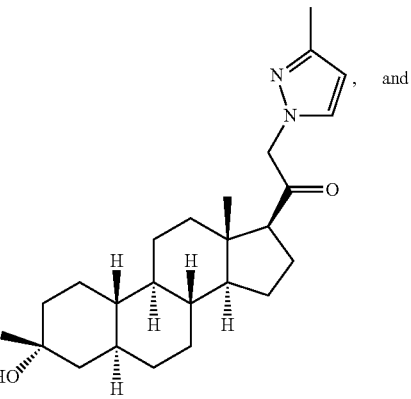
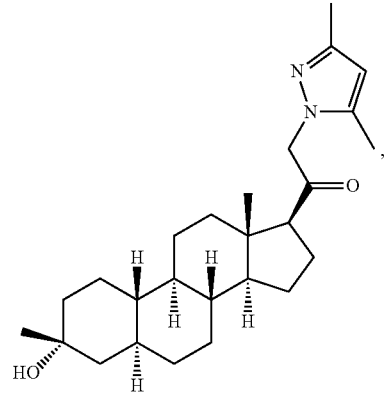
and pharmaceutically acceptable salts thereof.
In certain embodiments, a steroid of Formula (I) is selected from the group consisting of:

SD-1
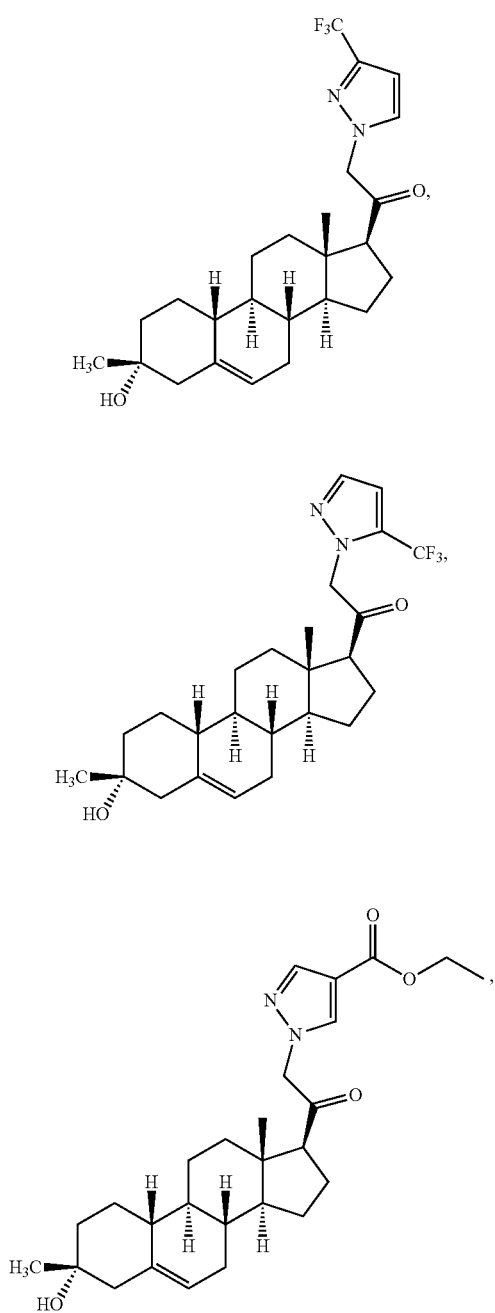
SD-2
SD-3
SD-4
SD-5
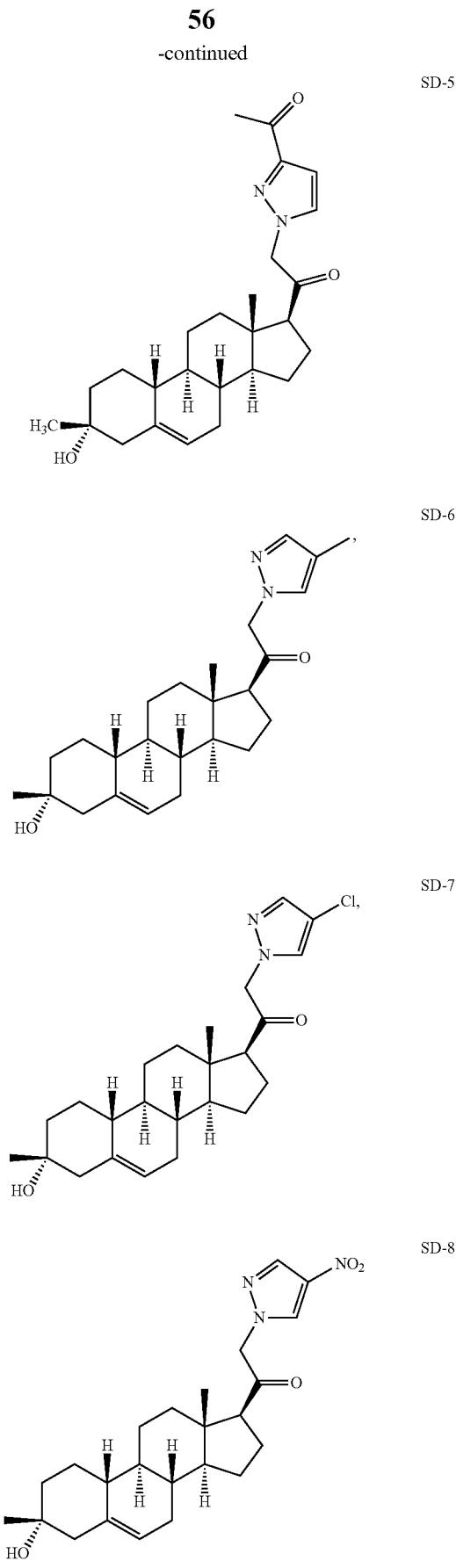
SD-6
SD-7
SD-8

SD-9 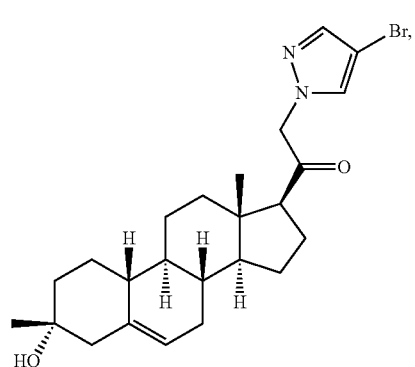
SD-10 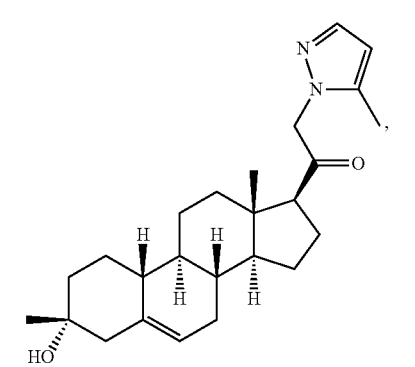
SD-11 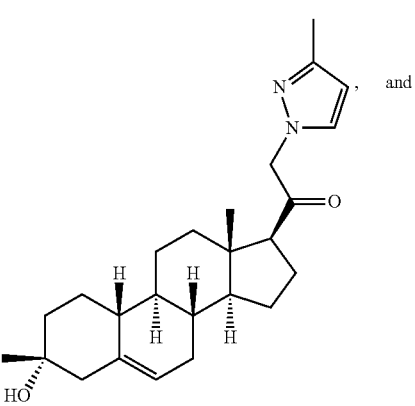 and
SD-12 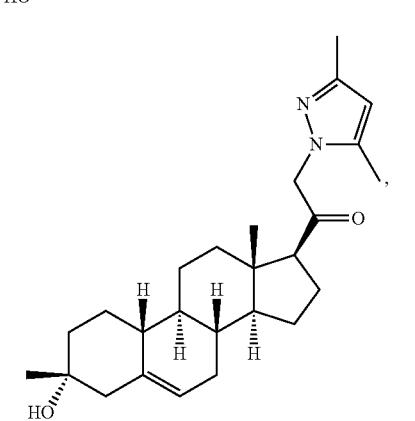
and pharmaceutically acceptable salts thereof.
In certain embodiments, a steroid of Formula (I) is selected from the group consisting of:
SU-1D 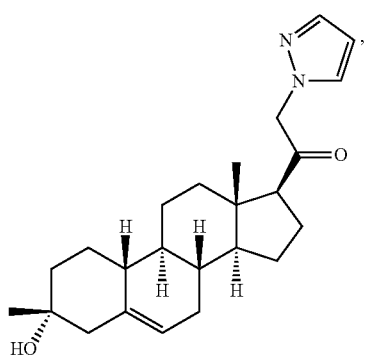
SU-2D 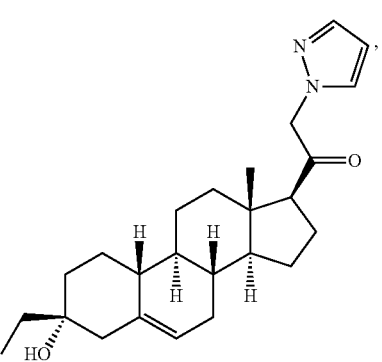
SU-3A 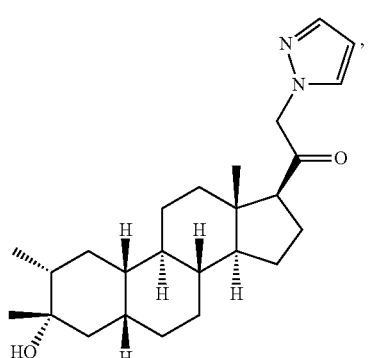
SU-3B 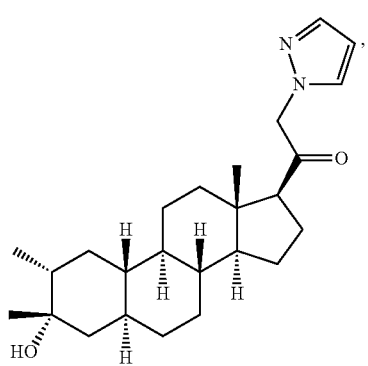

SU-3D
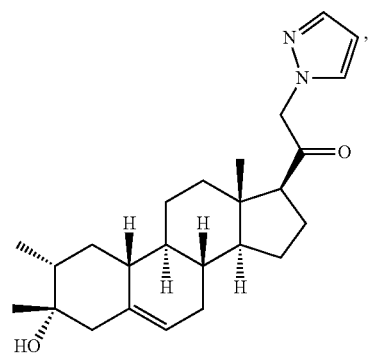
SU-4D
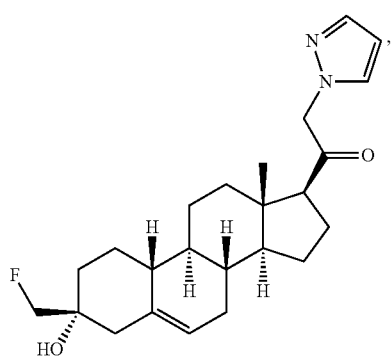
SU-5B
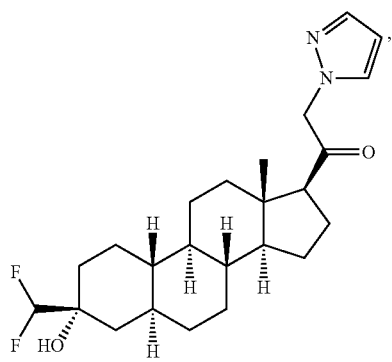
SU-5D
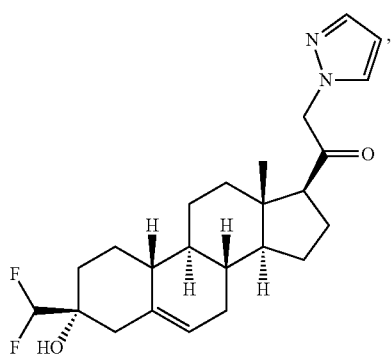
SU-6D
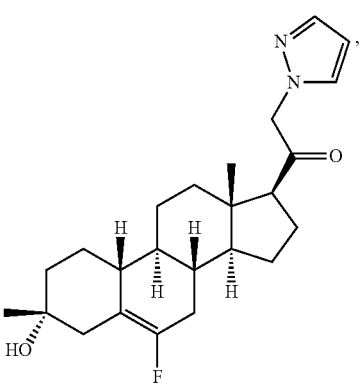
SU-7A
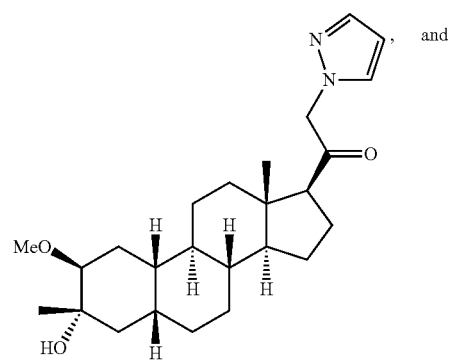
SU-7D
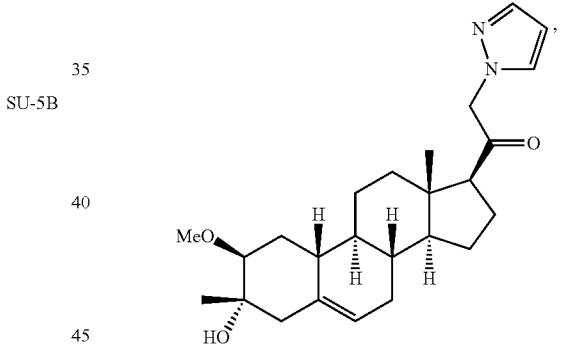
and pharmaceutically acceptable salts thereof.
In certain embodiments, a steroid of Formula (I) is selected from the group consisting of:
SA-1
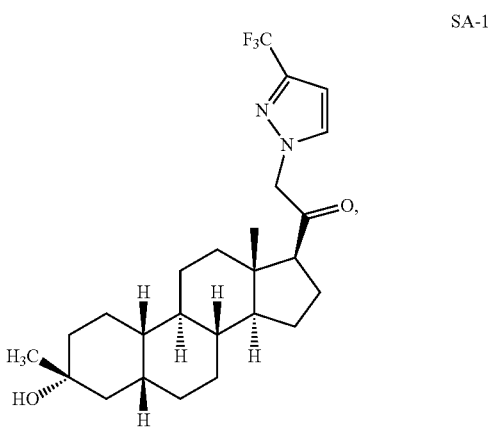

-continued
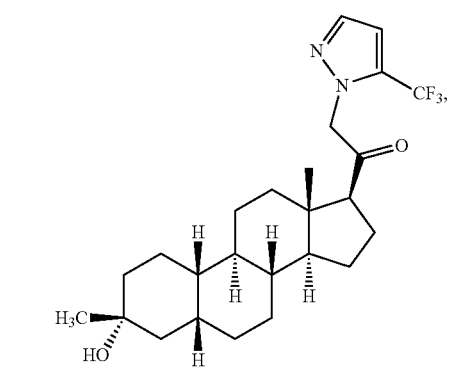
SA-2
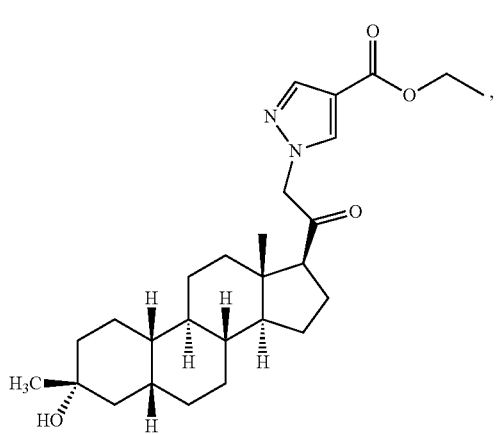
SA-3
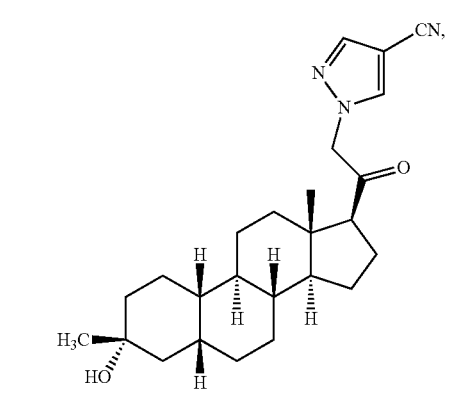
SA-4
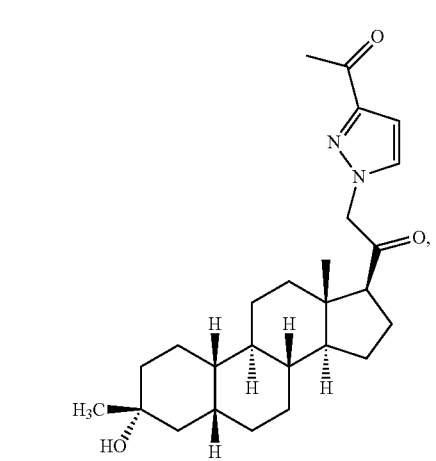
SA-5
-continued
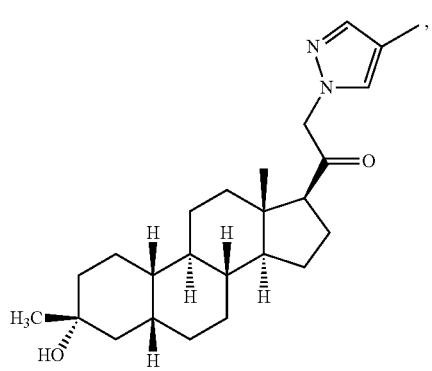
SA-6
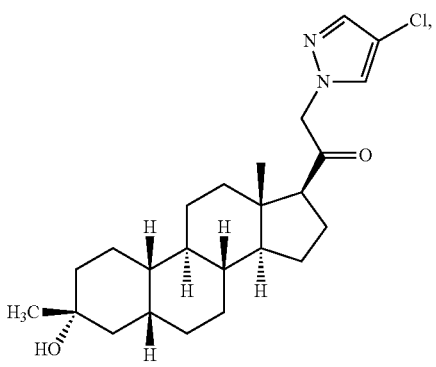
SA-7
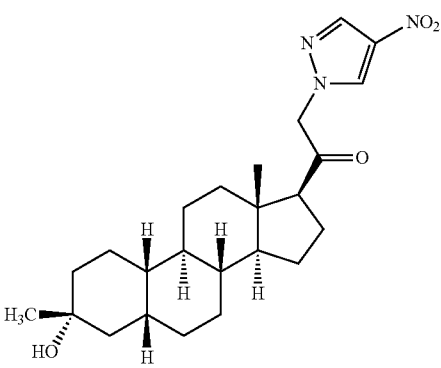
SA-8
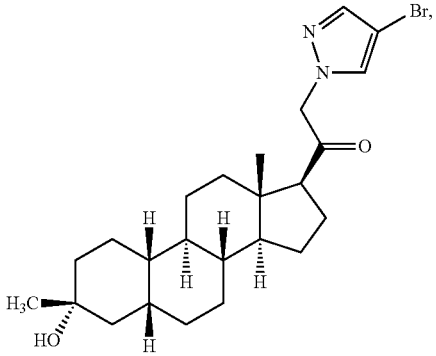
SA-9

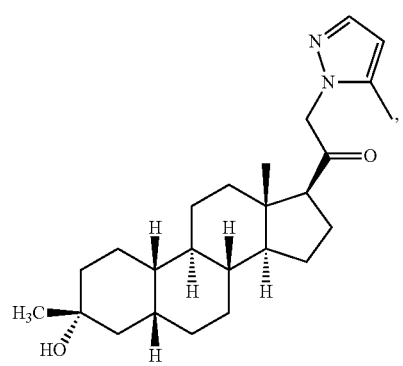
SA-10
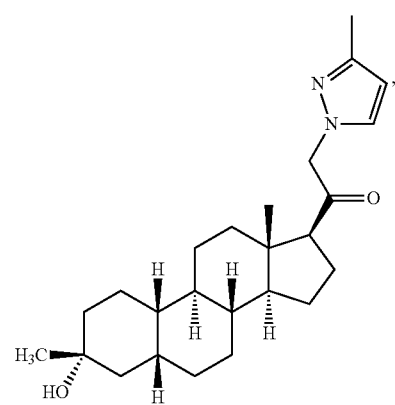
SA-11
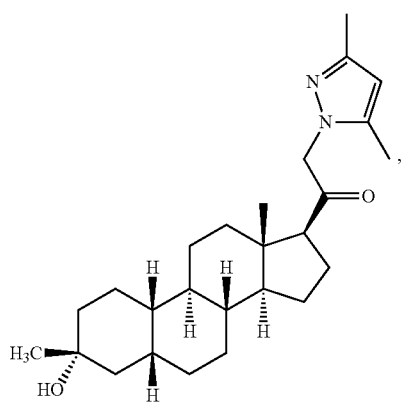
SA-12
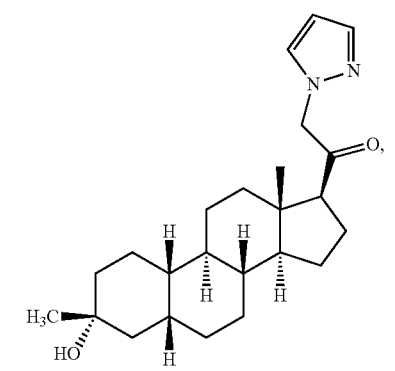
SA-13
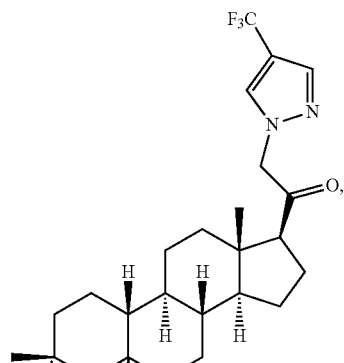
SA-14
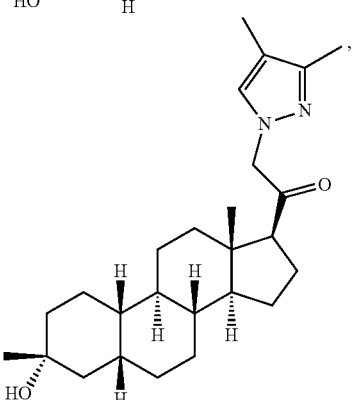
SA-15
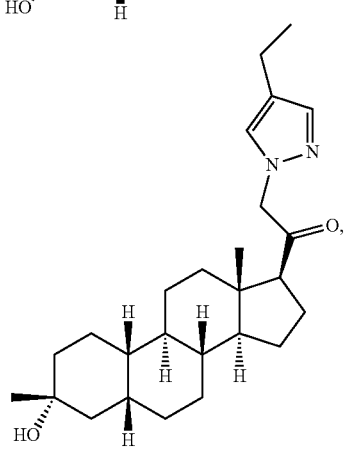
SA-16
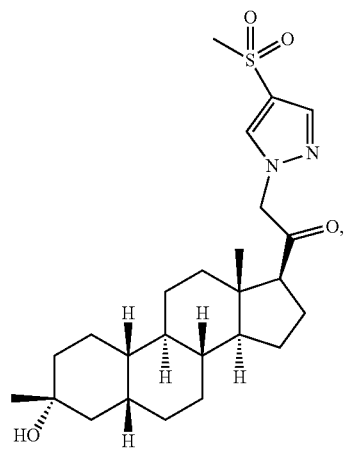
SA-17

-continued
SA-18
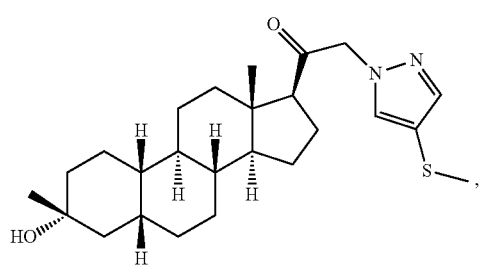
SA-24
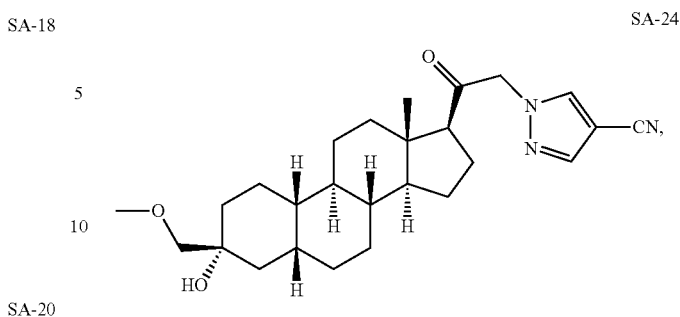
SA-20
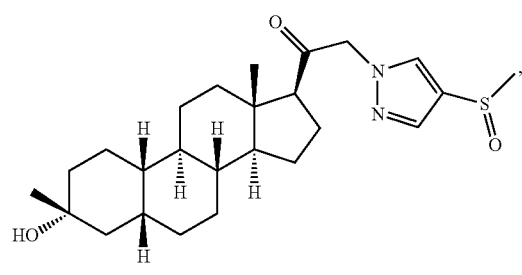
SA-25
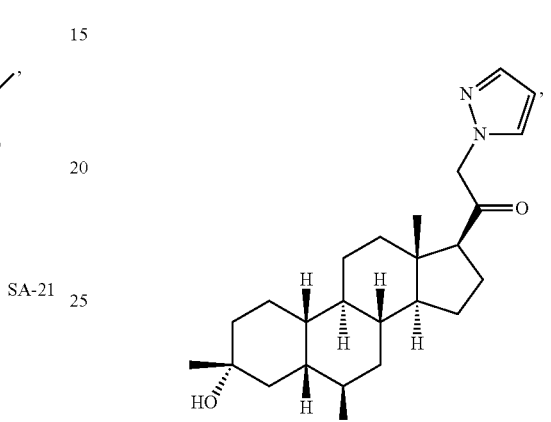
SA-21
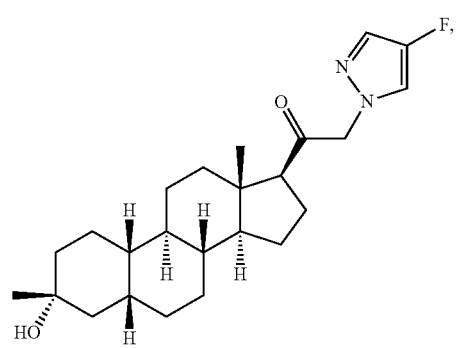
SA-22
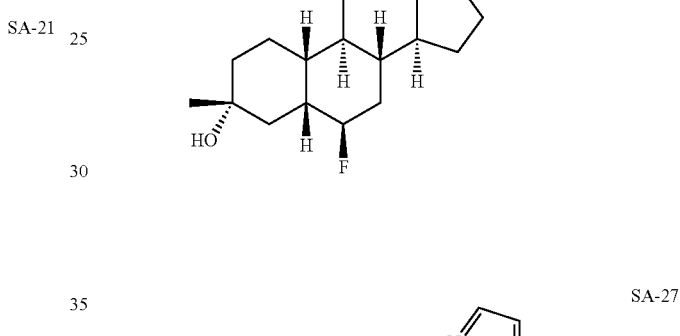
SA-27
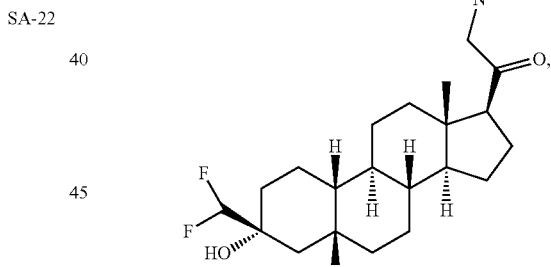
SA-23
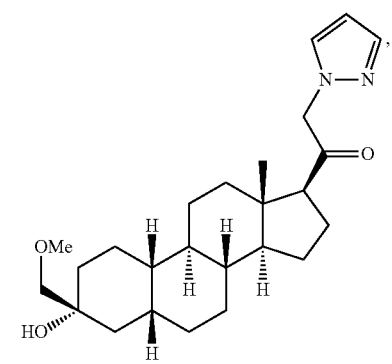
SA-28
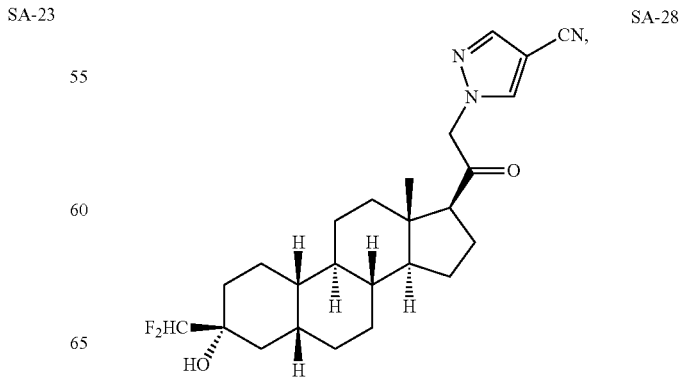

SA-29 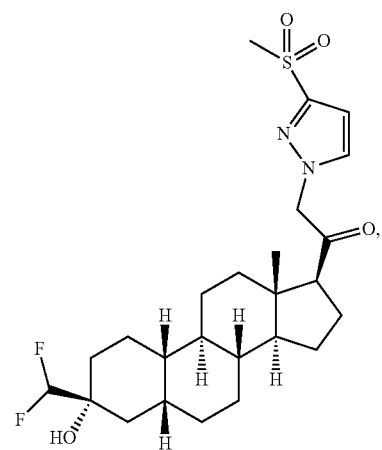
SA-30 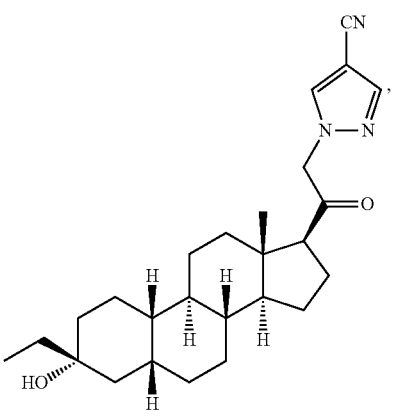
SA-31 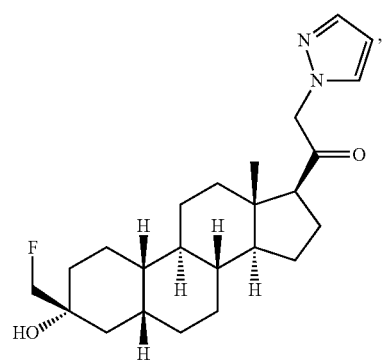
SA-32 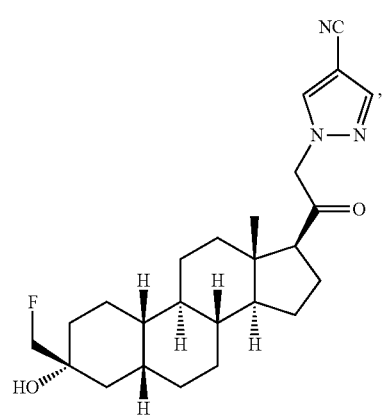
SA-33 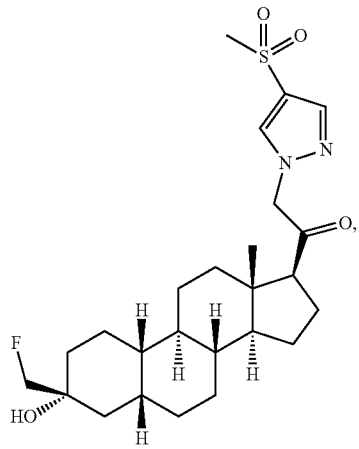
SA-34 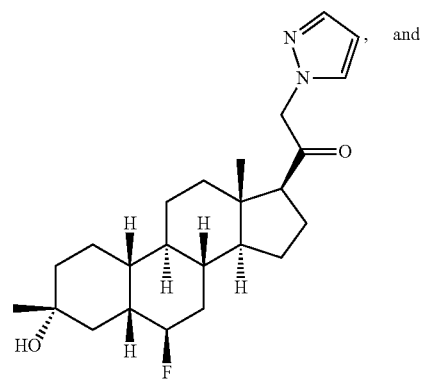
SA-35 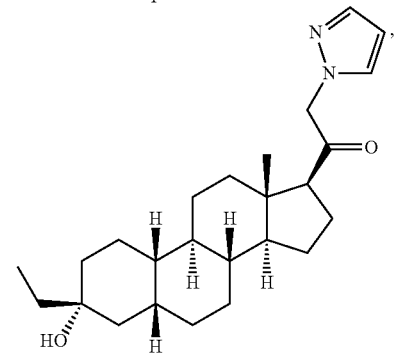
and pharmaceutically acceptable salts thereof.
In certain embodiments, a steroid of Formula (I) is selected from the group consisting of:
SB-1 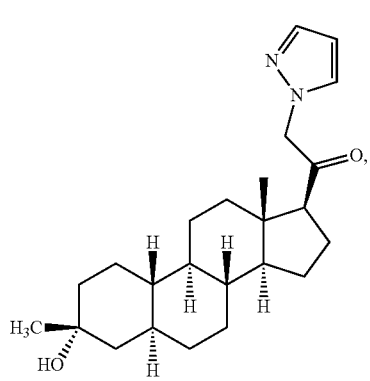

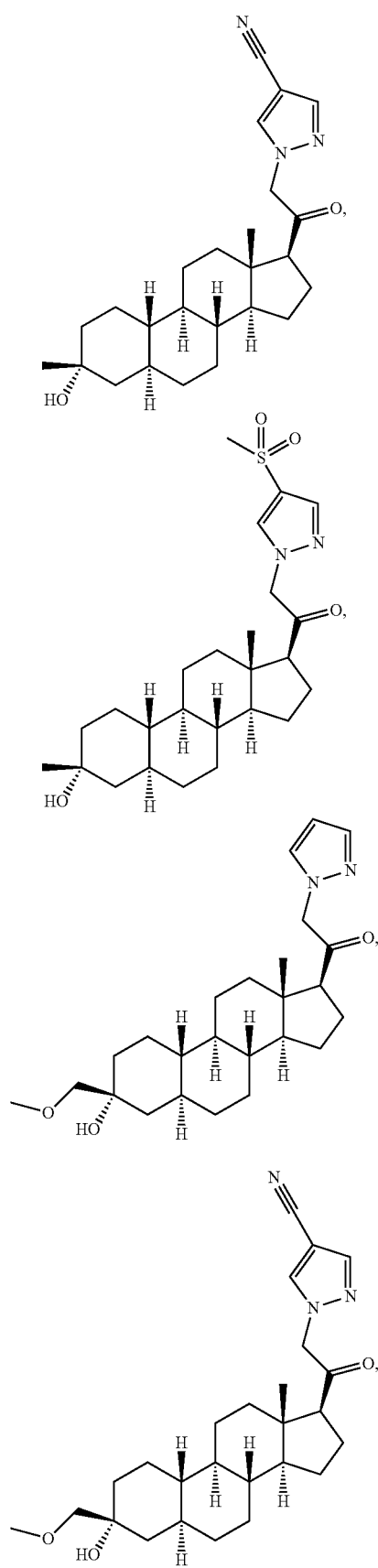
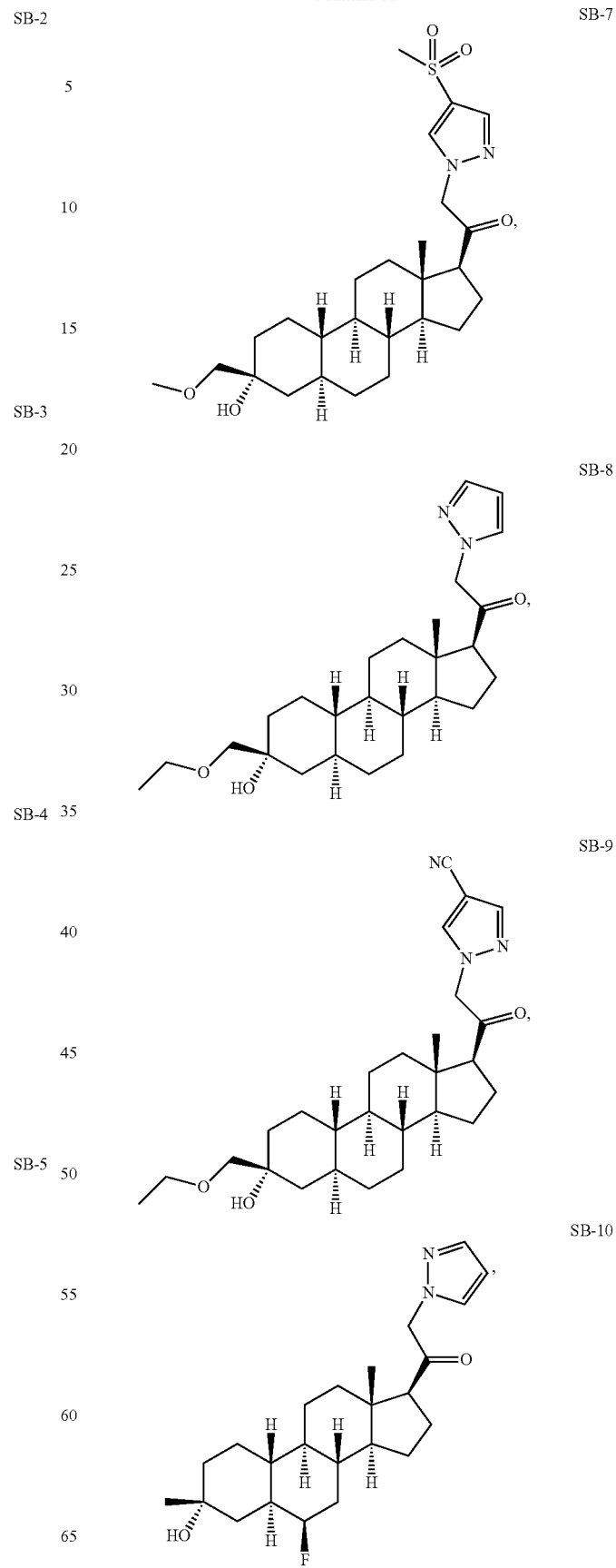

SB-11
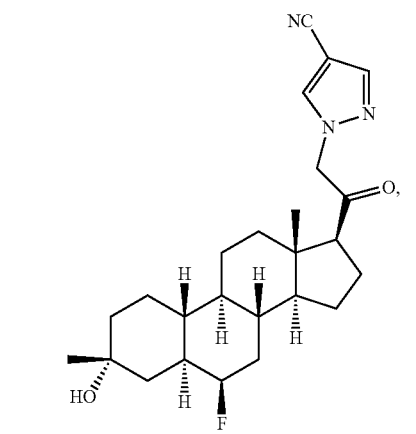
SB-12
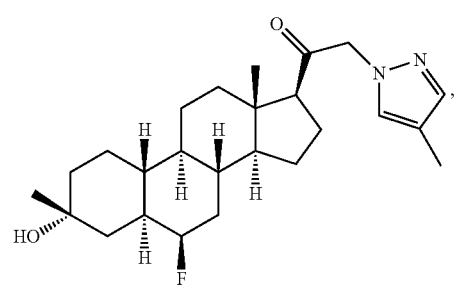
SB-13
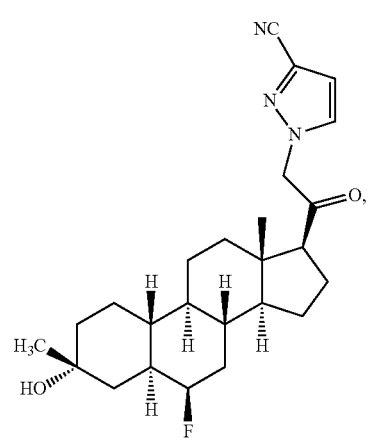
SB-14
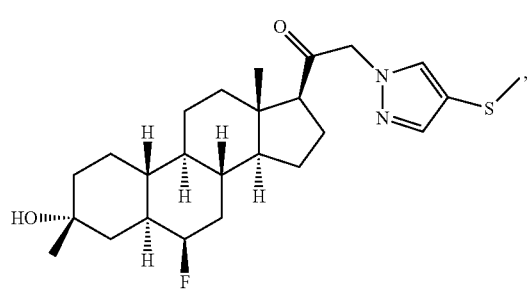
SB-15
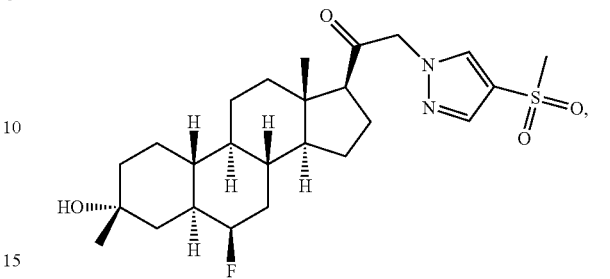
SB-18
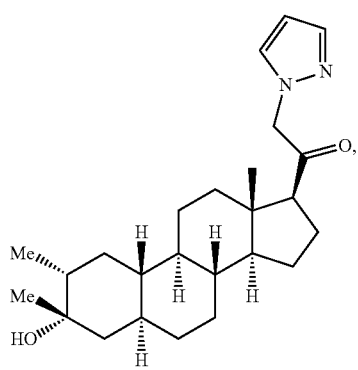
SB-19
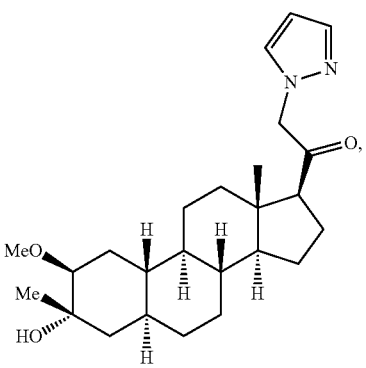
SB-20
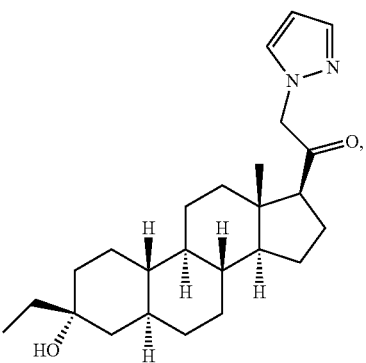

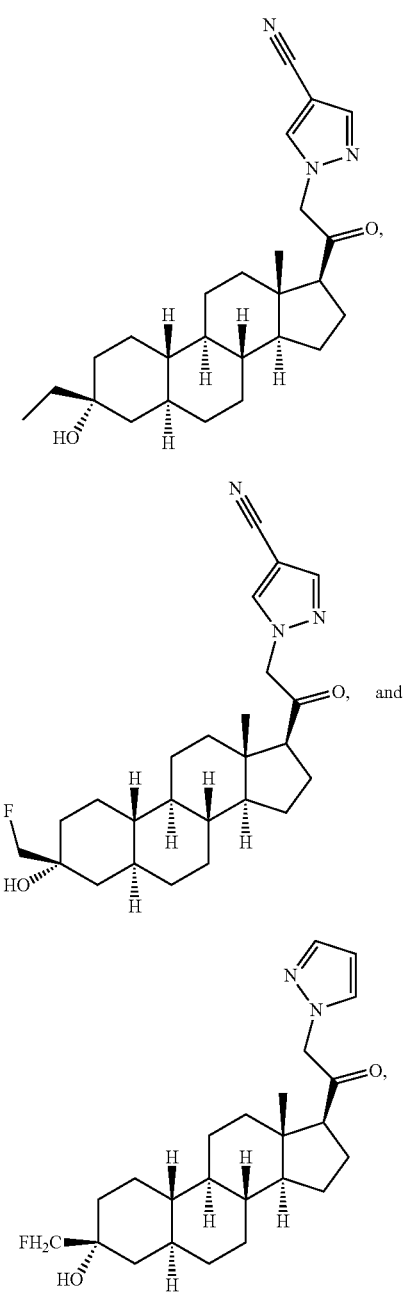

and pharmaceutically acceptable salts thereof.

Pharmaceutical Compositions

In another aspect, the invention provides a pharmaceutical composition comprising a compound of the present invention (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compostions of the present invention may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of the present invention can also be administered in sustained release forms or from sustained release drug delivery systems. A description of representative sustained release materials can be found in Remington's Pharmaceutical Sciences.

The present invention also relates to the pharmaceutically acceptable formulations of a compound of the present invention. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol®. See, e.g., U.S. Pat. No. 5,376,645. In certain embodiments, the formulation comprises hexapropyl-β-cyclodextrin (e.g., 10-50% in water).

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The following formulation examples illustrate representative pharmaceutical compositions that may be prepared in accordance with this invention. The present invention, however, is not limited to the following pharmaceutical compositions.

Exemplary Formulation 1—Tablets

A compound of the present invention may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 2—Capsules

A compound of the present invention may be admixed as a dry powder with a starch diluent in an approximate 1:1 weight ratio. The mixture is filled into 250 mg capsules (125 mg of active compound per capsule).

Exemplary Formulation 3—Liquid

A compound of the present invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 4—Tablets

A compound of the present invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 5—Injection

A compound of the present invention may be dissolved or suspended in a buffered sterile saline injectable aqueous medium to a concentration of approximately 5 mg/mL.

Exemplary Formulation 6—Tablets

A compound of the present invention may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 7—Tablets

A compound of the present invention may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 8—Tablets

A compound of the present invention may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 9—Tablets

A compound of the present invention may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 10—Tablets

A compound of the present invention may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Methods of Use and Treatment

As generally described herein, the present invention is directed to C21-substituted neuroactive steroids designed, for example, to act as GABA modulators. In certain embodiments, such compounds are envisioned to be useful as therapeutic agents for the inducement of anesthesia and/or sedation in a subject. In some embodiments, such compounds are envisioned to be useful as therapeutic agents for treating a CNS-related disorder (e.g., sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome).

Thus, in one aspect, the present invention provides a method of inducing sedation and/or anesthesia in a subject, comprising administering to the subject an effective amount of a compound of the present invention or a composition thereof. In certain embodiments, the compound is administered by intravenous administration.

Earlier studies (see, e.g., Gee et al., *European Journal of Pharmacology*, 136:419-423 (1987)) demonstrated that certain 3α-hydroxylated steroids are orders of magnitude more potent as modulators of the GABA receptor complex (GRC) than others had reported (see, e.g., Majewska et al., *Science* 232:1004-1007 (1986); Harrison et al., *J Pharmacol. Exp. Ther.* 241:346-353 (1987)). Majewska et al. and Harrison et al. taught that 3α-hydroxylated-5-reduced steroids are only capable of much lower levels of effectiveness. In vitro and in vivo experimental data have now demonstrated that the high potency of these steroids allows them to be therapeutically useful in the modulation of brain excitability via the GRC (see, e.g., Gee et al., *European Journal of Pharmacology*, 136:419-423 (1987); Wieland et al., *Psychopharmacology* 118(1):65-71 (1995)).

Various synthetic steroids have also been prepared as neuroactive steroids. See, for example, U.S. Pat. No. 5,232,917, which discloses neuroactive steroid compounds useful in treating stress, anxiety, insomnia, seizure disorders, and mood disorders, that are amenable to GRC-active agents, such as depression, in a therapeutically beneficial manner. Furthermore, it has been previously demonstrated that these steroids interact at a unique site on the GRC which is distinct from other known sites of interaction (e.g., barbiturates, benzodiazepines, and GABA) where therapeutically beneficial effects on stress, anxiety, sleep, mood disorders and seizure disorders have been previously elicited (see, e.g., Gee, K. W. and Yamamura, H. I., "Benzodiazepines and Barbiturates: Drugs for the Treatment of Anxiety, Insomnia and Seizure Disorders," in *Central Nervous System Disorders*, Horvell, ed., Marcel-Dekker, New York (1985), pp. 123-147; Lloyd, K. G. and Morselli, P. L., "Psychopharmacology of GABAergic Drugs," in *Psychopharmacology: The Third Generation of Progress*, H. Y. Meltzer, ed., Raven Press, N.Y. (1987), pp. 183-195; and Gee et al., *European Journal of Pharmacology*, 136:419-423 (1987). These compounds are desirable for their duration, potency, and oral activity (along with other forms of administration).

Compounds of the present invention, as described herein, are generally designed to modulate GABA function, and therefore to act as neuroactive steroids for the treatment and prevention of CNS-related conditions in a subject. Modulation, as used herein, refers to the inhibition or potentiation of GABA receptor function. Accordingly, the compounds and pharmaceutical compositions provided herein find use as therapeutics for preventing and/or treating CNS conditions in mammals including humans and non-human mammals. Thus, and as stated earlier, the present invention includes within its scope, and extends to, the recited methods of treatment, as well as to the compounds for such methods, and to the use of such compounds for the preparation of medicaments useful for such methods.

Exemplary CNS conditions related to GABA-modulation include, but are not limited to, sleep disorders [e.g., insomnia], mood disorders [e.g., depression, dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD))], schizophrenia spectrum disorders [e.g., schizophrenia, schizoaffective disorder], convulsive disorders [e.g., epilepsy (e.g., status epilepticus (SE)), seizures], disorders of memory and/or cognition [e.g., attention disorders (e.g., attention deficit hyperactivity disorder (ADHD)), dementia (e.g., Alzheimer's type dementia, Lewis body type dementia, vascular type dementia], movement disorders [e.g., Huntington's disease, Parkinson's disease], personality disorders [e.g., anti-social personality disorder, obsessive compulsive personality disorder], autism spectrum disorders (ASD) [e.g., autism, monogenetic causes of autism such as synaptophathy's, e.g., Rett syndrome, Fragile X syndrome, Angelman syndrome], pain [e.g., neuropathic pain, injury related pain syndromes, acute pain, chronic pain], traumatic brain injury (TBI), vascular diseases [e.g., stroke, ischemia, vascular malformations], substance abuse disorders and/or withdrawal syndromes [e.g., addition to opiates, cocaine, and/or alcohol], and tinnitus.

In yet another aspect, provided is a combination of a compound of the present invention and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In another aspect, provided is a method of treating or preventing brain excitability in a subject susceptible to or afflicted with a condition associated with brain excitability, comprising administering to the subject an effective amount of a compound of the present invention to the subject.

In yet another aspect, provided is a method of treating or preventing stress or anxiety in a subject, comprising administering to the subject in need of such treatment an effective amount of a compound of the present invention, or a composition thereof.

In yet another aspect, provided is a method of alleviating or preventing seizure activity in a subject, comprising administering to the subject in need of such treatment an effective amount of a compound of the present invention.

In yet another aspect, provided is a method of alleviating or preventing insomnia in a subject, comprising administering to the subject in need of such treatment an effective amount of a compound of the present invention, or a composition thereof.

In yet another aspect, provided is a method of inducing sleep and maintaining substantially the level of REM sleep that is found in normal sleep, wherein substantial rebound insomnia is not induced, comprising administering an effective amount of a compound of the present invention.

In yet another aspect, provided is a method of alleviating or preventing PMS or PND in a subject, comprising administering to the subject in need of such treatment an effective amount of a compound of the present invention.

In yet another aspect, provided is a method of treating or preventing mood disorders in a subject, comprising administering to the subject in need of such treatment an effective amount of a compound of the present invention. In certain embodiments the mood disorder is depression.

In yet another aspect, provided is a method of inducing anesthesia in a subject, comprising administering to the subject an effective amount of a compound of the present invention.

In yet another aspect, provided is a method of cognition enhancement or treating memory disorder by administering to the subject a therapeutically effective amount of a compound of the present invention. In certain embodiments, the disorder is Alzheimer's disease. In certain embodiments, the disorder is Rett syndrome.

In yet another aspect, provided is a method of treating attention disorders by administering to the subject a therapeutically effective amount of a compound of the present invention. In certain embodiments, the attention disorder is ADHD.

In certain embodiments, the compound is administered to the subject chronically. In certain embodiments, the compound is administered to the subject orally, subcutaneously, intramuscularly, or intravenously.

Anesthesia/Sedation

Anesthesia is a pharmacologically induced and reversible state of amnesia, analgesia, loss of responsiveness, loss of skeletal muscle reflexes, decreased stress response, or all of these simultaneously. These effects can be obtained from a single drug which alone provides the correct combination of effects, or occasionally with a combination of drugs (e.g., hypnotics, sedatives, paralytics, analgesics) to achieve very specific combinations of results. Anesthesia allows patients to undergo surgery and other procedures without the distress and pain they would otherwise experience.

Sedation is the reduction of irritability or agitation by administration of a pharmacological agent, generally to facilitate a medical procedure or diagnostic procedure.

Sedation and analgesia include a continuum of states of consciousness ranging from minimal sedation (anxiolysis) to general anesthesia.

Minimal sedation is also known as anxiolysis. Minimal sedation is a drug-induced state during which the patient responds normally to verbal commands. Cognitive function and coordination may be impaired. Ventilatory and cardiovascular functions are typically unaffected.

Moderate sedation/analgesia (conscious sedation) is a drug-induced depression of consciousness during which the patient responds purposefully to verbal command, either alone or accompanied by light tactile stimulation. No interventions are usually necessary to maintain a patent airway. Spontaneous ventilation is typically adequate. Cardiovascular function is usually maintained.

Deep sedation/analgesia is a drug-induced depression of consciousness during which the patient cannot be easily aroused, but responds purposefully (not a reflex withdrawal from a painful stimulus) following repeated or painful stimulation. Independent ventilatory function may be impaired and the patient may require assistance to maintain a patent airway. Spontaneous ventilation may be inadequate. Cardiovascular function is usually maintained.

General anesthesia is a drug-induced loss of consciousness during which the patient is not arousable, even to painful stimuli. The ability to maintain independent ventilatory function is often impaired and assistance is often required to maintain a patent airway. Positive pressure ventilation may be required due to depressed spontaneous ventilation or drug-induced depression of neuromuscular function. Cardiovascular function may be impaired.

Sedation in the intensive care unit (ICU) allows the depression of patients' awareness of the environment and reduction of their response to external stimulation. It can play a role in the care of the critically ill patient, and encompasses a wide spectrum of symptom control that will vary between patients, and among individuals throughout the course of their illnesses. Heavy sedation in critical care has been used to facilitate endotracheal tube tolerance and ventilator synchronization, often with neuromuscular blocking agents.

In some embodiments, sedation (e.g., long-term sedation, continuous sedation) is induced and maintained in the ICU for a prolonged period of time (e.g., 1 day, 2 days, 3 days, 5 days, 1 week, 2 week, 3 weeks, 1 month, 2 months). Long-term sedation agents may have long duration of action. Sedation agents in the ICU may have short elimination half-life.

Procedural sedation and analgesia, also referred to as conscious sedation, is a technique of administering sedatives or dissociative agents with or without analgesics to induce a state that allows a subject to tolerate unpleasant procedures while maintaining cardiorespiratory function.

Anxiety Disorders

Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of Phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Neurodegenerative Diseases and Disorders

The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cycloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Epilepsy

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grand-mal seizures on awakening, West syndrome, Lennox-Gastaut syndrome, partial epilepsy, e.g., temporal lobe epilepsy, frontal lobe epilepsy, benign focal epilepsy of childhood.

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

Compositions described herein can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pres sures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative pyrazoles that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

$^1$H-NMR reported herein (e.g., for intermediates) may be a partial representation of the full NMR spectrum of a compound, e.g., a compound described herein. For example, the reported $^1$H NMR may exclude the region between δ (ppm) of about 1 to about 2.5 ppm. Copies of full $^1$H-NMR spectrum for representative examples are provided in the Figures.

Exemplary general method for preparative HPLC: Column: Waters RBridge prep 10 μm C18, 19*250 mm. Mobile phase: aectonitrile, water (NH$_4$HCO$_3$) (30 L water, 24 g NH$_4$HCO$_3$, 30 mL NH$_3$.H$_2$O). Flow rate: 25 mL/min Exemplary general method for analytical HPLC: Mobile phase: A: water (10 mM NH$_4$HCO$_3$), B: acetonitrileGradient: 5%-95% B in 1.6 or 2 min Flow rate: 1.8 or 2 mL/min; Column: XBridge C18, 4.6*50 mm, 3.5 μm at 45 C.

Synthetic Procedures

The compounds of the invention can be prepared in accordance with methods described in the art (Upasani et al., *J. Med. Chem.* 1997, 40:73-84; and Hogenkamp et al., *J. Med. Chem.* 1997, 40:61-72) and using the appropriate reagents, starting materials, and purification methods known to those skilled in the art. In some embodiments, compounds described herein can be prepared using methods shown in general Schemes 1-4, comprising a nucleophilic substitution of 19-nor pregnane bromide with a neuclophile. In certain embodiments, the nucleophile reacts with the 19-nor pregnane bromide in the presence of K$_2$CO$_3$ in THF.

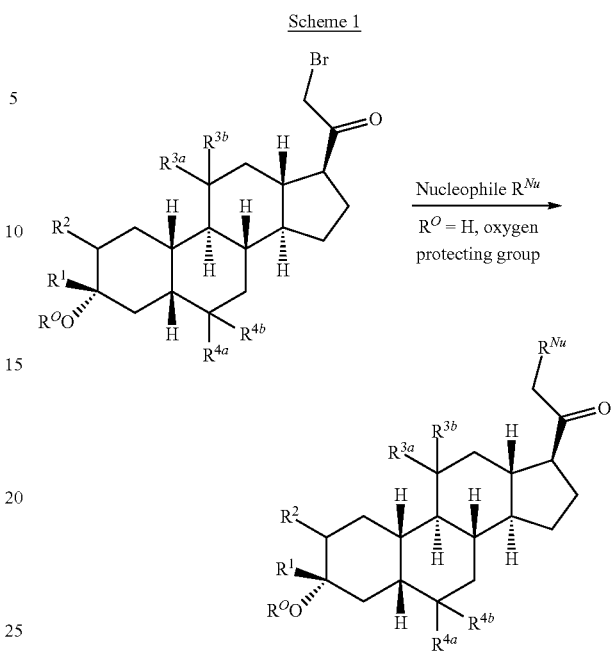

Scheme 1

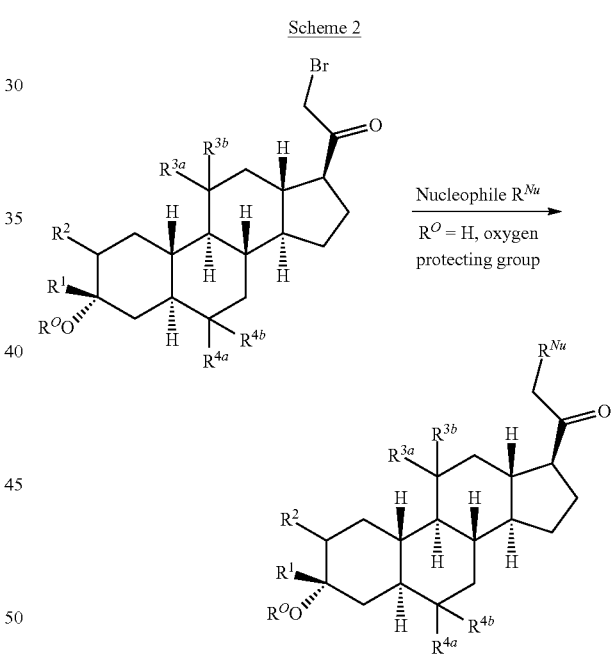

Scheme 2

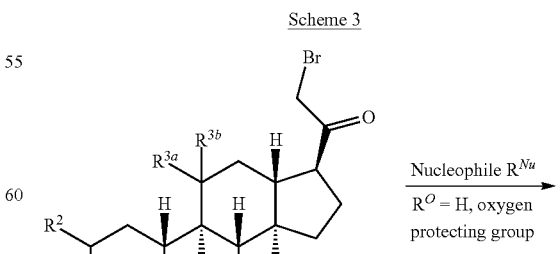

Scheme 3

Example 1. Synthesis of SA and SA Intermediates

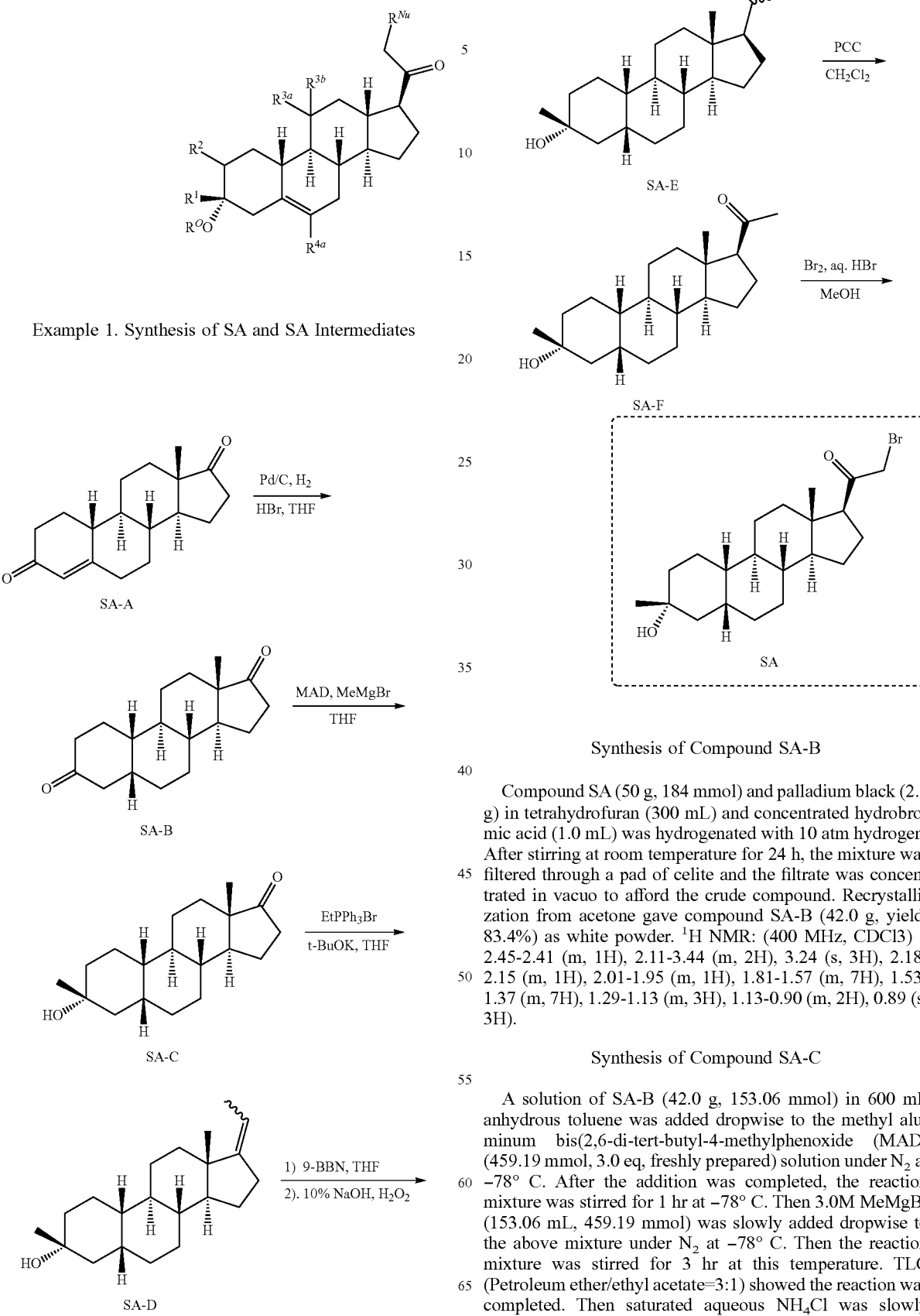

Synthesis of Compound SA-B

Compound SA (50 g, 184 mmol) and palladium black (2.5 g) in tetrahydrofuran (300 mL) and concentrated hydrobromic acid (1.0 mL) was hydrogenated with 10 atm hydrogen. After stirring at room temperature for 24 h, the mixture was filtered through a pad of celite and the filtrate was concentrated in vacuo to afford the crude compound. Recrystallization from acetone gave compound SA-B (42.0 g, yield: 83.4%) as white powder. $^1$H NMR: (400 MHz, CDCl3) δ 2.45-2.41 (m, 1H), 2.11-3.44 (m, 2H), 3.24 (s, 3H), 2.18-2.15 (m, 1H), 2.01-1.95 (m, 1H), 1.81-1.57 (m, 7H), 1.53-1.37 (m, 7H), 1.29-1.13 (m, 3H), 1.13-0.90 (m, 2H), 0.89 (s, 3H).

Synthesis of Compound SA-C

A solution of SA-B (42.0 g, 153.06 mmol) in 600 mL anhydrous toluene was added dropwise to the methyl aluminum bis(2,6-di-tert-butyl-4-methylphenoxide (MAD) (459.19 mmol, 3.0 eq, freshly prepared) solution under $N_2$ at −78° C. After the addition was completed, the reaction mixture was stirred for 1 hr at −78° C. Then 3.0M MeMgBr (153.06 mL, 459.19 mmol) was slowly added dropwise to the above mixture under $N_2$ at −78° C. Then the reaction mixture was stirred for 3 hr at this temperature. TLC (Petroleum ether/ethyl acetate=3:1) showed the reaction was completed. Then saturated aqueous $NH_4Cl$ was slowly added dropwise to the above mixture at −78° C. After the addition was completed, the mixture was filtered, the filter cake was washed with EtOAc, the organic layer was washed with water and brine, dried over anhydrous Na$_2$SO$_4$, filtered and concentrated, purified by flash Chromatography on silica gel (Petroleum ether/ethyl acetate 20:1 to 3:1) to afford compound SA-C (40.2 g, yield: 90.4%) as white powder. $^1$H NMR: (400 MHz, CDCl3) δ 2.47-2.41 (m, 1H), 2.13-2.03 (m, 1H), 1.96-1.74 (m, 6H), 1.70-1.62 (m, 1H), 1.54-1.47 (m, 3H), 1.45-1.37 (m, 4H), 1.35-1.23 (m, 8H), 1.22-1.10 (m, 2H), 1.10-1.01 (m, 1H), 0.87 (s, 3H).

Synthesis of Compound SA-D

To a solution of PPh$_3$EtBr (204.52 g, 550.89 mmol) in THF (500 mL) was added a solution of t-BuOK (61.82 g, 550.89 mmol) in THF (300 mL) at 0° C. After the addition was completed, the reaction mixture was stirred for 1 h 60° C., then SA-C (40.0 g, 137.72 mmol) dissolved in THF (300 mL) was added dropwise at 60° C. The reaction mixture was heated to 60° C. for 18 h. The reaction mixture was cooled to room temperature and quenched with Sat. NH$_4$Cl, extracted with EtOAc (3*500 mL). The combined organic layers were washed with brine, dried and concentrated to give the crude product, which was purified by a flash column chromatography (Petroleum ether/ethyl acetate 50:1 to 10:1) to afford compound SA-D (38.4 g, yield: 92%) as a white powder. $^1$H NMR: (400 MHz, CDCl3) δ 5.17-5.06 (m, 1H), 2.42-2.30 (m, 1H), 2.27-2.13 (m, 2H), 1.89-1.80 (m, 3H), 1.76-1.61 (m, 6H), 1.55-1.43 (m, 4H), 1.42-1.34 (m, 3H), 1.33-1.26 (m, 6H), 1.22-1.05 (m, 5H), 0.87 (s, 3H).

Synthesis of Compound SA-E

To a solution of SA-D (38.0 g, 125.62 mmol) in dry THF (800 mL) was added dropwise a solution of BH$_3$.Me$_2$S (126 mL, 1.26 mol) under ice-bath. After the addition was completed, the reaction mixture was stirred for 3 h at room temperature (14-20° C.). TLC (Petroleum ether/ethyl acetate 3:1) showed the reaction was completed. The mixture was cooled to 0° C. and 3.0M aqueous NaOH solution (400 mL) followed by 30% aqueous H$_2$O$_2$ (30%, 300 mL) was added. The mixture was stirred for 2 h at room temperature (14-20° C.), and then filtered, extracted with EtOAc (3*500 mL). The combined organic layers were washed with saturated aqueous Na$_2$S$_2$O$_3$, brine, dried over Na$_2$SO$_4$ and concentrated in vacuum to give the crude product (43 g, crude) as colorless oil. The crude product was used in the next step without further purification.

Synthesis of Compound SA-F

To a solution of SA-E (43.0 g, 134.16 mmol) in dichloromethane (800 mL) at 0° C. and PCC (53.8 g, 268.32 mmol) was added portion wise. Then the reaction mixture was stirred at room temperature (16-22° C.) for 3 h. TLC (Petroleum ether/ethyl acetate 3:1) showed the reaction was completed, then the reaction mixture was filtered, washed with DCM. The organic phase was washed with saturated aqueous Na$_2$S$_2$O$_3$, brine, dried over Na$_2$SO$_4$ and concentrated in vacuum to give the crude product. The crude product was purified by a flash column chromatography (Petroleum ether/ethyl acetate 50:1 to 8:1) to afford compound SA-F (25.0 g, yield: 62.5%, over two steps) as a white powder. $^1$H NMR (SA-F): (400 MHz, CDCl3) δ 2.57-2.50 (m, 1H), 2.19-2.11 (m, 4H), 2.03-1.97 (m, 1H), 1.89-1.80 (m, 3H), 1.76-1.58 (m, 5H), 1.47-1.42 (m, 3H), 1.35-1.19 (m, 10H), 1.13-1.04 (m, 3H), 0.88-0.84 (m, 1H), 0.61 (s, 3H).

Synthesis of Compound SA

To a solution of SA-F (10 g, 31.4 mmol) and aq. HBr (5 drops, 48% in water) in 200 mL of MeOH was added dropwise bromine (5.52 g, 34.54 mmol). The reaction mixture was stirred at 17° C. for 1.5 h. The resulting solution was quenched with saturated aqueous NaHCO$_3$ at 0° C. and extracted with EtOAc (150 mL×2). The combined organic layers were dried and concentrated. The residue was purified by column chromatography on silica gel eluted with (PE:EA=15:1 to 6:1) to afford compound SA (9.5 g, yield: 76.14%) as a white solid. LC/MS: rt 5.4 min; m/z 379.0, 381.1, 396.1.

Example 2. Synthesis of SB and SB Intermediates

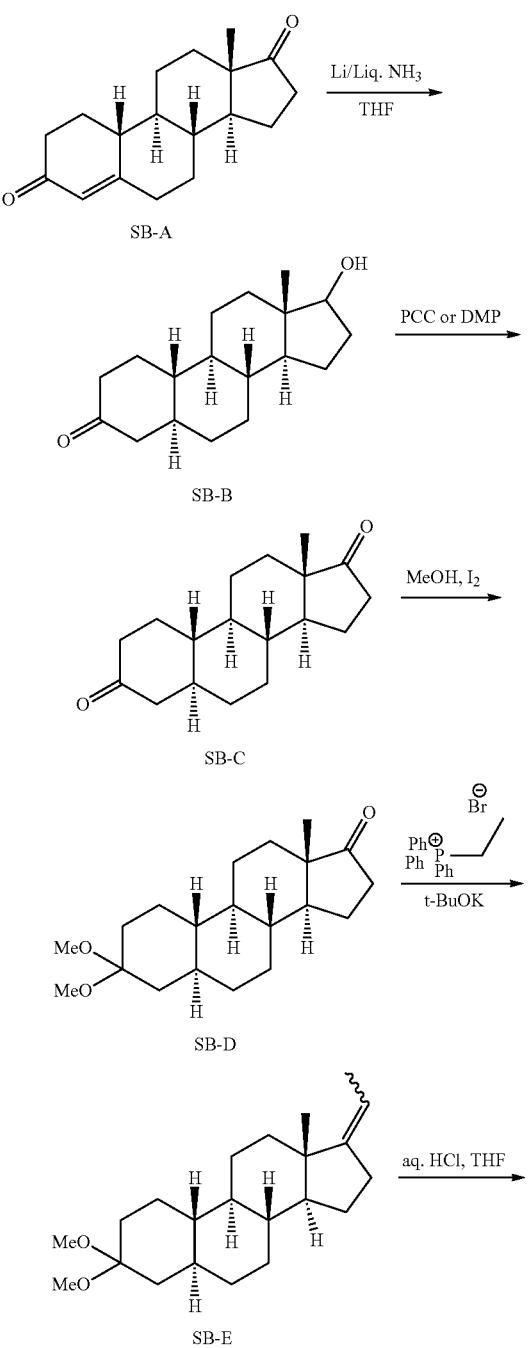

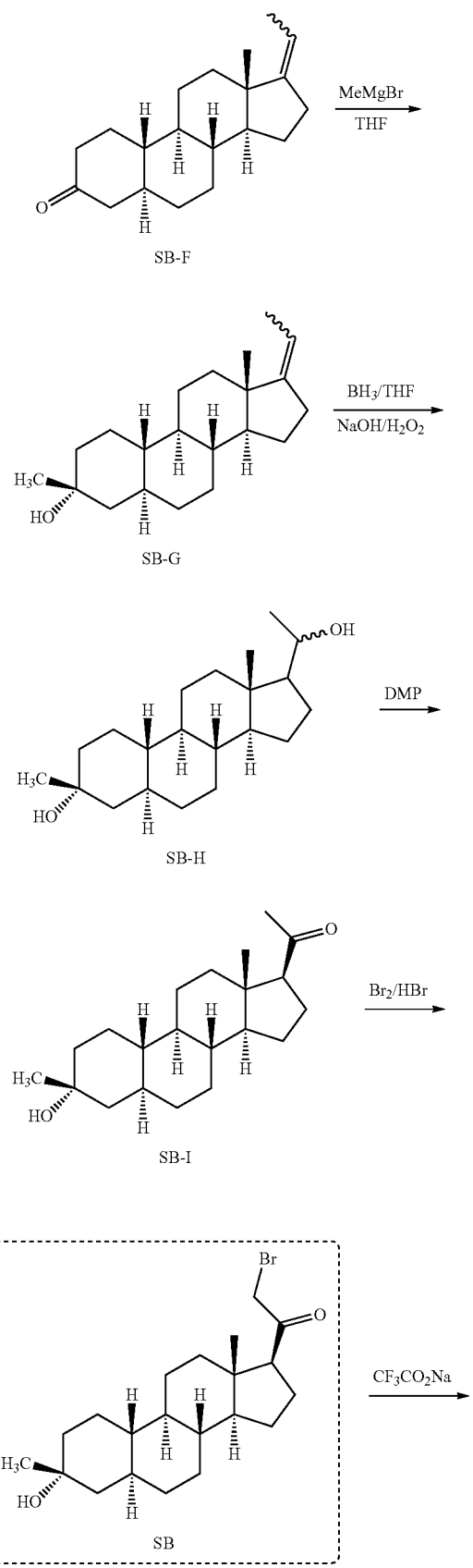

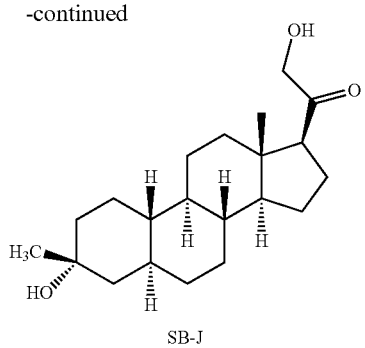

Synthesis of Compounds SB-B and SB-C

Small pieces of lithium (7.63 g, 1.1 mol) were added to 2.7 L of condensed ammonia in a three neck flask at −70° C. As soon as all lithium was dissolved, the blue solution was warmed to −50° C. A solution of 19-norandrost-4-ene-3,17-dione SB-A (1, 30 g, 110 mmol) and tert-BuOH (8.14 g, 110 mmol) in 800 ml of anhydrous tetrahydrofuran was added dropwise and stirred for 90 min until the reaction mixture turned light yellow. Ammonium chloride (70 g) was added and excess ammonia was left to evaporate. The residue was extracted with 0.5N HCl (500 mL) and dichloromethane (500 mL×2). The combined organic layers were washed with saturated NaHCO$_3$ solution, dried over Na$_2$SO$_4$, filtered and concentrated to give a mixture of SB-B and SB-C (21 g, 70%) which was directly used in the next step without further purification. A solution of SB-B and SB-C (21 g, 76 mmol) in 50 mL of anhydrous dichloromethane was added to a suspension of pyridinium chlorochromate (PCC) (32.8 g, 152 mmol) in 450 mL of dichloromethane. After stirring at room temperature for 2 h, 2N NaOH solution (500 mL) was added to the dark brown reaction mixture and stirred for another 10 min. The resulting solution was extracted with dichloromethane, the combined organic layers were washed with 2N HCl, brine, dried over Na$_2$SO$_4$, filtered and concentrated. The residue was purified by chromatography on silica gel (pertroleum ether/ethyl acetate=20:1 to 10:1) to afford title compound SB-C (16.8 g, 80%) as a white solid. $^1$H NMR of SB-B (400 MHz, CDCl$_3$), δ (ppm), 3.65 (t, 1H, 1H), 0.77 (s, 3H). $^1$H NMR of SB-C (400 MHz, CDCl$_3$), δ (ppm), 0.88 (s, 3H).

Synthesis of Compound SB-D

To a solution of compound SB-C (16.8 g, 61.3 mmol) in methanol (250 mL) was added iodine (1.54 g, 6.1 mmol). After stirring at 60° C. for 12 h, the solvent was removed in vacuo. The crude product was dissolved in dichloromethane (200 mL) and washed with saturated NaHCO$_3$ (150 mL), brine, dried over Na$_2$SO$_4$, filtered and concentrated. The residue was purified by chromatography on basic alumina (pertroleum ether/ethyl acetate=100:1) to give compound SB-D (14 g, 43.8 mmol, 71%). $^1$H NMR (400 MHz, CDCl$_3$), δ (ppm), 3.18 (s, 3H), 3.12 (s, 3H), 0.85 (s, 3H).

Synthesis of Compound SB-E

To a suspension of t-BuOK (7.36 g, 65.7 mmol) in THF (100 mL) at 0° C. was added ethyltriphenylphosphonium bromide (26 g, 70 mmol) slowly. After stirring at 60° C. for 3 h, compound SB-D (7 g, 21.9 mmol) was added and the mixture was stirred at 60° C. for another 2 h. After cooling to room temperature, the reaction mixture was poured into saturated ammonium chloride and extracted with EtOAc (2×500 mL). The combined organic layers were washed with brine, dried over sodium sulfate, filtered and concentrate to afford the crude compound SB-E (7.36 g, 100%). The crude product was used in the next step without further purification.

Synthesis of Compound SB-F

A solution of crude compound SB-E (7.36 g, 21.9 mmol) in THF (50 mL) was acidified to pH=3 by 1N aqueous HCl. After stirring at room temperature for 12 h, the reaction mixture was extracted with ethyl acetate (250 mL×3). The combined organic layers were washed with brine, dried over sodium sulfate, filtered and concentrated. The residue was purified by column chromatography (pertroleum ether/ethyl acetate=30:1 to 20:1) to afford compound SB-F (4.8 g, 16.7 mmol, 76% for two steps). $^1$H NMR (400 MHz, CDCl$_3$), δ (ppm), 5.12-5.10 (m, 1H), 0.77 (s, 3H).

Synthesis of Compound SB-G

To a solution of MeMgBr (28 mmol, 1M in THF) in THF (50 mL) at 0° C. was added a solution of compound SB-F (4.8 g, 16.8 mmol) in dry THF (10 mL) via syringe pump over 30 min. After stirring at 0° C. for 5 h, the reaction mixture was allowed to warm up and stirred at room temperature overnight. The reaction mixture was quenched with iced-cold water and extracted with ethyl acetate (150 mL×3). The combined organic layers were washed with brine, dried over sodium sulfate, filtered and concentrated. The white residue was purified by flash column chromatography (pertroleum ether/ethyl acetate=20:1 to 10:1) to give compound SB-G (2.5 g, 8.28 mmol, 49%; Rf=0.35, petroleum ether/ethyl acetate=10:1). $^1$H NMR (400 MHz, CDCl$_3$), δ (ppm), 5.05-5.03 (m, 1H), 1.21 (s, 3H), 0.90 (s, 3H).

Synthesis of Compound SB-H

To a solution of compound SB-G (2 g, 6.62 mmol) in dry THF (50 mL) was added borane-tetrahydrofuran complex (20 mL; 1.0M solution in THF). After stirring at room temperature for 1 hour, the reaction mixture was cooled in an ice bath then quenched slowly with 10% aqueous NaOH (10 mL) followed by 30% aqueous solution of H$_2$O$_2$ (12 mL). After stirring at room temperature for one hour, the mixture was extracted with EtOAc (3×100 mL). The combined organic layers were washed with 10% aqueous Na$_2$S$_2$O$_3$ (100 mL), brine (100 mL), dried over MgSO$_4$, filtered and concentrated to afford crude compound SB-H (2 g, 100%). The crude product was used in the next step without further purification.

Synthesis of Compound SB-I

To a solution of crude compound SB-H (2 g, 6.62 mmol) in 60 mL of wet dichloromethane (dichloromethane had been shaken with several milliliters of H$_2$O then separated from the water layer) was added Dess-Martin periodinate (5.5 g, 13 mmol). After stirring at room temperature for 24 h, the reaction mixture was extracted with dichloromethane (3×100 mL). The combined organic layers were washed with 10% aqueous Na$_2$S$_2$O$_3$ (100 mL), brine (100 mL), dried over MgSO$_4$, filtered and concentrated. The residue was purified by chromatography on silica gel (pertroleum ether/ethyl acetate=10:1 to 5:1) to afford compound SB-I (1 g, 3.14 mmol, 47% for two steps) as a white solid. $^1$H NMR (400 MHz, CDCl$_3$), δ (ppm), 2.56 (t, 1H), 2.11 (s and m, 4H), 2.0 (dt, 1H), 1.8 (dm, 2H), 1.54 (m, 6H) 1.43 (m, 1H), 1.34 (m, 2H), 1.20 (m, 12H), 0.7 (m, 2H), 0.62 (s, 3H).

Synthesis of Compound SB

To a solution of compound SB-I (600 mg, 1.89 mmol) in MeOH (20 mL) was added 5 drops of HBr (48%) followed by bromine (302 mg, 1.89 mmol). After stirring at room temperature for 1 h, the reaction mixture was poured into ice-water then extracted with ethyl acetate (100 mL×3). The combined organic layers were washed with brine (200 mL), dried over MgSO$_4$, filtered and concentrated to give crude compound SB (600 mg).

Synthesis of Compound SB-J

A solution of compound SB (600 mg, 1.5 mmol) in acetone 10 mL was treated with CF$_3$COOH (6.8 mL) and Et$_3$N (9.5 mL). After refluxed for 30 min, CF$_3$COONa salt (4.49 g, 33 mmol) was added in parts over a period of 10 hr. The reaction mixture was allowed to cool to room temperature and the solvent was removed in vaccuo. The residue was extracted with ethyl acetate, dried over MgSO$_4$, filtered and concentrated. The mixture was purified by chromatography on silica gel (pertroleum ether/ethyl acetate=10:1 to 3:1) to afford SB-J (300 mg, yield: 50% for two steps). $^1$H NMR (400 MHz, CDCl$_3$), δ (ppm), 4.23-4.13 (m, 2H), 2.48-2.44 (m), 0.64 (s, 3H).

Example 3. Synthesis of SA-V Compound

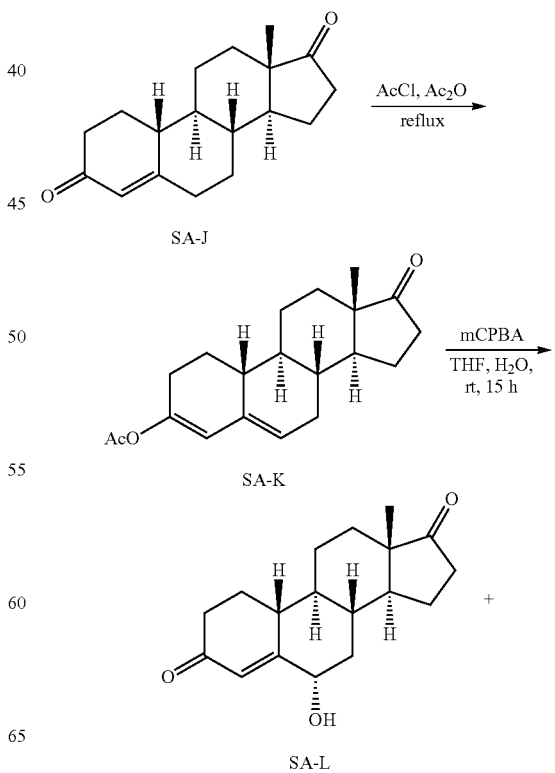

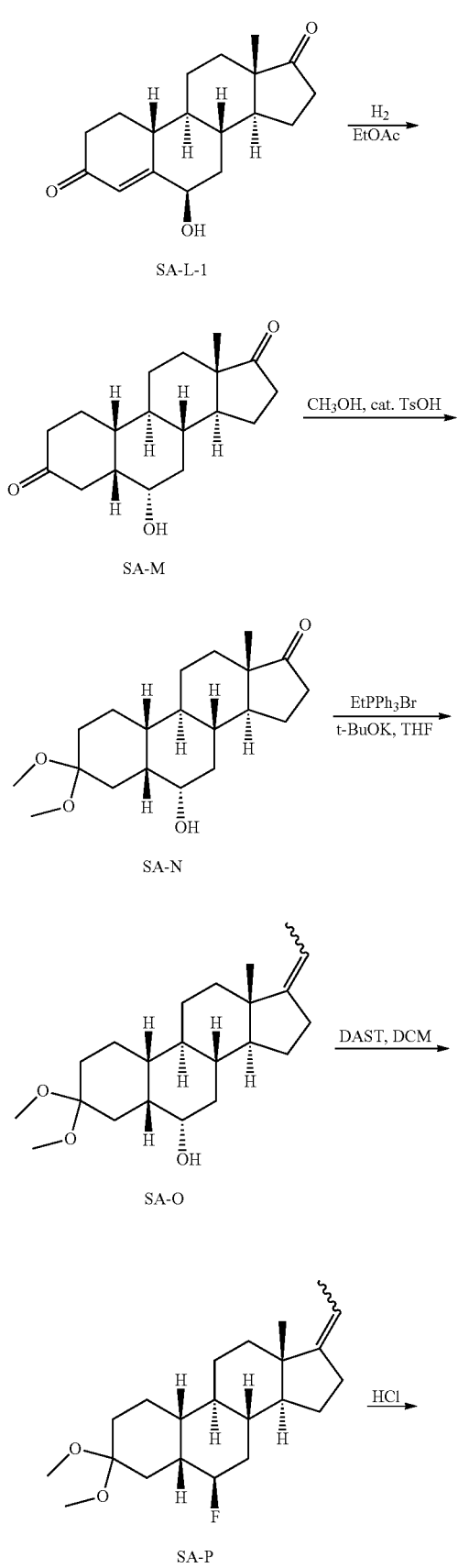
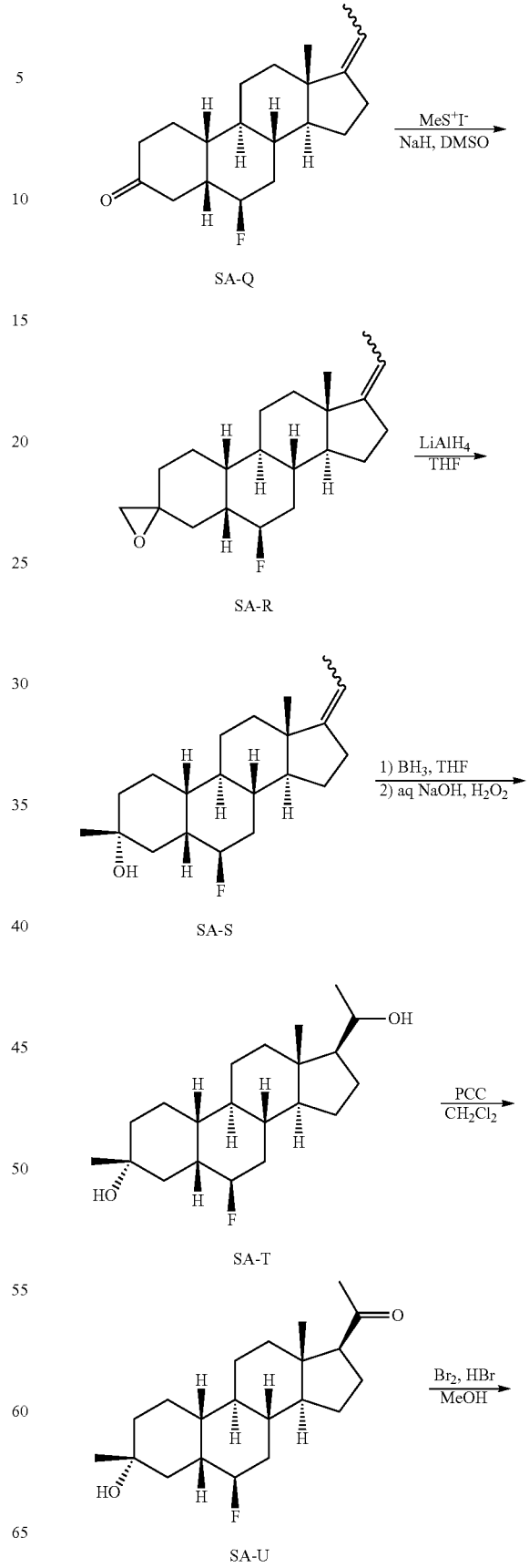

-continued

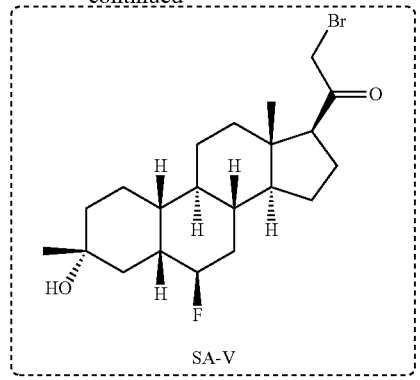

SA-V

Synthesis of Compound SA-K

Compound SA-J (10 g, 36.7 mmol) was added to 50 mL acetyl chloride and 50 mL acetic anhydride. The reaction mixture was heated to 120° C. for 5 h, evaporated in vacuo to afford SA-K as a white solid (10 g, 87% yield). $^1$H NMR (400 MHz, CDCl$_3$), δ (ppm), 5.78 (s, 1H), 5.55 (s, 1H), 2.4 (2H, dd), 2.13 (s, 3H), 0.90 (s, 3H).

Synthesis of Compound SA-L

To a solution of reactant SA-K (10 g, 31.8 mmol) in 200 mL THF and 20 mL H$_2$O, was added mCPBA (11 g, 63.6 mmol) at 0° C., stirred at rt for 15 h, the reaction mixture was extracted 500 mL EtOAc, washed with 100 mL saturated Na$_2$SO$_3$, 100 mL saturated NaHCO$_3$ and 100 mL brine and evaporated in vacuo then purified by silica gel flash chromatography on silica gel (Petroleum ether/ethyl acetate=5:1) to afford SA-L-1 as a white solid (2.2 g, 24% yield) (eluted first) and SA-L as the white solid (1.1 g, 12% yield) (eluted second). SA-L-1: 1H NMR (400 MHz, CDCl3), δ (ppm), 5.92 (s, 1H), 4.44 (s, 1H), 0.95 (s, 3H). SA-L: 1H NMR (400 MHz, CDCl3), δ (ppm), 6.25 (s, 1H), 4.28-4.25 (m, 1H), 0.93 (s, 3H).

Synthesis of Compound SA-M

To a solution of SA-L (2 g, 6.94 mmol) in 50 mL EtOAc, was added Pd\C 200 mg. The reaction mixture was hydrogenated in 1 atm H$_2$ for 15 h. The reaction mixture was evaporated in vacuo then purified by chromatography (Petroleum ether/ethyl acetate=1:2) to afford SA-M as a white solid (1.5 g, 75% yield). $^1$H NMR (400 MHz, CDCl$_3$), δ (ppm), 3.97 (td, 11H), 0.88 (s, 311).

Synthesis of Compound SA-N

To a solution of SA-M (1 g, 3.4 mmol) in 100 mL MeOH, was added TsOH 50 mg, heated to 60° C. for 2 h. The reaction mixture was extracted 500 mL EtOAc, washed with 100 mL sat. NaHCO$_3$, 100 mL brine solution and evaporated in vacuo to afford SA-N as a white solid (1 g, 91% yield).

Synthesis of Compound SA-O

To a solution of ethyltriphenylphosphonium bromide (10.67 g, 28.84 mmol) in 30 mL THF, was added KOt-Bu (3.23 g, 28.80 mmol). The reaction was heated to 60° C. for 1 h. SA-N (3.23 g, 9.6 mmol) was added to the mixture, stirred at 60° C. for 15 h. The reaction mixture was extracted 500 mL EtOAc, washed with brine solutions, and evaporated in vacuo evaporated then purified by chromatography (Petroleum ether/ethyl acetate=3:1) to afford SA-O as a white solid (2 g, 62% yield). $^1$H NMR (400 MHz, MeOD), δ (ppm) 5.15-5.12 (m, 1H), 3.80-3.78 (m, 1H), 3.21 (s, 3H), 3.15 (s, 3H), 1.67 (d, 3H), 0.95 (s, 3H).

Synthesis of Compound SA-P

To a solution of SA-O (0.5 g, 1.43 mmol) in 10 mL DCM, was added DAST 0.5 mL at −78° C. The reaction mixture was stirred at −78° C. for 30 min, then was quenched with 5 mL sat. NaHCO$_3$, extracted with 50 mL DCM, washed with brine, dried and concentrated in vacuo, purified by chromatography (Petroleum ether/ethyl acetate=30:1) to afford SA-P as a white solid 175 mg, 35% yield.

Synthesis of Compound SA-Q

To a solution of SA-P (350 mg, 1 mmol) in 20 mL THF, was added 2M HCl 2 mL, stirred at rt for 1 h. The reaction mixture was quenched with 5 mL H$_2$O and extracted with 100 mL EtOAc, washed with brine and evaporated in vacuo then purified by chromatography (Petroleum ether/ethyl acetate=10:1) to afford SA-Q as a white solid (210 mg, 60% yield). $^1$H NMR (400 MHz, CDCl$_3$), δ (ppm) 5.17-5.14 (m, 1H), 4.80-4.66 (m, 1H), 2.61-2.57 (m, 1H), 1.79 (d, 3H), 0.93 (s, 3H).

Synthesis of Compound SA-R

To a stirred solution of trimethylsulfonium iodide (3.2 g, 16 mmol) in 10 mL of DMSO was added NaH (60%; 400 mg, 16 mmol). After stirring at room temperature for 1 h, a suspension of SA-Q (486 mg, 1.6 mmol) in 5 mL of DMSO was added dropwise. After 15 h, the reaction mixture was poured into ice-cold water (100 mL) and extracted with 300 mL EtOAc, washed with 100 mL brine solution, and evaporated in vacuo then purified by chromatography (Petroleum ether/ethyl acetate=10:1) to afford SA-R and its isomer as a white solid (290 mg, 58% yield).

Synthesis of Compound SA-S

To a solution of SA-R and its isomer (300 mg, 0.94 mmol) in 10 mL THF, was added LiAH$_4$ (100 mg, 2.7 mmol), stirred at rt for 1 h. The reaction mixture was quenched with 5 mL H$_2$O and extracted with 100 mL EtOAc, washed with brine and evaporated in vacuo then purified by chromatography (Petroleum ether/ethyl acetate=3:1) to afford SA-S as a white solid (140 mg, 48% yield). $^1$H NMR (400 MHz, CDCl$_3$), δ (ppm) 5.15-5.12 (m, 1H), 4.72-4.60 (m, 1H), 1.70 (apparent d within m), 1.27 (apparent s within m), 0.92 (s, 3H).

Synthesis of Compound SA-T

To a solution of SA-S (100 mg, 0.3 mmol) in dry THF (5 mL) was added borane-tetrahydrofuran complex (1 mL; 1.0M solution in THF). After stirring at room temperature for 1 hour, the reaction mixture was cooled in an ice bath then quenched slowly with 10% aqueous NaOH (1 mL) followed by 30% aqueous solution of H$_2$O$_2$ (1 mL). After stirring at room temperature for one hour, the mixture was extracted with EtOAc (3×100 mL). The combined organic layers were washed with 10% aqueous Na$_2$S$_2$O$_3$ (100 mL), brine (100 mL), dried over MgSO$_4$, filtered and concentrated to afford SA-T as a white solid (100 mg, 91%). The crude product was used in the next step without further purification.

Synthesis of Compound SA-U

To a solution of SA-T (100 mg, 0.29 mmol in 20 mL DCM, was added PCC (190 mg, 0.87 mmol), stirred at rt for 2 h. The reaction mixture was quenched with 5 mL H$_2$O and extracted with 100 mL EtOAc, washed with brine and evaporated in vacuo then purified by chromatography (Petroleum ether/ethyl acetate=3:1) to afford SA-U as a white solid (53 mg, 53% yield). $^1$H NMR (400 MHz, CDCl$_3$), δ (ppm) 4.71-4.57 (m, 1H), 2.54 (1H, t), 1.28 (apparent s within m), 0.58 (s, 3H).

Synthesis of Compound SA-V

To a solution of SA-U (40 mg, 0.11 mmol) in MeOH (5 mL) was added 2 drops of HBr (48%) followed by bromine (150 mg, 0.33 mmol). After stirring at room temperature for 1 h, the reaction mixture was poured into ice-water then extracted with EtOAc (10 mL×3). The combined organic layers were washed with brine (20 mL), dried over MgSO$_4$, filtered and concentrated to give crude compound SA-V as a white solid (40 mg, 80% yield). The crude product was used in the next step without further purification.

Example 4. Synthesis of SB-W Compound

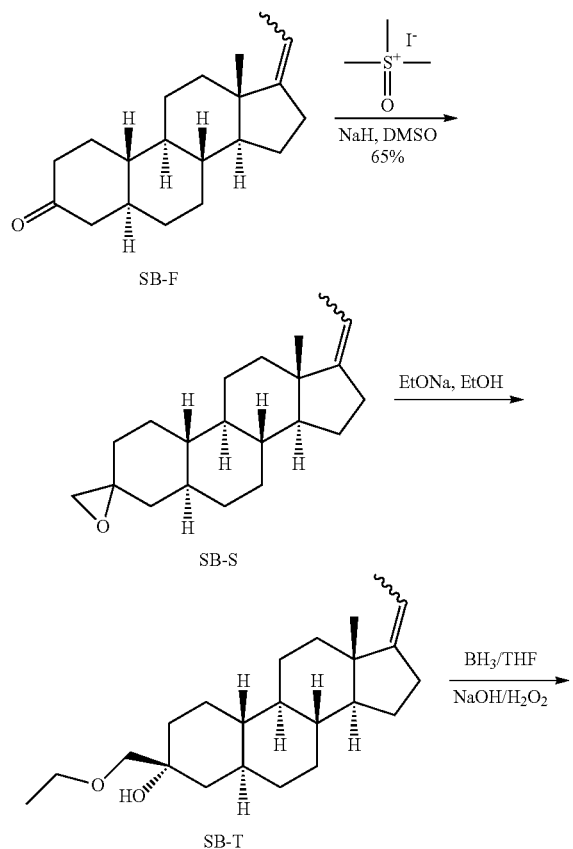

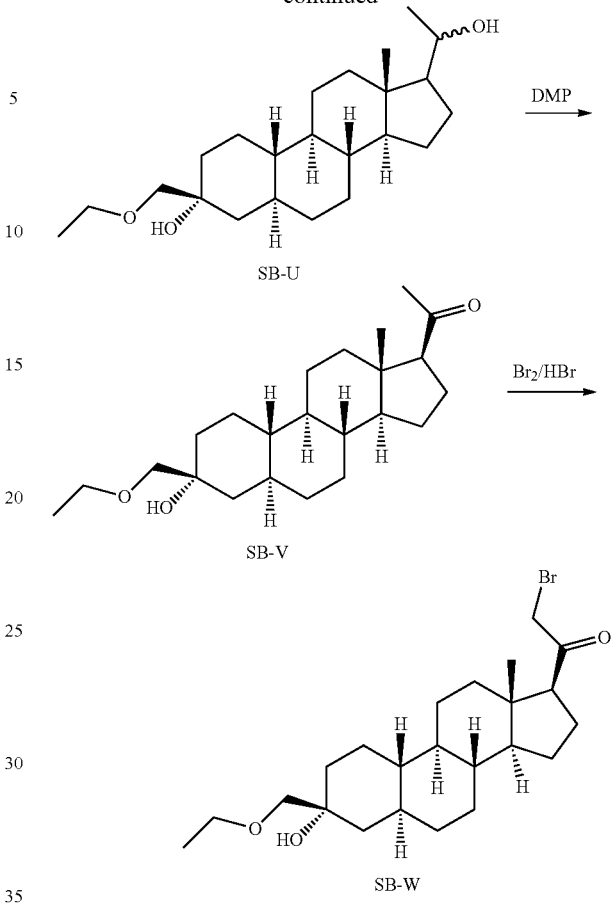

To a stirred solution of trimethylsulfonium iodide (8.1 g, 36.9 mmol) in 100 mL of DMSO was added NaH (60%; 1.26 g, 31.5 mmol). After stirring at room temperature for 1 h, a suspension of compound SB-F (2.2 g, 7.2 mmol) in DMSO (20 mL) was added dropwise. The mixture was stirred for another 2.5 h, then poured into ice-cold water and extracted with ether (100 mL×3). The combined ether layers were then washed with brine (100 mL×3), dried over MgSO$_4$, filtered, and concentrated to give the crude product SB-S (2.2 g). The crude product was used in the next step without further purification.

Synthesis of Compound SB-T

Compound SB-S (2.2 g, 7.3 mmol) was dissolved in dry ethanol (250 mL), and Na (672 mg, 29.2 mmol) was added. The solution was stirred reflux for 6 h. Ethanol was evaporated off and the residue was dissolved in dichloromethane and washed with H$_2$O (3×50 mL) and brine (100 mL), dried over MgSO$_4$, filtered, and concentrated. The crude target compound was purified by via silica gel chromatography (pertroleum ether/ethyl acetate=10:1 to 5:1), and concentrated to give SB-T (1.8 g, 82%) as a white solid. $^1$H NMR (500 MHz, CDCl$_3$), δ (ppm), 5.03-5.01 (m, 1H), 3.43 (q, 2H), 3.13 (s, 2H), 0.80 (s, 3H).

Synthesis of Compound SB-U

To a solution of compound SB-T (1.8 g, 5.2 mmol) in dry THF (50 mL) was added borane-tetrahydrofuran complex (20 mL of 1.0M solution in THF). After stirring at room temperature for 1 hour, the reaction mixture was cooled in an ice bath then quenched slowly with 10% aqueous NaOH (10 mL) followed 30% aqueous solution of H₂O₂ (12 mL). The mixture was allowed to stir at room temperature for 1 hour then extracted with EtOAc (3×100 mL). The combined organic layers were washed with 10% aqueous Na₂S₂O₃ (100 mL), brine (100 mL), dried over MgSO₄, filtered and concentrated to afford crude compound SB-U (1.8 g, 100%). The crude product was used in the next step without further purification.

Synthesis of Compound SB-V

To a solution of crude compound SB-U (1.8 g, 5.2 mmol) was dissolved in 60 mL of H₂O saturated dichloromethane (dichloromethane had been shaken with several milliliters of H₂O then separated from the water layer) was added Dess-Martin periodinate (4.4 g, 10.4 mmol). After stirring at room temperature for 24 h, the reaction mixture was extracted with dichloromethane (3×100 mL). The combined organic layers were washed with 10% aqueous Na₂S₂O₃ (100 mL), brine (100 mL), dried over MgSO₄, filtered and concentrated. The residue was purified by chromatography on silica gel (petroleum ether/ethyl acetate=10:1 to 5:1) to afford SB-V (1 g, 2.8 mmol, 56% for two steps) as a white solid. $^1$H NMR (400 MHz, CDCl₃), δ (ppm), 3.52 (q, 2H), 3.21 (s, 2H), 2.54 (t, 2H), 2.11 (s, 3H), 1.20 (t, 3H), 0.61 (s, 3H). LCMS: Rt=7.25 min. m/z=345.1 [M-17]⁺.

Synthesis of Compound SB-W

To a solution of compound SB-V (600 mg, 1.65 mmol) in MeOH (20 mL) was added 5 drops of HBr (48%) followed by bromine (264 mg, 1.65 mmol). After stirring at room temperature for 1 h, the reaction mixture was poured into ice-water then extracted with ethyl acetate (100 mL×3). The combined organic layers were washed with brine (200 mL), dried over MgSO₄, filtered and concentrated to give crude compound SB-W (600 mg, 100%). The crude product was used in the next step without further purification. LCMS: Rt=7.25 min. m/z=463.1 [M+Na]⁺.

Example 5. Synthesis of SA-AA Compound

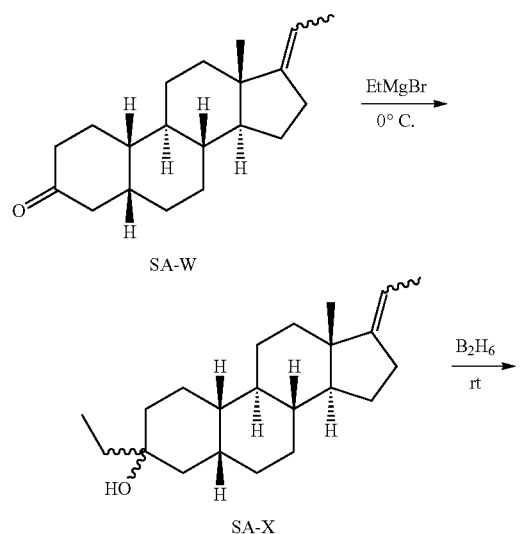

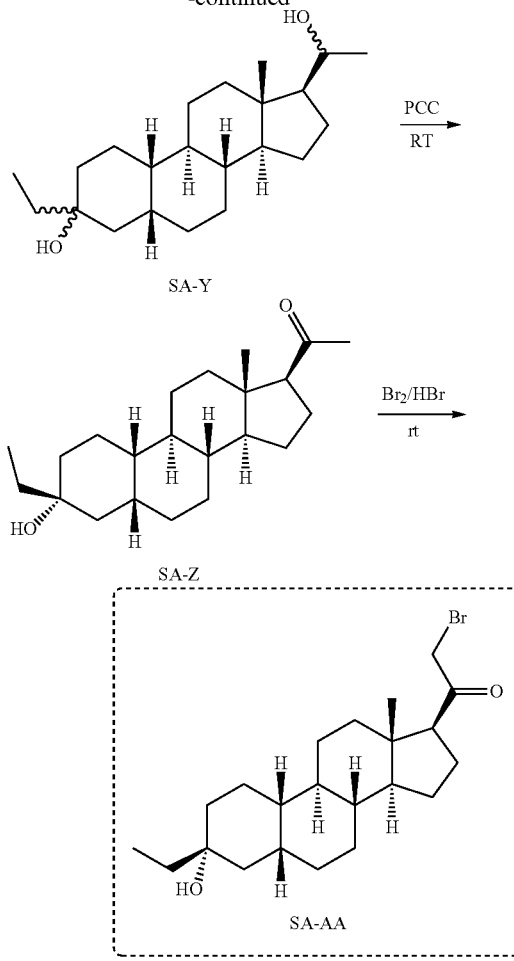

Synthesis of Compound SA-X

To a solution of EtMgBr (5 mmol, 1M in THF) in THF (20 mL) at 0° C. was added a solution of compound SA-W (858 mg, 3 mmol) in dry THF (5 mL) via syringe pump over 30 min. After stirring at 0° C. for 5 h, the reaction mixture was allowed to warm up and stirred at room temperature overnight. The reaction mixture was quenched with iced-cold water and extracted with EtOAc (15 mL×3). The combined organic layers were washed with brine, dried over sodium sulfate, filtered and concentrated. The white residue was purified by flash column chromatography (petroleum ether/ethyl acetate=20:1 to 10:1) to give compound SA-X (900 mg).

Synthesis of Compound SA-Y

To a solution of compound SA-X (200 mg, 0.66 mmol) in dry THF (5 mL) was added borane-tetrahydrofuran complex (2 mL of 1.0M solution in THF). After stirring at room temperature for 1 hour, the reaction mixture was cooled in an ice bath then quenched slowly with 10% aqueous NaOH (1 mL) followed by 30% aqueous solution of H₂O₂ (1.2 mL). The mixture was allowed to stir at room temperature for 1 hour then extracted with EtOAc (3×10 mL). The combined organic layers were washed with 10% aqueous Na₂S₂O₃ (10 mL), brine (10 mL), dried over MgSO₄, filtered and concentrated to afford compound SA-Y (260 mg, crude). The crude product was used in the next step without further purification.

Synthesis of Compound SA-Z

To a solution of compound SA-Y (260 mg, crude) was dissolved in 10 mL dichloromethane was added PCC (449 mg,). After stirring at room temperature for 24 h, the reaction mixture was extracted with dichloromethane (3×10 mL). The combined organic layers were washed with 10% aqueous NaCl (10 mL), brine (10 mL), dried over MgSO$_4$, filtered and concentrated. The residue was purified by chromatography on silica gel (petroleum ether/ethyl acetate=4:1 to 2:1) to afford title SA-Z (15 mg), as a white solid. $^1$H NMR (500 MHz, CDCl$_3$), δ (ppm), 2.49 (1H, t), 0.84 (t, 3H), 0.59 (s, 3H).

Synthesis of Compound SA-AA

To a solution of compound SA-Z (30 mg, 0.09 mmol) in MeOH (5 mL) was added 2 drops of HBr (48%) followed by bromine (100 mg, 0.62 mmol). After stirring at room temperature for 1 h, the reaction mixture was poured into ice-water then extracted with ethyl acetate (15 mL×3), The combined organic layers were washed with brine (20 mL), dried over MgSO$_4$, filtered and concentrated to give compound SA-AA (36 mg crude). The crude product was used in the next step without further purification.

Example 6. Synthesis of SA-JJ Compound

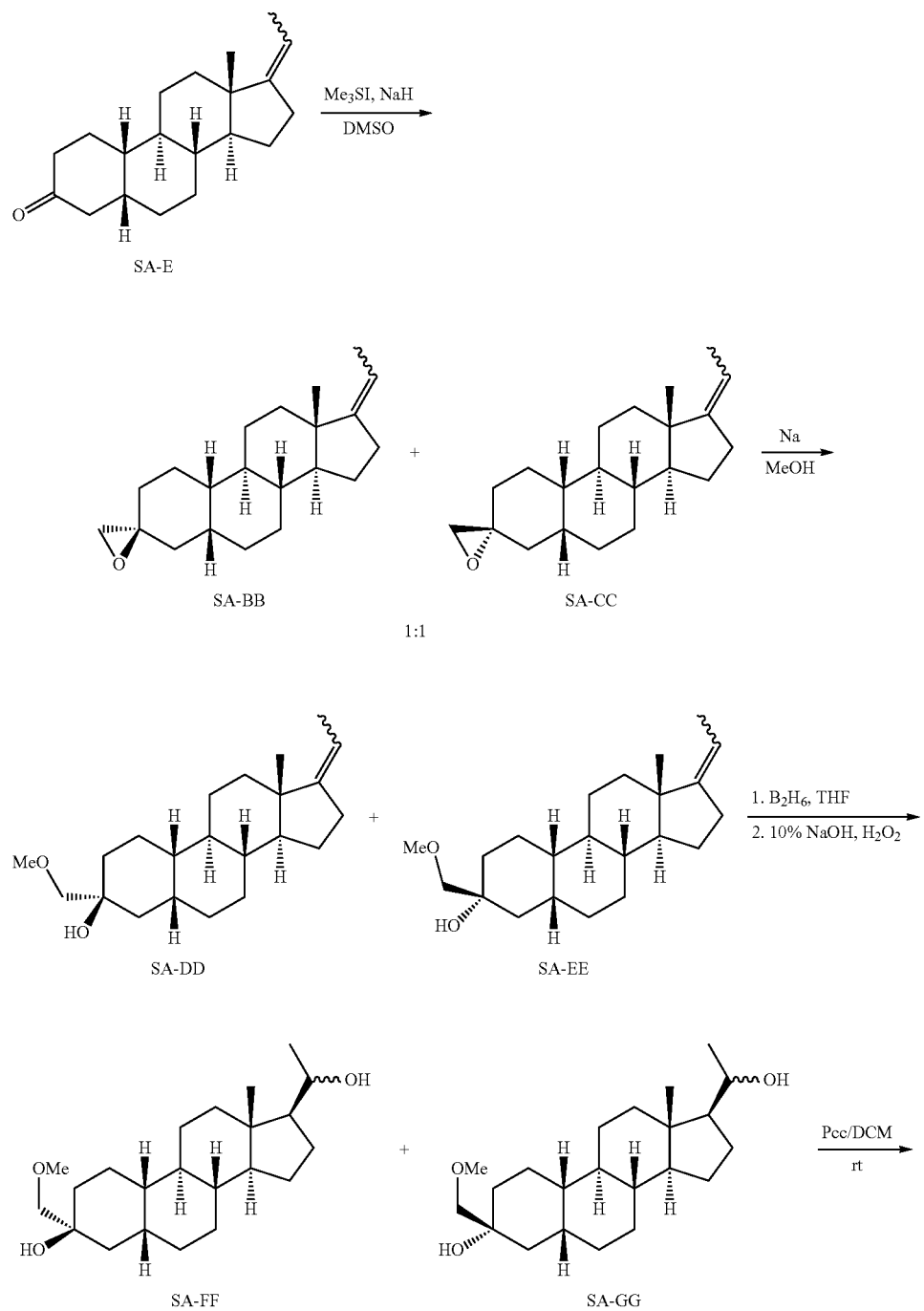

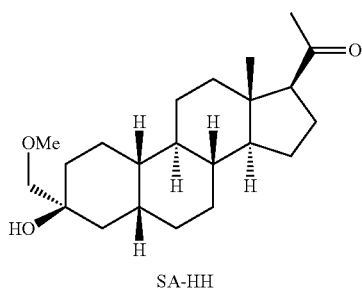

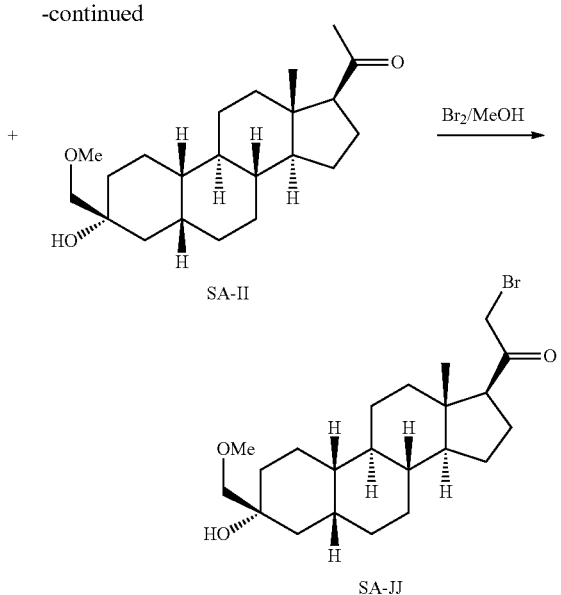

Synthesis of Compound SA-DD and SA-EE

Compound mixture SA-BB and SA-CC (5.0 g, 16.7 mmol) was dissolved in dry methanol (250 mL), and Na metal (1.2 g, 50.0 mmol) was added and the solution was refluxed for 16 h. Methanol was then evaporated off and the residue was dissolved in dichloromethane and washed with $H_2O$ (3×50 mL) and brine (100 mL), dried over $MgSO_4$, filtered, and concentrated. The crude target compound was purified by via silica gel chromatography (petroleum ether/ethyl acetate=10:1 to 5:1), and concentrated to give the product mixture SA-DD and SA-EE (4.6 g, 83%) as a white solid.

Synthesis of Compound SA-FF and SA-GG

To a solution of reactant mixture SA-DD and SA-EE (4.6 g, 13.9 mmol) in anhydrous THF (30 mL) was added $BH_3$.THF (1.0M, 27.7 mL, 27.7 mmol), the solution was stirred at 25° C. overnight, then the reaction was quenched by addition of water (5 mL). 2M NaOH solution (30 mL) was added followed by 30% $H_2O_2$ (30 mL). The mixture was stirred at room temperature for 1 hour. The mixture was diluted with ethyl acetate (200 mL) and resulting solution was washed with brine (2×100 mL), dried over magnesium sulfate and concentrated in vacuo. The crude product mixture was used directly in the next step without further purification.

Synthesis of Compound SA-HH and SA-II

To a solution of crude reactant mixture SA-FF and SA-GG (4.9 g, 13.9 mmol, theoretical amount) in dichloromethane (40 mL) was added Pyridinium chlorochromate (PCC) in portions (6.0 g, 27.8 mmol). The solution was stirred at 25° C. overnight then the mixture was filtered through a short pad of silica gel and the silica gel was washed with dichloromethane (3×50 mL). All filtrates were combined and concentrated in vacuo. The residue was purified by flash chromatography (petroleum ether/ethyl acetate=15:1) to afford product SA-HH (2.1 g, 6.03 mmol, Yield=43% (2 steps)) as white solid and product SA-II (2.2 g, 6.32 mmol, Yield=45% (2 steps)) as white solid. Compound SA-HH: $^1$HNMR (500 MHz, CDCl3) δ (ppm): 3.40 (s, 3H), 3.20 (s, 2H), 2.62-2.51 (m, 2H), 2.11 (s, 3H), 2.02-1.99 (m, 2H), 0.62 (s, 3H). Compound SA-II: $^1$HNMR (500 MHz, CDCl3) δ (ppm): 3.42 (AB, 1H), 3.38 (AB, 1H), 3.40 (s, 3H), 2.65 (s, 1H), 2.54 (t, 1H), 2.16-2.14 (m, 1H), 2.11 (s, 3H), 2.02-1.98 (m, 1H), 0.61 (s, 3H).

Synthesis of Compound SA-JJ

To a solution of reactant SA-II (100 mg, 0.301 mmol) in methanol (10 mL) was added 48% hydrobromic acid (152 mg, 0.903 mmol) followed by bromine (241 mg, 0.077 mL, 1.51 mmol). The solution was heated at 25° C. for 1.5 hours then the mixture was poured into cold water (50 mL) and the resulting solid was extracted with ethyl acetate (2×50 mL). The combined organic extracts were washed with brine (50 mL), dried over magnesium sulfate and concentrated in vacuo. The crude product SA-JJ was used directly without further purification in the next step.

Example 8. Synthesis of SB-R Compound

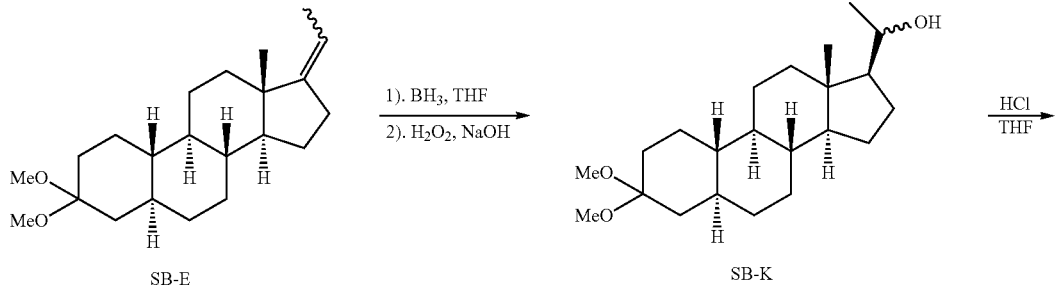

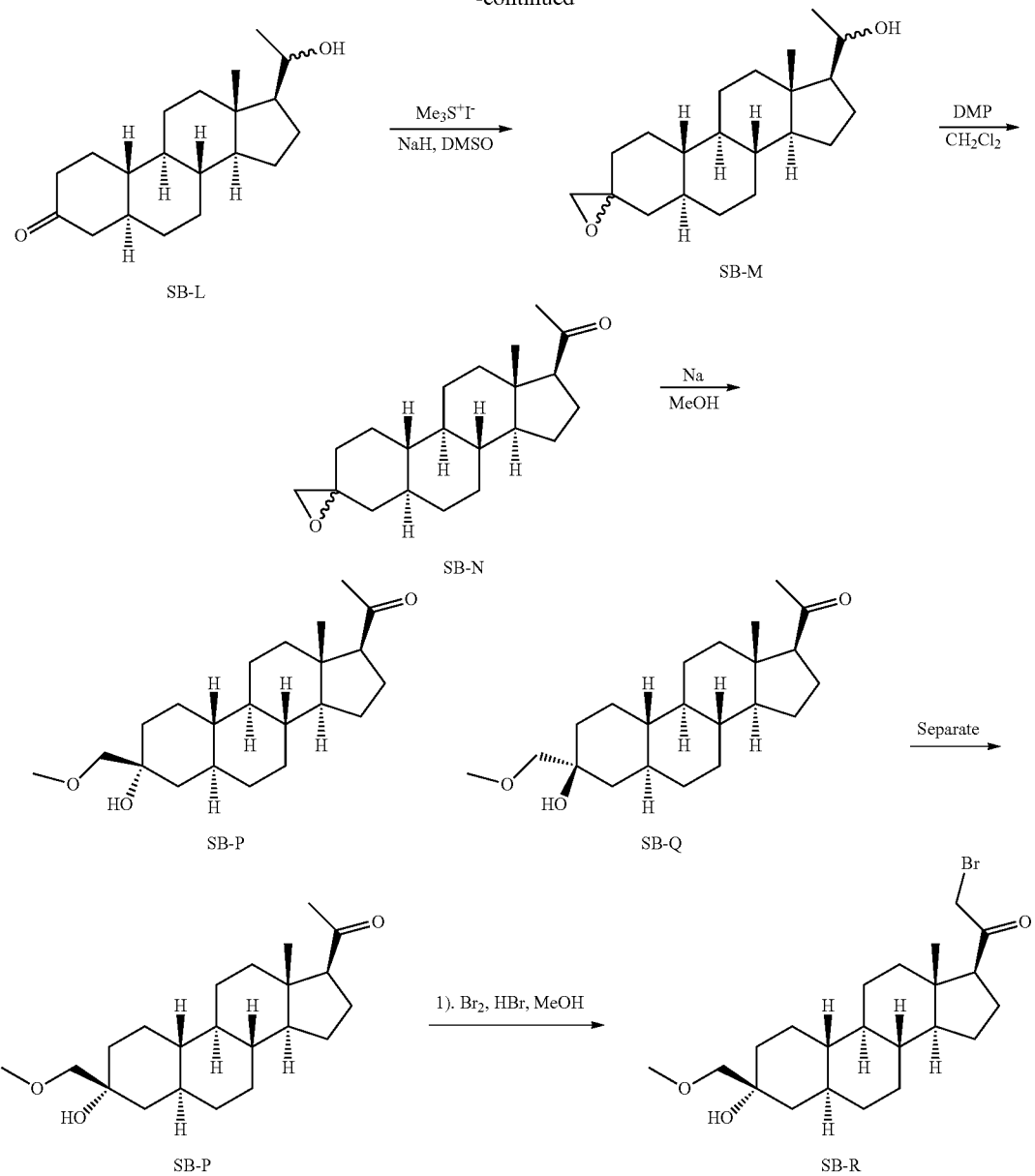

Synthesis of Compound SB-K

To a solution of compound SB-E (5 g, 15 mmol) in dry THF (20 mL) was added borane-tetrahydrofuran complex (30 mL of 1.0M solution in THF) and the reaction mixture was stirred at ambient temperature for 1 hour then 10% aqueous NaOH (56 mL) was slowly added. The mixture was cooled in ice and 30% aqueous solution of $H_2O_2$ (67 mL) was slowly added. The mixture was stirred at ambient temperature for 1 hour and then extracted with EtOAc (3×100 mL). The combined EtOAc extracts were washed with 10% aqueous $Na_2S_2O_3$ (100 mL), brine (100 mL), dried over $MgSO_4$. Filtration and removal of the solvent gave the crude product 3.2 g for next step reaction.

Synthesis of Compound SB-L

To a solution of compound SB-K (3.2 g, 9 mmol) in THF (40 mL) was added 2M HCl (3 mL). The reaction solution was stirred at RT for 12 h then the solvent was removed under reduced pressure. The crude target compound was purified by silica gel chromatography (petroleum ether/ethyl acetate=10:1 to 5:1) to give 2.2 g of the product as a white solid, yield: 81.40%.

Synthesis of Compound SB-M

To a stirred solution of trimethylsufonium iodide (6.43 g, 31.5 mmol) in 100 mL of DMSO was added 60 wt % NaH (1.26 g, 31.5 mmol). After stirring at room temperature (15° C.) for 1 h, a solution of compound SB-L (2.2 g, 7.2 mmol) in 20 mL of DMSO was added dropwise. After 2.5 h, the reaction mixture was poured into ice-cold water and extracted with ether (100 mL×3). The combined ether layers were then washed with brine (100 mL×3), dried ($MgSO_4$), filtered, and concentrated to give the crude product 1.6 g for next step reaction.

Synthesis of Compound SB-N

Compound SB-M (1.6 g, 5 mmol) was dissolved in 60 mL of H₂O saturated CH₂Cl₂. (Using a separatory funnel, the CH₂Cl₂ had been shaken with several milliliters of H₂O and then separated from the water layer). DMP was added (4.2 g, 10 mmol), and the resultant reaction mixture was vigorously stirred for 24 h. The reaction solution was diluted with DCM (100 mL), washed with 10% aqueous Na₂S₂O₃ (100 mL), brine (100 mL), dried over MgSO₄, filtered, and concentrated. The residue was purified by chromatography on silica gel (petroleum ether/ethyl acetate=20:1 to 10:1) to afford title compound (1.2 g, 3.79 mmol, 75%) as a white solid. ¹H NMR (400 MHz, CDCl3) δ (ppm): 2.63 (s, 1H), 2.59 (s, 1H), 2.12 (s, 3H), 0.63 (s, 3H).

Synthesis of SB-P and SB-Q

Compound SB-N (1.2 g, 3.8 mmol) was dissolved in dry methanol (250 mL), and Na (262 mg, 11.4 mmol) was added. The solution was refluxed for 16 h. Methanol was evaporated off and the residue was dissolved in dichloromethane and washed with H₂O (3×50 mL) and brine (100 mL), dried over MgSO₄, filtered, and concentrated. The crude target compound was purified by silica gel chromatography (petroleum ether/ethyl acetate=10:1 to 5:1) to give SB-P (300 mg, 25%, SB-Q (300 mg, 25%) as a white solid. SB-P: 1H NMR (400 MHz, CDCl3) δ (ppm): 3.39 (s, 3H), 3.19 (s, 2H), 2.54 (t, 1H), 0.61 (s, 3H). SB-Q: 1H NMR (400 MHz, CDCl3) δ (ppm): 3.39 (s, 5H), 3.37 (s, 2H), 2.52 (t, 1H), 0.62 (s, 3H).

Synthesis of Compound SB-R

To a solution of reactant SB-P (190 mg, 0.545 mmol) in methanol (15 mL) was added 48% hydrobromic acid (275 mg, 1.635 mmol) followed by bromine (435 mg, 0.139 mL, 2.725 mmol). The solution was heated at 25° C. for 1.5 hours. Then the mixture was poured into cooled water (50 mL). The resulting solution was extracted with ethyl acetate (2×100 mL). The combined organic extracts were washed with brine (100 mL), dried over magnesium sulfate and concentrated in vacuo. The crude product was used directly without further purification in the next step.

Example 9. Synthesis of SB-FF Compound

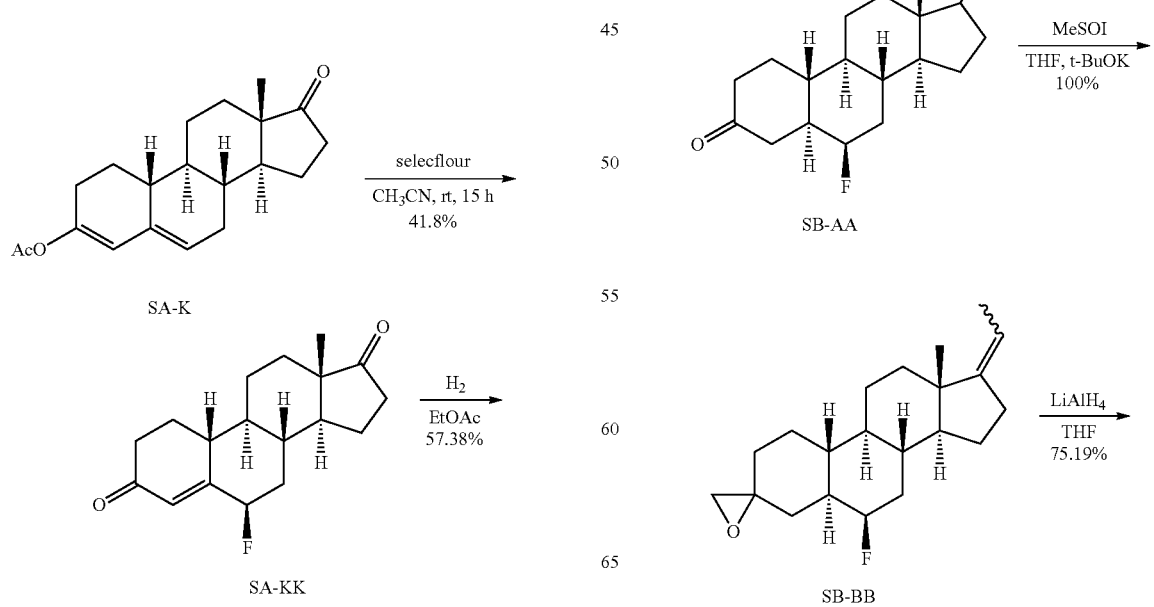

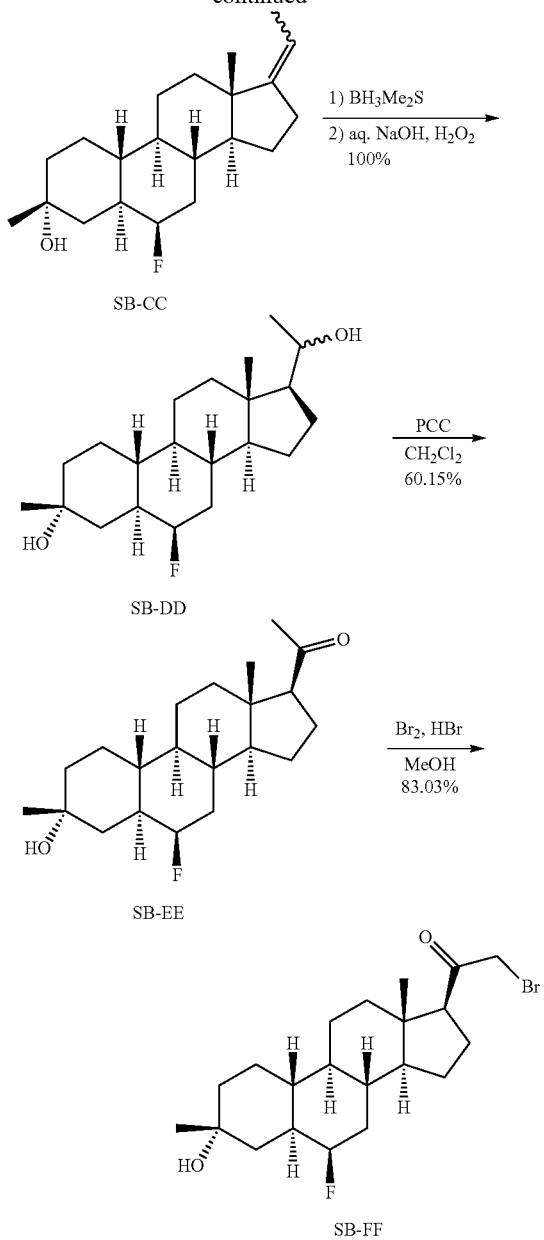

Synthesis of Compound SB-KK

To a solution of SA-K (68 g, 216.27 mmol) in 600 mL CH₃CN, was added selectflour (90.22 g, 324.4 mmol) in portions at −4° C. The resulting reaction mixture was stirred at −4° C. for 3 h. After the TLC showed the reaction was completed, then the mixture was filtered and concentrated. The product was purified by column chromatograph on silica gel eluted with (Petroleum ether/ethyl acetate 20:1-15:1-10:1-8:1-6:1-5:1) to afford SB-KK (26.3 g, 41.8% yield) as white solid. $^1$H NMR (SB-KK) (400 MHz, CDCl₃), δ (ppm), 6.02-5.94 (m, 1H), 5.20-5.01 (m, 1H), 2.55-2.26 (m, 6H), 2.16-2.05 (m, 1H), 2.01-1.83 (m, 4H), 1.48-1.22 (m, 5H), 0.98-0.78 (m, 6H).

Synthesis of Compound SB-X

To a solution of SB-KK (27 g, 92.98 mmol) in EtOAc (350 mL) at 20° C., then Pd/C (2.7 g, 5%) was added in the mixture. The solution was stirred at 20° C., 1 atm for 10 h under hydrogen. After the LCMS showed the reaction was completed, and then the mixture was filtered and concentrated. The product was purified by column chromatograph on silica gel eluted with (Petroleum ether/ethyl acetate 40:1-35:1-30:1-25:1-20:1-15:1-10:1-6:1) to give SB-X (15.6 g, 56.38%) as white solid. $^1$H NMR (SB-X) (400 MHz, CDCl₃), δ (ppm)=4.68-4.56 (m, 1H), 2.64-2.51 (m, 1H), 2.53-2.03 (m, 8H), 1.97-1.80 (m, 4H), 1.49-1.20 (m, 6H), 0.96-0.92 (m, 21H), 0.88-0.78 (m, 11H).

Synthesis of Compound SB-Y

To a solution of SB-X (47 g, 160.75 mmol) in MeOH (600 mL) at 23° C., then 2.35 g of TsOH was added in the mixture. The solution was stirred at 60° C. for 1.5 h. After the TLC showed the reaction was completed, and then the mixture was filtered and concentrated to give SB-Y (35 g, 64.33%) as white solid. $^1$H NMR (SB-Y) (400 MHz, CDCl₃), δ (ppm)=4.74-4.57 (m, 1H), 3.16 (s, 3H), 3.10 (s, 3H), 2.47-2.35 (m, 1H), 2.15-2.09 (m, 1H), 2.06-1.82 (m, 6H), 1.77-1.15 (m, 11H), 1.05-0.96 (m, 1H), 0.89 (s, 3H), 0.83-0.77 (m, 1H).

Synthesis of Compound SB-Z

To a solution of ethyltriphenylphosphonium bromide (115.17 g, 310.23 mmol) in 150 mL THF, was added KOt-Bu (34.81 g, 310.23 mmol). The reaction mixture was heated to 60° C. for 1 h and SB-Y (35 g, 103.41 mmol) was added to the mixture which was stirred at 60° C. for an additional 15 h. The reaction mixture was cooled and extracted 1500 mL EtOAc, washed with brine and concentrated to afford SB-Z as the white solid (120 g, crude). $^1$H NMR (SB-Z) (400 MHz, CDCl₃), δ (ppm)=5.13-5.07 (m, 1H), 4.67-4.54 (m, 1H), 3.14 (s, 3H), 3.09 (s, 3H), 2.42-2.15 (m, 3H), 1.92-1.79 (m, 3H), 1.67-1.61 (m, 4H), 1.57-1.50 (m, 2H), 1.45-1.15 (m, 10H), 1.01-0.94 (m, 1H), 0.92 (s, 3H), 0.90-0.84 (m, 1H).

Synthesis of Compound SB-AA

To a solution of SB-Z (120 g, crude) in 600 mL THF, was added 2M aqueous HCl 90 mL. the reaction mixture was stirred at 22° C. for 1 h. After the TLC showed the reaction was completed, then the reaction was quenched with aq.NaHCO₃. The reaction was extracted with 500 mL EtOAc, washed with brine and evaporated in vacuo. The resulting residue was purified by chromatography (Petroleum ether/ethyl acetate=150:1-125:1-100:1-80:1-60:1-50:1) to afford SB-AA as the white solid (24 g, 76.23% yield). $^1$H NMR (SB-AA) (400 MHz, CDCl₃), δ (ppm)=5.13 (m, 1H), 4.65-4.48 (m, 1H), 2.62-2.42 (m, 1H), 2.44-2.07 (m, 81-H), 1.92-1.80 (m, 1H), 1.72-1.55 (nm, 81H), 1.36-1.08 (m, 61H), 0.92 (s, 3H), 0.83-0.73 (m, 1H).

Synthesis of Compound SB-BB

To a solution of Me₃SOI (78.07 g, 354.75 mmol) in 50 mL THF, was added a solution of t-BuOK (39.81 g, 354.75 mmol) in 50 mL THF. The reaction mixture was stirred at 60° C. for 1.5 h. Then a solution of SB-AA (24 g, 78.83 mmol) in THF (300 mL) was added in the reaction. The reaction was stirred for 2.5 h at 23° C. After the TLC showed the reaction was completed, then the reaction was quenched with ice water. The reaction was extracted with 500 mL EtOAc, washed with brine and evaporated in vacuo to afford SB-BB as crude product (50 g). $^1$H NMR (SB-BB) (400 MHz, CDCl$_3$), δ (ppm)=5.20-5.11 (m, 1H), 4.65-4.52 (m, 1H), 2.74-2.68 (m, 2H), 2.48-1.81 (m, 9H), 1.72-1.64 (m, 4H), 1.55-1.06 (m, 10H), 0.97-0.89 (m, 3H), 0.85-0.77 (m, 1H).

Synthesis of Compound SB-CC

To a solution of SB-BB (50 g, crude) in 300 mL THF, was added LiAlH$_4$ (8.99 g, 236.49 mmol) at 0° C. the reaction mixture was stirred at 23° C. for 1.5 h. After the TLC showed the reaction was completed, then the reaction was quenched with water. The reaction was extracted with 1000 mL EtOAc, washed with brine and evaporated in vacuo. The resulting residue was purified by chromatography (Petroleum ether/ethyl acetate=100:1-80:1-60:1-50:1-40:1-30:1) to afford SB-CC as the white solid (19 g, 75.19% yield). $^1$H NMR (SB-CC) (400 MHz, CDCl$_3$), δ (ppm)=5.17-5.07 (m, 1H), 4.66-4.48 (m, 1H), 2.41-2.32 (m, 1H), 2.28-2.15 (m, 2H), 2.09-2.05 (m, 1H), 1.88-1.75 (m, 2H), 1.68-1.64 (m, 3H), 1.40-1.31 (m, 1H), 1.25-1.13 (m, 9H), 0.89 (s, 3H), 0.81-0.72 (m, 11H).

Synthesis of Compound SB-DD

To a solution of SB-CC (19 g, 59.29 mmol) in dry THF (500 mL) was added C$_2$H$_9$BS (59.29 mL; 10M solution in THF) at 0° C. After stirring at room temperature for 2 hour, the reaction mixture was cooled in an ice bath then quenched slowly with 3M aqueous NaOH (160 mL) followed by 30% aqueous solution of H$_2$O$_2$ (100 mL). After stirring at 20° C. for 1.5 h, the mixture filtered and extracted with EtOAc (300 mL). The combined organic layers was treated with aq.Na$_2$S$_2$O$_3$, extracted, dried and concentrated to afford SB-DD as the crude (21 g, crude). The crude product was used in the next step without further purification.

Synthesis of Compound SB-EE

To a solution of SB-DD (21 g, 59.29 mmol) in 200 mL CH$_2$Cl$_2$, was added PCC (25.56 g, 118.58 mmol) at 0° C., stirred at 22° C. for 2 h. The reaction mixture was filtered and extracted with 20 mL CH$_2$Cl$_2$, washed with aq.NaHCO$_3$, aq.Na$_2$S$_2$O$_3$, brine and evaporated in vacuo. The residue was purified by chromatography (Petroleum ether/ethyl acetate=15:1-10:1-6:1) to afford SB-EE as the white solid (12 g, 60.15% yield). $^1$H NMR (SB-EE) (400 MHz, CDCl$_3$), δ (ppm)=4.65-4.46 (m, 1H), 2.55-2.51 (m, 1H), 2.22-2.09 (m, 4H), 2.06-1.97 (m, 32H), 1.88-1.77 (m, 2H), 1.69-1.54 (m, 5H), 1.48-1.30 (m, 3H), 1.28-1.05 (m, 11H), 0.83-0.72 (m, 1H), 0.63 (s, 3H).

Synthesis of Compound SB-FF

To a solution of SB-EE (12 g, 35.66 mmol) in 1500 mL MeOH, was added HBr (5 drops) and Br$_2$ (2.01 mL, 39.23 mmol) at 0° C. The reaction was stirred at 16° C. for 2 h. The reaction mixture was quenched with aq.NaHCO$_3$ and concentrated. Then the mixture was extracted with 1000 ml EtOAc, washed with brine and evaporated in vacuo. The product was purified by column chromatograph on silica gel eluted with (Petroleum ether/ethyl acetate=12:1-10:1-8:1-6:1-3:1) to afford SB-FF as the white solid (12.3 g, 83.03% yield). $^1$H NMR (SB-FF) (400 MHz, CDCl$_3$), δ (ppm)=4.64-4.47 (m, 1H), 3.95-3.86 (m, 2H), 2.89-2.80 (m, 1H), 2.23-2.16 (m, 1H), 2.07-1.64 (m, 8H) 1.46-1.06 (m, 14H), 0.83-0.74 (m, 11H), 0.67 (s, 3H).

Example 12. Synthesis of SC-O Compound

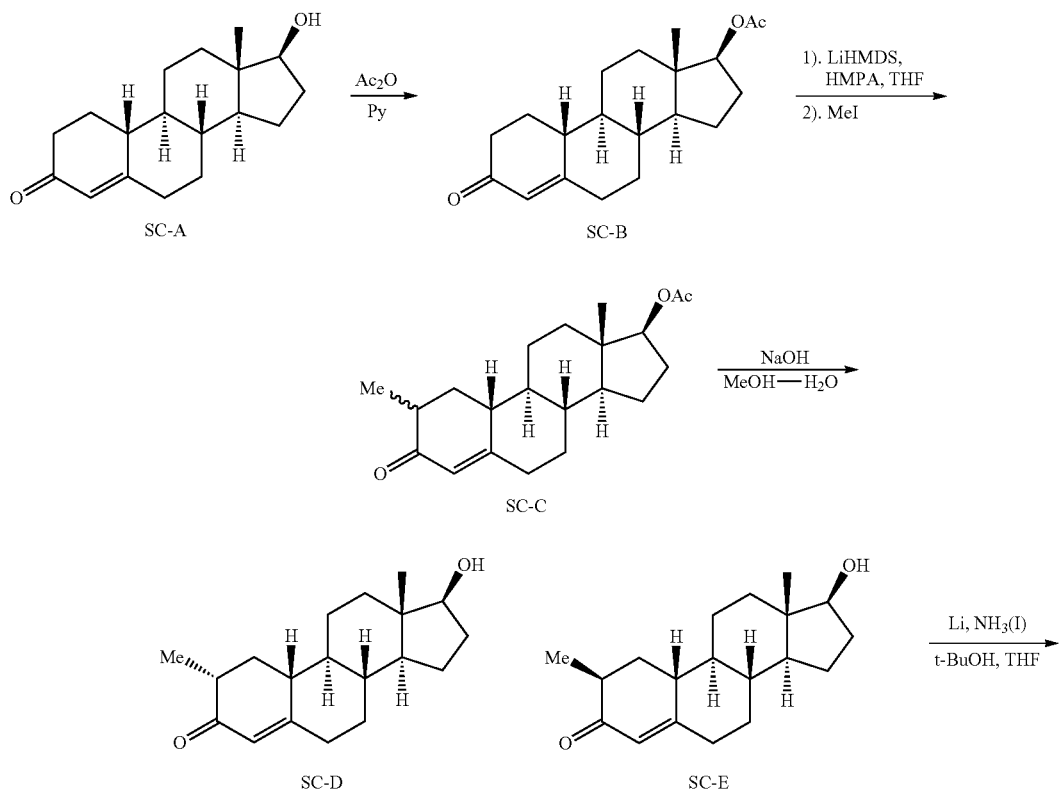

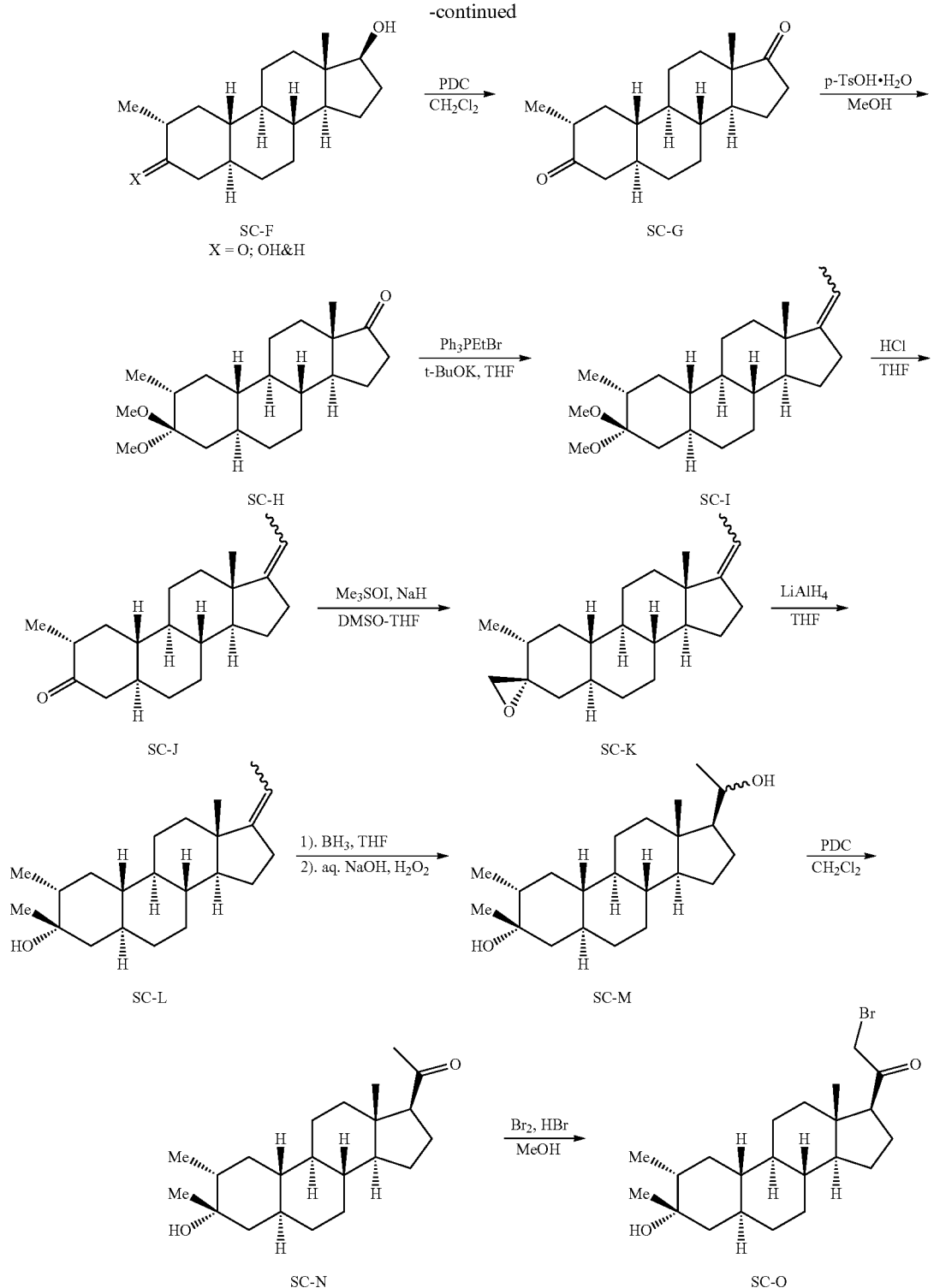

Synthesis of Compound SC-B

To a solution of reactant SC-A (10.0 g, 36.44 mmol) in pyridine (30 mL) was added acetic anhydride (5.0 mL, 52.89 mmol). The mixture was stirred at 60° C. overnight. Then the solution was poured into ice-water (200 mL). The white precipitate was filtered and dissolved in ethyl acetate (300 mL). The resulting solution was washed with sat. $CuSO_4·5H_2O$ solution (2×200 mL) in order to remove residual pyridine. The organic layer was further washed with brine (200 mL), dried over magnesium sulfate and concentrated in vacuo. The residue was purified by flash chromatography (petroleum ether/ethyl acetate=4:1) to afford product SC-B (11.125 g, 35.16 mmol, Yield=96%) as white solid. $^1$HNMR (500 MHz, $CDCl_3$) δ(ppm): 5.83 (1H, s), 4.62 (1H, dd), 2.05 (3H, s), 0.86 (3H, s).

Synthesis of Compound SC-C

To a solution of reactant SC-B (4.68 g, 14.79 mmol) in THF (150 mL) was added LiHMDS (1.0M in THF solution, 17.74 mL, 17.74 mmol) at −78° C. The solution was stirred at −78° C. for 30 minutes. Then HMPA (3.09 mL, 17.74 mmol) was added. The solution was stirred at −78° C. for another 30 minutes. Then iodomethane (2.76 mL, 44.37 mmol) was added. The solution was further stirred at −78° C. for 2 hours and warmed to room temperature and stirred for 1 hour. The reaction was quenched by addition of water (10 mL). Most THF solvent was removed in vacuo. Then the residue was diluted with ethyl acetate (300 mL) and the resulting solution was washed with brine (2×200 mL), dried over magnesium sulfate. Removal of solvent in vacuo afforded crude product SC-C (4.50 g, 13.62 mmol, Yield=92%) as thick oil. The crude product was used in the next step without further purification. $^1$HNMR (500 MHz, CDCl$_3$) δ(ppm): 5.75 (1H, s), 4.62 (1H, t), 2.05 (3H, s), 1.10 (3H, d), 0.86 (3H, s).

Synthesis of Compound SC-D & SC-E

To a solution of crude reactant SC-C (11.62 g, 35.16 mmol, theoretical amount) in methanol (100 mL) and water (20 mL) was added sodium hydroxide (2.81 g, 70.32 mmol). The solution was heated at 60° C. for 1 hour. Then most methanol solvent was removed in vacuo. The residual solution was acidified by 2M HCl to pH 5-6. The aqueous layer was extracted with ethyl acetate (3×100 mL). The combined organic extracts were washed with brine (200 mL), dried over magnesium sulfate and concentrated in vacuo. The residue was purified by flash chromatography (petroleum ether/ethyl acetate=5:1) to afford pure product SC-D (2.354 g, 8.162 mmol, Yield=23%) and pure product SC-E (5.306 g, 18.40 mmol, Yield=50%) as white solid. Compound SC-D: $^1$HNMR (500 MHz, CDCl$_3$) δ(ppm): 5.81 (1H, s), 3.67 (1H, t), 1.11 (3H, d), 0.81 (3H, s).

Compound SC-E: $^1$HNMR (500 MHz, CDCl$_3$) δ(ppm): 5.74 (1H, s), 3.67 (1H, t, J=8.5 Hz), 1.11 (3H, d), 0.81 (3H, s).

Synthesis of Compound SC-F

To liquid ammonia (200 mL) was added lithium (1.80 g, 260 mmol) at −78° C. The liquid then turned to deep blue. Then a solution of reactant SC-D (3.0 g, 10.40 mmol) in t-BuOH (1.0 mL, 10.40 mmol) and THF (100 mL) was added to Li-ammonia solution. The mixture was stirred at −78° C. for 4 hours. Then NH$_4$Cl solid (20 g) was added to quench the reaction. The mixture was turned from deep blue to white. The mixture was allowed to warm to room temperature and ammonia was evaporated in a hood overnight. To the residue was added water (300 mL). The mixture was acidified by conc. HCl to pH 6-7. Then ethyl acetate (300 mL) was added. The separated aqueous layer was further extracted with ethyl acetate (2×100 mL). The combined organic extracts were washed with brine (300 mL), dried over magnesium sulfate and concentrated in vacuo. The crude product SC-F was used directly without further purification in the next step.

Synthesis of Compound SC-G

To a solution of crude reactant SC-F (1.749 g, 6.022 mmol) in dichloromethane (60 mL) was added pyridinium dichromate (PDC) (3.398 g, 9.033 mmol). The mixture was stirred at room temperature overnight. The solution was filtered through a short pad of celite. The celite was washed with CH$_2$Cl$_2$ (3×50 mL). The combined CH$_2$Cl$_2$ solution was concentrated in vacuo. The residue was purified by flash chromatography (petroleum ether/ethyl acetate=5:1) to afford product SC-G (1.298 g, 4.50 mmol, Yield=75%) as white solid. Compound SC-G: $^1$HNMR (400 MHz, CDCl$_3$) δ(ppm): 1.02 (3H, d), 0.91 (3H, s).

Synthesis of Compound SC-H

To a solution of reactant SC-G (1.948 g, 6.754 mmol) in anhydrous methanol (50 mL) was added p-toluenesulfonic acid monohydrate (128 mg, 0.6754 mmol). The solution was heated at 70° C. for 3 hours. The reaction was quenched by addition of sat. Na$_2$CO$_3$ solution (10 mL). Most methanol solvent was removed in vacuo. Then the residue was diluted with ethyl acetate (200 mL). The resulting solution was washed with sat. Na$_2$CO$_3$ solution (2×100 mL). The combined aqueous layers were extracted with ethyl acetate (50 mL). The combined organic extracts were washed with brine (100 mL), dried over magnesium sulfate and concentrated in vacuo. The residue was purified by flash chromatography (petroleum ether/ethyl acetate=10:1, added 0.1% NEt$_3$) to afford product SC-H (652 mg, 1.949 mmol, Yield=29%) as white solid. Furthermore, starting material (1.338 g) was also recovered. So the yield based on recovered starting material is 92%. $^1$H NMR (500 MHz, d6-acetone) δ(ppm): 3.079 (3H, s), 3.075 (3H, s), 2.38 (1H, dd), 1.98 (1H, dd), 0.91 (3H, d), 0.85 (3H, s).

Synthesis of Compound SC-I

To a solution of ethyltriphenylphosphonium bromide (8.795 g, 23.69 mmol) in anhydrous THF (20 mL) was added t-BuOK (2.658 g, 23.69 mmol). The solution then became reddish in color and was heated at 70° C. for 2 hours. Then the reactant SC-H (1.642 g, 4.909 mmol) was added in one portion. The solution was heated at 70° C. overnight. The reaction was quenched by the addition of water (10 mL). The mixture was diluted with ethyl acetate (200 mL) and the resulting solution was washed with brine (2×100 mL), dried over magnesium sulfate and concentrated in vacuo. The crude product SC-I was used directly in the next step without further purification.

Synthesis of Compound SC-J

To the crude product SC-I (1.702 g, 4.909 mmol, theoretical amount) in THF (30 mL) was added 2M HCl (3 mL). The solution was stirred at ambient temperature for 1 hour. The mixture was diluted with ethyl acetate (300 mL) and the resulting solution was washed with sat. Na$_2$CO$_3$ solution (2×100 mL). The combined aqueous layers were extracted with ethyl acetate (100 mL). The combined organic extracts were washed with brine (100 mL), dried over magnesium sulfate and concentrated in vacuo. The residue was purified by flash chromatography (petroleum ether/ethyl acetate=100:3) to afford crude product SC-J (1.746 g) as white solid which was contaminated with some inseparated PPh$_3$. Judged by the integration of $^1$HNMR spectrum, the ratio of desired product to PPh$_3$ is 3:1, so the amount of desired product SC-J is 1.354 g (4.506 mmol), the yield is 92%. $^1$H NMR (500 MHz, CDCl3) δ(ppm): 5.13 (1H, qt), 1.66 (3H, dt), 1.02 (3H, d), 0.91 (3H, s).

Synthesis of Compound SC-K

To a solution of trimethylsulfoxonium iodide (5.213 g, 23.69 mmol) in anhydrous DMSO (30 mL) was added sodium hydride (60% wt, 948 mg, 23.69 mmol). The mixture was stirred at 25° C. for 1 hour. Then a solution of crude reactant (1.746 g, contaminated with some residual PPh3, theoretical amount, 1.354 g, 4.506 mmol) in anhydrous THF (10 mL) was added. The mixture was stirred at 25° C. overnight. The reaction was quenched by addition of water (5 mL). The mixture was diluted with ethyl acetate (300 mL) and the resulting solution was washed with water (2×100 mL), followed by brine (100 mL) dried over magnesium sulfate and concentrated in vacuo. The crude product SC-K was used directly in the next step without further purification.

Synthesis of Compound SC-L

To a solution of crude reactant SC-K (theoretical amount, 1.417 g, 4.506 mmol) in anhydrous THF (30 mL) was added lithium aluminum hydride (342 mg, 9.012 mmol) in portions. The suspension was stirred at 25° C. for 1 hour. Then the reaction was quenched by addition of ethyl acetate (5 mL) followed by water (5 mL). A white solid was filtered and thoroughly washed with ethyl acetate (5×100 mL). The combined filtrate was washed with brine (200 mL), dried over magnesium sulfate and concentrated in vacuo. The residue was purified by flash chromatography (petroleum ether/ethyl acetate=20:1) to afford product SC-L (458 mg, 1.447 mmol, 2 steps total yield=32%) as white solid.

Synthesis of Compound SC-M

To a solution of reactant SC-L (458 mg, 1.447 mmol) in anhydrous THF (15 mL) was added $BH_3.THF$ (1.0M, 7.23 mL, 7.23 mmol), The solution was stirred at 25° C. overnight. Then the reaction was quenched by addition of water (5 mL). 2M NaOH solution (10 mL) was added followed by 30% $H_2O_2$ (10 mL). The mixture was stirred at room temperature for 1 hour. The mixture was diluted with ethyl acetate (200 mL) and resulting solution was washed with brine (2×100 mL), dried over magnesium sulfate and concentrated in vacuo. The crude product was used directly in the next step without further purification.

Synthesis of Compound SC-N

To a solution of crude reactant SC-M (484 mg, 1.447 mmol, theoretical amount) in dichloromethane (40 mL) was added pyridinium dichromate (PDC) in portions (1633 mg, 4.341 mmol). The solution was stirred at 25° C. overnight. Then the mixture was filtered through a short pad of silica gel and the silica gel was washed with dichloromethane (3×50 mL). All filtrate was combined and concentrated in vacuo. The residue was purified by flash chromatography (petroleum ether/ethyl acetate=8:1) to afford product SC-N (305 mg, 0.917 mmol, Yield=63% (2 steps)) as white solid. $^1H$ NMR (500 MHz, CDCl3) δ(ppm): 2.54 (1H, t), 2.12-2.19 (1H, m), 2.12 (3H, s 0.92 (3H, d), 0.61 (3H, s). $^{13}C$ NMR (100 MHz, CDCl3) δ(ppm): 209.75, 71.09, 63.96, 55.89, 47.96, 47.80, 47.00, 44.35, 41.19, 40.22, 39.05, 37.95, 34.49, 33.14, 31.54, 30.92, 28.46, 25.82, 24.22, 22.76, 15.14, 13.45.

Synthesis of Compound SC-O

To a solution of reactant SC-N (100 mg, 0.301 mmol) in methanol (10 mL) was added 48% hydrobromic acid (152 mg, 0.903 mmol) followed by bromine (241 mg, 0.077 mL, 1.505 mmol). The solution was heated at 25° C. for 1.5 hours. Then the mixture was poured into cooled water (50 mL). The resulting solid was extracted with ethyl acetate (2×50 mL). The combined organic extracts were washed with brine (50 mL), dried over magnesium sulfate and concentrated in vacuo. The crude product SC-O was used directly without further purification in the next step.

Example 13. Synthesis of SC-Y Compound

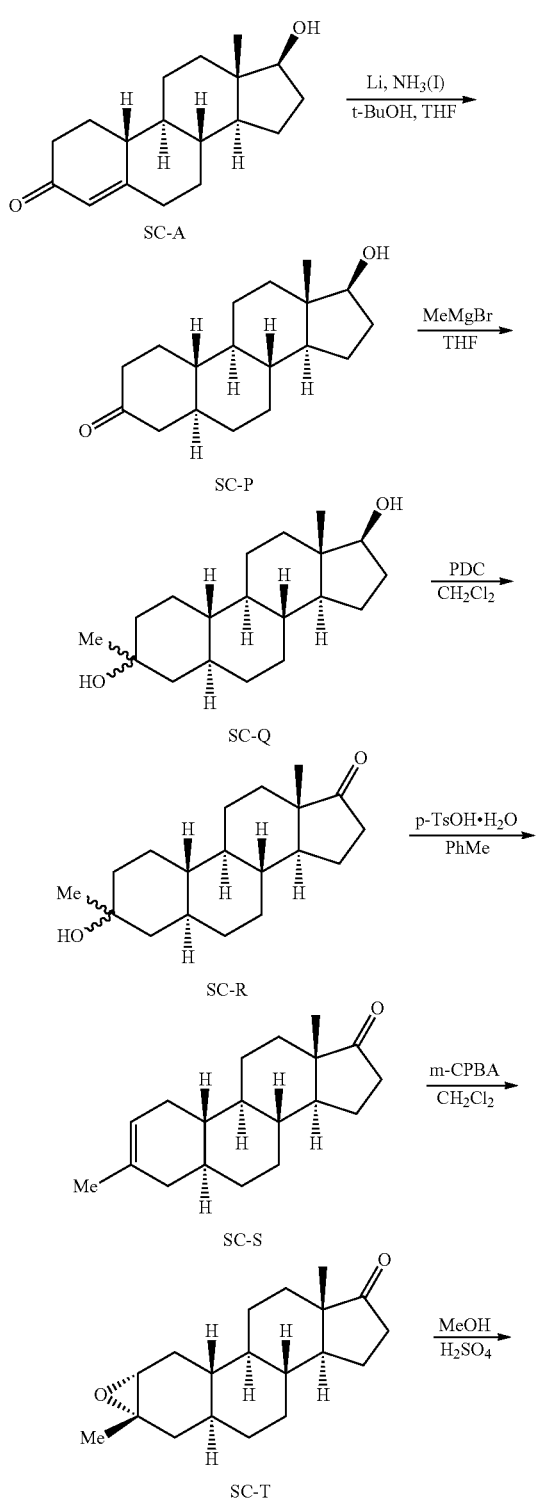

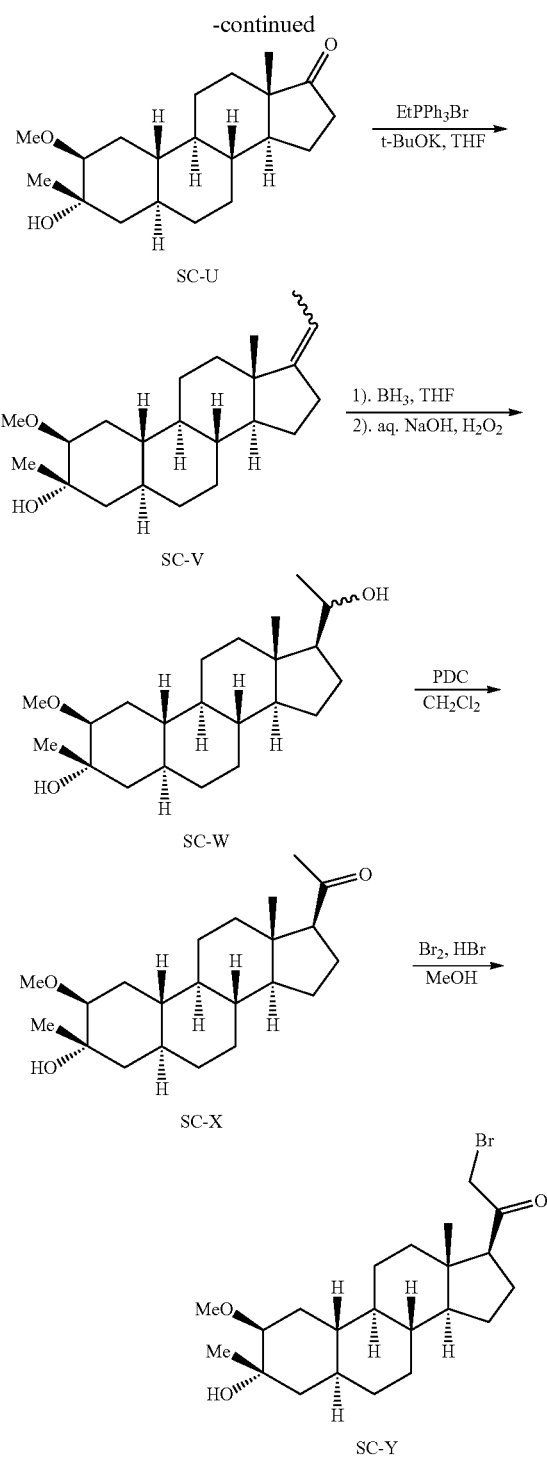

Synthesis of Compound SC-P

To NH$_3$ (liquid, 2.0 L) was added lithium (7.0 g, 1 mol) at −78° C. After the liquid was turned to deep blue, a solution of compound SC-A (27.0 g, 100 mmol) in t-BuOH (7.4 g, 100 mmol) and THF (20 mL) was added dropwise. The mixture was stirred at −78° C. for 4 hours. Then NH$_4$Cl solid (50 g) was added to quench the reaction. The mixture was turned from deep blue to white. The mixture was allowed to warm to room temperature and ammonia was evaporated overnight. The residue was dissolved in 0.5N aqueous HCl (50 mL) and extracted with dichloromethane (200 mL×3). The combined organic layers were washed with saturated NaHCO$_3$ (200 mL) and brine (200 mL), dried over magnesium sulfate and concentrated in vacuo. The crude product was purified by flash chromatography (Petroleum ether/ethyl acetate=4:1) to get product SC-P (18.98 g, 68.7%) as white solid. $^1$H NMR (500 MHz, CDCl$_3$) δ(ppm): 3.66 (1H, t), 2.29-2.27 (2H, m), 2.12-2.07 (2H, m), 1.83-1.81 (2H, m), 1.50 (1H, s), 0.77 (3H, s).

Synthesis of Compound SC-Q

A sample of 19.0 g compound SC-P (68.84 mmol) was dissolved in 50 mL THF at 0° C. Then 70 mL MeMgBr in THF (3M) was added dropwise in 30 min. The reaction was kept at 0° C. for 8 h. The reaction mixture was quenched with ice-cold water and extracted with EtOAc (200 mL×3). The combined organic layers were washed with brine, dried over sodium sulfate, filtered and concentrated. The white residue was purified by flash column chromatography (Petroleum ether/ethyl acetate=5:1) to give product SC-Q (19.0 g, 94%) as white solid. $^1$H NMR (500 MHz, CDCl$_3$) δ (ppm): 5.78 (1H, br), 5.36 (1H, t), 3.67 (1H, t), 1.73 (3H, s), 0.77 (3H, s).

Synthesis of Compound SC-R

To a solution of compound SC-Q (19.0 g, 65.07 mmol) in dichloromethane (100 mL) was added pyridinium dichromate (PDC) (48.9 g, 130.14 mmol). The mixture was stirred at room temperature overnight. The solution was filtered through a short pad of celite. The celite was washed with CH$_2$Cl$_2$ (3×100 mL). The combined CH$_2$Cl$_2$ solution was concentrated in vacuo. The residue was purified by flash chromatography (Petroleum ether/ethyl acetate=5:1) to afford product SC-R (10.0 g, 53%) as white solid. $^1$H NMR (500 MHz, CDCl$_3$) δ (ppm): 2.44 (1H, dd), 2.07 (1H, m), 1.21 (3H, s), 0.87 (3H, s).

Synthesis of Compound SC-S

To a solution of compound SC-R (5.0 g, 17.2 mmol) in anhydrous toluene (100 mL) was added to the p-toluenesulfonic acid on sillica gel (80 g), the mixture was stirred under 45° C. for 1 hour. The insoluble bi-products were removed from sillica gel by elution with Petroleum ether/ethyl acetate (10/1). The crude product SC-S (3.20 g, 11.75 mmol) was used in the next step without further purification.

Synthesis of Compound SC-T

To a solution of compound SC-S (3.20 g, 11.75 mmol) in 10 mL anhydrous dichloromethane was added mCPBA (4.04 g, 23.50 mmol), and the reaction mixture was stirred over night at room temperature. The reaction mixture then was extracted with CH$_2$Cl$_2$, the combined organic layer was washed twice with NaHCO$_3$ (100 mL) and brine, dried over Na$_2$SO$_4$ and concentrated. The crude product SC-T was used in the next step without further purification.

Synthesis of Compound SC-U

To a solution of compound SC-T (11.75 mmol) in methanol was added H$_2$SO$_4$ (0.5 mL), and the reaction mixture was stirred for 2 h at room temperature. The reaction solution was then extracted with CH$_2$Cl$_2$ (200 mL×3), the combined organic layer was washed with NaHCO$_3$ (100 mL) and brine, dried over Na$_2$SO$_4$ and concentrated. The residue was purified by chromatography (Petroleum ether/ethyl acetate=10:1) to afford compound SC-U (3.30 g, 10.30 mmol, Yield=87% for two steps) as white solid.

Synthesis of Compound SC-V

To a solution of ethyltriphenylphosphonium bromide (11.52 g, 31.0 mmol) in anhydrous THF (20 mL) was added t-BuOK (3.48 g, 31.0 mmol). The solution was turned to reddish and heated at 70° C. for 3 hours. Then compound SC-U (3.30 g, 10.30 mmol) was added in one portion. The reaction solution was heated at 70° C. overnight, then was quenched by the addition of water (10 mL). The mixture was diluted with EtOAc (200 mL) and the resulting solution was washed with brine (2×100 mL), dried over magnesium sulfate and concentrated in vacuo. The crude product SC-V (1.90 g) was used directly in the next step without further purification.

Synthesis of Compound SC-W

To a solution of compound SC-V (1.90 g, 5.72 mmol) in dry THF (20 mL) was added BH$_3$-THF (18 mL of 1.0M solution in THF). After stirring at room temperature for 1 h, the reaction mixture was cooled in an ice bath then quenched slowly with 10% aqueous NaOH (12 mL) followed by 30% H$_2$O$_2$ (20 mL). The mixture was allowed to stir at room temperature for 1 h then extracted with EA (100 mL×3). The combined organic layer was washed with 10% aqueous Na$_2$S$_2$O$_3$ (50 mL), brine, dried over Na$_2$SO$_4$, filtered and concentrated to afford crude compound SC-W (1.86 g, 5.31 mmol). The crude product was used in the next step without further purification.

Synthesis of Compound SC-X

To a solution of crude compound SC-W (1.86 g, 5.31 mmol) in dichloromethane (50 mL) was added pyridinium dichromate (PDC) in portions (3.98 g, 10.62 mmol). The solution was stirred at 25° C. overnight. Then the mixture was filtered through a short pad of silica gel and the silica gel was washed with dichloromethane (3×50 mL). All filtrate was combined and concentrated in vacuo. The residue was purified by flash chromatography (Petroleum ether/ethyl acetate=10:1) to afford product SC-X (1.20 g, 3.45 mmol, 65%) as white solid. $^1$HNMR (500 MHz, CDCl3) δ(ppm): 3.33 (3H, s), 3.04 (1H, s), 2.53 (1H, t), 2.12 (3H, s within m), 1.26 (3H, s within m), 0.62 (3H, s)

Synthesis of Compound SC-Y

To a solution of reactant SC-X (100 mg, 0.287 mmol) in methanol (10 mL) was added 48% HBr (152 mg, 0.903 mmol) followed by bromine (0.08 mL, 1.505 mmol). The solution was heated at 25° C. for 1.5 hours. Then the mixture was poured into cooled water (50 mL). The resulting solid was extracted with ethyl acetate (2×50 mL). The combined organic extracts were washed with brine (50 mL), dried over magnesium sulfate and concentrated in vacuo. The crude product SC-Y was used directly without further purification in the next step.

Example 14. Synthesis of SC-EE Compound

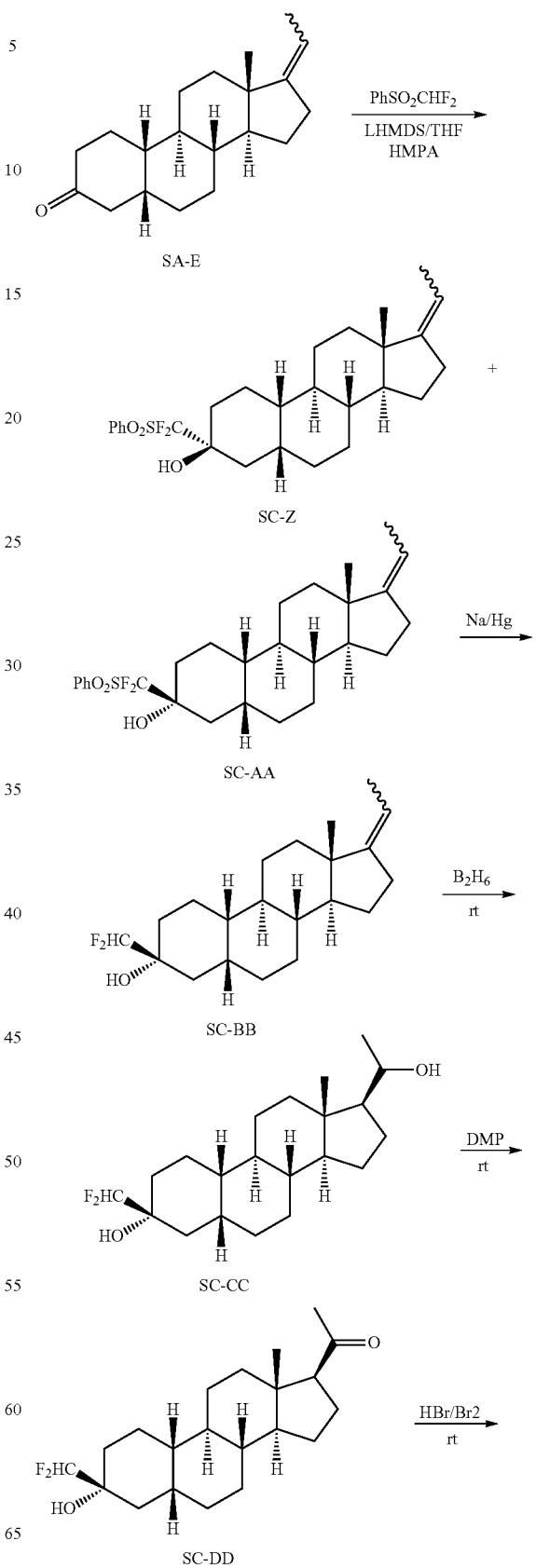

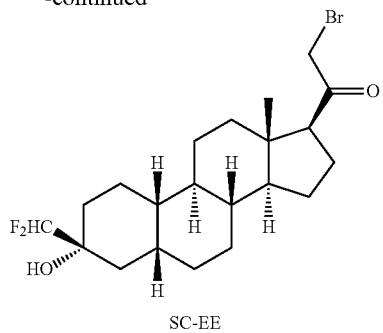

SC-EE

Synthesis of Compound SC-Z and SC-AA

To a solution of compound SA-E (800 mg, 2.79 mmol) and PhSO$_2$CF$_2$H (540 mg, 2.79 mmol) in THF (25 mL) and HMPA (0.5 mL) at −78° C. under N$_2$ was added LHMDS (4 mL, 1M in THF) dropwise. After stirring at −78° C. for 2 h, the reaction mixture was quenched with saturated aqueous NH$_4$Cl solution (10 mL) and allowed to warm to room temperature then extracted with Et$_2$O (20 mL×3). The combined organic layers were washed with brine, dried over sodium sulfate, filtered and concentrate. The residue was purified by silica gel column chromatography (pertroleum ether/ethyl acetate=10/1) to give the mixture of compound SC-Z and SC-AA (700 mg). The mixture was further purified by chiral-HPLC to afford compound SC-Z (200 mg, t=4.31 min). $^1$H NMR (400 MHz, CDCl$_3$), δ (ppm), 7.99-7.97 (d, 2H), 7.77-7.75 (m, 1H), 7.64-7.60 (m, 2H), 5.14-5.08 (m, 1H), 0.88 (s, 3H): compound SC-AA (260 mg, t=5.66 min). $^1$H NMR (400 MHz, CDCl$_3$), δ (ppm), 8.00-7.98 (d, 2H), 7.77-7.75 (m, 1H), 7.64-7.60 (m, 2H), 5.14-5.09 (m, 1H), 0.88 (s, 3H).

Synthesis of Compound SC-BB

To a solution of compound SC-AA (100 mg, 0.209 mmol) and anhydrous Na$_2$HPO$_4$ (100 mg) in anhydrous methanol (5 mL) at −20° C. under N$_2$ was added Na/Hg amalgam (500 mg). After stirring at −20° C. to 0° C. for 1 h, the methanol solution was decanted out and the solid residue was washed with Et$_2$O (5×3 mL). The combined organic layers were washed with brine (20 mL), dried over MgSO$_4$, filtered and concentrated. The residue was purified by silica gel chromatography (pertroleum ether/ethyl acetate=10/1) to give compound SC-BB (36 mg, 0.106 mmol, 51%). $^1$H NMR (400 MHz, CDCl$_3$), δ (ppm), 6.02-5.88 (t, 1H), 5.17-5.15 (m, 1H), 0.88 (s, 3H).

Synthesis of Compound SC-CC

To a solution of compound SC-BB (150 mg, 0.443 mmol) in dry THF (5 mL) was added borane-tetrahydrofuran complex (1.34 mL of 1.0M solution in THF). After stirring at room temperature for 1 hour, the reaction mixture was cooled in an ice bath then quenched slowly with 10% aqueous NaOH (1 mL) followed 30% aqueous solution of H$_2$O$_2$ (1.2 mL). The mixture was allowed to stir at room temperature for 1 hour then extracted with EtOAc (3×10 mL). The combined organic layers were washed with 10% aqueous Na$_2$S$_2$O$_3$ (10 mL), brine (10 mL), dried over MgSO$_4$, filtered and concentrated to afford crude compound SC-CC (210 mg). The crude product was used in the next step without further purification.

Synthesis of Compound SC-DD

To a solution of crude compound SC-CC (210 mg) was dissolved in 10 mL of H$_2$O saturated dichloromethane (dichloromethane had been shaken with several milliliters of H$_2$O then separated from the water layer) was added Dess-Martin periodinate (380 mg, 0.896 mmol). After stirring at room temperature for 24 h, the reaction mixture was extracted with dichloromethane (3×10 mL). The combined organic layers were washed with 10% aqueous Na$_2$S$_2$O$_3$ (10 mL), brine (10 mL), dried over MgSO$_4$, filtered and concentrated. The residue was purified by chromatography on silica gel (pertroleum ether/ethyl acetate=5:1) to afford compound SC-DD (90 mg, 0.254 mmol, 57%) as a white solid. $^1$H NMR (400 MHz, CDCl$_3$), δ (ppm), 6.01-5.73 (t, 1H), 2.55-2.54 (m, 1H), 2.12 (s, 3H), 0.62 (S, 3H).

Synthesis of Compound SC-EE

To a solution of compound SC-DD (80 mg, 0.226 mmol) in MeOH (5 mL) was added 2 drops of HBr (48%) followed by bromine (100 mg, 0.63 mmol). After stirring at room temperature for 1 h, the reaction mixture was poured into ice-water then extracted with ethyl acetate (15 mL×3), The combined organic layers were washed with brine (20 mL), dried over MgSO4, filtered and concentrated to give crude compound SC-EE (95 mg). The crude product was used in the next step without further purification.

Example 15. Synthesis of SC-II Compound

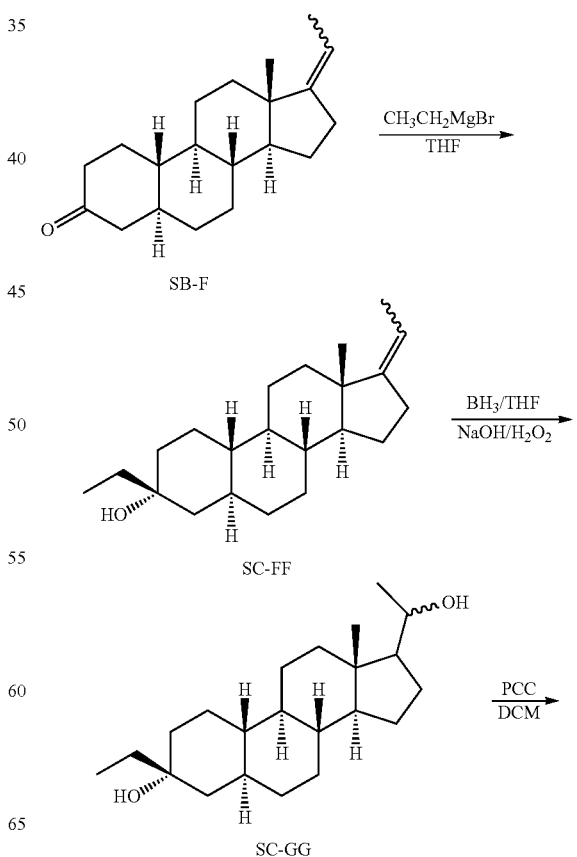

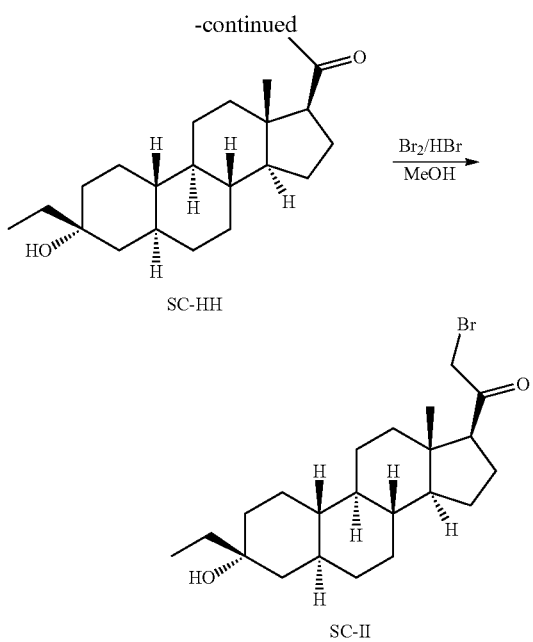

product SC-HH (2.5 g, 7.53 mmol, yield 39%) as a white solid. $^1$HNMR (500 MHz, CDCl3) δ(ppm): 2.54 (1H, t), 2.11 (3H, s), 1.42-1.45 (2H, q), 0.91 (3H, t), 0.62 (3H, s).

Synthesis of Compound SC-II

To a solution of reactant SC-HH (80 mg, 0.24 mmol) in methanol (5 mL) was added 48% hydrobromic acid (148 mg, 0.884 mmol) followed by bromine (241 mg, 0.077 mL, 1.505 mmol). The solution was heated at 25° C. for 1.5 hours, then the mixture was poured into cooled water (50 mL). The resulting solid was extracted with ethyl acetate (2×50 mL). The combined organic extracts were washed with brine (20 mL), dried over magnesium sulfate and concentrated in vacuo. The crude product SC-II was used directly without further purification in the next step.

Example 16. Synthesis of SC-SS Compound

Synthesis of Compound SC-FF

To a solution of reactant SB-F (4.4 g, 15.38 mmol) in dry THF (50 mL) was added ethylmagnesium bromide (3M in THF, 51.28 mL) dropwise at 0° C. The solution was then slowly warmed and stirred at ambient temperature for 15 h. Sat. NH$_4$Cl solution (20 mL) was added to quench the reaction and the resulting solution was extracted with ethyl acetate (3×100 mL). The extracts were washed with brine, dried over Na$_2$SO$_4$ and concentrated in vacuo. The residue was purified by flash chromatography (petroleum ether: ethyl acetate=10:1) to afford product SC-FF (3.15 g, 10.00 mmol, 64.8%) as a white solid.

Synthesis of Compound SC-GG

To a solution of reactant SC-FF (500 mg, 1.58 mmol) in anhydrous THF (10 mL) was added BH$_3$.THF (1.0M, 7.23 mL, 7.23 mmol) at room temperature, and the solution was stirred at 25° C. overnight. Then the reaction was quenched by addition of water (5 mL), 2M NaOH solution (10 mL) was added followed by 30% H$_2$O$_2$ (10 mL). The resulting mixture was stirred at room temperature for 1 hour. Then the mixture was diluted with ethyl acetate (200 mL) and resulting solution was washed with brine (2×100 mL), dried over magnesium sulfate and concentrated in vacuo. The crude product SC-GG was used directly in the next step without further purification.

Synthesis of Compound SC-HH

To a solution of reactant SC-GG (6.53 g, 19.67 mmol) in anhydrous DCM (100 mL) cooled in an ice-water cooling bath was added pyridinium chlorochromate (8.48 g, 39.34 mol) in portions. The mixture was stirred at ambient temperature overnight. The solution was then diluted with DCM (50 mL) and filtered. The combined organic solutions were washed with brine (100 mL), dried over Na$_2$SO$_4$ and concentrated in vacuo. The residue was purified by flash chromatography (petroleum ether:elthyl acetate=10:1) to afford

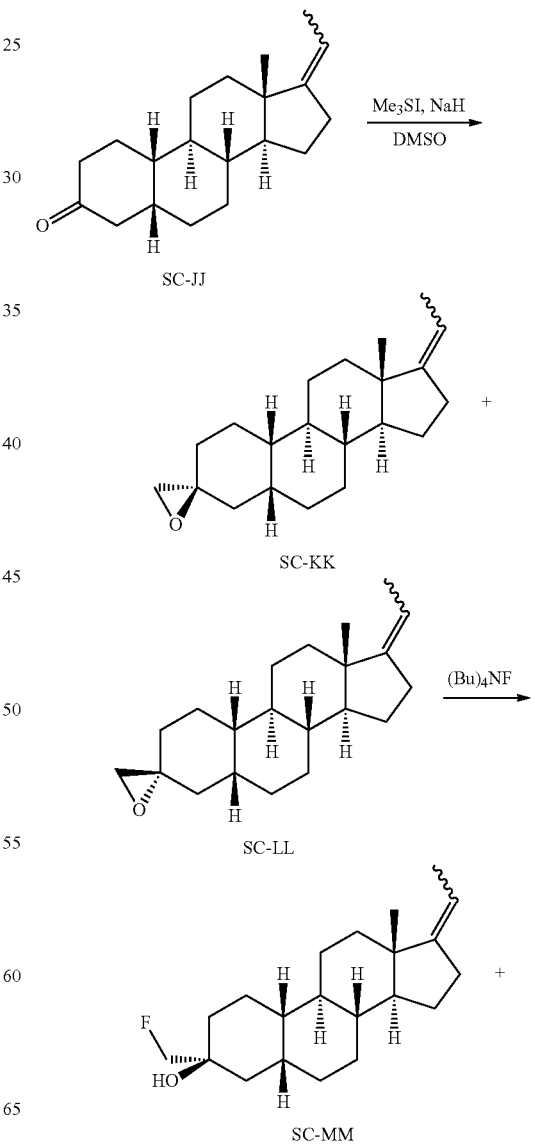

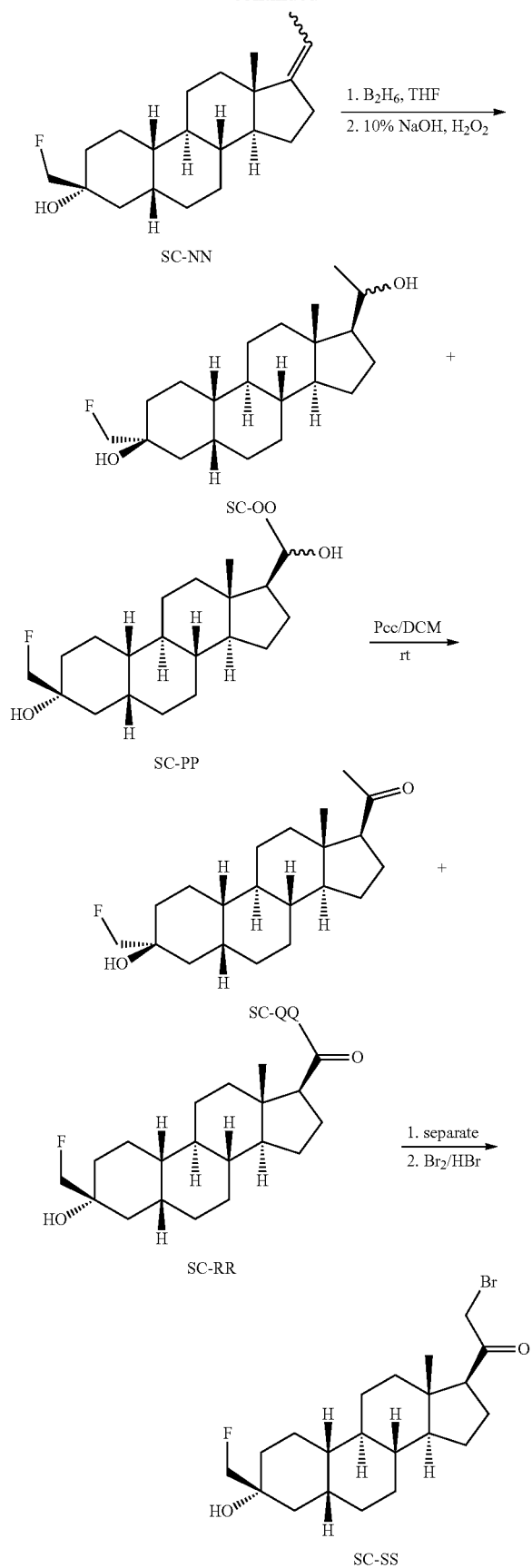

Synthesis of Compound SC-MM and SC-NN

A mixture of reactant mixture SA-KK and SA-LL (3.0 g, 10.0 mmol, 1:1) was added dry $(Bu)_4NF$, then the mixture was heated 100° C. overnight. The residual mixture was poured in to 50 mL $H_2O$ and extracted with EtOAc (2×50 mL). The combined organic layers were washed with brine solution, dried over sodium sulfate, filtered and concentrated. The residue was purified by flash chromatography (petroleum ether/ethyl acetate=20:1) to afford product mixture SC-MM and SC-NN (2.1 g, 6.5 mmol, 65%) as white solid.

Synthesis of Compound SC-OO and SC-PP

To a solution of reactant mixture SC-MM and SC-NN (2.1 g, 6.5 mmol) in anhydrous THF (30 mL) was added $BH_3$.THF (1.0M, 13.0 mL, 13.0 mmol), the solution was stirred at 25° C. overnight. Then the reaction was quenched by addition of water (5 mL). 2M NaOH solution (20 mL) was added followed by 30% $H_2O_2$ (20 mL). The mixture was stirred at room temperature for 1 hour. The mixture was diluted with ethyl acetate (200 mL) and resulting solution was washed with brine (2×100 mL), dried over magnesium sulfate and concentrated in vacuo. The crude product mixture was used directly in the next step without further purification.

Synthesis of Compound SC-QQ and SC-RR

To a solution of crude reactant mixture SC-OO and SC-PP (2.2 g, 6.5 mmol, theoretical amount) in dichloromethane (40 mL) was added Pyridinium chlorochromate (Pcc) in portions (2.8 g, 13.0 mmol). The solution was stirred at 25° C. overnight. Then the mixture was filtered through a short pad of silica gel and the silica gel was washed with dichloromethane (3×50 mL). All filtrate was combined and concentrated in vacuo. The residue was purified by flash chromatography (petroleum ether/ethyl acetate=15:1) to afford product SC-QQ (910 mg, 2.7 mmol, Yield=41% (2 steps)) as white solid and product SC-RR (850 mg, 2.5 mmol, Yield=39% (2 steps)) as white solid. Compound SC-QQ: $^1$HNMR (500 MHz, CDCl3) δ(ppm): 4.17 (d, 2H), 2.53 (t, 1H), 2.17-2.13 (m, 2H), 2.11 (s, 3H), 2.03-2.00 (m, 1H), 0.62 (s, 3H). Compound SC-RR: $^1$HNMR (500 MHz, CDCl3) δ(ppm): 4.45 (AB×d, 1H), 4.39 (AB×d, 1H), 2.54 (t, 1H), 0.62 (s, 3H).

Synthesis of Compound SC-SS

To a solution of reactant SC-RR (100 mg, 0.301 mmol) in methanol (10 mL) was added 48% hydrobromic acid (152 mg, 0.903 mmol) followed by bromine (241 mg, 0.077 mL, 1.505 mmol). The solution was heated at 25° C. for 1.5 hours. Then the mixture was poured into cooled water (50 mL). The resulting solid was extracted with ethyl acetate (2×50 mL). The combined organic extracts were washed with brine (50 mL), dried over magnesium sulfate and concentrated in vacuo. The crude product SC-SS was used directly without further purification in the next step.

Example 17. Synthesis of SA-ZZ Compound

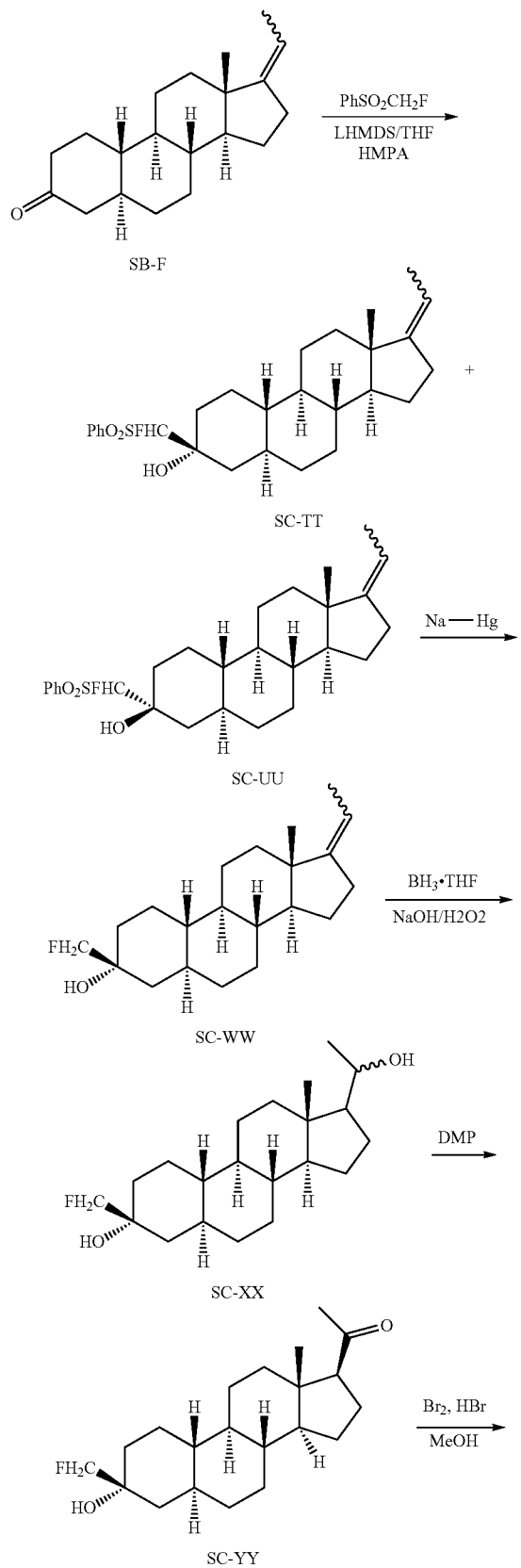

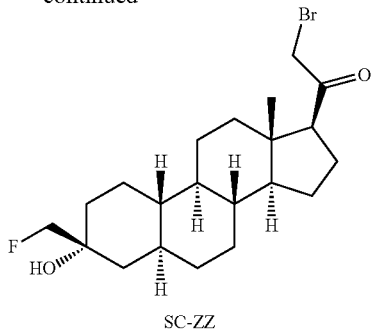

Synthesis of Compound SC-TT and SC-UU

To a solution of compound SB-F (1.3 g, 4.5 mmol) and PhSO$_2$CH$_2$F (790 mg, 4.5 mmol) in THF (25 mL) and HMPA (0.5 mL) at −78° C. under N$_2$ was added LHMDS (5.5 mL, 1M in THF) dropwise. After stirring at −78° C. for 2 h, the reaction mixture was quenched with saturated aqueous NH$_4$Cl solution (10 mL) and allowed to warm to room temperature then extracted with Et$_2$O (20 mL×3). The combined organic layers were washed with brine, dried over sodium sulfate, filtered and concentrate. The residue was purified by silica gel column chromatography (pertroleum ether/ethyl acetate=10/1) to give the mixture of compound SC-TT and SC-UU (1.53 g). The mixture was further purified by chiral-HPLC to afford compound SC-TT-1 (220 mg, t=3.41 min). $^1$H NMR (500 MHz, CDCl3), δ (ppm), 7.99-7.97 (m, 2H), 7.75-7.74 (m, 1H), 7.62-7.55 (m, 2H), 5.13-5.09 (m, 1H), 4.86-4.78 (d, 1H), 0.88 (s, 3H); SC-TT-2 (200 mg, t=3.66 min); $^1$H NMR (500 MHz, CDCl3), δ (ppm), 7.96-7.95 (m, 1H), 7.71-7.69 (m, 1H), 7.62-7.58 (m, 2H), 5.13-5.09 (m, 1H), 4.87-4.77 (d, 1H), 0.88 (s, 3H); SC-UU-1 (235 mg, t=4.9 min). $^1$H NMR (500 MHz, CDCl3), δ (ppm), 7.99-7.97 (m, 1H), 7.72-7.70 (m, 1H), 7.62-7.59 (m, 2H), 5.29-5.20 (d, 1H), 4.88-4.78 (m, 1H), 0.88 (s, 3H); SC-UU-2 (220 mg, t=5.2 min). $^1$H NMR (500 MHz, CDCl3), δ (ppm), 7.99-7.97 (m, 2H), 7.72 (m, 1H), 7.62-7.59 (m, 2H), 5.30-5.20 (d, 1H), 5.09-5.08 (m, 1H), 0.88 (s, 3H).

Synthesis of Compound SC-WW

To a solution of compound SC-TT-1 (200 mg, 0.434 mmol) and anhydrous Na$_2$HPO$_4$ (100 mg) in anhydrous methanol (15 mL) at −20° C. under N$_2$ was added Na/Hg amalgam (400 mg). After stirring at −20° C. to 0° C. for 1 h, the methanol solution was decanted out and the solid residue was washed with Et$_2$O (5×3 mL). The solvent of combined organic phase was removed under vacuum, and 20 ml brine was added, followed by extracting with Et2O. The combined ether phase was dried with MgSO4, and the ether was removed to give the crude product, which was further purified by silica gel chromatography (petroleum ether/ethyl acetatE=10/1) to give product 99 mg, 69%. $^1$H NMR (500 MHz, CDCl3), δ (ppm), 5.12-5.10 (m, 1H), 4.21-24.11 (d, 2H), 0.88 (s, 3H).

Synthesis of Compound SC-XX

To a solution of compound SC-WW (95 mg, 0.296 mmol) in dry THF (5 mL) was added borane-tetrahydrofuran complex (1 mL of 1.0M solution in THF). After stirring at room temperature for 1 hour, the reaction mixture was cooled in an ice bath then quenched slowly with 10% aqueous NaOH (1 mL) followed by 30% aqueous solution of $H_2O_2$ (1.2 mL). The mixture was allowed to stir at room temperature for 1 hour then extracted with EtOAc (3×10 mL). The combined organic layers were washed with 10% aqueous $Na_2S_2O_3$ (10 mL), brine (10 mL), dried over $MgSO_4$, filtered and concentrated to afford compound SC-XX (120 mg crude). The crude product was used in the next step without further purification.

Synthesis of Compound SC-YY

To a solution of compound SC-XX (120 mg crude) was dissolved in 10 mL of wet dichloromethane (dichloromethane had been shaken with several milliliters of $H_2O$ then separated from the water layer) was added Dess-Martin periodinate (300 mg, 707 mmol). After stirring at room temperature for 24 h, the reaction mixture was extracted with dichloromethane (3×10 mL). The combined organic layers were washed with 10% aqueous $Na_2S_2O_3$ (10 mL), brine (10 mL), dried over $MgSO_4$, filtered and concentrated. The residue was purified by chromatography on silica gel (pertroleum ether/ethyl acetate=1:5) to afford compound SC-YY (70 mg, 70% for two steps) as a white solid. $^1H$ NMR (500 MHz, CDCl3), δ (ppm), 4.21-4.11 (d, 2H), 2.19 (s, 3H), 0.62 (s, 3H).

Synthesis of Compound SC-ZZ

To a solution of reactant (200 mg, 0.594 mmol) in methanol (5 mL) was added 48% hydrobromic acid (300 mg, 1.782 mmol) followed by bromine (475 mg, 0.152 mL, 2.97 mmol). The solution was heated at 25° C. for 2 hours. Then the mixture was poured into cooled water (50 mL). The resulting solid was extracted with ethyl acetate (2×100 mL). The combined organic extracts were washed with brine (100 mL), dried over magnesium sulfate and concentrated in vacuo. The crude product was used directly without further purification in the next step.

Example 18. Synthesis of Compounds SA-1 and SA-2

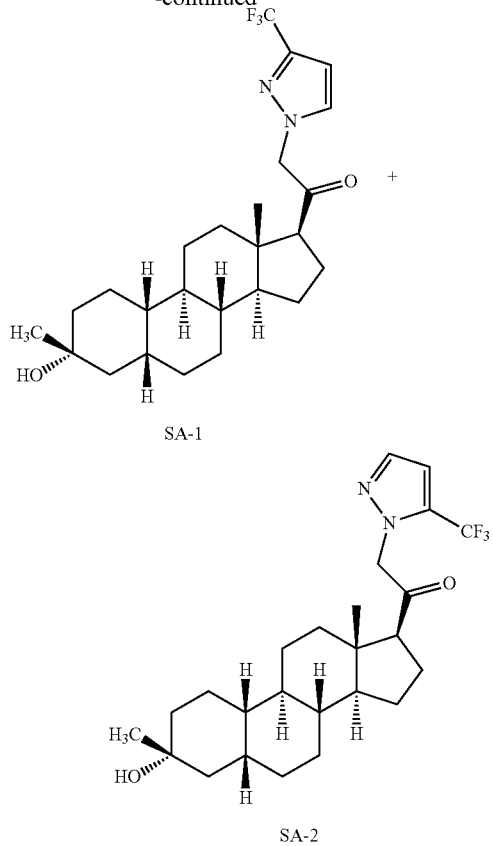

To a suspension of $K_2CO_3$ (50 mg, 0.36 mmol) in THF (5 mL) was added 5-(trifluoromethyl)-1H-pyrazole (80 mg, 0.59 mmol) and SA (100 mg, 0.25 mmol). The mixture was stirred at rt for 15 h. The reaction mixture was poured into 5 mL $H_2O$ and extracted with EtOAc (2×10 mL). The combined organic layers were washed with brine, dried over sodium sulfate, filtered and concentrated. The residue mixture was purified with by reverse-phase prep-HPLC to afford the title compound as a white solid SA-1 (15 mg, 13.2%). SA-2 (5 mg, 4.4%). SA-1: $^1H$ NMR (500 MHz, CDCl$_3$), δ (ppm), 7.47 (d, 1H), 6.59 (d, 1H), 4.99 (1H, AB), 4.95 (1H, AB), 2.58 (1H, t), 1.00-2.20 (m, 24H), 0.68 (s, 3H). SA-2: $^1H$ NMR (500 MHz, CDCl$_3$), δ (ppm), 7.57 (d, 1H), 6.66 (d, 1H), 5.03 (1H, AB), 4.93 (1H, AB), 2.77 (1H, t), 1.00-2.2 (m, 24H), 0.9 (s, 3H).

Example 19. Synthesis of Compound SA-3

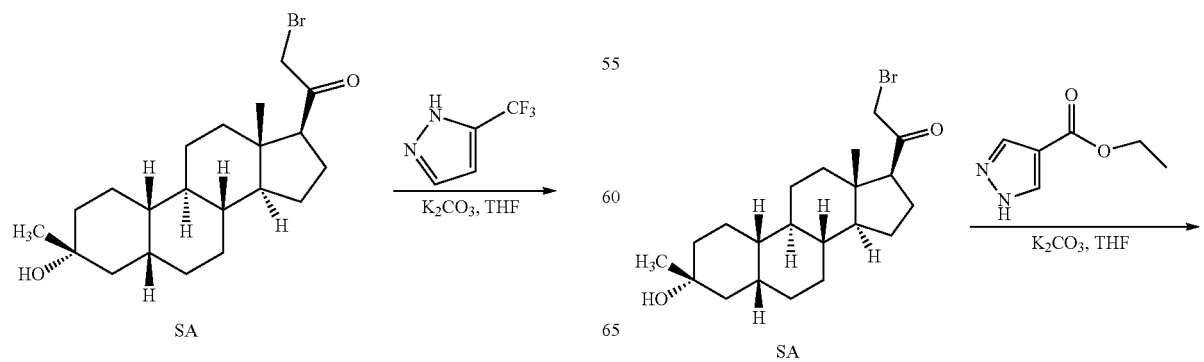

-continued

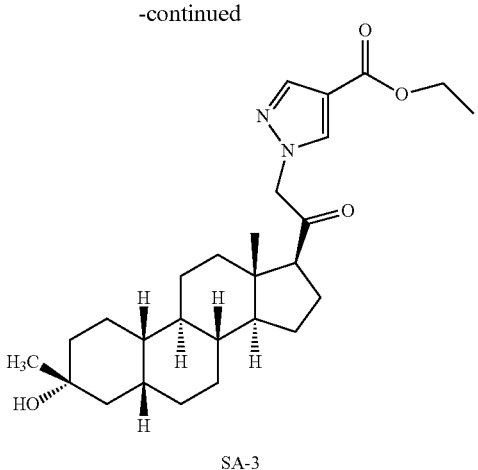

SA-3

To a suspension of K₂CO₃ (50 mg, 0.36 mmol) in THF (5 mL) was added ethyl 1H-pyrazole-4-carboxylate (100 mg, 0.71 mmol) and SA (72 mg, 0.18 mmol). The mixture was stirred at rt for 15 h. The reaction mixture was poured in to 5 mL H₂O and extracted with EtOAc (2×10 mL). The combined organic layers were washed with brine, dried over sodium sulfate, filtered and concentrated. The residue mixture was purified with by reverse-phase prep-HPLC to afford the title compound as a white solid (18 mg, 21.6%). ¹H NMR (500 MHz, CDCl₃), δ (ppm) 7.93 (s, 1H), 7.91 (s, 1H), 4.97 (1H, AB), 4.86 (1H, AB), 4.28 (q, 2H), 2.60 (1H, t), 1.34 (t, 3H), 1.00-2.25 (m, 24H), 0.67 (s, 3H).

Example 20. Synthesis of Compound SA-4

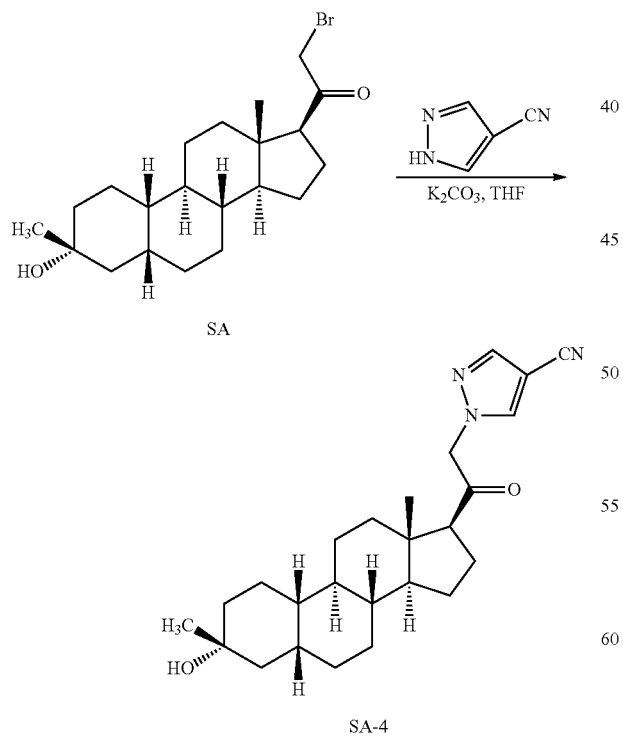

SA-4

To a suspension of K₂CO₃ (50 mg, 0.36 mmol) in THF (5 mL) was added ethyl 1H-pyrazole-4-carbonitrile (100 mg, 0.97 mmol) and SA (50 mg, 0.12 mmol). The mixture was stirred at rt for 15 h. The reaction mixture was poured in to 5 mL H₂O and extracted with EtOAc (2×10 mL). The combined organic layers were washed with brine, dried over sodium sulfate, filtered and concentrated. The residue mixture was purified with by reverse-phase prep-HPLC to afford the title compound as a white solid (9 mg, 17.4%). ¹H NMR (500 MHz, CDCl₃), δ (ppm) 7.87 (1H, s), 7.82 (1H, s), 5.02 (1H, AB), 4.92 (1H, AB), 2.61 (1H, t), 2.16-2.24 (1H, m), 2.05 (1H, d×t), 1.70-1.88 (6H, m), 1.61-1.69 (2H, m), 1.38-1.52 (6H, m), 1.23-1.38 (5H, m), 1.28 (3H, s), 1.06-1.17 (3H, m), 0.67 (3H, s). LCMS: rt=2.24 min, m/z=410.1 [M+H]⁺.

Example 21. Synthesis of Compound SA-5

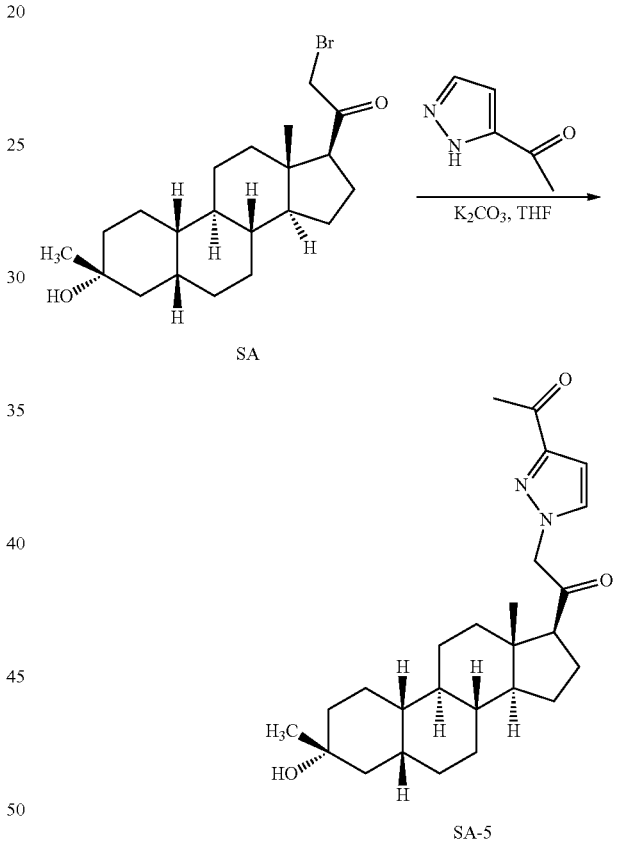

SA-5

To a suspension of K₂CO₃ (50 mg, 0.36 mmol) in THF (5 mL) was added ethyl 1-(1H-pyrazol-5-yl)ethanone (100 mg, 0.91 mmol) and SA (50 mg, 0.12 mmol). The mixture was stirred at rt for 15 h. The reaction mixture was poured in to 5 mL H₂O and extracted with EtOAc (2×10 mL). The combined organic layers were washed with brine, dried over sodium sulfate, filtered and concentrated. The residue mixture was purified with by reverse-phase prep-HPLC to afford the title compound as a white solid (37 mg, 65%): ¹H NMR (500 MHz, CDCl₃), δ (ppm) 7.41 (d, 1H), 6.85 (d, 1H), 4.98 (1H, AB), 4.86 (1H, AB), 2.59 (t, 1H), 2.55 (s, 3H), 1.00-2.25 (m, 24H), 0.69 (s, 3H).

Example 22. Synthesis of Compound SA-6

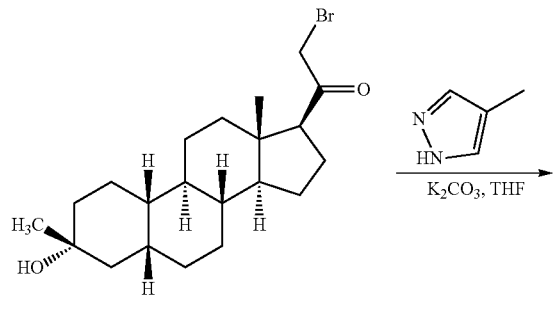

SA

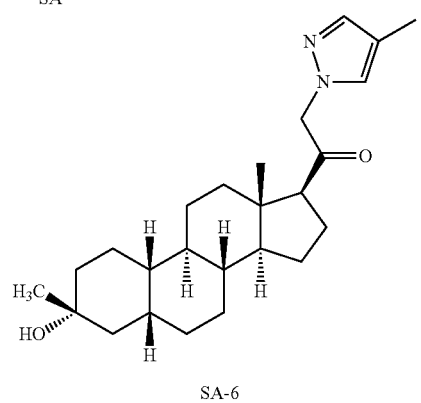

SA-6

A solution of SA (350 mg, 0.88 mmol) and K$_2$CO$_3$ (243.5 mg, 1.76 mmol) in 10 mL dry DMF was added 4-methyl-1H-pyrazole (144.6 mg, 1.76 mmol) under N$_2$ at room temperature. The reaction mixture was stirred for 18 h at this temperature. The reaction mixture was poured to water, extracted with EtOAc (2*50 mL), the organic layers were washed with brine, dried over anhydrous Na$_2$SO$_4$, filtered and concentrated, purified by flash chromatography silica column (petroleum ether/ethyl acetate 10:1 to 2:1) to afford SA-6 (230 mg, yield: 65.5%) as a white powder. $^1$H NMR (400 MHz, CDCl$_3$), δ (ppm), 7.35 (s, 1H), 7.18 (s, 1H), 4.92-4.79 (m, 2H), 2.59-2.55 (m, 1H), 2.23-2.15 (m, 1H), 2.10 (s, 3H), 2.07-2.03 (m, 1H), 1.88-1.80 (m, 3H), 1.76-1.61 (m, 6H), 1.49-1.22 (m, 16H), 1.13-1.05 (m, 3H), 0.68 (s, 3H). LCMS: rt=1.29 min, m/z=399.2 [M+H]$^+$.

Example 23. Synthesis of Compound SA-7

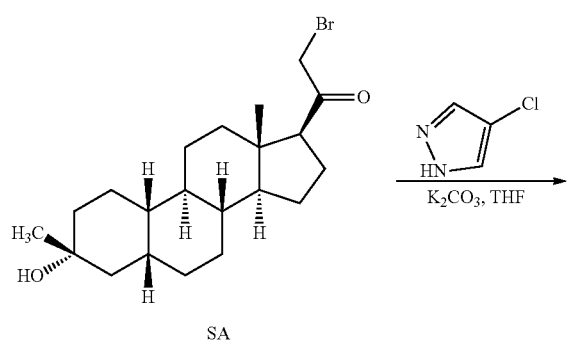

SA

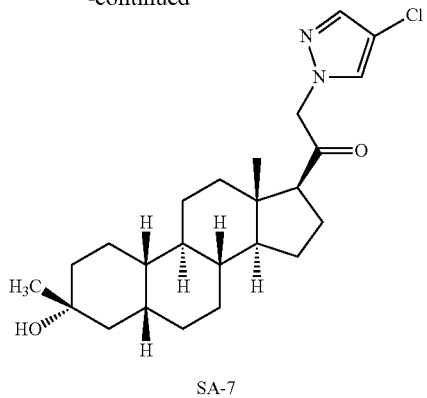

SA-7

To a suspension of K$_2$CO$_3$ (25 mg, 0.18 mmol) in THF (5 mL) was added 4-chloro-4H-pyrazole (21 mg, 0.21 mmol) and SA (36 mg, 0.09 mmol). The mixture was stirred at RT for 15 h. The residue mixture was poured in to 5 mL H$_2$O and extracted with EtOAc (2×10 mL). The combined organic layers were washed with brine, dried over sodium sulfate, filtered and concentrated. The residue mixture was purified with by reverse-phase prep-HPLC to afford the title compound as a white solid (8 mg, 21%): $^1$H NMR (500 MHz, CDCl$_3$), δ (ppm), 7.45 (s, 1H), 7.41 (s, 1H), 4.90 (AB, 1H), 4.81 (AB, 1H), 2.57 (t, 1H), 2.22-2.16 (m, 1H), 2.05-2.01 (m, 1H), 1.00-1.90 (m, 22H), 0.67 (s, 3H). LCMS: rt=2.52 min, m/z=419.1 [M+H]+

Example 24. Synthesis of Compound SA-8

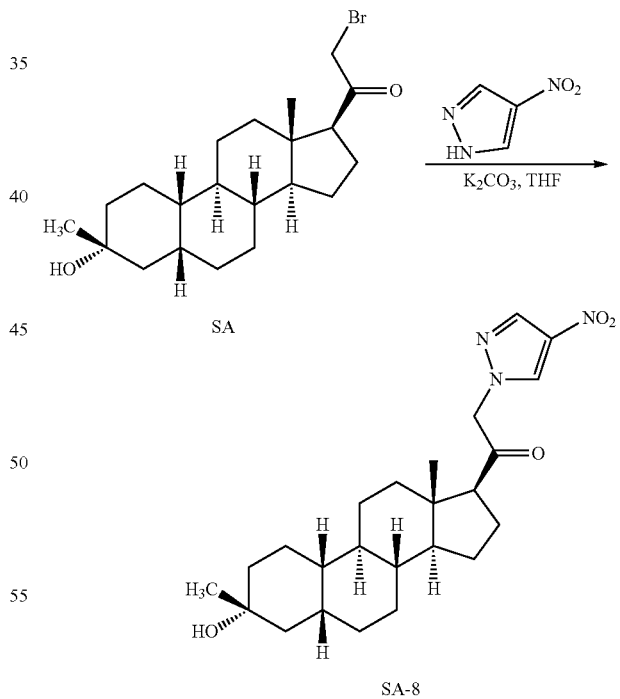

SA

SA-8

To a suspension of K$_2$CO$_3$ (25 mg, 0.18 mmol) in THF (5 mL) was added 4-nitro-4H-pyrazole (20 mg, 0.18 mmol) and SA (36 mg, 0.09 mmol). The mixture was stirred at RT for 15 h. The residue mixture was poured in to 5 mL H$_2$O and extracted with EtOAc (2×10 mL). The combined organic layers were washed with brine, dried over sodium sulfate, filtered and concentrated. The residue mixture was purified with by reverse-phase prep-HPLC to afford the title compound as a white solid (12 mg, 31%): ¹H NMR (500 MHz, CDCl₃), δ (ppm) 8.11 (s, 1H), 8.01 (s, 1H), 4.93 (AB, 1H), 4.83 (AB, 1H), 2.55 (t, 1H), 2.15-2.10 (m, 1H), 1.99-1.96 (m, 1H), 1.00-1.80 (m, 22H), 0.68 (s, 3H).

Example 25. Synthesis of Compound SA-9

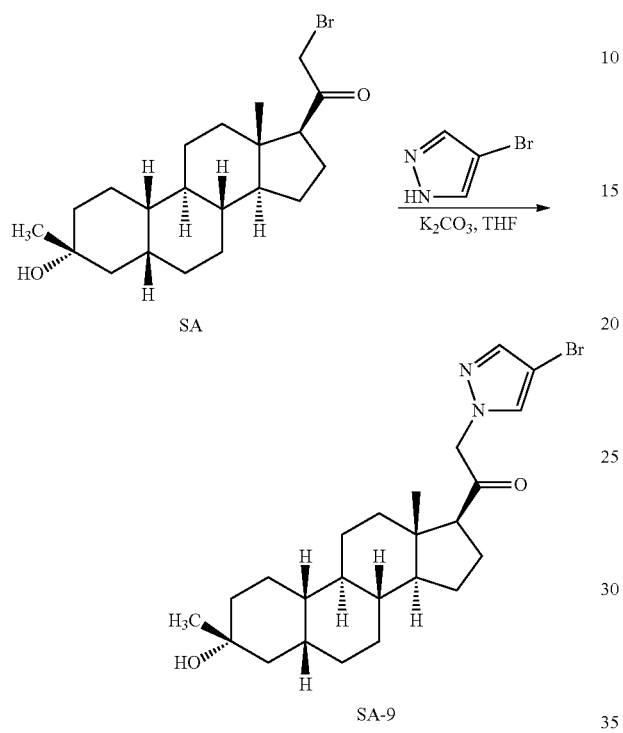

To a suspension of K₂CO₃ (25 mg, 0.18 mmol) in THF (5 mL) was added 4-bromo-4H-pyrazole (26 mg, 0.18 mmol) and SA (36 mg, 0.09 mmol). The mixture was stirred at RT for 15 h. The residue mixture was poured in to 5 mL H₂O and extracted with EtOAc (2×10 mL). The combined organic layers were washed with brine, dried over sodium sulfate, filtered and concentrated. The residue mixture was purified with by reverse-phase prep-HPLC to afford the SA-9 as a white solid (9 mg, 22%): ¹H NMR (500 MHz, CDCl₃), δ (ppm), 7.41 (s, 1H), 7.37 (s, 1H), 4.85 (AB, 1H), 4.77 (AB, 1H), 2.59 (t, 1H), 2.22-2.18 (m, 1H), 2.06-2.01 (m, 1H), 0.90-1.80 (m, 22H), 0.68 (s, 3H). 0.90-1.80 (m, 22H).

Example 26. Synthesis of Compounds SA-10 and SA-11

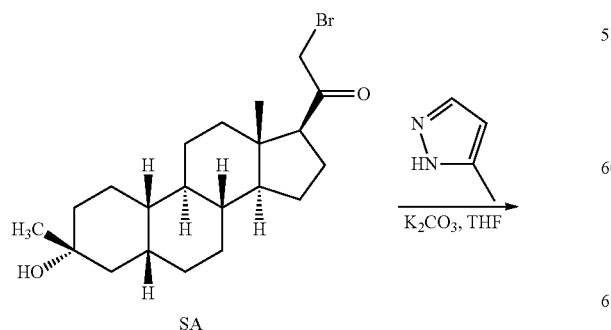

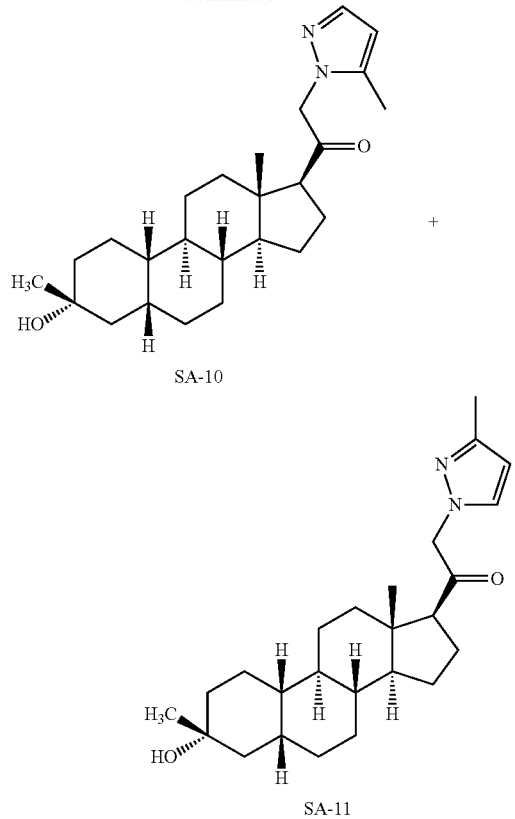

To a suspension of K₂CO₃ (55 mg, 0.4 mmol) in THF (5 mL) was added 3-methyl-4H-pyrazole (33 mg, 0.4 mmol) and SA (79 mg, 0.2 mmol). The mixture was stirred at RT for 15 h. The residue mixture was poured in to 5 mL H₂O and extracted with EtOAc (2×10 mL). The combined organic layers were washed with brine, dried over sodium sulfate, filtered and concentrated. The residue mixture was purified with by reverse-phase prep-HPLC to afford SA-10 as a white solid (9 mg, 11%) and SA-11 as a white solid (11 mg, 14%). Compound SA-10: 1H NMR (400 MHz, CDCl₃), δ (ppm), 7.41 (d, 1H), 6.07 (s, 1H), 4.85 (s, 2H), 2.84-2.83 (m, 1H), 2.59 (t, 1H), 2.17 (s, 3H), 2.07-2.04 (m, 1H), 1.00-1.90 (m, 22H), 0.69 (s, 3H). Compound SA-11: 1H NMR (400 MHz, CDCl₃), δ (ppm), 7.28 (s, 1H), 6.09 (d, 1H), 4.84 (AB, 1H), 4.83 (AB, 1H), 2.56 (t, 1H), 2.27 (s, 3H), 2.22-2.14 (m, 1H), 2.05-2.02 (m, 1H), 1.00-1.90 (m, 22H), 0.67 (s, 3H), 1.00-1.90 (m, 22H).

Example 27. Synthesis of Compound SA-12

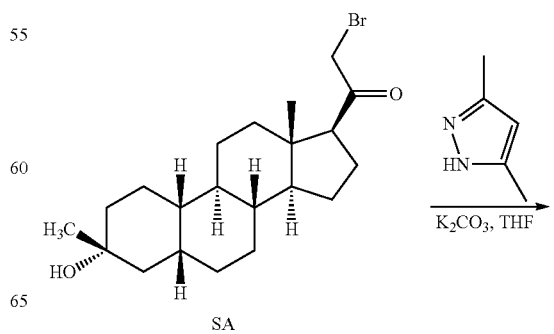

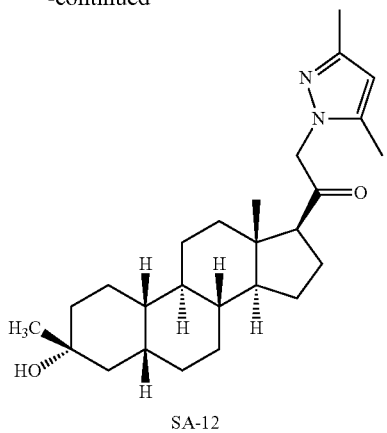

SA-12

To a suspension of K$_2$CO$_3$ (25 mg, 0.18 mmol) in THF (5 mL) was added 3,5-dimethyl-4H-pyrazole (17 mg, 0.18 mmol) and SA (36 mg, 0.09 mmol). The mixture was stirred at RT for 15 h. The residue mixture was poured in to 5 mL H$_2$O and extracted with EtOAc (2×10 mL). The combined organic layers were washed with brine, dried over sodium sulfate, filtered and concentrated. The residue mixture was purified with by reverse-phase prep-HPLC to afford the title compound as a white solid (11 mg, 30%): $^1$H NMR (500 MHz, CDCl$_3$), δ (ppm), 5.86 (s, 1H), 4.79 (AB, 1H), 4.74 (AB, 1H), 2.57 (t, 1H), 2.21 (s, 3H), 2.18-2.16 (m, 1H), 2.11 (s, 3H), 2.05-2.02 (m, 1H), 0.90-1.80 (m, 22H), 0.68 (s, 3H).

Example 28. Synthesis of Compound SA-13

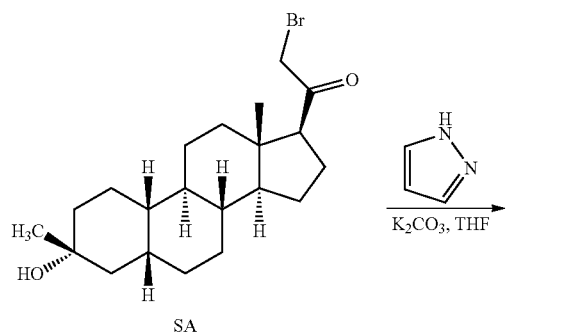

SA-13

To a suspension of K$_2$CO$_3$ (50 mg, 0.36 mmol) in THF (6 mL) was added 3H-pyrazole (16 mg, 0.23 mmol) and SA (36 mg, 0.09 mmol). The mixture was stirred at RT for 15 h. The reaction mixture was poured into 5 mL H$_2$O and extracted with EtOAc (2×10 mL). The combined organic layers were washed with brine, dried over sodium sulfate, filtered and concentrated. The residue was purified with by reverse-phase prep-HPLC to afford the title compound as a white solid (11 mg, 31.3%). $^1$HNMR (400 MHz, CDCl$_3$), δ (ppm), 7.56 (d, 1H), 7.44 (d, 1H), 6.35 (s, 1H), 4.95 (AB, 1H), 4.92 (AB, 1H), 2.60 (1H, t), 1.00-2.25 (m, 24H), 0.68 (s, 3H).

Example 29. Synthesis of Compound SA-14

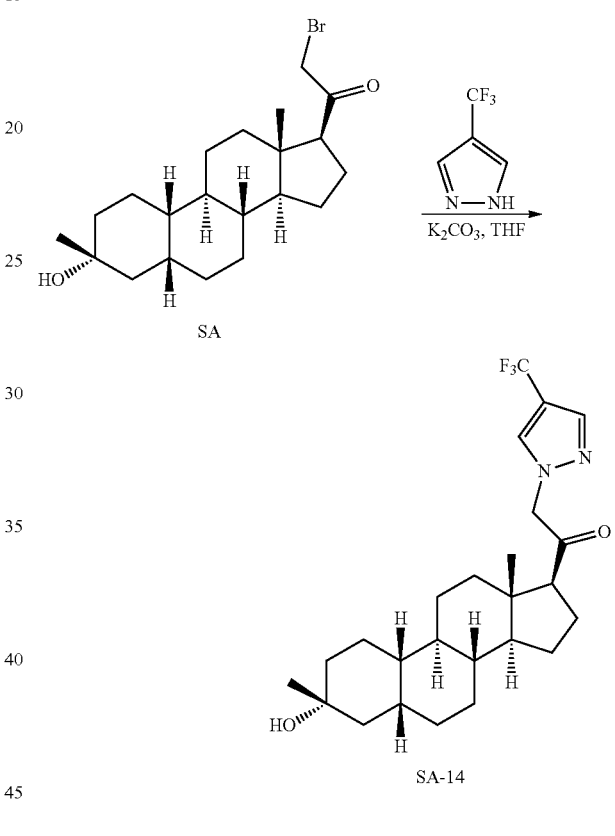

SA-14

To a solution of crude reactant (124.8 mg, 0.315 mmol, theoretical amount) in anhydrous THF (2.5 mL) was added 4-(trifluoromethyl)-1H-pyrazole (85.5 mg, 0.628 mmol) followed by potassium carbonate (86.8 mg, 0.628 mmol). The solution was heated at room temperature overnight then the solution was diluted with ethyl acetate (100 mL). The resulting solution was washed with brine (2×50 mL), dried over magnesium sulfate and concentrated in vacuo. The crude product was purified by silica gel chromatography (petroleum ether/ethyl acetate=1:1) to afford product (69 mg, 0.152 mmol, Yield=48% (2 steps)) as white solid. $^1$HNMR (500 MHz, CDCl$_3$) δ(ppm): 7.72 (2H, s), 4.99 (1H, AB), 4.89 (1H, AB), 2.61 (1H, t), 2.2 (bq, 1H), 1.00-2.10 (23H, m), 0.69 (3H, s). 1.00-2.10 (24H, m). $^{19}$FNMR (376 MHz, CDCl$_3$) δ(ppm): −56.46. LCMS: rt=2.52 min, m/z=453.2 [M+H]$^+$

Example 30. Synthesis of Compound SA-15

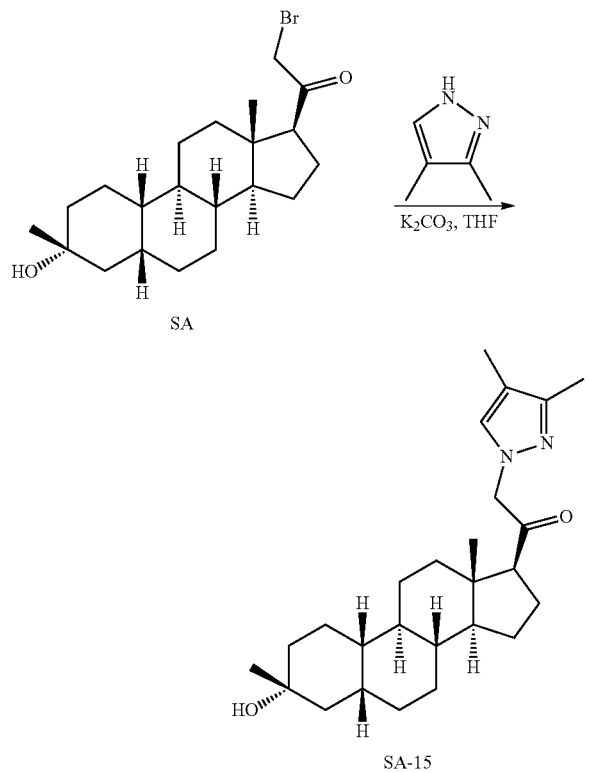

To a solution of crude reactant (249.5 mg, 0.629 mmol, theoretical amount) in anhydrous THF (5 mL) was added 3.4-dimethyl-1H-pyrazole (120.7 mg, 1.256 mmol) followed by potassium carbonate (173.6 mg, 1.256 mmol). The solution was stirred at 25° C. overnight then the solution was diluted with ethyl acetate (200 mL). The resulting solution was washed with brine (2×100 mL), dried over magnesium sulfate and concentrated in vacuo. The crude product was purified by silica gel chromatography (petroleum ether/ethyl acetate=1:3) to afford product (56 mg, 0.136 mmol, Yield=22% (2 steps)) as white solid. $^1$HNMR (400 MHz, CDCl$_3$) δ(ppm): 7.08 (1H, s), 4.77 (1H, AB), 4.76 (1H, AB), 2.55 (1H, t), 2.18 (3H, s), 1.00-2.20 (24H, m). 0.67 (3H, s). LCMS: rt=2.41 min, m/z=413.2 [M+H]$^+$ Synthesis of 4-ethyl-1H-pyrazole

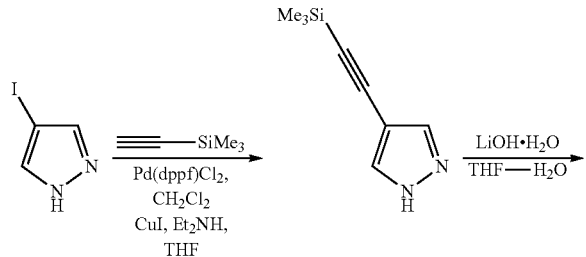

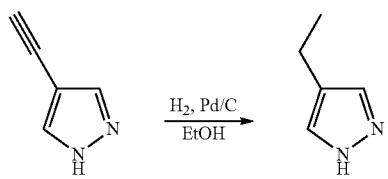

Synthesis of 4-ethynyltrimethylsilane-1H-pyrazole

To a solution of reactant (3.88 g, 20 mmol), Pd(dppf)Cl$_2$.CH$_2$Cl$_2$ (2.45 g, 3 mmol), CuI (0.571 g, 3 mmol) in Et$_2$NH (30 mL) and THF (30 mL) was added ethynyltrimethylsilane (9.823 g, 14.1 mL, 100 mmol) under N$_2$ atmosphere and the mixture was stirred at room temperature overnight. Then the black solution was diluted with ethyl acetate (300 mL) and the resulting solution was washed with brine (2×100 mL), dried over magnesium sulfate and concentrated in vacuo. The residue was purified by silica gel chromatography (: petroleum ether/ethyl acetate=7.5:1) to afford product (1.90 g, 11.57 mmol, Yield=58%) as brownish solid. $^1$HNMR (500 MHz, DMSO-d6) δ(ppm): 13.12 (1H, br), 8.07 (1H, s), 7.65 (1H, s), 0.19 (9H, s).

Synthesis of 4-ethynyl-1H-pyrazole

To a solution of reactant (1.90 g, 11.57 mmol) in THF (20 mL) and water (4 mL) was added lithium hydroxide hydrate (970 mg, 23.14 mmol). The solution was stirred at room temperature overnight then most THF solvent was removed in vacuo. The solution was neutralized by addition of acetic acid and the resulting mixture was diluted with dichloromethane (200 mL) and brine (50 mL). The organic layer was separated, dried over magnesium sulfate and concentrated in vacuo. The residue was purified by silica gel chromatography (: petroleum ether/ethyl acetate=4:1) to afford product (828 mg, 8.99 mol, Yield=78%) as pale brownish solid. $^1$HNMR (500 MHz, DMSO-d6) δ(ppm): 13.11 (1H, br), 8.05 (1H, s), 7.65 (1H, s), 3.95 (1H, s).

Synthesis of 4-ethyl-1H-pyrazole

To a solution of reactant (828 mg, 8.99 mmol) in ethanol (50 mL) was added 10 wt % Pd/C on carbon (165.6 mg, 0.16 mmol). The reaction mixture was hydrogenated with a hydrogen balloon overnight. A small sample solution was filtered, concentrated in vacuo and characterized by $^1$HNMR to determine that the reaction was complete. All reaction mixture was filtered by celite and the celite was washed with ethanol (20 mL). The combined filtrate was concentrated in vacuo. The residue was purified by a short pad of silica gel (: petroleum ether/ethyl acetate=3:1) to afford product (643 mg, 6.69 mmol, Yield=74%) as pale yellow liquid. $^1$HNMR (500 MHz, DMSO-d6) δ(ppm): 12.48 (1H, s), 7.39 (2H, s), 2.43 (2H, q, J=7.6 Hz), 1.13 (3H, t, J=7.6 Hz).

Example 31. Synthesis of Compound SA-16

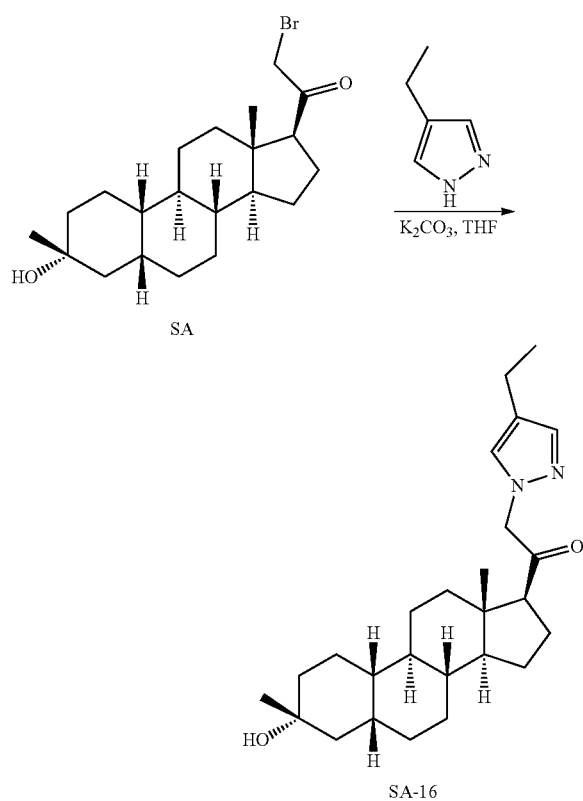

To a solution of crude reactant (249.5 mg, 0.629 mmol, theoretical amount) in anhydrous THF (5 mL) was added 4-ethyl-1H-pyrazole (120.7 mg, 1.256 mmol) followed by potassium carbonate (173.6 mg, 1.256 mmol). The solution was stirred at 25° C. overnight and then the solution was diluted with ethyl acetate (200 mL). The resulting solution was washed with brine (2×100 mL), dried over magnesium sulfate and concentrated in vacuo. The crude product was purified by silica gel chromatography (: petroleum ether/ethyl acetate=2:3) to afford product (29.5 mg, 0.0714 mmol, Yield=11% (2 steps)) as white solid. $^1$HNMR (400 MHz, CDCl$_3$) δ(ppm): 7.38 (1H, s), 7.18 (1H, s), 4.89 (1H, AB), 4.82 (1H, AB), 2.57 (1H, t), 2.51 (2H, q), 0.80-2.20 (24H, m), 0.68 (3H, s). LCMS: rt=2.34 min, m/z=413.1 [M+H]$^+$ Synthesis of 4-methylsulfonyl-1H-pyrazole

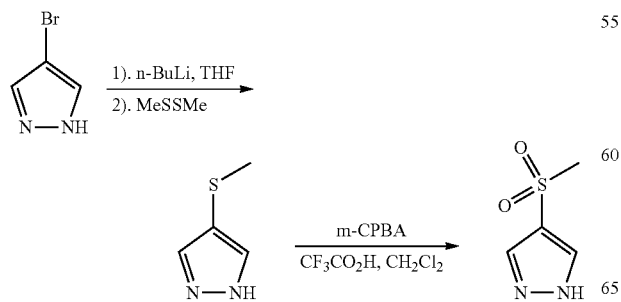

Synthesis of 4-methylthio-1H-pyrazole

To a solution of 4-bromo-1H-pyrazole (200 mg, 1.361 mmol) in anhydrous THF (5 mL) was added n-BuLi (2.5M, 1.8 mL, 4.5 mmol) at 0° C. The solution was stirred at room temperature for 1 hour. The MeSSMe (128 mg, 0.12 mL, 1.361 mmol) was added at 0° C. and reaction solution was stirred at room temperature for 2 hours. The reaction was poured into ethyl acetate (50 mL) and water (50 mL). The separated organic layer was washed brine (50 mL), dried over magnesium sulfate and concentrated in vacuo. Due to its smell, the crude product was used in next oxidation reaction without further purification.

Synthesis of 4-methylsulfonyl-1H-pyrazole

To a solution of the crude reactant (155.4 mg, 1.361 mmol, theoretical amount) in dichloromethane (2.7 mL) was added trifluoroacetic acid (0.1 mL) at 0° C. Then 3-chloroperbenzoic acid (m-CPBA, 85% wt, 863 mg, 4.25 mmol) was added in portions and the solution was stirred at room temperature overnight. The solution was diluted with ethyl acetate (100 mL) and the resulting solution was washed with sat. Na$_2$CO$_3$ solution (3×50 mL) followed by brine (50 mL), dried over magnesium sulfate and concentrated in vacuo. The crude product was purified by silica gel chromatography (ethyl acetate to ethyl acetate:methanol=10:1) to afford product (51 mg, 0.349 mmol, Yield=26% (2 steps)) as pale yellow thick oil. $^1$HNMR (500 MHz, CDCl$_3$) δ(ppm): 8.04 (2H, s), 3.14 (3H, s).

Example 32. Synthesis of Compound SA-17

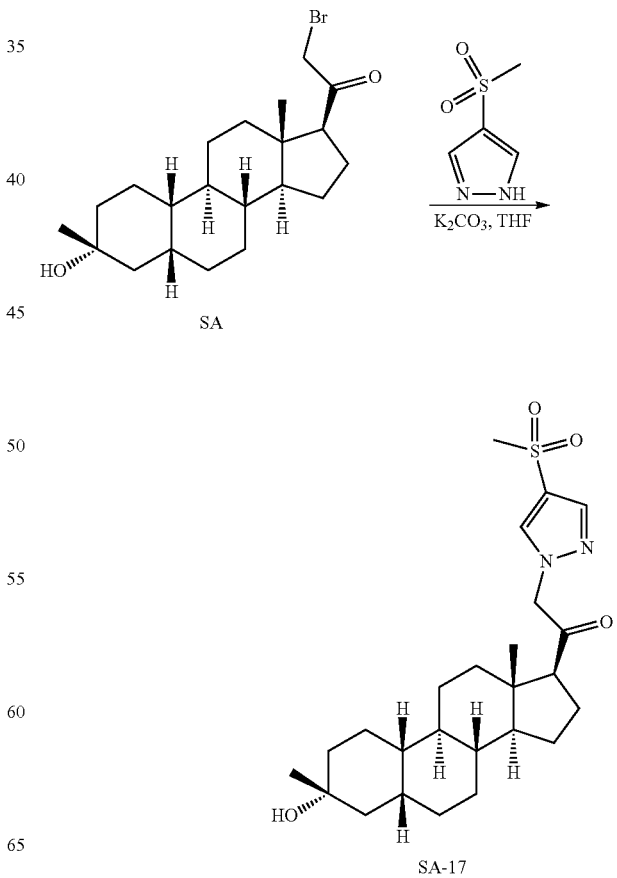

To a solution of crude reactant (124.8 mg, 0.315 mmol, theoretical amount) in anhydrous THF (2.5 mL) was added 4-(methylsulfonyl)-1H-pyrazole (51 mg, 0.349 mmol) followed by potassium carbonate (48 mg, 0.349 mmol). The solution was heated at 40° C. for 2 hours then the solution was diluted with ethyl acetate (100 mL). The resulting solution was washed with brine (2×50 mL), dried over magnesium sulfate and concentrated in vacuo. The crude product was purified by reverse phase prep-HPLC to afford product SA-17 (4 mg, 0.00865 mmol, Yield=2.8% (2 steps) as a white solid. $^1$HNMR (400 MHz, CDCl$_3$) δ(ppm): 7.93 (1H, s), 7.87 (1H, s), 5.02 (1H, AB), 4.92 (1H, AB), 3.14 (3H, s), 2.63 (1H, t), 2.17-2.26 (1H, s), 2.04 (1H, d×t), 1.70-1.89 (6H, m), 1.56-1.69 (1H, m), 1.20-1.54 (12H, m), 1.27 (3H, s), 1.04-1.18 (3H, m), 0.68 (3H, s). LCMS: rt=2.35 min, m/z=463.1 [M+H]$^+$ (b)

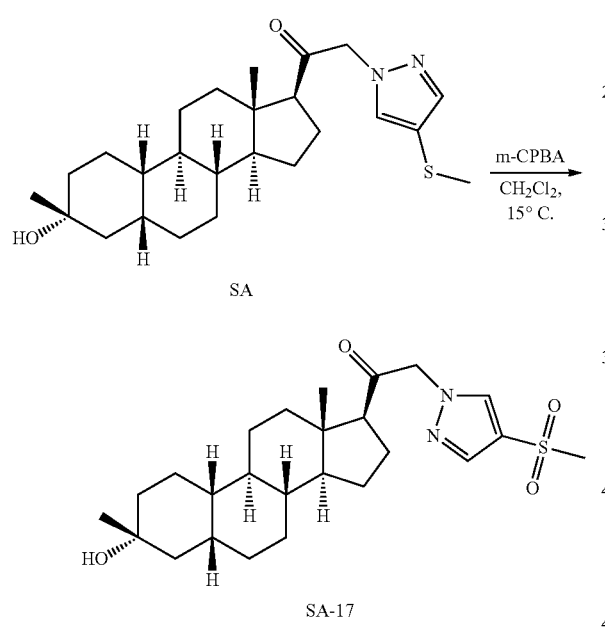

To a solution of SA (200 mg, 0.46 mmol) in 30 mL of DCM was added m-CPBA (236 mg, 1.16 mmol) at room temperature (15-19° C.). The reaction mixture was stirred for 6 hr at the same temperature. TLC showed the reaction was complete. The reaction mixture was poured into saturated aqueous Na$_2$S$_2$O$_3$ and extracted with DCM (50 mL×2). The organic layers were washed with saturated aqueous Na$_2$S$_2$O$_3$ (10 mL), brine (10 mL), dried over anhydrous Na$_2$SO$_4$ and concentrated in vacuum. The residue was purified by silica gel column (petroleum ether/ethyl acetate 5/1-1/2) to give SA-17 (140.5 mg, yield: 65%) as a white solid. $^1$H NMR: (400 MHz, CDCl3) δ 7.92 (s, 1H), 7.86 (s, 1H), 5.04-4.89 (m, 2H), 3.13 (s, 3H), 2.64-2.59 (m, 1H), 2.24-2.16 (m, 1H), 2.06-2.03 (m, 1H), 1.87-1.75 (m, 6H), 1.64-1.42 (m, 11H), 1.35-1.27 (m, 7H), 1.16-1.06 (m, 3H), 0.67 (s, 3H).

Example 33. Synthesis of Compound SA-18

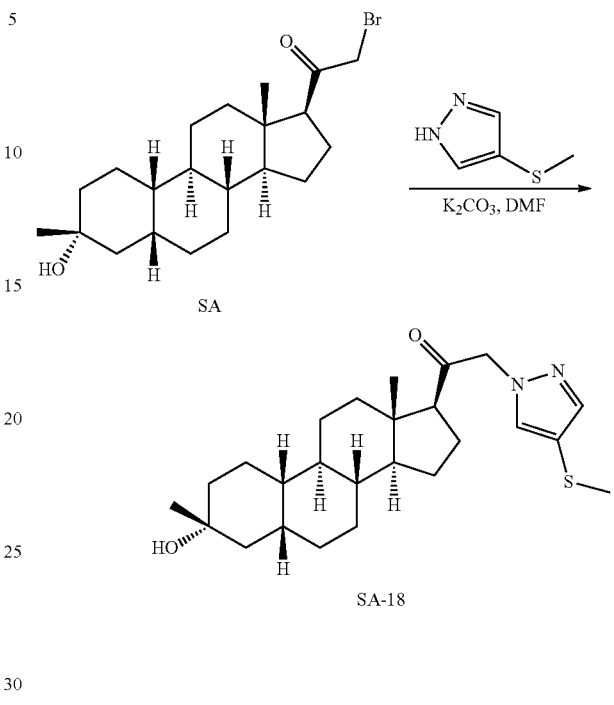

To a mixture of SA (200 mg, 0.50 mmol) and K$_2$CO$_3$ (138.2 mg, 1.00 mmol) in 5 mL dry DMF was added 4-(methylthio)-1H-pyrazole (114.2 mg, 1.00 mmol) under N$_2$ at room temperature (25° C.). The reaction mixture was stirred at the same temperature for 18 h. The reaction mixture was poured into water and extracted with EtOAc (50 mL×2). The organic layers were washed with brine, dried over Na$_2$SO$_4$, filtered and concentrated in vacuum. The residue was purified by silica gel column (Petroleum ether/ethyl acetate 10/1 to 2/1) to give Compound SA-18 (165 mg, yield: 76%) as white powder. $^1$H NMR: (400 MHz, CDCl3) δ 7.53 (s, 1H), 7.42 (s, 1H), 4.94-4.80 (m, 2H), 2.60-2.56 (m, 1H), 2.34 (s, 3H), 2.23-2.16 (m, 1H), 2.06-2.02 (m, 1H), 1.87-1.58 (m, 12H, contained H$_2$O), 1.49-1.27 (m, 14H), 1.15-1.07 (m, 2H), 0.67 (s, 3H). LCMS: rt=1.32 min, m/z=431.2 [M+H]$^+$ Example 35. Synthesis of Compound SA-20

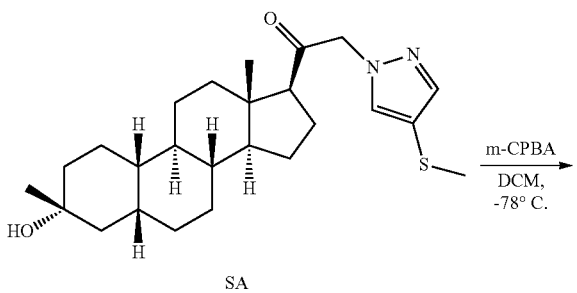

-continued

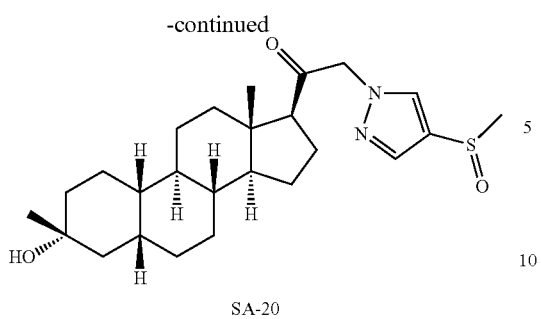

SA-20

To a solution of SA (100.0 mg, 0.23 mmol) in 10 mL of DCM was added m-CPBA (51.86 mg, 0.26 mmol) at −78° C. Then the reaction mixture was stirred at −78° C. for 3 h. LCMS indicated the reaction was complete. Then saturated aqueous $Na_2S_2O_3$ was added to the mixture at −78° C. Then the reaction was allowed warm to room temperature (16-22° C.). The resulting mixture was extracted with EtOAc (50 mL×2), washed with water (10 mL), brine (10 mL), dried over anhydrous $Na_2SO_4$, and concentrated in vacuum. The residue was purified by silica gel column (Petroleum ether/ethyl acetate=1/1 to EtOAc) to give SA-20 (90 mg, yield: 72.3%) as a white solid. $^1$H NMR: (400 MHz, CDCl3) δ 7.82 (s, 1H), 7.81 (s, 1H), 5.05-4.88 (m, 2H), 2.89 (d, 3H), 2.64-2.59 (m, 1H), 2.25-2.17 (m, 1H), 2.06-2.03 (m, 1H), 1.87-1.74 (m, 6H), 1.65-1.58 (m, 2H, contained $H_2O$), 1.48-1.40 (m, 7H), 1.33-1.28 (m, 8H), 1.15-1.07 (m, 3H), 0.68 (s, 3H). LCMS: rt=1.14 min, m/z=429.2 [M−$H_2O$], 469.2 [M+Na].

Example 36. Synthesis of Compound SA-21

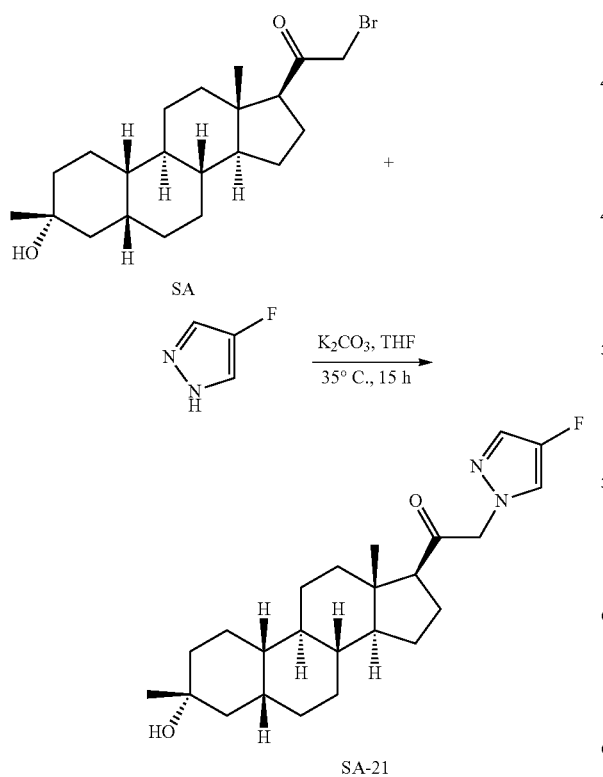

SA-21

To a suspension of Compound SA (100 mg, 0.25 mmol) in THF (25 mL) was added 4-fluoro-1H-pyrazole (64.5 mg, 0.75 mmol) and $K_2CO_3$ (103 mg, 0.75 mmol). The mixture was stirred at 35° C. for 15 h. Then the reaction mixture was extracted 50 mL EtOAc, washed with 100 mL $H_2O$ and 100 mL brine and evaporated in vacuo. The residue was purified by reverse-phase prep-HPLC to afford SA-21 as a white solid (19 mg, 0.05 mmol, 20% yield). $^1$H NMR (500 MHz, CDCl$_3$), δ (ppm), 7.37 (1H, d), 7.30 (1H, d), 4.85 (1H, AB), 4.77 (1H, AB), 2.57 (t, 1H), 2.2 (bq, 1H), 2.1 (bd, 1H), 1.00-1.9 (22H, m), 0.67 (s, 3H). LCMS: Rt=2.31 min, MS (ESI) m/z: 403.4 [M+H]$^+$.

Example 37. Synthesis of Compound SA-22

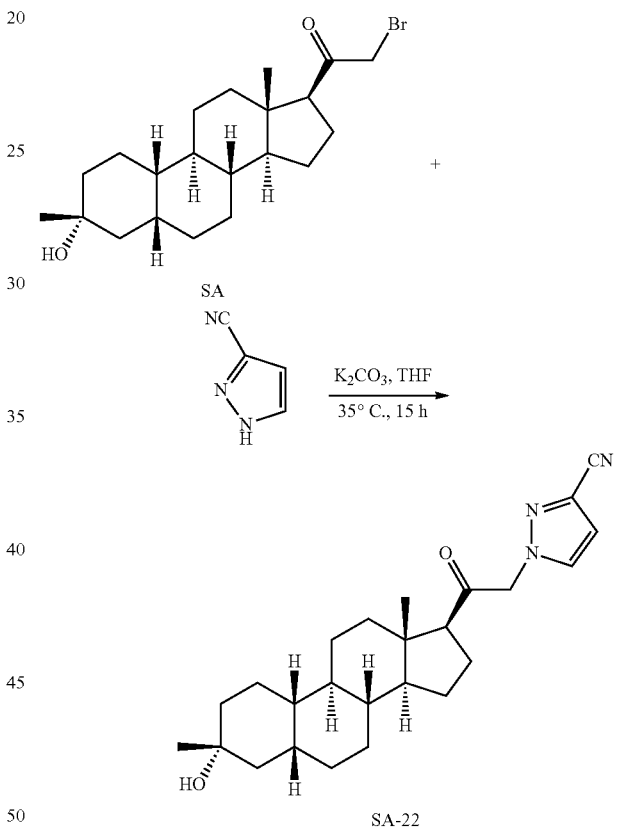

SA-22

To a suspension of Compound SA (100 mg, 0.25 mmol) in THF (25 mL) was added 1H-pyrazole-3-carbonitrile (70 mg, 0.75 mmol) and $K_2CO_3$ (103 mg, 0.75 mmol). The mixture was stirred at 35° C. for 15 h. Then the reaction mixture was extracted 50 mL EtOAc, washed with 100 mL $H_2O$ and 100 mL brine and evaporated in vacuo. The resulting residue was purified by reverse-phase prep-HPLC to afford SA-22 as a white solid (23 mg, 0.056 mnol, 24% yield). $^1$H NMR (500 MHz, CDCl$_3$), δ (ppm), 7.48 (d, 1H), 6.73 (d, 1H), 5.03 (1H, AB), 4.93 (1H, AB), 2.60 (t, 1H), 1.00-2.25 (24H, m), 0.68 (s, 3H). LCMS: Rt=2.38 min, MS (ESI) m/z: 410.2 [M+H]$^+$.

Example 38. Synthesis of Compound SA-23

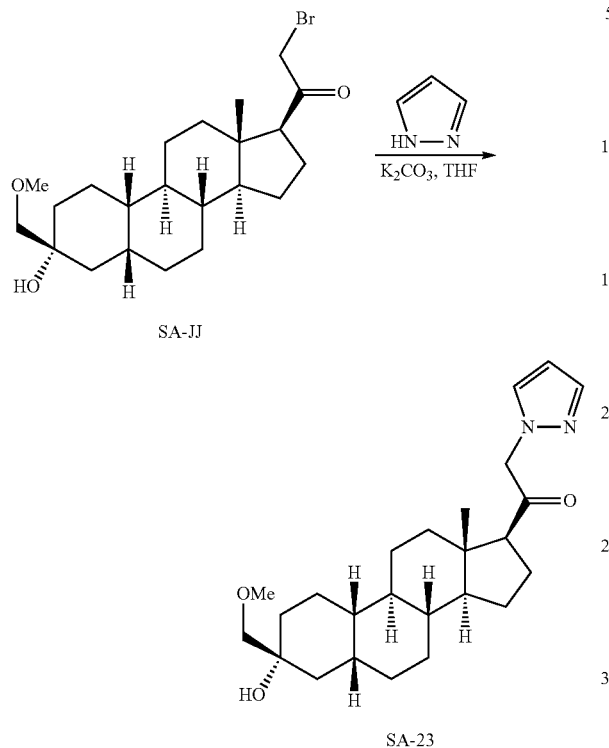

To a suspension of K$_2$CO$_3$ (55 mg, 0.4 mmol) in THF (5 mL) was added 1H-pyrazole (28 mg, 0.4 mmol) and Compound SA-JJ (85 mg, 0.2 mmol). The mixture was stirred at RT for 15 h then the residue mixture was poured into 5 mL H$_2$O and extracted with EtOAc (2×10 mL). The combined organic layers were washed with brine, dried over sodium sulfate, filtered and concentrated. The residue mixture was purified by reverse-phase prep-HPLC to afford SA-23 as a white solid (29 mg, 35%). $^1$HNMR (500 MHz, CDCl3) δ (ppm): 7.55 (d, 1H), 7.41 (d, 1H), 6.33 (t, 1H), 4.97 (AB, 1H), 4.88 (AB, 1H), 3.42-3.37 (m, 5H), 2.58 (t, 1H), 2.22-2.16 (m, 1H), 2.06-2.03 (m, 1H), 1.00-1.90 (m, 22H), 0.68 (s, 3H). LC-MS: rt=2.27 min, m/z=415.3 [M+H]$^+$

Example 39. Synthesis of Compound SA-24

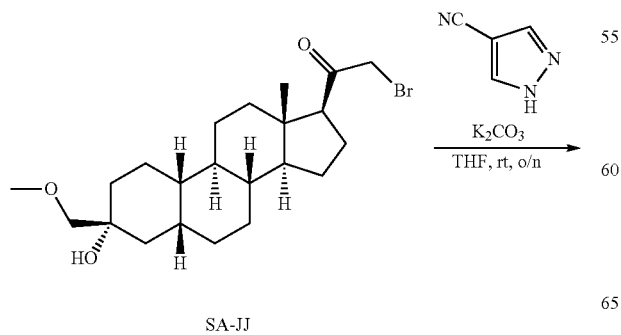

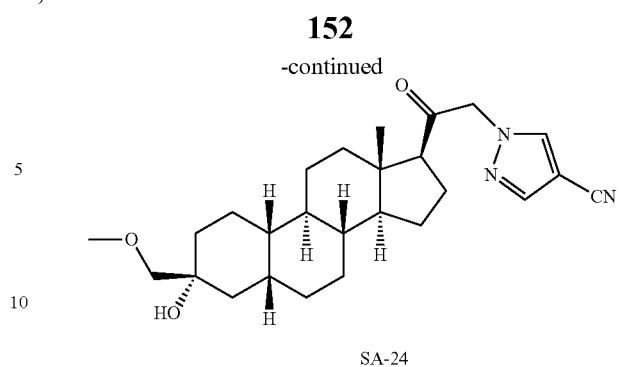

To a solution of compound SA-JJ (120 mg, 0.28 mmol) in THF (3 mL) was added K$_2$CO$_3$ (190 mg, 1.4 mmol) and 1H-pyrazole-4-carbonitrile (130 mg, 1.4 mmol). The resulting solution was stirred at room temperature overnight, then the reaction was diluted with EtOAc (20 mL). The resulting solution was washed with brine (10 mL), dried over Na$_2$SO$_4$ and concentrated in vacuo. The residue was purified by prep-HPLC to give SA-24 (30 mg, 24%) as a white solid. 1H NMR: (500 MHz, CDCl$_3$), δ (ppm), 7.86 (1H, s), 7.81 (1H, s), 5.0 (1H, AB), 4.88 (1H, AB), 3.39 (3H, s), 3.19 (2H, s), 2.59 (1H, t), 2.2 (m, 1H), 0.69 (3H, s), 0.60-2.1 (23H, m). LC-MS: rt=2.25 min; m/z=440.4 (M+H)$^+$

Example 40. Synthesis of Compound SA-25

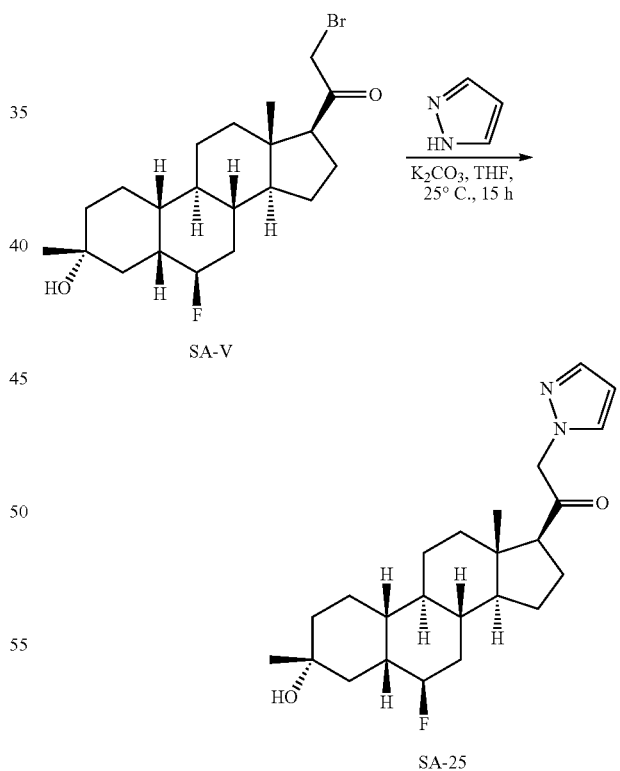

To a suspension of SA-V (20 rag, 0.04 mmol) in THF (5 mL) was added pyrazole (30 mg, 0.45 mmol) and K$_2$CO$_3$ (60 mg, 0.45 mmol). The mixture was stirred at 25° C. for 15 h. Then the reaction mixture was purified with by reverse-phase prep-HPLC to afford SA-25 as a white solid (11 mg, 57% yield). $^1$H NMR (500 MHz, CDCl$_3$), δ (ppm), 7.56 (s, 1H), 7.42 (s, 1H), 6.33 (s, 1H), 4.97 (1H, AB), 4.89 (1H, AB), 4.86-4.69 (m, 1H), 2.60 (1H, t), 1.00-2.20 (22H, m), 0.72 (s, 3H).

Example 42. Synthesis of Compound SA-27

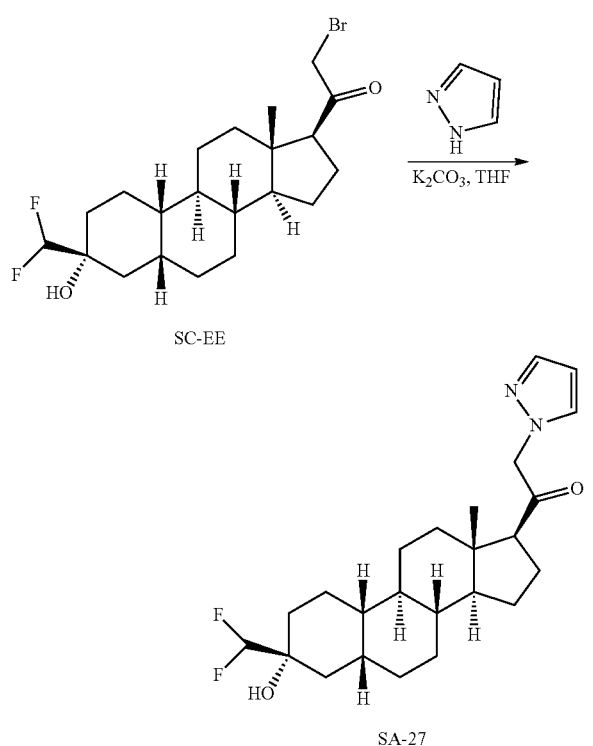

To a suspension of K$_2$CO$_3$ (25 mg, 0.18 mmol) in THF (5 mL) was added 3H-pyrazole (16 mg, 0.23 mmol) and SC-EE (36 mg, 0.08 mmol). The mixture was stirred at rt for 15 h. The reaction mixture was poured in to 5 mL H$_2$O and extracted with EtOAc (2×10 mL). The combined organic layers were washed with brine, dried over sodium sulfate, filtered and concentrated. The residue mixture was purified with by reverse-phase prep-HPLC to afford the title compound as a white solid (12 mg, 34.3%). $^1$HNMR (500 MHz, CDCl3) δ(ppm), 7.55 (d, 1H), 7.42-7.41 (d, 1H), 6.34 (t, 1H), 5.87 (t, 1H), 4.97 (1H, AB), 4.88 (1H, AB), 2.55 (t, 1H), 0.69 (s, 3H), 1.10-2.25 (m, 24H), 0.69 (s, 3H).

Example 43. Synthesis of Compound SA-28

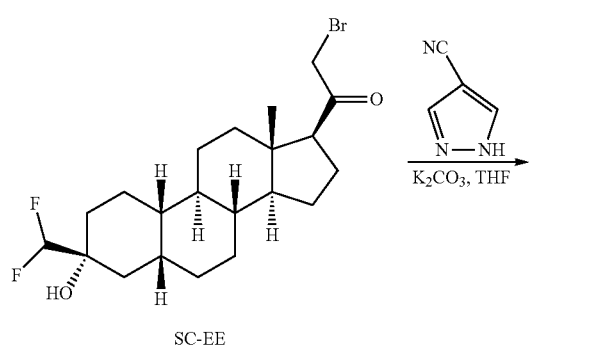

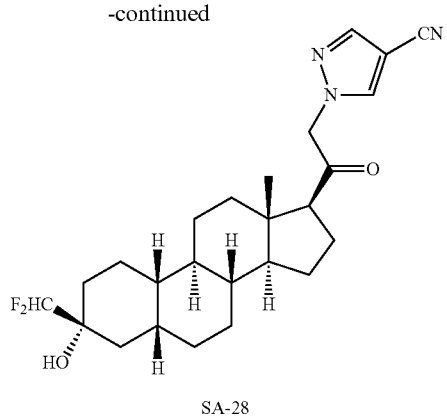

To a suspension of K$_2$CO$_3$ (25 mg, 0.18 mmol) in THF (5 mL) was added 1H-pyrazole-4-carbonitrile (20 mg, 0.23 mmol) and SC-EE (36 mg, 0.09 mmol). The mixture was stirred at rt for 15 h. The reaction mixture was poured into 5 mL H$_2$O and extracted with EtOAc (2×10 mL). The combined organic layers were washed with brine, dried over sodium sulfate, filtered and concentrated. The residue was purified with by reverse-phase prep-HPLC to afford the title compound as a white solid (22 mg, 61.6%). $^1$HNMR (400 MHz, CDCl$_3$), δ (ppm): 7.86 (s, 1H), 7.81 (s, 1H), 5.87 (t, 1H), 5.02 (AB, 1H), 4.90 (AB, 1H), 2.61 (t, 1H), 1.00-2.25 (m, 24H), 0.68 (s, 3H). LC-MS: rt=2.30 min, m/z=446.2 (M+1).

Example 44. Synthesis of Compound SA-29

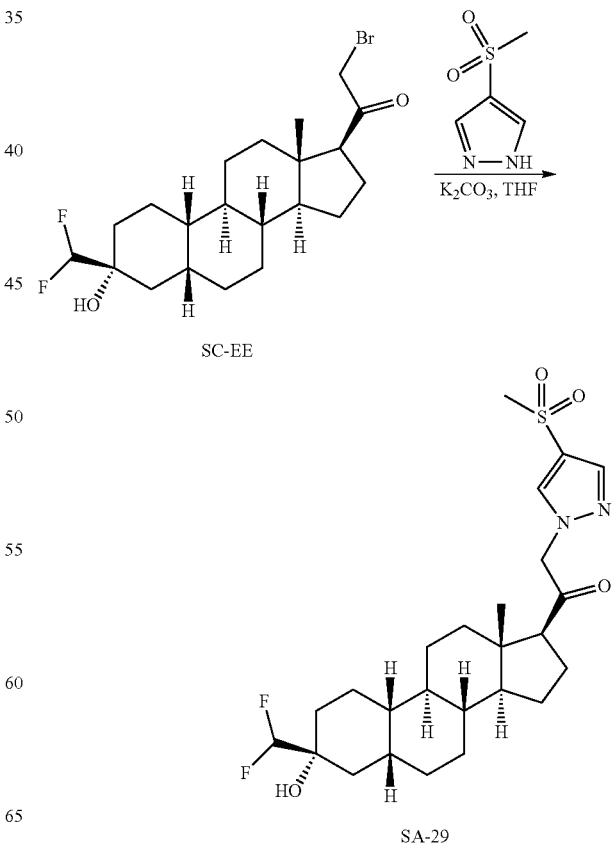

To a suspension of $K_2CO_3$ (127 mg, 0.92 mmol) in THF (5 mL) was added 4-(methylsulfonyl)-1H-pyrazole (67 mg, 0.46 mmol) and the reactant (200 mg, 0.46 mmol) and the resulting mixture was stirred at room temperature for 15 h. Then the mixture was poured in to 20 mL $H_2O$ and extracted with EtOAc (2×50 mL). The combined organic layers were washed with brine (50 mL), dried over sodium sulfate, filtered and concentrated in vacuo. The residual mixture was purified with by reverse-phase prep-HPLC to afford the title compound SA-29 as a white solid (46 mg, 0.0923 mmol, yield=20%). $^1$HNMR (500 MHz, $CDCl_3$) δ (ppm): 7.93 (s, 1H), 7.87 (s, 1H), 5.87 (t, 1H), 5.02 (AB, 1H), 4.92 (AB, 1H), 3.14 (s, 3H), 2.63 (t, 1H), 2.25-2.17 (m, 1H), 2.08-2.04 (m, 1H), 1.00-2.00 (m, 22H), 0.69 (s, 3H). LC-MS: rt=2.10 min, m/z=499.3 $[M+H]^+$ Example 61. Synthesis of Compound SA-30

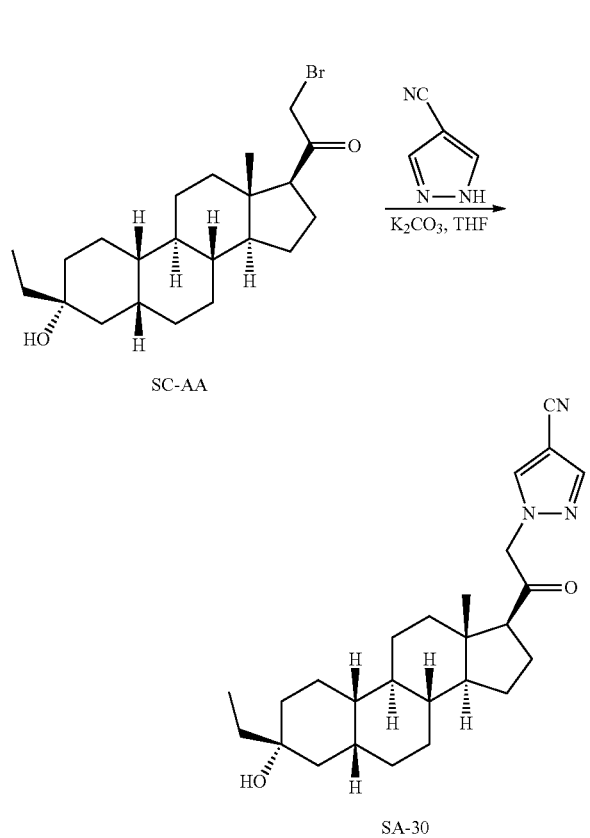

SA-30

To a suspension of $K_2CO_3$ (25 mg, 0.18 mmol) in THF (5 mL) was added 1H-pyrazole-4-carbonitrile (20 mg, 0.21 mmol) and SA-AA (36 mg, 0.087 mmol). The mixture was stirred at rt for 15 h. Then the reaction mixture was poured into 5 mL $H_2O$ and extracted with EtOAc (2×10 mL). The combined organic layers were washed with brine, dried over sodium sulfate, filtered and concentrated. The residue was purified with by reverse-phase prep-HPLC to afford the title compound as a white solid (10 mg, 27.0%). $^1$HNMR (400 MHz, $CDCl_3$), δ (ppm): 7.86 (s, 1H), 7.81 (s, 1H), 5.99 (AB, 1H), 5.85 (AB, 1H), 2.65 (t, 1H), 1.59 (q, 2H), 0.88 (t, 3H), 1.00-2.25 (m, 24H), 0.89 (t, 3H), 0.68 (s, 3H). LC-MS: rt=2.45 min, m/z=424.3 ($M^+$+1).

Example 45. Synthesis of Compound SA-31

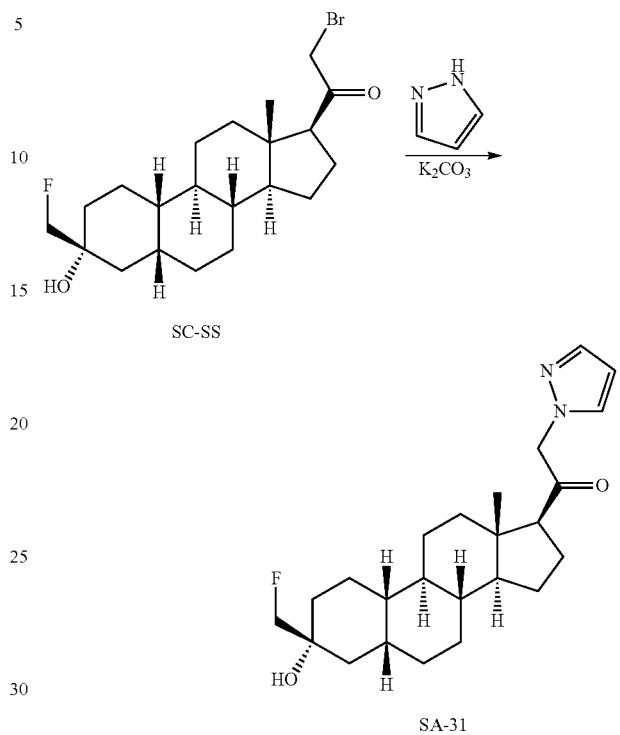

To a suspension of $K_2CO_3$ (55 mg, 0.4 mmol) in THF (5 mL) was added 1H-pyrazole (28 mg, 0.4 mmol) and Compound SC-SS (83 mg, 0.2 mmol). The mixture was stirred at RT for 15 h then the residue mixture was poured into 5 mL $H_2O$ and extracted with EtOAc (2×10 mL). The combined organic layers were washed with brine, dried over sodium sulfate, filtered and concentrated. The residue mixture was purified by reverse-phase prep-HPLC to afford SA-31 as a white solid (7 mg, 9%). Compound SA-31: $^1$HNMR (500 MHz, CDCl3) δ (ppm): 7.55 (d, 1H), 7.41 (d, 1H), 6.33 (t, 1H), 4.97 (AB, 1H), 4.88 (AB, 1H), 4.48 (AB×d, 1H), 4.38 (AB×d, 1H), 2.59 (t, 1H), 2.23-2.16 (m, 1H), 2.09-2.05 (m, 1H), 1.00-1.90 (22H, m), 0.68 (s, 3H). LC-MS: rt=2.15 min, m/z=403.3 [M+H]

Example 46. Synthesis of Compound SA-32

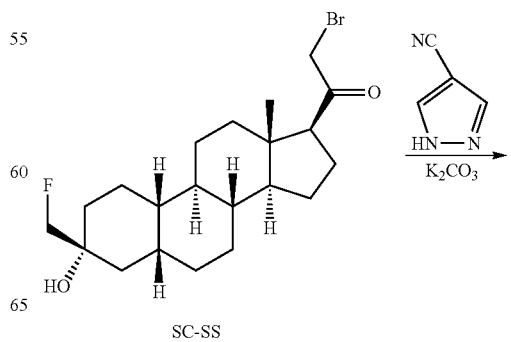

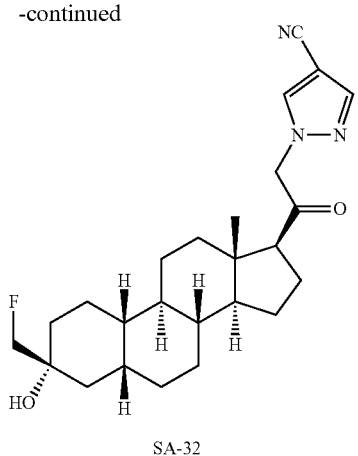

SA-32

To a suspension of K₂CO₃ (55 mg, 0.4 mmol) in THF (5 mL) was added 1H-pyrazole-4-carbonitrile (37 mg, 0.4 mmol) and Compound SC-SS (83 mg, 0.2 mmol). The mixture was stirred at RT for 15 h then the residue mixture was poured into 5 mL H₂O and extracted with EtOAc (2×10 mL). The combined organic layers were washed with brine, dried over sodium sulfate, filtered and concentrated. The residue mixture was purified by reverse-phase prep-HPLC to afford SA-32 as a white solid (20 mg, 23%). Compound SA-32: ¹HNMR (500 MHz, CDCl3) δ (ppm): 7.86 (s, 1H), 7.81 (s, 1H), 5.02 (AB, 1H), 4.91 (AB, 1H), 4.48 (ABxd, 1H), 4.38 (ABxd, 1H), 2.61 (t, 1H), 2.23 (s, 1H), 2.21-2.17 (m, 1H), 2.07-2.03 (m, 1H), 1.00-1.90 (m, 21H), 0.67 (s, 3H). LC-MS: rt=2.22 min, m/z=428.3 [M+H]⁺

Example 47. Synthesis of Compound SA-33

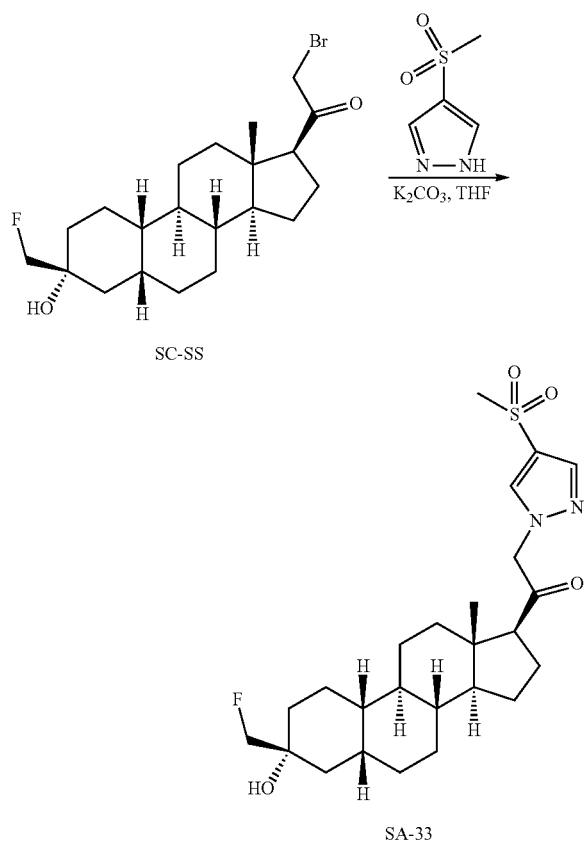

To a suspension of K₂CO₃ (119 mg, 0.86 mmol) in THF (5 mL) was added 4-(methylsulfonyl)-1H-pyrazole (63 mg, 0.43 mmol) and reactant SC-SS (180 mg, 0.43 mmol) and the mixture was stirred at RT for 15 h. The residual mixture was poured in to 20 mL H₂O and extracted with EtOAc (2×50 mL). The combined organic layers were washed with brine (50 mL), dried over sodium sulfate, filtered and concentrated in vacuo. The residual mixture was purified with by reverse-phase prep-HPLC to afford the title compound SA-33 as a white solid (53 mg, 0.110 mmol, Yield=25.6%). ¹HNMR (500 MHz, CDCl₃) δ (ppm): 7.93 (s, 1H), 7.87 (s, 1H), 5.02 (AB, 1H), 4.92 (AB, 1H), 4.48 (ABxd, 4.39 (ABxd, 1H), 3.14 (s, 1H), 2.63 (t, 1H), 2.24-2.17 (m, 1H), 2.07-2.04 (m, 1H), 1.00-1.90 (m, 24H), 0.68 (s, 3H). LC-MS: rt=2.06 min, m/z=481.2 [M+H]⁺

Example 49. Synthesis of Compound SA-35

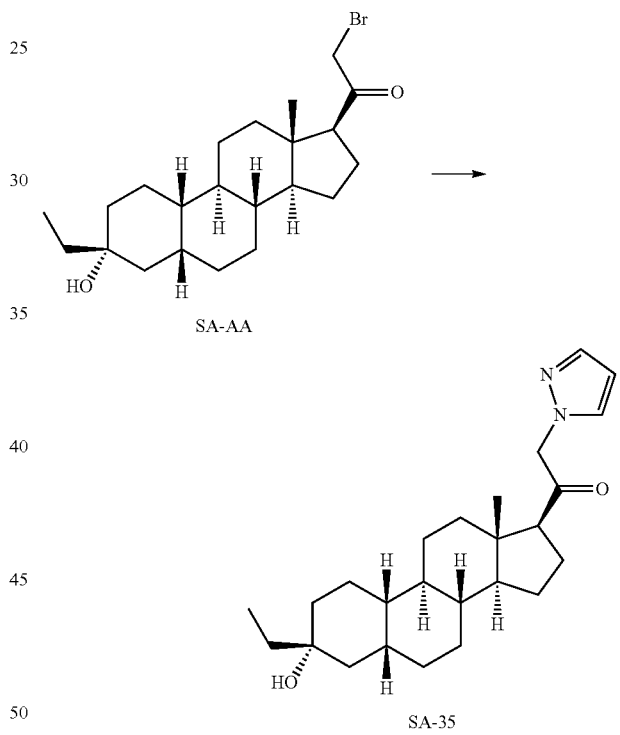

To a suspension of K₂CO₃ (25 mg, 0.18 mmol) in THF (5 mL) was added 1H-pyrazole (20 mg, 0.23 mmol) and SA-AA (36 mg, 0.09 mmol). The mixture was stirred at rt for 15 h. The reaction mixture was poured in to 5 mL H₂O and extracted with EtOAc (2×10 mL). The combined organic layers were washed with brine, dried over sodium sulfate, filtered and concentrated. The residue was purified with by reverse-phase prep-HPLC to afford SA-35 as a white solid (8 mg, 21.6%). ¹H NMR (400 MHz, CDCl₃), δ (ppm), 7.53 (1H, s), 7.41 (1H, s) 6.33 (s, 1H), 4.97 (AB, 1H), 4.88 (AB, 1H), 2.58 (1H, t), 1.00-2.25 (24H, m), 0.88 (3H, t), 0.68 (s, 3H). LC-MS: rt=2.39 min, m/z=399.4 (M⁺+1).

Example 50. Synthesis of Compound SB-1

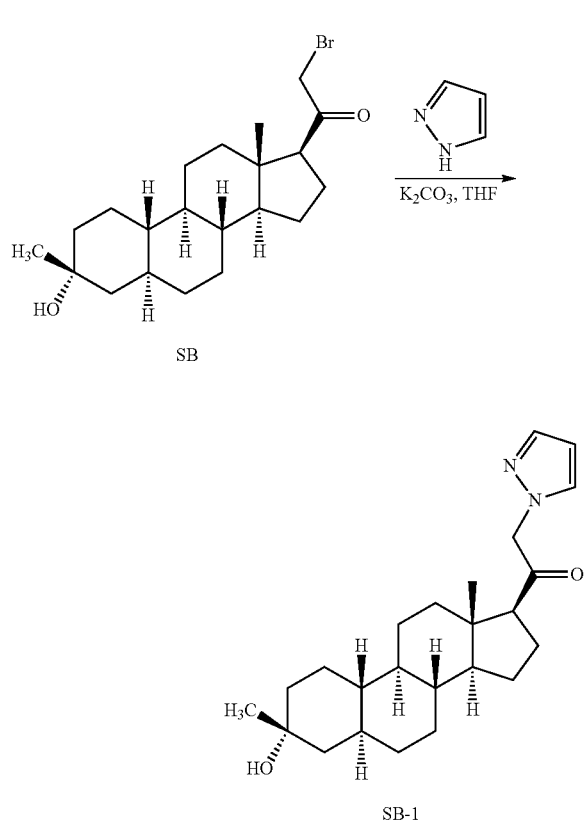

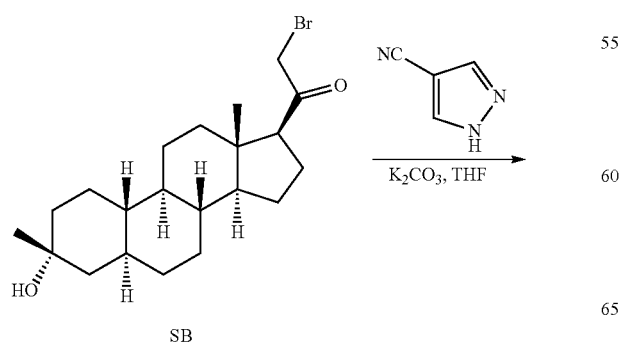

To a suspension of K$_2$CO$_3$ (25 mg, 0.18 mmol) in THF (5 mL) was added pyrazole (13 mg, 0.18 mmol) and compound SB (36 mg, 0.09 mmol). After stirring at room temperature for 15 h, the reaction mixture was poured in to 5 mL H$_2$O and extracted with EtOAc (2×10 mL). The combined organic layers were washed with brine, dried over sodium sulfate, filtered and concentrate. The reaction mixture was purified with by reverse-phase prep-HPLC to 7.54 (d, 1H), 7.41 (d, 1H), 6.33 (t, 1H), 4.97 (AB, 1H), 4.87 (AB, 1H), 2.58 (t, 1H), 0.90-2.25 (m, 21H), 0.69 (s, 3H).

Example 51. Synthesis of Compound SB-2

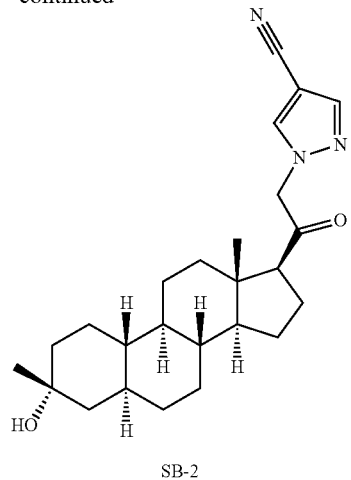

To a solution of crude SB (124.8 mg, 0.314 mmol, theoretical amount) in anhydrous THF (3 mL) was added 4-cyanopyrazole (58.5 mg, 0.628 mmol) followed by potassium carbonate (86.8 mg, 0.628 mmol). The solution was heated at 50° C. for 2 hours. Then the solution was diluted with ethyl acetate (200 mL). The resulting solution was washed with brine (2×100 mL), dried over magnesium sulfate and concentrated in vacuo. The crude product was purified by reverse phase prep-HPLC to afford desired product (34.6 mg, 0.0845 mmol, two steps overall yield=27%) as a white solid. $^1$HNMR (400 MHz, CDCl$_3$) δ(ppm): 7.86 (1H, s), 7.82 (1H, s), 5.01 (1H, AB), 4.91 (1H, AB), 2.61 (1H, t), 2.16-2.26 (2H, m), 2.04 (1H, m), 1.00-1.90 (21H, m), 0.68 (3H, s). LCMS: rt=2.26 min, m/z=410.2 [M+H]$^+$

Example 52. Synthesis of Compound SB-3

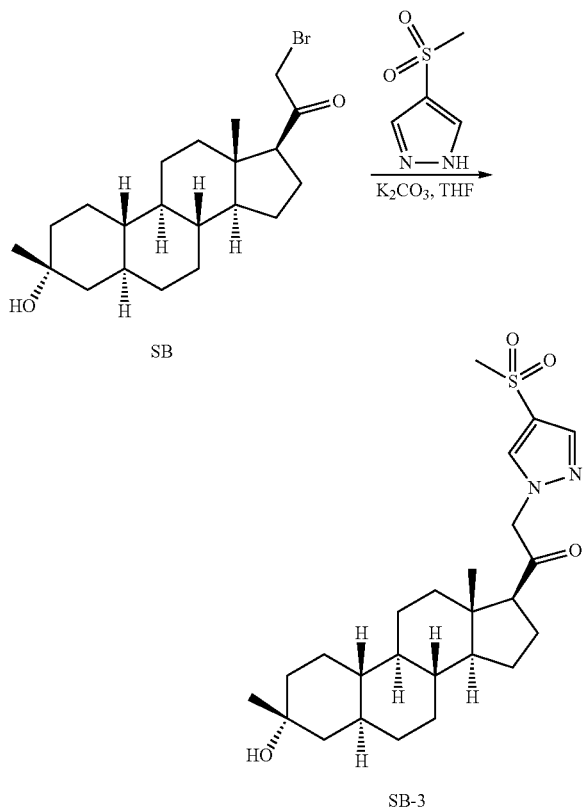

To a solution of crude reactant (374.3 mg, 0.942 mmol, theoretical amount) in anhydrous THF (7.5 mL) was added 4-methylsulfonyl-1H-pyrazole (110 mg, 0.754 mmol) followed by potassium carbonate (130 mg, 0.942 mmol). The solution was heated at 25° C. overnight and then the solution was diluted with dichloromethane (200 mL). The resulting solution was washed with brine (2×50 mL), dried over magnesium sulfate and concentrated in vacuo. The crude product was purified by silica gel chromatography (petroleum ether/ethyl acetate=1:3) to afford crude product which was contaminated with 4-methylsulfonyl-1H-pyrazole. The crude product was then re-crystallized from ethyl acetate to afford pure product (38.4 mg, 0.083 mmol, two steps overall yield=8.8%) as white solid. $^1$HNMR (500 MHz, CDCl$_3$) δ(ppm): 7.92 (1H, s), 7.87 (1H, s), 5.02 (1H, AB), 4.91 (1H, AB), 3.14 (3H, s), 2.63 (1H, t), 0.9-2.25 (21H, m), 0.68 (3H, s). LCMS: rt=2.15 min, m/z=463.3 [M+H]$^+$ Example 53. Synthesis of Compound SB-4

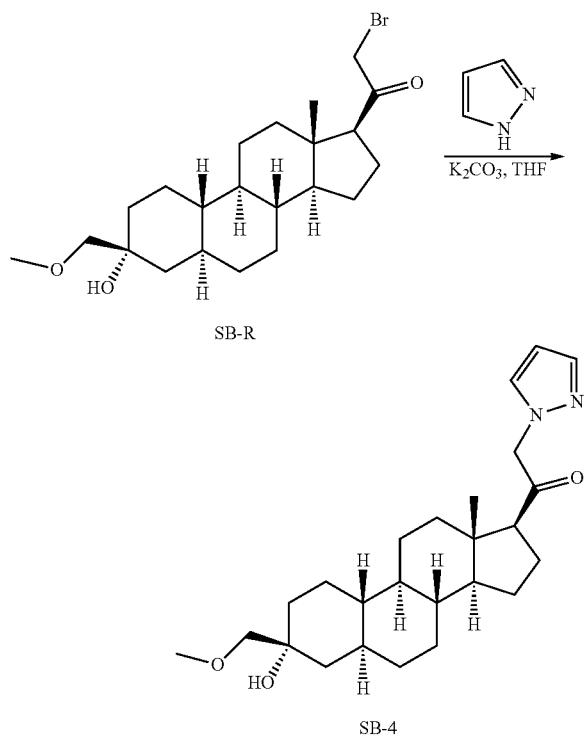

SB-4

To a solution of crude reactant (61.1 mg, 0.143 mmol, theoretical amount) in anhydrous THF (5 mL) was added 1H-pyrazole (97 mg, 1.43 mmol) followed by potassium carbonate (198 mg, 1.43 mmol). The solution was heated at 50° C. overnight. Then the solution was diluted with ethyl acetate (100 mL). The resulting solution was washed with brine (2×50 mL), dried over magnesium sulfate and concentrated in vacuo. The crude product was purified by reverse phase prep-HPLC to afford product SB-4 (7 mg, 0.0169 mmol, two steps overall yield=12%) as white solid. $^1$HNMR (400 MHz, CDCl$_3$) δ (ppm) 7.55 (1H, d), 7.42 (1H, d), 6.33 (1H, t), 4.97 (1H, AB), 4.88 (1H, AB), 3.39 (3H, s), 3.19 (2H, s), 2.59 (1H, t, J=8.9 Hz), 0.69 (3H, s), 0.60-2.25 (24H, m). LC-MS: rt=2.31 min, m/z=415.3 [M+H]$^+$ Example 54. Synthesis of Compounds SB-5

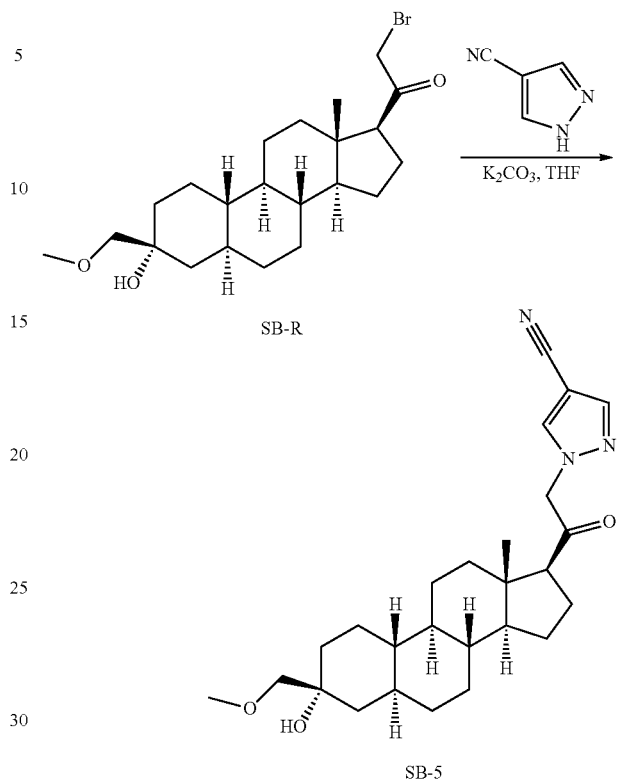

SB-5

To a solution of crude reactant (122.6 mg, 0.287 mmol, theoretical amount) in anhydrous THF (3 mL) was added 4-cyanopyrazole (134 mg, 1.435 mmol) followed by potassium carbonate (198 mg, 1.435 mmol). The solution was heated at 60° C. overnight. Then the solution was diluted with ethyl acetate (200 mL). The resulting solution was washed with brine (2×100 mL), dried over magnesium sulfate and concentrated in vacuo. The crude product was purified by reverse phase prep-HPLC to afford desired product SB-5 (12.4 mg, 0.0282 mmol, two steps overall yield=9.8%) and by-product (4.2 mg, 0.00955 mmol, two steps overall yield=3.3%) as white solid. Compound SB-5 $^1$HNMR (400 MHz, CDCl$_3$) δ(ppm): 7.86 (s, 1H), 7.81 (s, 1H), 5.02 (AB, 1H), 4.90 (AB, 1H), 3.42 (AB, 1H), 3.40 (S, 3H), 3.39 (AB, 1H), 2.64 (s, 1H), 2.61 (t, 1H), 1.00-2.25 (m, 23H), 0.67 (s, 3H). LC-MS: rt=2.32 min, m/z=440.2 [M+H]$^+$ Example 55. Synthesis of Compound SB-7

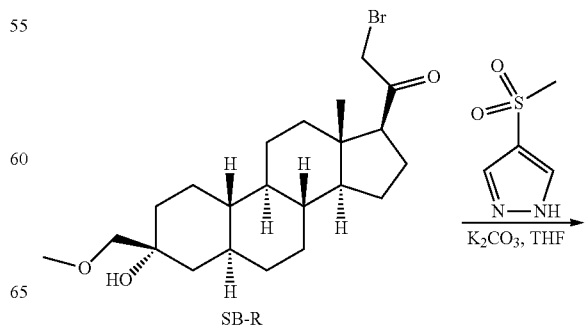

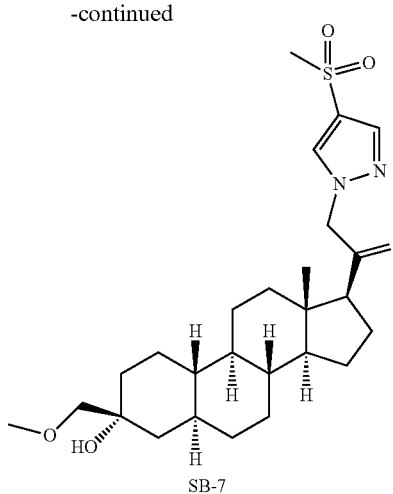

SB-7

To a solution of crude reactant (368 mg, 0.861 mmol, theoretical amount) in anhydrous THF (7.5 mL) was added 4-methylsulfonyl-1H-pyrazole (126 mg, 0.861 mmol) followed by potassium carbonate (119 mg, 0.861 mmol). The solution was heated at 25° C. overnight then the solution was diluted with dichloromethane (200 mL) and the resulting solution was washed with brine (2×50 mL), dried over magnesium sulfate and concentrated in vacuo. The crude product was purified by silica gel chromatography (petroleum ether/ethyl acetate=1:3) to afford crude product which was contaminated with 4-methylsulfonyl-1H-pyrazole. The crude product was then re-crystallized from ethyl acetate to afford pure product (50 mg, 0.101 mmol, two steps overall yield=12%) as white solid. $^1$HNMR (500 MHz, CDCl$_3$) δ(ppm): 7.92 (1H, s), 7.87 (1H, s), 5.02 (1H, AB), 4.91 (1H, AB), 3.39 (3H, s), 3.19 (2H, s), 3.14 (3H, s), 2.63 (1H, t), 0.9-2.25 (21H, m), 0.68 (3H, s). LCMS: rt=2.13 min, m/z=493.0 [M+H]$^+$ Example 56. Synthesis of Compound SB-8

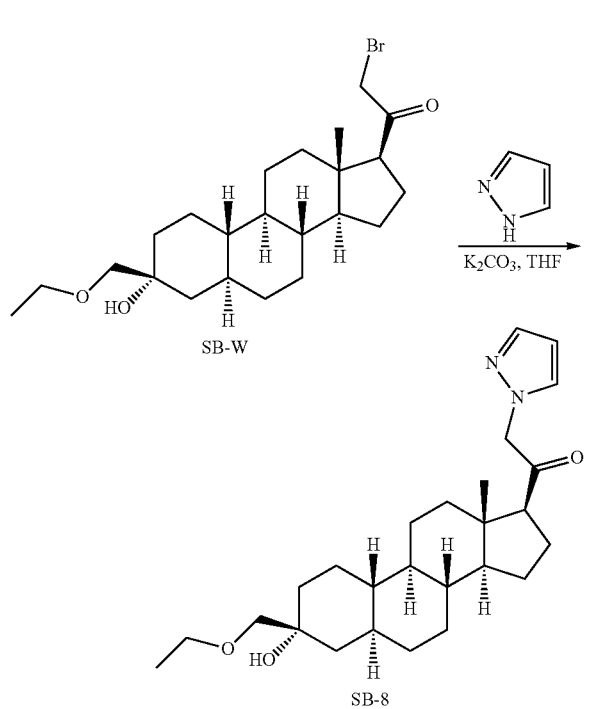

To a suspension of K$_2$CO$_3$ (25 mg, 0.18 mmol) in THF (5 mL) was added pyrazole (13 mg, 0.18 mmol) and compound SB-W (36 mg, 0.09 mmol). After stirring at room temperature for 15 h, the reaction mixture was poured in to 5 mL H$_2$O and extracted with EtOAc (2×10 mL). The combined organic layers were washed with brine, dried over sodium sulfate, filtered and concentrated. The reaction mixture was purified with by reverse-phase prep-HPLC to afford the title compound as a white solid (15.6 mg, 0.073 mmol, 40.4%). $^1$HNMR (500 MHz, CDCl$_3$) δ (ppm): 7.54 (d, 1H), 7.41 (d, 1H), 6.33 (t, 1H), 4.97 (AB, 1H), 4.87 (AB, 1H), 3.52 (q, 2H), 3.21 (s, 2H), 2.59 (t, 1H), 0.69 (s, 3H), 0.69-2.25 (m, 24H). LCMS: Rt=2.35 min. m/z=429.4 [M+H]$^+$.

Example 57. Synthesis of Compound SB-9

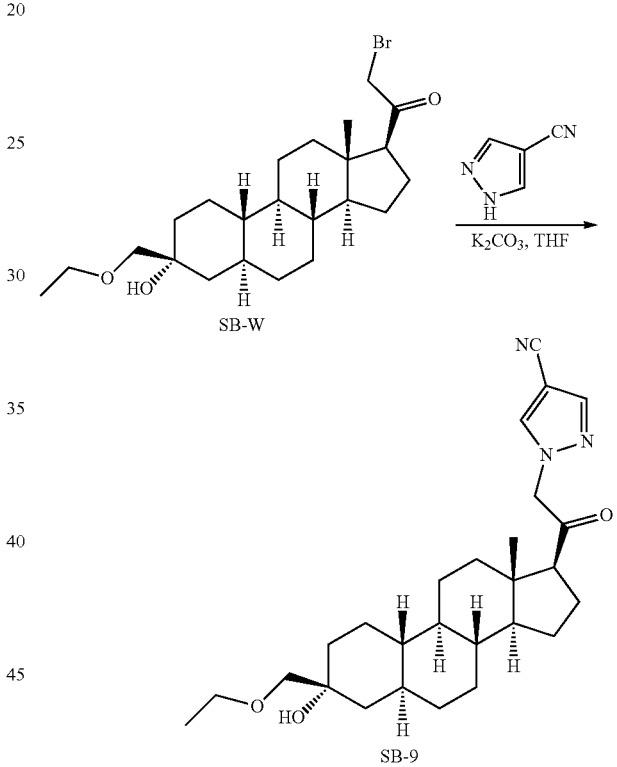

To a suspension of K$_2$CO$_3$ (63 mg, 0.46 mmol) in THF (10 mL) was added 4-cyanopyrazole (43 mg, 0.46 mmol) and compound SB-W (100 mg, 0.23 mmol). After stirring at room temperature for 15 h, the reaction mixture was poured into 5 mL H$_2$O and extracted with EtOAc (2×10 mL). The combined organic layers were washed with brine (2×10 mL), dried over sodium sulfate, filtered and concentrated under vacuum. The residue was purified by reverse-phase prep-HPLC to afford SB-9 as a white solid (43.5 mg, 0.095 mmol, 41.7%). $^1$HNMR (500 MHz, CDCl$_3$) δ (ppm 7.86 (1H, s), 7.82 (1H, s), 5.01 (1H, AB), 4.91 (1H, AB), 3.53 (2H, q), 3.22 (2H, s), 2.61 (1H, t), 0.67 (3H, s), 0.67-2.25 (24H, m). LCMS: Rt=2.37 min. m/z=454.4 [M+H]$^+$.

Example 58. Synthesis of Compound SB-10

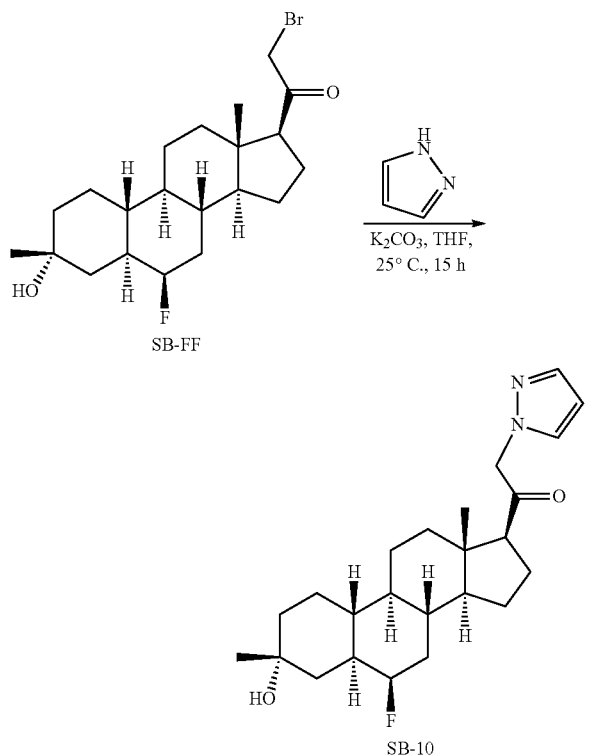

To a suspension of SB-FF (40 mg, 0.09 mmol) in THF (5 mL) was added 1H-pyrazole (30 mg, 0.45 mmol) and K$_2$CO$_3$ (60 mg, 0.45 mmol). The mixture was stirred at 25° C. for 15 h. The solution was then diluted with ethyl acetate (100 mL) and the resulting solution was washed with brine (100 mL), dried over sodium sulfate and concentrated in vacuo. The reaction mixture was purified with by reverse-phase prep-HPLC to afford SB-10 as a white solid (15 mg, 38% yield). $^1$H NMR (400 MHz, CDCl$_3$), δ (ppm), 7.55 (s, 1H), 7.41 (s, 1H), 6.33 (s, 1H), 4.99-4.95 (AB, 1H), 4.90-4.87 (AB, 1H), 4.55 (1H, d, 1H), 2.60 (t, 1H), 0.70-2.25 (m, 22H), 0.71 (s, 3H).

Example 59. Synthesis of Compound SB-11

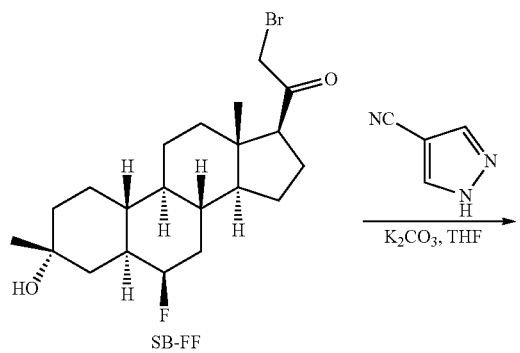

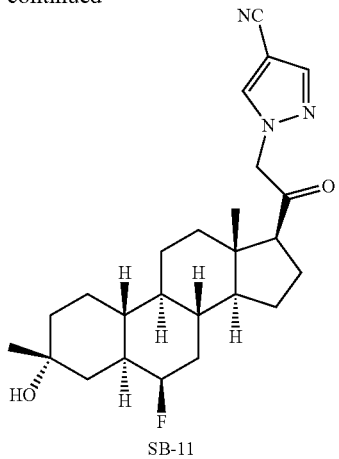

To a solution of crude reactant SB-FF (50.7 mg, 0.122 mmol, theoretical amount) in anhydrous THF (1.5 mL) was added 4-cyanopyrazole (22.7 mg, 0.244 mmol) followed by potassium carbonate (33.7 mg, 0.244 mmol). The solution was stirred at 25° C. overnight. Then the solution was diluted with ethyl acetate (100 mL). The resulting solution was washed with brine (2×50 mL), dried over magnesium sulfate and concentrated in vacuo. The crude product was purified by reverse phase prep-HPLC to afford desired product (14.2 mg, 0.0332 mmol, two steps overall yield=27%) as white solid. $^1$HNMR (400 MHz, CDCl$_3$) δ(ppm): 7.85 (s, 1H), 7.81 (s, 1H), 5.03-4.87 (m, 2H), 4.62-4.50 (m, 1H), 2.63-2.62 (m, 1H), 2.30-2.20 (m, 1H), 2.05-1.95 (m, 2H), 1.90-1.60 (m, 6H), 1.50-1.20 (m, 15H), 0.70 (s, 3H). $^{19}$FNMR (376 MHz, CDCl$_3$) δ(ppm): −193.13. LCMS: rt=2.13 min, m/z=428.0 [M+H]$^+$

Example 60. Synthesis of Compound SB-12

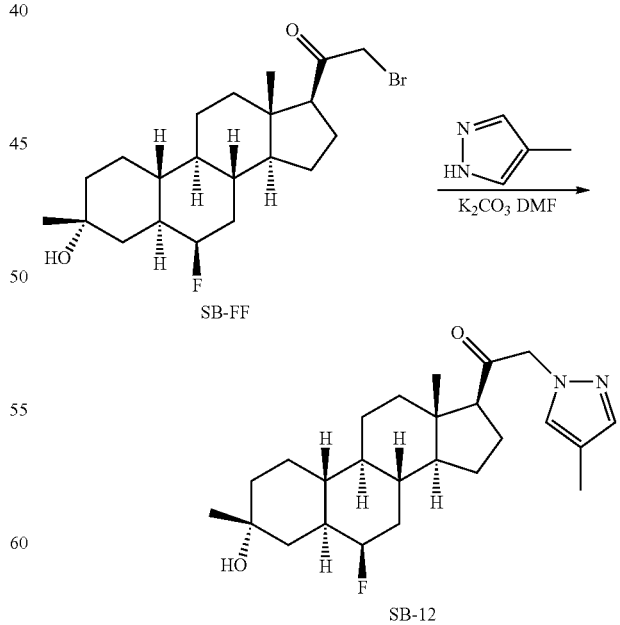

To a solution of SB-FF (85 mg, 0.20 mmol) in 2 mL of DMF was added 4-methyl-1H-pyrazole (33.6 mg, 0.41 mmol) and K$_2$CO$_3$ (84.84 mg, 0.61 mmol). The reaction mixture was stirred at 28° C. for 1 h. The resulting solution was quenched with water (10 mL) and extracted with EtOAc (15 mL×2). The combined organic layers were dried and concentrated in vacuum. The residue was purified by column chromatography on silica gel eluted with (petroleum ether/ethyl acetate=12/1 to 2/1) to give SB-12 (23.1 mg, yield: 31.6%) as a white solid. $^1$H NMR (SB-12): (400 MHz, CDCl$_3$) δ 7.34 (s, 1H), 7.17 (s, 1H), 4.92-4.75 (m, 2H), 4.66-4.47 (m, 1H), 2.60-2.56 (m, 1H), 2.25-1.99 (m, 6H), 1.91-1.61 (m, 6H), 1.54-1.03 (m, 15H), 0.84-0.74 (m, 1H), 0.70 (s, 3H). LCMS: rt=1.23 min, m/z=417.2 [M+H]$^+$.

Example 61. Synthesis of Compound SB-13

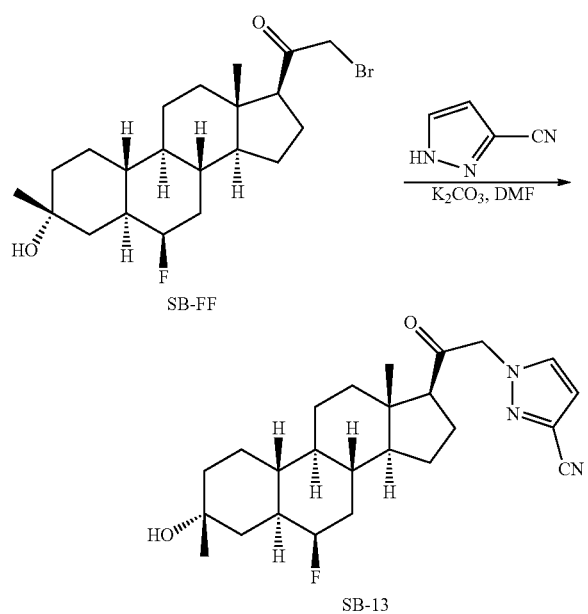

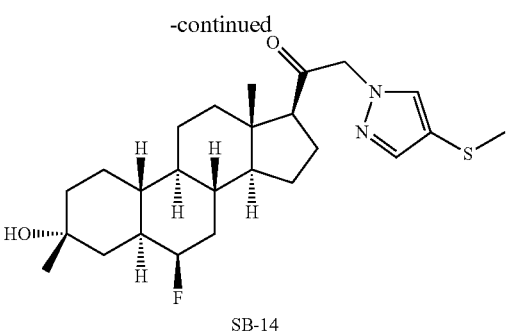

A mixture of SB-FF (100 mg, 0.241 mmol), 1H-pyrazole-3-carbonitrile (45 mg, 0.48 mmol), K$_2$CO$_3$ (66 mg, 0.48 mmol) and DMF (3 mL) were stirred at room temperature for 2 h. TLC showed the reaction was finished. The reaction mixture was poured into brine (10 mL) and extracted with EtOAc (10 mL×2). Combined the organic layers and dried over Na$_2$SO$_4$, concentrated to give crude product, which was purified by silica gel column to give SB-13 (30 mg, yield: 28%) as a white solid. $^1$H NMR: (400 MHz, CDCl$_3$) δ 7.48 (s, 1H), 6.73 (s, 1H), 4.79-4.97 (m, 2H), 4.47-4.65 (m, 1H), 2.56-2.63 (m, 1H), 2.30-2.20 (m, 1H), 2.10-2.00 (m, 1H), 1.90-1.60 (m, 6H), 1.50-1.20 (m, 15H), 0.85-0.75 (m, 1H), 0.70 (s, 3H). LCMS: rt=1.23 min, m/z=428.2 [M+H]$^+$.

Example 62. Synthesis of SB-14

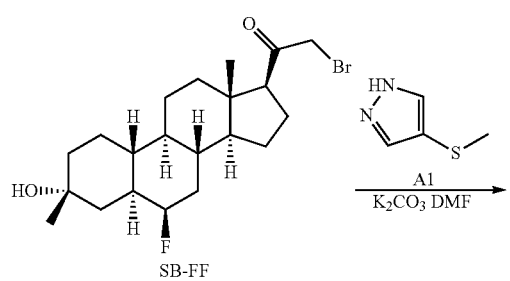

To a solution of SB-FF (100 mg, 0.24 mmol) in DMF (2 mL) was added A1 (55 mg, 0.48 mmol) and K$_2$CO$_3$ (100 mg, 0.72 mmol) at 19° C. The reaction was stirred at 19° C. for 16 h. The resulting mixture was poured into water (3 ml). The mixture was extracted with EtOAc (2 mL×3). The combined organic layers was washed with brine (5 mL), dried over Na$_2$SO$_4$ and concentrated in vacuum. The residue was purified by silica gel column (Petroleum ether/ethyl acetate=10/1 to 3/1) to give SB-14 (80 mg, yield: 74%) as a pink solid. $^1$H NMR: (400 MHz, CDCl$_3$) δ 7.53 (s, 1H), 7.43 (s, 1H), 4.79-4.97 (m, 2H), 4.47-4.65 (m, 1H), 2.56-2.63 (m, 1H), 2.35 (s, 3H), 2.19-2.26 (m, 1H), 2.00-2.08 (m, 2H), 1.63-1.92 (m, 5H), 1.35-1.57 (m, 5H), 1.20-1.1.32 (m, 5H), 1.07-1.18 (m, 5H), 0.75-0.91 (m, 1H), 0.71 (s, 3H). LCMS: rt=1.25 min, m/z=449.2 [M+H]$^+$.

Example 63. Synthesis of SB-15

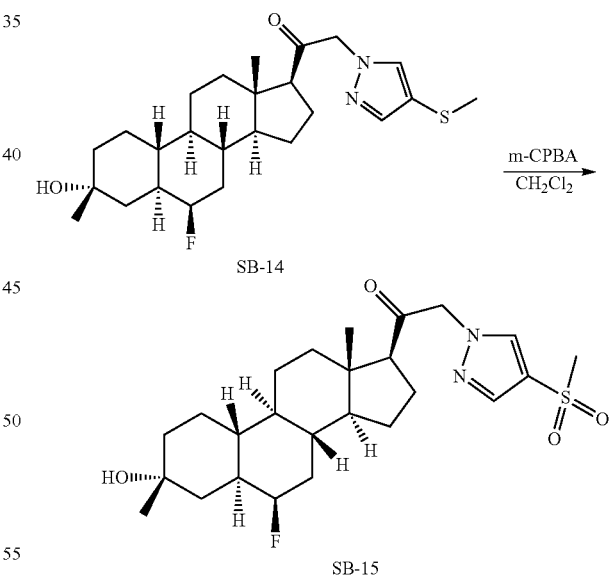

To a solution of SB-14 (80 mg, 0.19 mmol) in DCM (5 mL) was added m-CPBA (90 mg, 0.45 mmol) at 0° C. The reaction mixture was stirred at 20° C. for 2 h. Saturated aqueous NaS$_2$O$_3$ solution (5 mL) was added. The resulting mixture was stirred at 20° C. for 30 min, and extracted with EtOAc (5 mL×3). The combined organic layers were washed with brine (10 mL), dried over Na$_2$SO$_4$ and concentrated in vacuum. The residue was purified by silica gel column (Petroleum ether/ethyl acetate=1/2) to give SB-15 (30 mg, 47%) as a white solid. $^1$H NMR: (400 MHz, CDCl$_3$)

δ7.93 (s, 1H), 7.87 (s, 1H), 4.87-5.07 (m, 2H), 4.48-4.66 (m, 1H), 3.14 (s, 3H), 2.58-2.68 (m, 1H), 2.17-2.30 (m, 1H), 1.97-2.12 (m, 2H), 1.65-1.90 (m, 6H), 1.45-1.55 (m, 3H), 1.05-1.40 (m, 12H), 0.80-0.91 (m, 1H), 0.71 (s, 3H). LCMS: rt=0.85 min, m/z=481.2 [M+H]$^+$.

Example 66. Synthesis of Compound SB-18

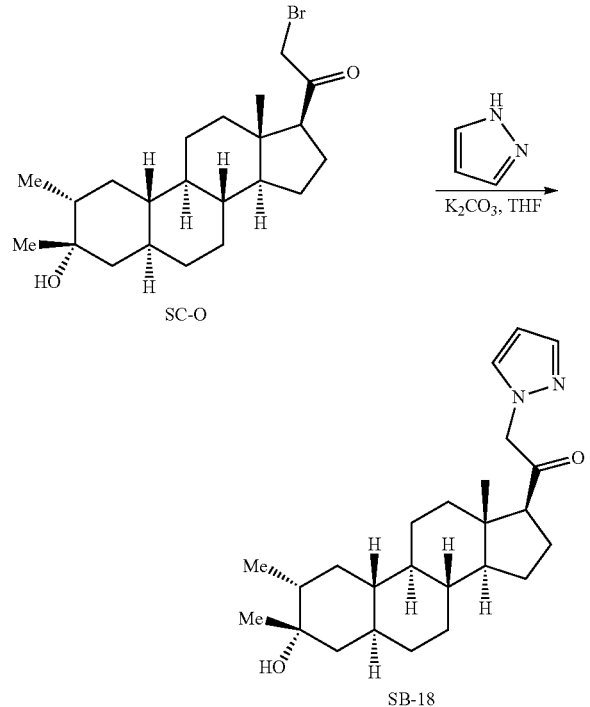

To a solution of crude reactant SC-O (62 mg, 0.150 mmol) in anhydrous THF (5 mL) was added 1H-pyrazole (20.4 mg, 0.30 mmol) followed by potassium carbonate (41.5 mg, 0.30 mmol). The solution was heated at 50° C. overnight. Then the solution was diluted with ethyl acetate (100 mL). The resulting solution was washed with brine (2×50 mL), dried over magnesium sulfate and concentrated in vacuo. The crude product was purified by reverse phase prep-HPLC to afford product SB-18 (10 mg, 0.0251 mmol, Yield=17%) as white solid. $^1$HNMR (500 MHz, CDCl3) δ(ppm): 7.55 (1H, s), 7.41 (1H, s), 6.33 (1H, s), 4.97 (1H, AB), 4.89 (1H, AB), 2.59 (1H, t), 2.20 (1H, dd), 0.60-2.05 (22H, m), 0.69 (3H, s).

Example 67. Synthesis of SB-19

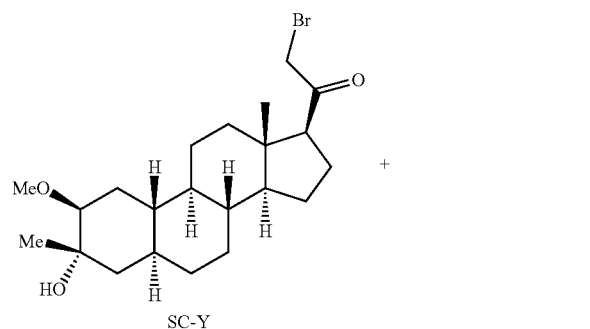

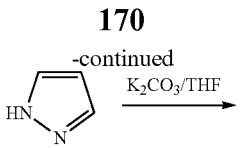

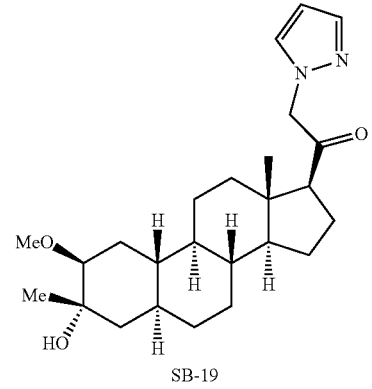

To a solution of compound SC-Y (60 mg, crude) in dry THF (2 mL) was added potassium carbonate (100 mg) and 1H-pyrazole (60 mg, 0.09 mmol). The reaction mixture was stirred at ambient temperature for 16 hour, and then extracted with EtOAc (3×10 mL). The combined organic layers were washed with brine (10 mL), dried over MgSO$_4$, filtered, and concentrated. The residue was purified by preparative HPLC to afford title compound SB-19 (7 mg, 12%) as white solid. $^1$H NMR (500 MHz, CDCl3) δ (ppm): 7.54 (1H, d), 7.41 (1H, d), 6.33 (1H, t), 4.96 (1H, AB), 4.88 (1H, AB), 3.33 (3H, s), 3.04 (1H, s), 2.58 (1H, t), 0.60-2.20 (22H, m), 0.68 (3H, s).

Example 68. Synthesis of Compound SB-20

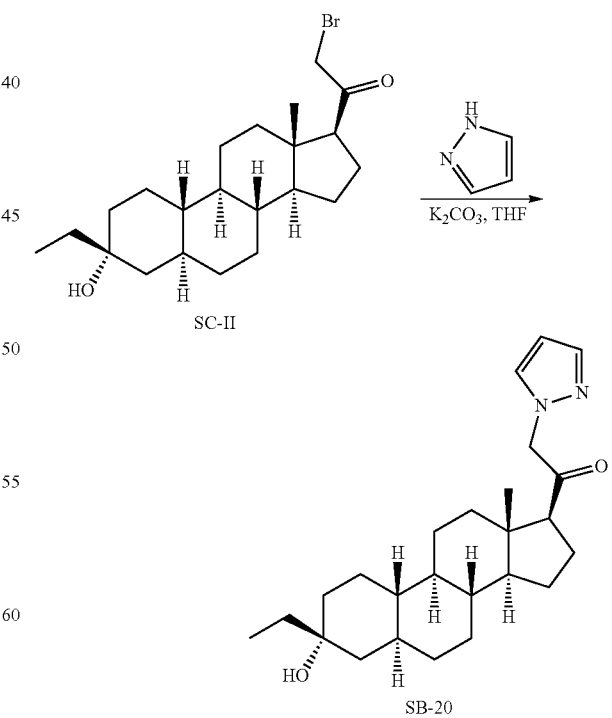

To a solution of crude reactant SC-II (100 mg, 0.241 mmol) in anhydrous THF (5 mL) was added 3H-pyrazole (82 mg, 1.2 mmol) followed by potassium carbonate (170 mg, 1.2 mmol) and the solution was heated at 60° C. for 2 h. Then the reaction mixture was diluted with ethyl acetate (100 mL). The resulting solution was washed with brine (2×50 mL), dried over magnesium sulfate and concentrated in vacuo. The crude product was purified by reverse phase prep-HPLC to afford product SB-20 (24 mg, 0.06 mmol, Yield=25%) as white solid. $^1$HNMR (500 MHz, CDCl3) δ(ppm): 7.55 (1H, d), 7.41 (1H, d), 6.33 (1H, t), 4.95 (1H, AB), 4.89 (1H, AB), 2.59 (1H, t), 0.69 (3H, s), 0.69-2.25 (24H, m). LCMS: rt=2.46 min, m/z=399.2 [M+H]$^+$ Example 69. Synthesis of Compound SB-21

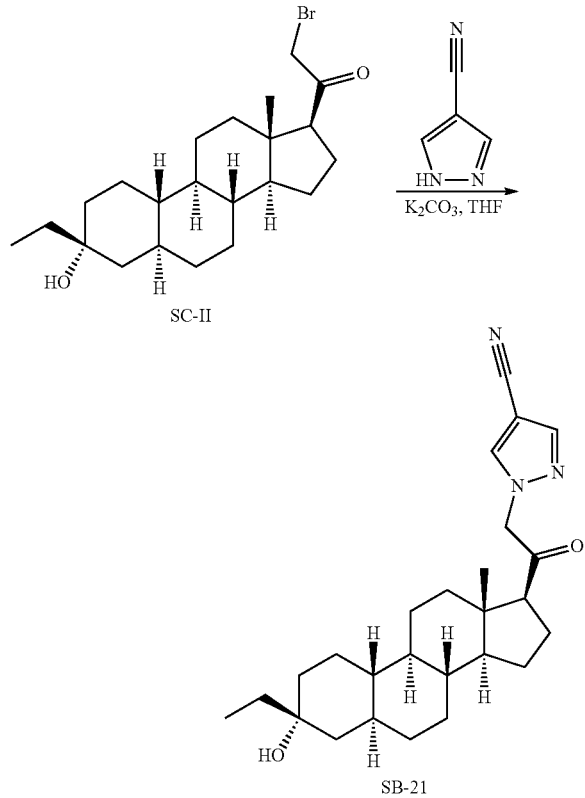

SC-II

SB-21

To a solution of crude reactant SC-II (100 mg, 0.241 mmol) in anhydrous THF (5 mL) was added 1H-pyrazole-4-carbonitrile (112 mg, 1.2 mmol) followed by potassium carbonate (170 mg, 1.2 mmol) and the solution was heated at 60° C. for 2 h. Then the reaction mixture was diluted with ethyl acetate (100 mL). The resulting solution was washed with brine (2×50 mL), dried over magnesium sulfate and concentrated in vacuo. The crude product was purified by reverse phase prep-HPLC to afford product SB-21 (46 mg, 0.109 mmol, Yield=45%) as a white solid. $^1$HNMR (500 MHz, CDCl3) δ(ppm): 7.86 (1H, s), 7.81 (1H, s), 5.00 (1H, AB), 4.92 (1H, AB), 2.61 (1H, t), 0.67 (3H, s), 0.67-2.25 (24H, m). LCMS: rt=2.47 min, m/z=424.2 [M+H]$^+$ Example 70. Synthesis of Compound SB-22

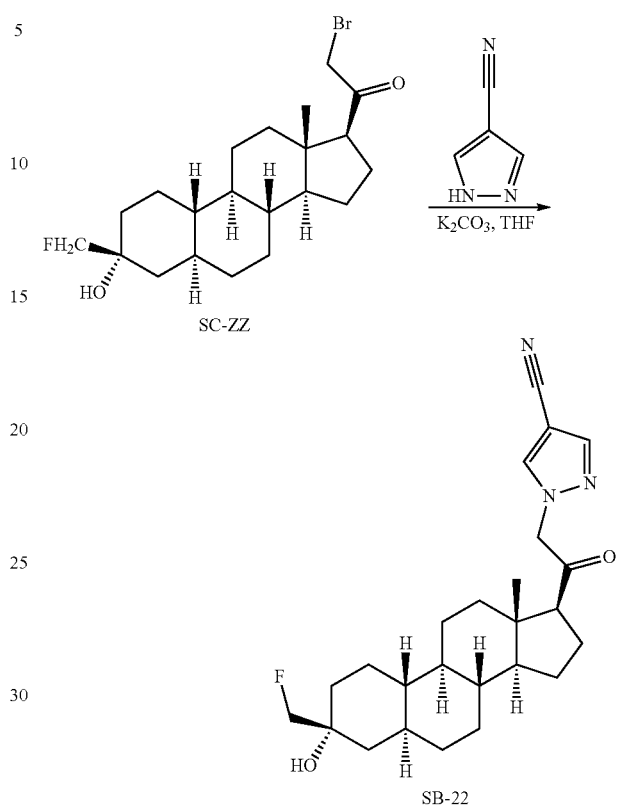

SC-ZZ

SB-22

To a solution of crude reactant SC-ZZ (100 mg, 0.241 mmol) in anhydrous THF (5 mL) was added 1H-pyrazole-4-carbonitrile (112 mg, 1.2 mmol) followed by potassium carbonate (170 g, 1.2 mmol). The solution was heated at 60° C. for 2 h then the solution was cooled to room temperature and diluted with ethyl acetate (100 mL). The resulting solution was washed with brine (2×50 mL), dried over magnesium sulfate and concentrated in vacuo. The crude product was purified by reverse phase prep-HPLC to afford product SB-22 (38 mg, 0.09 mmol, Yield=38%) as white solid. $^1$HNMR (500 MHz, CDCl3) δ(ppm): 7.86 (1H, s), 7.81 (1H, s), 5.87 (2H, d), 5.02 (1H, AB), 4.90 (1H, AB), 4.17 (2H, d), 2.61 (1H, t), 0.70-2.25 (22H, m), 0.68 (3H, s). LCMS: rt=2.24 min, m/z=428 [M+H]$^+$ Example 71. Synthesis of SB-23

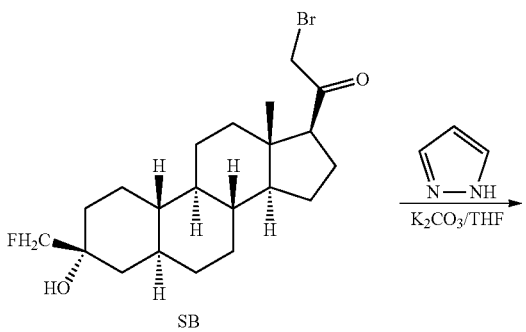

SB

-continued

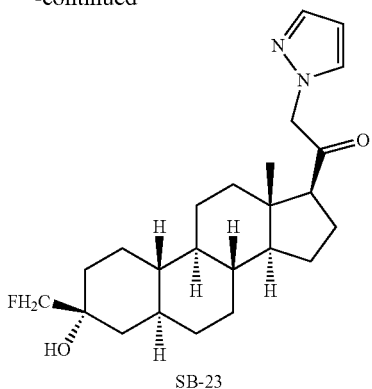

SB-23

To a suspension of K$_2$CO$_3$ (19 mg, 0.14 mmol) in THF (5 mL) was added Pyrazole (10 mg, 0.14 mmol) and compound SB (30 mg, 0.07 mmol). After stirring at room temperature for 15 h, the reaction mixture was poured into 5 mL H$_2$O and extracted with EtOAc (2×10 mL). The combined organic layers were washed with brine (2×10 mL), dried over sodium sulfate, filtered and concentrated under vacuum. The residue was purified by reverse-phase prep-HPLC to afford SB-23 as a white solid (19.3 mg, 66%). 1H NMR (500 MHz, CDCl$_3$), δ (ppm), 7.55 (d, 1H), 7.41 (d, 1H), 6.33 (t, 1H), 4.97 (AB, 1H), 4.88 (AB, 1H), 4.17 (d, 2H), 2.59 (t, J=9.0 Hz, 1H), 0.69 (s, 3H), 0.60-2.20 (m, 24H). LCMS: Rt=2.27 min. m/z=403.2 [M+H]$^+$.

Assay Methods

Compounds provided herein can be evaluated using various assays; examples of which are described below.

Steroid Inhibition of TBPS Binding

[35S]-t-Butylbicyclophosphorothionate (TBPS) binding assays using rat brain cortical membranes in the presence of 5 μM GABA has been described (Gee et al, *J. Pharmacol. Exp. Ther.* 1987, 241, 346-353; Hawkinson et al, *Mol. Pharmacol.* 1994, 46, 977-985; Lewin, A. H et al., *Mol. Pharmacol.* 1989, 35, 189-194).

Briefly, cortices are rapidly removed following decapitation of carbon dioxide-anesthetized Sprague-Dawley rats (200-250 g). The cortices are homogenized in 10 volumes of ice-cold 0.32M sucrose using a glass/teflon homogenizer and centrifuged at 1500×g for 10 min at 4° C. The resultant supernatants are centrifuged at 10,000×g for 20 min at 4° C. to obtain the P2 pellets. The P2 pellets are resuspended in 200 mM NaCl/50 mM Na—K phosphate pH 7.4 buffer and centrifuged at 10,000×g for 10 min at 4° C. This washing procedure is repeated twice and the pellets are resuspended in 10 volumes of buffer. Aliquots (100 μL) of the membrane suspensions are incubated with 3 nM [$^{35}$S]-TBPS and 5 μL aliquots of test drug dissolved in dimethyl sulfoxide (DMSO) (final 0.5%) in the presence of 5 μM GABA. The incubation is brought to a final volume of 1.0 mL with buffer. Nonspecific binding is determined in the presence of 2 μM unlabeled TBPS and ranged from 15 to 25%. Following a 90 min incubation at room temp, the assays are terminated by filtration through glass fiber filters (Schleicher and Schuell No. 32) using a cell harvester (Brandel) and rinsed three times with ice-cold buffer. Filter bound radioactivity is measured by liquid scintillation spectrometry. Non-linear curve fitting of the overall data for each drug averaged for each concentration is done using Prism (GraphPad). The data are fit to a partial instead of a full inhibition model if the sum of squares is significantly lower by F-test. Similarly, the data are fit to a two component instead of a one component inhibition model if the sum of squares is significantly lower by F-test. The concentration of test compound producing 50% inhibition (IC$_{50}$) of specific binding and the maximal extent of inhibition (I$_{max}$) are determined for the individual experiments with the same model used for the overall data and then the means±SEM.s of the individual experiments are calculated. Picrotoxin serves as the positive control for these studies as it has been demonstrated to robustly inhibit TBPS binding.

Various compounds are or can be screened to determine their potential as modulators of [$^{35}$S]-TBPS binding in vitro. These assays are or can be performed in accordance with the above discussed procedures.

Patch Clamp Electrophysiology of Recombinant α$_1$β$_2$γ$_2$ and α$_4$β$_3$δ GABA$_A$ Receptors Cellular electrophysiology is used to measure the pharmacological properties of our GABA$_A$ receptor modulators in heterologous cell systems. Each compound is tested for its ability to affect GABA mediated currents at a submaximal agonist dose (GABA EC$_{20}$=2 μM). LTK cells are stably transfected with the α$_1$β$_2$γ$_2$ subunits of the GABA receptor and CHO cells are transiently transfected with the α$_4$β$_3$δ subunits via the Lipofecatamine method. Cells were passaged at a confluence of about 50-80% and then seeded onto 35 mm sterile culture dishes containing 2 ml culture complete medium without antibiotics or antimycotics. Confluent clusters of cells are electrically coupled (Pritchett et al., Science, 1988, 242, 1306-1308.). Because responses in distant cells are not adequately voltage clamped and because of uncertainties about the extent of coupling (Verdoorn et al., Neuron 1990, 4, 919-928.), cells were cultivated at a density that enables the recording of single cells (without visible connections to other cells).

Whole cell currents were measured with HEKA EPC-10 amplifiers using PatchMaster software or by using the high throughput QPatch platform (Sophion). Bath solution for all experiments contained (in mM): NaCl 137 mM, KCl 4 mM, CaCl$_2$ 1.8 mM, MgCl$_2$ 1 mM, HEPES 10 mM, D-Glucose 10 mM, pH (NaOH) 7.4. In some cases 0.005% cremophor was also added. Intracellular (pipette) solution contained: KCl 130 mM, MgCl$_2$ 1 mM, Mg-ATP 5 mM, HEPES 10 mM, EGTA 5 mM, pH 7.2. During experiments, cells and solutions were maintained at room temperature (19° C.-30° C.). For manual patch clamp recordings, cell culture dishes were placed on the dish holder of the microscope and continuously perfused (1 ml/min) with bath solution. After formation of a Gigaohm seal between the patch electrodes and the cell (pipette resistance range: 2.5 MΩ-6.0 MΩ; seal resistance range: >1 GΩ) the cell membrane across the pipette tip was ruptured to assure electrical access to the cell interior (whole-cell patch-configuration). For experiments using the QPatch system, cells were transferred as suspension to the QPatch system in the bath solution and automated whole cell recordings were performed.

Cells were voltage clamped at a holding potential of −80 mV. For the analysis of test articles, GABA receptors were stimulated by 2 μM GABA after sequential pre-incubation of increasing concentrations of the test article. Pre-incubation duration was 30 s and the duration of the GABA stimulus was 2 s. Test articles were dissolved in DMSO to form stock solutions (10 mM). Test articles were diluted to 0.01, 0.1, 1, and 10 μM in bath solution. All concentrations of test articles were tested on each cell. The relative percentage potentiation was defined as the peak amplitude in response to GABA $EC_{20}$ in the presence of the test article divided by the peak amplitude in response to GABA $EC_{20}$ alone, multiplied by 100.

Loss of Righting Reflex in Rats

The plasma pharmacokinetics and a qualitative assessment of sedation were obtained in male Sprague Dawley rats according to the following procedure. Rats were dosed by intravenous bolus dose (60 seconds) via the foot dorsal vein at doses ranging from 5 to 15 mg/kg in an appropriate vehicle. In order to assess sedation, rats were gently restrained by hand to a lateral position for dose administration. If decreased muscle tone was observed during dose administration, restraint was gradually reduced. If the animal was unable to return to an upright position, the time was recorded as the onset of loss of righting reflex (LRR). In the event that LRR did not occur during dosing, the animals were evaluated at 5 minute intervals thereafter by being placed in dorsal recumbency. Sluggish or incomplete righting twice consecutively within a 30 second interval qualifies as a loss of righting reflex. After onset of LRR, animals were assessed every 5 minutes in the same manner. Recovery of righting reflex is defined as the ability of a rat to right itself completely within 20 seconds of being placed in dorsal recumbency. The duration of LRR is defined as the time interval between LRR and the return of righting reflex.

Acute PTZ Method

The anticonvulsant effect of test compounds were assessed in the pentylenetetazol-induced seizure assay in mice similar to methods described in Giardina & Gasior (2009) *Curr Protoc Pharmacol.*, Chapter 5. Male CD-1 mice were housed in groups of five under controlled conditions (temperature of 22±2° C. and 12:12 light-dark cycle, lights on at 8:00 am) and water and food were available ad libitum. The mice were housed for 1 week prior to behavioral testing, at which time they weighed 25-35 g. Pentylenetetrazol (PTZ, Sigma) was dissolved in sterile 0.9% saline at a concentration of 12 mg/mL concentration for subcutaneous administration. Test compounds were formulated and administered via oral gavage or intraperitoneal injection at a predetermined time-point (typically 30 or 60 minutes) prior to PTZ injection. All solutions were made fresh and were given in a volume of 10 ml/kg body weight.

Mice were acclimated to the test room for at least 30 min before compound administration. Mice were randomized into at least four test groups (vehicle and at least three doses of the test compound) with 10 mice per group. After compound administration, mice were observed for qualitative assessment of sedation for a pre-determined time point (30 or 60 minutes). Following the drug pretreatment time the mice were injected s.c. with PTZ (120 mg/kg). Immediately following the PTZ injection, mice were individually placed into observation chambers (25×15×15 cm) and a three-channel timer was started. Each mouse was continuously observed for 30 min and the following behaviors were recorded by observers blinded to the treatments: 1) latency to clonic convulsions that persist for 3 sec and followed by an absence of righting reflex 2) latency to tonic convulsions, characterized by the rigid extension of all four limbs that exceeded a 90 degree angle with the body 3) latency to death 4) number of clonic and tonic convulsions. Data are presented as mean±S.E.M and one-way analysis of variance with Dunnett's or Bonferroni's post-hoc test was used to detect significant differences in latency and number between the vehicle and dose group. p values<0.05 were regarded as statistically significant.

TABLE 1

TBPS binding of the exemplary compounds.

| Name | TBPS $IC_{50}$ (nM)* |
|---|---|
| SA-1 | A |
| SA-2 | C |
| SA-3 | A |
| SA-4 | A |
| SA-5 | A |
| SA-6 | B |
| SA-7 | B |
| SA-8 | B |
| SA-9 | B |
| SA-10 | C |
| SA-11 | B |
| SA-12 | B |
| SA-13 | B |
| SA-23 | D |
| SA-24 | B |
| SA-25 | E |
| SA-27 | D |
| SA-29 | E |
| SA-31 | D |
| SA-32 | B |
| SA-33 | E |
| SA-35 | D |
| SB-1 | D |
| SB-3 | E |
| SB-4 | D |
| SB-5 | B |
| SB-7 | E |
| SB-8 | E |
| SB-10 | D |
| SB-18 | D |
| SB-19 | D |
| SB-20 | E |
| SB-22 | D |
| SB-23 | D |

For Table 1:
TBPS: "A" indicates an $IC_{50}$ <10 nM, "B" indicates an $IC_{50}$ 10 to <50 nM, "C" indicates an $IC_{50}$ 50 nM to <100 nM, "D" indicates an $IC_{50}$ 100 nM to <500 nM, and "E" indicates $IC_{50}$ greater than or equal to 500 nM.

TABLE 2

Electrophysiological evaluation of the exemplary compounds at $GABA_A$-R

| Name | $EC_{50}$ (nM)** | Emax (%) |
|---|---|---|
| SA-1 | D | B |
| SA-2 | E | B |
| SA-4 | B | A |
| SA-5 | E | D |
| SA-6 | B | A |
| SA-7 | D | A |
| SA-8 | D | A |
| SA-9 | B | A |
| SA-10 | E | A |
| SA-11 | D | B |
| SA-13 | C | A |

For Table 2:
$EC_{50}$: "A" indicates an $EC_{50}$ <100 nM, "B" indicates an $EC_{50}$ 100 to less than or equal to 500 nM, "C" indicates an $EC_{50}$ >500 nM to 1000 nM, "D" indicates $IC_{50}$ >1000 nM to 2000 nM, and "E" indicates $EC_{50}$ >2000 nM.
Emax: "A" indicates an Emax of 0 to 500, "B" indicates an Emax of >500 to 1000, "C" indicates an Emax of >1000.

TABLE 3

Electrophysiological evaluation of the exemplary compounds at $GABA_A$-R.

| Name | GABA (α1β2γ2) Qpatch in Ltk, % efficacy at 10 μM | GABA (α4β3δ) Manual patch in CHO, % efficacy at 10 μM |
|---|---|---|
| SB-1 | B | B |
| SA-13 | B | C |
| SB-10 | B | B |
| SA-6 | B | C |
| SA-7 | C | C |
| SA-8 | B | D |
| SA-9 | B | C |
| SA-10 | B | D |
| SA-11 | C | D |
| SA-12 | B | D |
| SA-1 | C | D |
| SA-2 | C | D |
| SA-3 | C | D |
| SA-4 | B | B |
| SA-5 | C | D |
| SB-18 | B | D |
| SA-27 | B | D |
| SB-19 | C | D |
| SA-23 | C | D |
| SB-4 | C | D |
| SB-23 | B | D |
| SA-35 | B | D |
| SA-31 | B | D |
| SB-5 | C | B |
| SA-32 | C | C |
| SB-22 | C | D |
| SA-30 | B | D |
| SA-28 | C | D |
| SB-2 | B | B |
| SA-21 | C | D |
| SA-24 | C | C |
| SA-22 | C | B |
| SB-21 | B | D |
| SB-9 | B | D |
| SA-17 | B | B |
| SB-11 | B | C |
| SA-14 | B | D |
| SA-18 | C | D |
| SB-12 | B | D |
| SA-20 | B | D |
| SB-14 | B | D |
| SB-15 | B | C |
| SA-15 | B | D |
| SB-13 | B | D |
| SA-16 | C | D |

For Table 3:
GABAA receptors α1β2γ2 and α4β3δ % effiicacy: "A" 10-100, "B" >100-500, "C" >500; D indicates the data is not available or has not been determined.

TABLE 4

Loss of Righting Reflex (Rat IV, 5 mpk)

| Compound | Duration of Rat LRR |
|---|---|
| SA-6 | A |
| SA-4 | C |
| SA-22 | B |

A <15 min; B 15-60 min; C >60 min
LRR: Loss of Righting Reflex

TABLE 5

Minimal effective anticonvulsant doses are defined as the lowest dose which significantly reduces the latency to tonic seizures in PTZ-treated mice

| Compound | Anticonvulsive Effect Dose |
|---|---|
| SA-13 | B (IP) |
| SA-4 | A (PO) |
| SA-22 | A (PO) |
| SA-17 | A (PO) |

A <3 mpk; B ≥3 mpk

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A method for positively modulating a $GABA_A$ receptor in a subject in need thereof, comprising administering to the subject an effective amount of a compound of the formula

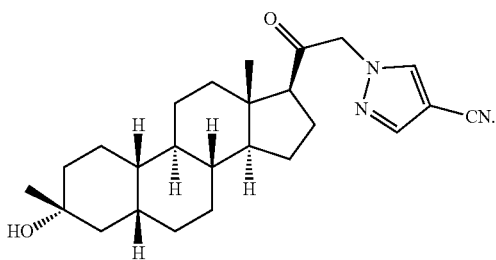

2. The method of claim 1, wherein the compound is administered orally, subcutaneously, intravenously, or intramuscularly.

3. The method of claim 1, wherein the compound is administered chronically.

4. The method of claim 1, wherein the subject has a CNS-related disorder.

5. The method of claim 2, wherein the compound is administered orally.

6. The method of claim 2, wherein the compound is administered intravenously.

7. A method for positively modulating a $GABA_A$ receptor in a subject in need thereof, comprising administering to the subject a pharmaceutical composition comprising an effective amount of a compound of the formula

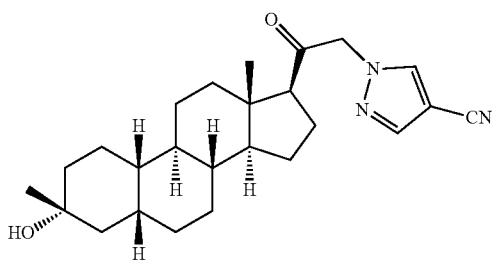

and a pharmaceutically acceptable excipient.

8. The method of claim 7, wherein the pharmaceutical composition is administered orally, subcutaneously, intravenously, or intramuscularly.

9. The method of claim 7, wherein the compound is administered chronically.

10. The method of claim 7, wherein the subject has a CNS-related disorder.

11. The method of claim 8, wherein the pharmaceutical composition is administered orally.

12. The method of claim 8, wherein the pharmaceutical composition is administered intravenously.

* * * * *